(12) United States Patent
Ikeda et al.

(10) Patent No.: US 8,766,243 B2
(45) Date of Patent: Jul. 1, 2014

(54) HETEROCYCLE-CONTAINING ASYMMETRIC AROMATIC COMPOUND, COMPOUND FOR ORGANIC THIN FILM TRANSISTOR, AND ORGANIC THIN FILM TRANSISTOR USING THE SAME

(75) Inventors: Yoichi Ikeda, Sodegaura (JP); Masatoshi Saito, Sodegaura (JP); Hidetsugu Ikeda, Sodegaura (JP); Hiroaki Nakamura, Sodegaura (JP); Hirofumi Kondo, Sodegaura (JP); Naoki Kurihara, Sodegaura (JP); Kota Terai, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 211 days.

(21) Appl. No.: 13/508,034

(22) PCT Filed: Nov. 2, 2010

(86) PCT No.: PCT/JP2010/006455
§ 371 (c)(1),
(2), (4) Date: Jul. 2, 2012

(87) PCT Pub. No.: WO2011/055529
PCT Pub. Date: May 12, 2011

(65) Prior Publication Data
US 2012/0273768 A1   Nov. 1, 2012

(30) Foreign Application Priority Data

Nov. 5, 2009 (JP) ................................ 2009-254004
Jul. 2, 2010 (JP) ................................ 2010-152256
Sep. 22, 2010 (JP) ................................ 2010-211824

(51) Int. Cl.
*H01L 35/24* (2006.01)
(52) U.S. Cl.
USPC .................................. 257/40; 257/E51.001
(58) Field of Classification Search
USPC ........................................ 257/40, E51.001
See application file for complete search history.

(56) References Cited

U.S. PATENT DOCUMENTS 3,896,184 A   7/1975   Bergfjord et al.
2010/0012929 A1   1/2010   Nakano et al.

FOREIGN PATENT DOCUMENTS

| CN | 101523631 | 9/2009 |
|---|---|---|
| JP | 50-36452 A | 4/1975 |
| JP | 05-55568 A | 3/1993 |
| JP | 2001-094107 A | 4/2001 |
| JP | 2009-218333 A | 9/2009 |
| JP | 2009-267140 A | 11/2009 |
| JP | 2010-177637 A | 8/2010 |

OTHER PUBLICATIONS

Written Opinion mailed Feb. 8, 2011 in corresponding application No. PCT/JP2010/006455.
International Search Report mailed Feb. 8, 2011 in corresponding application No. PCT/JP2010/006455.
Tetsuo Otsuki et al., "Novel Photochemical Synthesis of 5-Arylbenzo[b]chrysene Derivatives", Yuki Gosei Kagaku Kyokaishi, 1978, pp. 318-321, vol. 36, No. 4.
Kazuhiro Maruyama et al., "Facile Photochemical Synthesis of Polycyclic Aromatic compounds", The Journal of Organic Chemistry, 1980, pp. 1424-1428, vol. 45.
E. Clar et al., "Kekule Structures and the Benzylic Coupling of o-Dimethyl-Derivatives", Tetrahedron, 1971, pp. 5943-5951, vol. 27.
Kaitei So et al., Journal of the Chemical Society (Kagaku Gakuho),1982, vol. 40, stage 6, pp. 481-487.
Subodh Kumar, "Synthesis of *trans*-3, 4-dihydroxy-3, 4-dihydrophenanthro[3,2-*b*]-[1]benzothiophene, a potentially carcinogenic metabolite of sulfur heterocycle phenanthro[3,2-*b*][1]benzothiophene", Journal of the Chemical Society, Perkin Transactions 1, 2001, pp. 1018-1023, No. 9.
Gerhard Becker et al., "Gas chromatograph-atomic emission detection for quantification of polycyclic aromatic sulfur heterocycles", Analytica Chimica Acta 376, 1998, pp. 265-272.
J.N. Chatterjea et al., Syntheses of Furano Compounds: Part XLII—Cook-Schoental Cyclization of Some Substituted Benzo[b]furans & Benzo[*b*]phenanthro[I,2-*d*]furans, Indian Journal of Chemistry Section B, 17B(4), 1979, pp. 329-332.
Hideki Okamoto et al., "Air-assisted High-performance Field-effect Transistor with Thin Films of Picene", Journal of the American Chemical Society, Aug. 13, 2008, pp. 10470-10471, vol. 130.
Carruthers, et al. "The Constituents of High-boiling Petroleum Distillates. Part VIII. Identification of 1,2,3,4-Tetrahydro-2,2,9-trimethylpicene in an American Crude Oil", Journal of the Chemical Society, published on Jan. 1964, pp. 724-729.
Guillen, et al. "Polycyclic Aromatic Hydrocarbons and Olive Pomace Oil", Journal of Agricultural and Food Chemistry, 2004, vol. 52, pp. 2123-2132.
Liansheng, et al. "Partition Coefficients of PAHs and Di-Region Theory", Acta Scientiae Circumstantiae, Jun. 1987, vol. 7, No. 2, pp. 240-244.
Office Action in CN Appln. No: 201080060537.7 dated Dec. 27, 2013.

*Primary Examiner* — Anthony Ho
(74) *Attorney, Agent, or Firm* — Foley & Lardner LLP

(57) ABSTRACT

A compound represented by the following formula (I), provided that the compound in which all of $R^1$ to $R^{14}$ are hydrogen atoms is excluded.

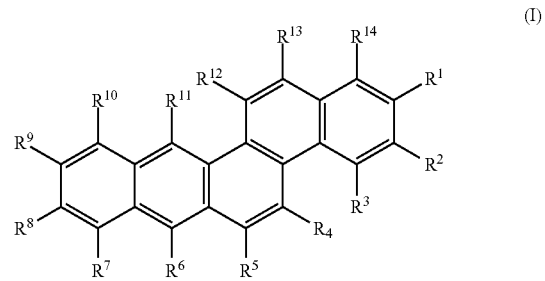

(I)

24 Claims, 3 Drawing Sheets

1: Organic thin film transistor
15: Gate electrode
14: Insulator layer
13: Organic semiconductor layer
12: Drain electrode
10: Substrate
11: Source electrode 2: Organic thin film transistor

HETEROCYCLE-CONTAINING ASYMMETRIC AROMATIC COMPOUND, COMPOUND FOR ORGANIC THIN FILM TRANSISTOR, AND ORGANIC THIN FILM TRANSISTOR USING THE SAME

TECHNICAL FIELD

The invention relates to a compound for an organic thin film transistor and an organic thin film transistor using the same. More particularly, the invention relates to a compound for an organic thin film transistor to which a coating process can be applied and an organic thin film transistor using it in an organic semiconductor layer. Further, the invention relates to a heterocyclic asymmetric aromatic compound, a compound for an organic thin film transistor and an organic thin film transistor using the same. More particularly, the invention relates to a compound for an organic thin film transistor which is a heterocyclic asymmetric aromatic compound to which a coating process can be applied and has excellent oxidization stability, and an organic thin film transistor using it in an organic semiconductor layer. The invention relates to a novel heterocyclic asymmetric aromatic compound, a compound for an organic thin film transistor to which a coating process can be applied and an organic thin film transistor using it in an organic semiconductor layer.

BACKGROUND TECHNOLOGY

A thin film transistor (hereinafter often abbreviated as TFT) has been widely used as a switching device for a display for a liquid crystal display device or the like. A representative TFT has a configuration in which a gate electrode, an insulator layer and a semiconductor layer are stacked in this sequence on a substrate, and has, on the semiconductor layer, a source electrode and a drain electrode being formed with a predetermined interval there between. The organic semiconductor layer constitutes a channel part, and an on-off operation is conducted by controlling electric current between the source electrode and the drain electrode by a voltage applied to the gate electrode.

Conventionally, this TFT was fabricated by using amorphous or polycrystalline silicon. However, a CVD (chemical vapor deposition) apparatus used for fabrication of a TFT using silicon is very expensive, and an increase in size of a display or the like using a TFT had a problem that the production cost increased significantly. Further, there was a problem that, since forming amorphous or polycrystalline silicon into a film requires significantly high temperatures, the type of a material which is usable as a substrate is limited, and hence, a lightweight plastic substrate or the like could not be used. There were also problems that plastic substrates or the like which were excellent in formativeness or flexibility could not be used.

In order to solve the problem, a TFT using an organic substance instead of amorphous or polycrystalline silicon has been proposed. As the film-forming method which is used when a TFT is fabricated by using an organic substance, a vacuum vapor deposition method, a wet coating method or the like are known. According to these methods, it is possible to realize an increase in size of a device while suppressing an increase in the production cost, and is also possible to allow the process temperature which is required at the time of film formation to be relatively low. Accordingly, in such an organic TFT, there are advantages that only small restrictions are imposed on the type of materials used for a substrate. Therefore, its practical use has been expected and research reports have been actively made.

As an organic semiconductor materials used for the active layer of the p-type field effect transistor (FET: field effect transistor), a polymer such as a conjugated polymer or thiophene, metal phthalocyanine compounds, and fused aromatic hydrocarbons such as pentacene or the like have been used singly or in the form of a mixture with other compounds. For the n-type FET materials, 1,4,5,8-naphthalenetetracarboxylic dianhydride (NTCDA), 11,11,12,12-tetracyanonaphtho-2,6-quinodimethane (TCNNQD), 1,4,5,8-naphthalene tetracarboxylic diimide (NTCDI) and fluorinated phthalocyanine are known, for example.

As the device which uses semiconductors as in the case of an organic TFT, an organic electroluminescence (EL) device is known. In an organic EL device, in general, electric charges are forced to inject into a super thin film of 10 nm or less by applying a strong electric field of $10^5$ V/cm or more across the film thickness direction. In the case of an organic TFT, since electric charges are required to be flown at a high speed for a relatively long distance of several μm or more with an electric field of $10^5$ V/cm or less, organic materials itself used in an organic TFT are required to have further conductivity than in an organic EL devices.

However, the above-mentioned organic semiconductor materials in conventional organic TFTs had small field effect mobility and a slow response speed, and hence were defective in high-speed response as a transistor. Moreover, the on-off ratio was also small.

In addition, the on-off ratio as referred to here means a value which is obtained by dividing a current flow between source and drain electrodes when a gate voltage is applied (ON) by a current flow between source and drain electrodes when a gate voltage is not applied (OFF). The on-current is normally means a current value at the time when the current flowing between source and drain electrodes is saturated (saturation current) after increasing the gate voltage.

Pentacene is known as a typical material for an organic TFT. An organic TFT which uses pentacene in an organic semiconductor layer is fabricated in Patent Documents 1 and 2. Since pentacene has a disadvantage that the stability in the atmosphere is low, although it shows a very high mobility immediately after the device fabrication, mobility will be lowered with the passage of time.

As a method to improve the stability in the atmosphere, a phenacene compound is used. For example, Non-Patent Document 1 proposes a picene ([5]phenacene) and Patent Document 3 proposes [5]-[11]phenacene. However, these compounds had a disadvantage that they had a low solubility in common organic solvents, and hence could not be applied to a wet coating process.

Patent Document 4 discloses an organic thin film transistor which is produced by a wet coating process and is provided with an organic semiconductor layer comprising a heterocyclic fused aromatic compound. Patent Document 4 states that this compound has excellent storage stability. However, in this document, the organic TFT for which the storage stability was evaluated were produced by the vacuum deposition method, and for organic TFTs which were produced by a wet coating process, evaluation of storage stability was not made.

As the method for improving the stability in the air, Patent Document 5 discloses a 5-membered fused ring structure in which thiophene rings are arranged on the both ends of a phenanthrene skeleton or a fused ring structure with 5 or more rings in which thiophene rings are arranged on one or both ends of a chrysene skeleton. However, there is neither a statement nor a suggestion on solubility.

RELATED ART DOCUMENTS

Patent Documents

Patent Document 1: JP-A-H05-55568
Patent Document 2: JP-A-2001-94107
Patent Document 3: JP-A-2009-218333
Patent Document 4: JP-A-2009-267140
Patent Document 5: JP-A-2010-177637

Non-Patent Documents

H. Okamoto et al., Journal of the American Chemical Society, vol. 130, page 10470, 2008

SUMMARY OF THE INVENTION

An object of the invention is to provide a compound for an organic thin film transistor to which a wet coating process can be applied and is excellent stability against oxidization.

An object of the invention is to provide an organic thin film transistor which has excellent transistor properties.

According to the invention, the following compound for an organic thin film transistor, or the like are provided.

1. A compound represented by the following formula (I):

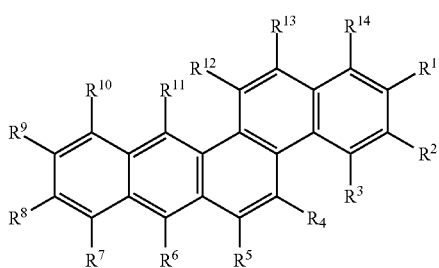

wherein $R^1$ to $R^{14}$ are independently a hydrogen atom, a halogen atom, an alkyl group having 2 to 30 carbon atoms, an alkenyl group having 3 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups further may have one or more substituents; and the two alkyl groups of the dialkylamino group having 2 to 60 carbon atoms may combine with each other to form a cyclic structure containing a nitrogen atom;

provided that the compound in which all of $R^1$ to $R^{14}$ are hydrogen atoms is excluded.

2. The compound according to 1 wherein at least one of $R^1$ to $R^{14}$ is
an alkenyl group having 3 to 30 carbon atoms, an alkynyl group having 2 to 30 carbon atoms, a halolalkyl group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an alkylsilyl group having 3 to 20 carbon atoms, an alkylsilylethynyl group having 5 to 60 carbon atoms or a cyano group.

3. A compound for an organic thin film transistor represented by the following formula (A-1):

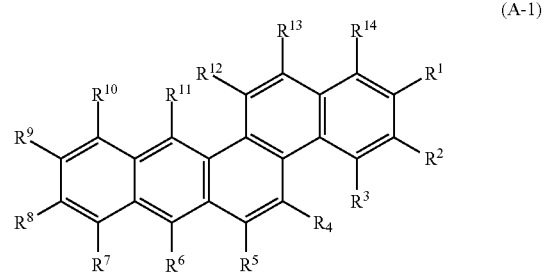

wherein $R^1$ to $R^{14}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups further may have one or more substituents; and the two alkyl groups of the dialkylamino group having 2 to 60 carbon atoms may combine with each other to form a cyclic structure containing a nitrogen atom;

provided that the compound in which all of $R^1$ to $R^{14}$ are hydrogen atoms is excluded.

4. A compound for an organic thin film transistor represented by the following formula (A-2):

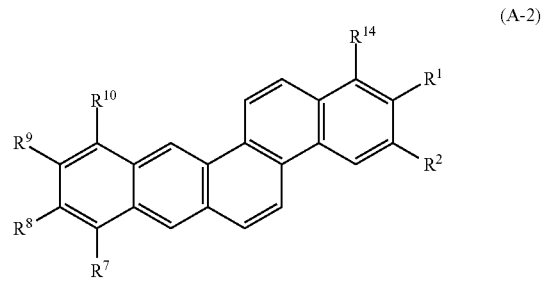

wherein $R^1$, $R^2$, $R^7$, $R^8$, $R^9$, $R^{19}$ and $R^{14}$ are the same as $R^1$, $R^2$, $R^7$, $R^8$, $R^9$, $R^{19}$ and $R^{14}$ in the formula (A-1).

5. An organic thin film transistor comprising the compound for an organic thin film transistor according to 3 or 4.

6. An organic thin film transistor comprising at least three terminals of a gate electrode, a source electrode and a drain electrode, an insulating layer and an organic semiconductor layer, on a substrate, current flowing between the source electrode and the drain electrode being controlled by applying a voltage to the gate electrode, the organic semiconductor layer comprising the compound for an organic thin film transistor according to 3 or 4.

7. An apparatus comprising the organic thin film transistor according to 5 or 6.

8. A compound represented by the following formula (B-1):

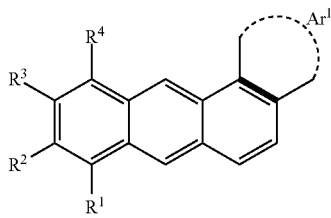

(B-1)

wherein $R^1$ to $R^4$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents;

the two alkyl groups of the above-mentioned dialkylamino group having 2 to 60 carbon atoms may combine with each other to form a ring structure containing a nitrogen atom; and the ring $Ar^1$ is a fused ring which is represented by any of the following formulas (B-2) to (B-5):

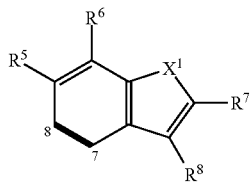

(B-2)

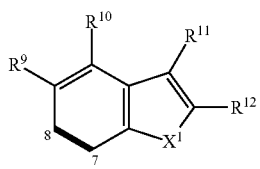

(B-3)

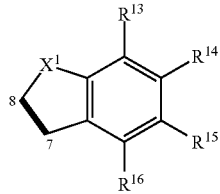

(B-4)

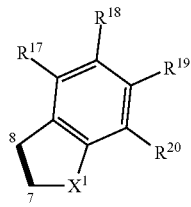

(B-5)

wherein the numerals 7 and 8 in a bold line respectively correspond to the $7^{th}$ and $8^{th}$ positions of the anthracene skeleton of the compound represented by the formula (B-1):

$X^1$ is —S—, —O—, or —N($R^{21}$)—;

$R^5$ to $R^{21}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that compounds in which all of $R^{13}$ to $R^{16}$ and all of $R^{17}$ to $R^{20}$ are hydrogen atoms are excluded.

9. A compound according to 8 which is represented by the following formula (B-6):

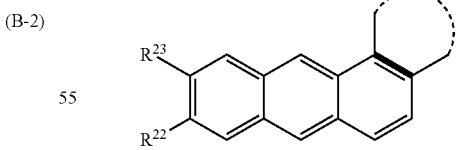

(B-6)

wherein $R^{22}$ and $R^{23}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, which groups may further have one or more substituents;

the two alkyl groups of the dialkylamino group having 2 to 60 carbon atoms may combine with each other to form a ring structure containing a nitrogen atom; and the ring $Ar^2$ is a fused ring represented by any of the following formulas (B-7) to (B-10):

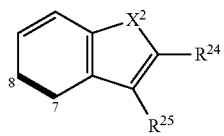
(B-7)

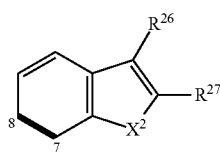
(B-8)

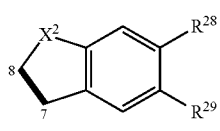
(B-9)

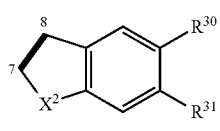
(B-10)

wherein the numerals 7 and 8 in a bold line respectively correspond to the $7^{th}$ and $8^{th}$ positions of the anthracene skeleton of the compound represented by the formula (B-6):

$X^2$ is —S—, —O—, or —N($R^{32}$)—;

$R^{24}$ to $R^{32}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that compounds in which all of $R^{28}$ to $R^{29}$ and all of $R^{39}$ to $R^{31}$ are hydrogen atoms are excluded.

10. A compound for an organic thin film transistor represented by the following formula (B-1):

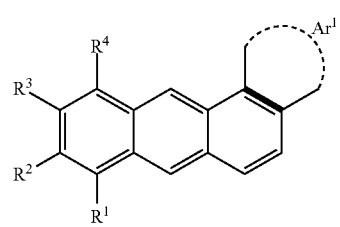
(B-1)

wherein $R^1$ to $R^4$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents;

the two alkyl groups of the dialkylamino group having 2 to 60 carbon atoms may combine with each other to form a ring structure containing a nitrogen atom; and the ring $Ar^1$ is a fused ring which is represented by any of the following formulas (B-2) to (B-5):

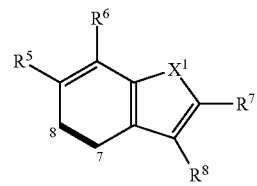
(B-2)

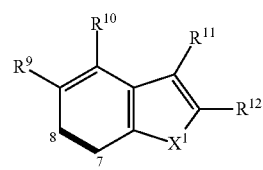
(B-3)

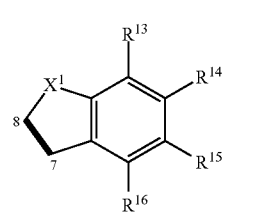
(B-4)

-continued (B-5)

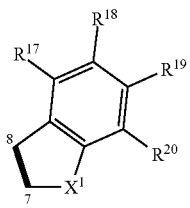

wherein the numerals 7 and 8 in a bold line respectively correspond to the $7^{th}$ and $8^{th}$ positions of the anthracene skeleton of the compound represented by the formula (B-1):

$X^1$ is —S—, —O—, or —N($R^{21}$)—;

$R^5$ to $R^{21}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that compounds in which all of $R^{13}$ to $R^{16}$ and all of $R^{17}$ to $R^{20}$ are hydrogen atoms are excluded.

11. A compound for an organic thin film transistor according to 10 which is represented by the following formula (B-6):

(B-6)

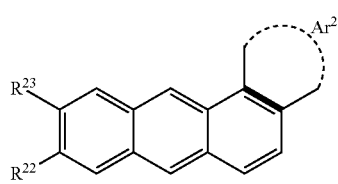

wherein $R^{22}$ and $R^{23}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, which groups may further have one or more substituents;

the two alkyl groups of the dialkylamino group having 2 to 60 carbon atoms may combine with each other to form a ring structure containing a nitrogen atom; and the ring $Ar^2$ is a fused ring represented by any of the following formulas (B-7) to (B-10):

(B-7)

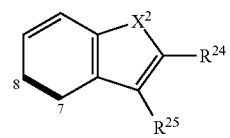

(B-8)

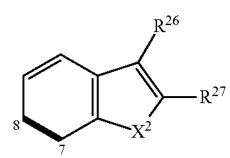

(B-9)

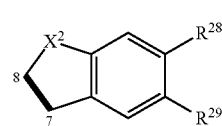

(B-10)

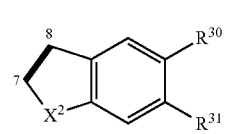

wherein the numerals 7 and 8 in a bold line respectively correspond to the $7^{th}$ and $8^{th}$ positions of the anthracene skeleton of the compound represented by the formula (B-6):

$X^2$ is —S—, —O—, or —N($R^{32}$)—;

$R^{24}$ to $R^{32}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the above-mentioned dialkylamino group having 2 to 60 carbon atoms may combine with each other to form a ring structure containing a nitrogen atom;

provided that compounds in which all of $R^{28}$ to $R^{29}$ and all of $R^{30}$ to $R^{31}$ are hydrogen atoms are excluded.

12. An organic thin film transistor comprising the compound for an organic thin film transistor according to 10 or 11.

13. An organic thin film transistor comprising at least three terminals of a gate electrode, a source electrode and a drain electrode, an insulating layer and an organic semiconductor layer, on a substrate, current flowing between the source electrode and the drain electrode being controlled by applying a voltage to the gate electrode, the organic semiconductor layer comprising the compound for an organic thin film transistor according to 10 or 11.

14. An apparatus comprising the organic thin film transistor according to 12 or 13.

15. A method for producing an organic thin film transistor wherein an organic semiconductor layer is formed by applying the compound for an organic thin film transistor according to 10 or 11.

16. A compound represented by the following formula (C-1) or (C-2):

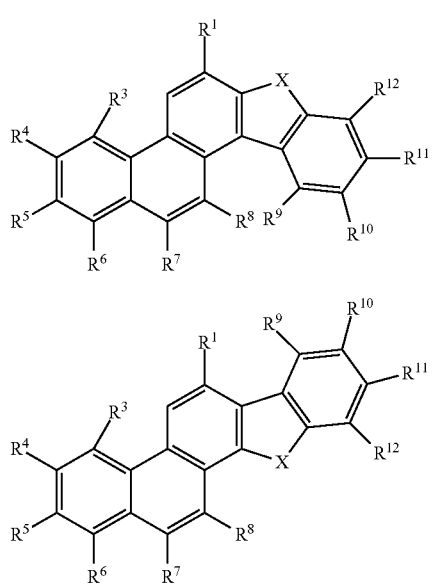

(C-1)

(C-2)

wherein $R^1$ to $R^8$ are independently a hydrogen atom, a halogen atom, an alkyl group having 2 to 30 carbon atoms, an alkenyl group having 2 to 30 carbon atoms, an alkynyl group having 2 to 30 carbon atoms, a haloalkyl group having 1 to 30 carbon atoms, an alkoxy group having 2 to 30 carbon atoms, a haloalkoxy group having 1 to 30 carbon atoms, an alkylthio group having 2 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms or an alkylsilylethynyl group having 5 to 60 carbon atoms, which groups may further have one or more substituents;

the two alkyl groups of the dialkylamino group having 2 to 60 carbon atoms may combine with each other to form a ring structure containing a nitrogen atoms;

X is —S—, —O—, or —N($R^{13}$)—;

$R^9$ to $R^{13}$ are independently a hydrogen atom, a halogen atom, an alkyl group having 2 to 30 carbon atoms ($R^{13}$ may be a methyl group), an alkenyl group having 2 to 30 carbon atoms, an alkynyl group having 2 to 30 carbon atoms, a haloalkyl group having 1 to 30 carbon atoms, an alkoxy group having 2 to 30 carbon atoms, a haloalkoxy group having 1 to 30 carbon atoms, an alkylthio group having 2 to 30 carbon atoms, a haloalkylthio group having 1 to 30 carbon atoms, an alkylamino group having 1 to 30 carbon atoms, a dialky-lamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that at least one of $R^1$ to $R^{12}$ is a group other than hydrogen.

17. The compound according to 16 wherein the compound represented by the formula (C-1) is a compound represented by the following formula (C-3) and the compound represented by the formula (C-2) is a compound represented by the following formula (C-4):

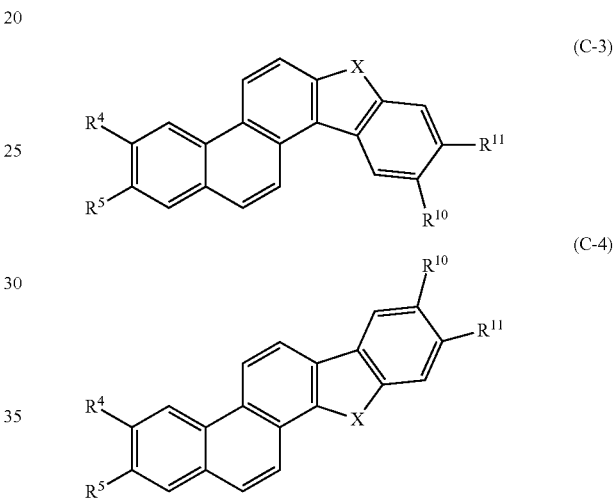

(C-3)

(C-4)

wherein X, $R^4$, $R^5$, $R^{19}$ and $R^{11}$ are the same as those in the formulas (C-1) and (C-2); and at least one of $R^4$, $R^5$, $R^{19}$ and $R^{11}$ is a group other than hydrogen.

18. The compound according to 16 or 17 which is a compound for an organic thin film transistor.

19. An organic thin film transistor which comprises the compound according to 18.

20. An organic thin film transistor comprising at least three terminals of a gate electrode, a source electrode and a drain electrode, an insulating layer and an organic semiconductor layer, on a substrate, current flowing between the source electrode and the drain electrode being controlled by applying a voltage to the gate electrode, the organic semiconductor layer comprising the compound according to 18.

21. An apparatus comprising the organic thin film transistor according to 19 or 20.

According to the invention, it is possible to provide a compound for an organic thin film transistor to which a coating process can be applied and is excellent in stability to oxidization.

According to the invention, it is possible to provide an organic thin film transistor which has excellent transistor properties.

MODE FOR CARRYING OUT THE INVENTION

Figure 1:
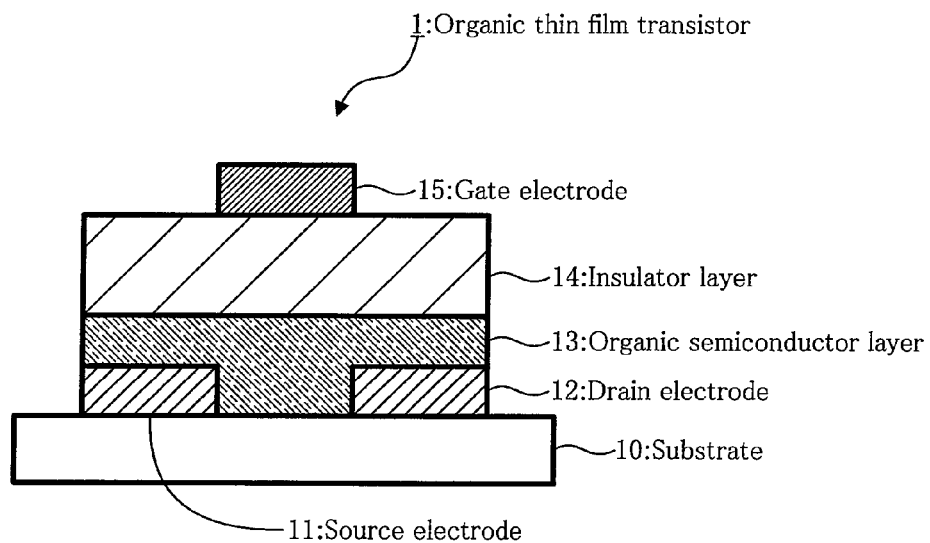
FIG. 1 is a view showing one embodiment of the thin film transistor of the invention.

The first embodiment of the invention will be explained herein below. The compound for an organic thin film transistor according to a first embodiment of the invention is a compound represented by the following formula (A-1).

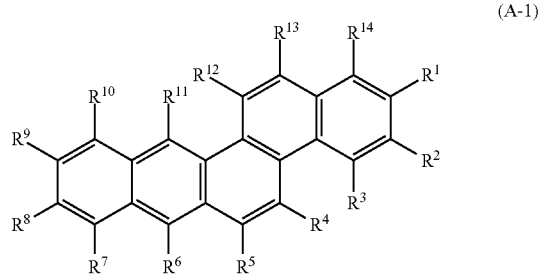

(A-1)

wherein $R^1$ to $R^{14}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups further may have one or more substituents; and the two alkyl groups of the dialkylamino group having 2 to 60 carbon atoms may combine with each other to form a cyclic structure containing a nitrogen atom;

provided that the compound in which all of $R^1$ to $R^{14}$ are hydrogen atoms is excluded.

The compound for an organic thin film transistor represented by the formula (A-1) (hereinafter may be referred to as a first compound of the invention) can provide a high mobility when used as a material for an organic thin film transistor due to enhanced intermolecular interaction by expanding the π-conjugated system. Further, by causing the structure to be asymmetric and/or introducing a substituent, the compound of the invention can have improved solubility in an organic solvent.

In addition, unlike a linear polyacene, the representative example of which is pentacene, in which benzene rings are fused in a straight line, the compound of the invention has a phenacene structure in which some of the benzene rings are arranged in a zig-zag manner, and hence has excellent stability against oxidization.

In the formula (A-1), it is preferred that at least one of $R^1$ to $R^{14}$ be a group selected from an alkenyl group having 3 to 30 carbon atoms, an alkynyl group having 2 to 30 carbon atoms, a haloalkyl group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an alkylsilyl group having 3 to 20 carbon atoms, an alkylsilyl group having 5 to 60 carbon atoms and a cyano group.

The first compound of the invention is preferably a compound for an organic thin film transistor represented by the following formula (A-2). Due to the structure represented by the formula (A-2), the first compound has a strong intermolecular interaction, whereby a high mobility can be expected.

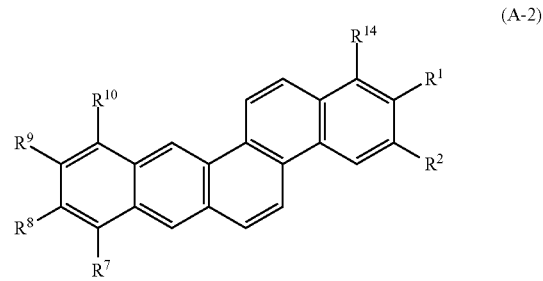

(A-2)

wherein $R^1$, $R^2$, $R^7$, $R^8$, $R^9$, $R^{19}$ and $R^{14}$ are the same as $R^1$, $R^2$, $R^7$, $R^8$, $R^9$, $R^{70}$ and $R^{14}$ in the formula (A-1).

Of the compounds represented by the formula (A-2), compounds in which only $R^1$ is a substituent other than a hydrogen atom and all of $R^2$, $R^7$, $R^8$, $R^9$, $R^{10}$ and $R^{14}$ are a hydrogen atom is an excellent compound since it can shorten the reaction process and the production thereof is easy.

In the above-mentioned case, $R^1$ is preferably an alkyl group having 1 to 30 carbon atoms, an alkenyl group having 2 to 30 carbon atoms, an alkynyl group having 2 to 30 carbon atoms, a haloalkyl group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents.

Herein below, each substituent of the first compound of the invention will be explained.

The alkyl group having 1 to 30 carbon atoms represented by $R^1$ to $R^{14}$ is preferably an alkyl group having 2 to 30 carbon atoms. Examples thereof include methyl, ethyl, propy, isopropyl, n-butyl, s-butyl, isobutyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, and n-octadecyl.

Of the above-mentioned alkyl groups, in respect of solubility, a straight-chain alkyl group is preferable. A straight-chain alkyl group having 3 to 18 carbon atoms is preferable, with a straight-chain alkyl group having 5 to 12 carbon atoms being particularly preferable. In the case of a straight-chain alkyl group having 19 or more carbon atoms, an organic thin film transistor using the same may have insufficient heat resistance.

The alkenyl group having 2 to 30 carbon atoms represented by $R^1$ to $R^{14}$ is preferably an alkenyl group having 3 to 30 carbon atoms. Examples thereof include ethenyl, propenyl, butenyl, pentenyl, pentadienyl, hexenyl, hexadienyl, heptenyl, octenyl, octadienyl, 2-ethylhexenyl and deceny.

As the alkynyl group having 2 to 30 carbon atoms represented by $R^1$ to $R^{14}$ include ethynyl, propynyl, 2-phenylethynyl, n-butynyl, n-pentynyl, n-hexynyl, n-heptynyl and n-octynyl can be given.

As the haloalkyl group having 1 to 30 carbon atoms represented by $R^1$ to $R^{14}$, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-iodoethyl group, a 1,3-iodoisopropyl group, a 2,3-diodo-t-butyl group, a 1,2,3-triiodopropyl group, a fluoromethyl group, a 1-fluoroethyl group, a 2-fluoroethyl group, a 2-fluoroisobutyl group, a 1,2-difluoroethyl group, a difluoromethyl group, a trifluoromethyl group, a pentafluoroethyl group, a perfluoroisopropyl group, a perfluorobutyl group, a perfluorocyclohexyl group, or the like can be given, for example.

The alkoxy group having 1 to 30 carbon atoms represented by $R^1$ to $R^{14}$ is a group represented by —$OX^1$, and the examples of $X^1$ include the same groups as exemplified in the above-mentioned alkyl group. The haloalkoxy group having 1 to 30 carbon atoms represented by $R^1$ to $R^{14}$ is a group represented by —$OX^2$, and the examples of $X^2$ include the same groups as those exemplified in the above-mentioned haloalkyl group.

The alkylthio group having 1 to 30 carbon atoms represented by $R^1$ to $R^{14}$ is a group represented by —$SX^1$, and the examples of $X^1$ include the same groups as exemplified in the above-mentioned alkyl group. The haloalkylthio group having 1 to 30 carbon atoms represented by $R^1$ to $R^{14}$ is a group represented by —$SX^2$, and the examples of $X^2$ include the same groups as those exemplified in the above-mentioned haloalkyl group.

The alkylamino group having 1 to 30 carbon atoms represented by $R^1$ to $R^{14}$ is a group represented by —$NHX^1$, a dialkylamino group is a group represented by —$NX^1X^3$, and the examples of $X^1$ and $X^3$ include the same groups as those exemplified by the above-mentioned alkyl group. In addition, the alkyl groups of the dialkylamino group having 2 to 60 carbon atoms represented by $R^1$ to $R^{14}$ may combine with each other to form a ring structure containing a nitrogen atom. Examples of the ring structure include pyrrolidine, piperidine, or the like.

As the arylamino group having 6 to 60 carbon atoms represented by $R^1$ to $R^{14}$, it suffices that at least one of the substituent(s) bonding to the amino group be an aryl group. Specific examples thereof include phenylamino, methylphenylamino, diphenylamino, di-p-tolylamino, di-m-tolylamino, phenyl-m-tolylamino, phenyl-1-naphthylamino, phenyl-2-naphthylamino, phenyl(sec-butylphenyl)amino, phenyl-t-butylamino, bis(4-methoxyphenyl)amino, and phenyl-4-carbazolylphenylamino.

The alkylsulfonyl group having 1 to 30 carbon atoms represented by $R^1$ to $R^{14}$ is a group represented by —$SO_2X^1$ and the examples of $X^1$ include the same groups as exemplified in the above-mentioned alkyl group. The haloalkylsulfonyl group having 1 to 30 carbon atoms represented by $R^1$ to $R^{14}$ is a group represented by —$SO_2X^2$ and the examples of $X^2$ include the same groups as those exemplified in the above-mentioned haloalkyl group.

As the aromatic hydrocarbon group having 6 to 60 carbon atoms represented by $R^1$ to $R^{14}$, a phenyl group, a naphthyl group, an anthryl group, a phenanthryl group, a fluorenyl group, a perylenyl group, a tetracenyl group, a pentacenyl group, or the like can be given, for example.

As the aromatic heterocyclic group having 3 to 60 carbon atoms represented by $R^1$ to $R^{14}$, a dithienophenyl group, a benzofuranyl group, a benzothiophenyl group, a quinolynyl group, a carbazolyl group, a dibenzofuranyl group, a dibenzothiophenyl group, a benzothiazonyl group or the like can be given, for example.

The alkylsilyl group having 3 to 20 carbon atoms represented by $R^1$ to $R^{14}$ is a group represented by —$SiX^1X^2X^3$ and the examples of $X^1$, $X^2$ and $X^3$ include the same groups as exemplified in the above-mentioned alkyl group.

As the alkylsilylethyl group having 5 to 60 carbon atoms represented by $R^1$ to $R^{14}$, a trimethylsilylethynyl group, a triethylsilylethynyl group, a triisopropylsilylethynyl, group, a tert-butylsilylethynyl or the like can be given.

As the substituent which $R^1$ to $R^{14}$ further have, an arylsulfonyl group can be given.

In each of the above-mentioned substituents, an alkyl group, an alkenyl group and an alkynyl group are preferable since both the mobility and the solubility are expected to be improved. An alkyl group is particularly preferable. Further, for the same reason, an arylalkyl group having 7 to 60 carbon atoms is preferable. As the aromatic hydrocarbon group and the alkyl group constituting the arylalkyl group, the above-mentioned groups can be given.

Specific examples of the first compound of the invention are given below.

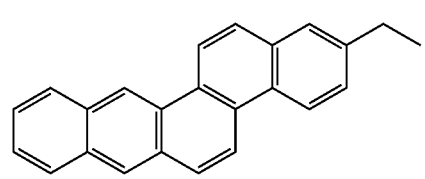

(A2)

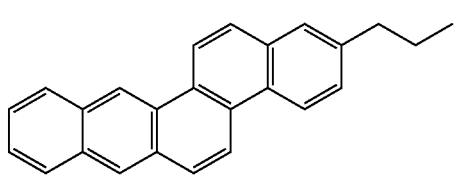

(A3)

-continued
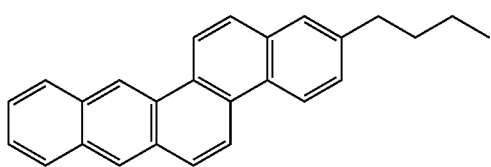 (A4)
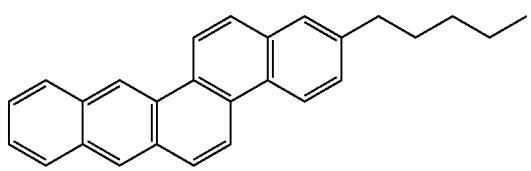 (A5)
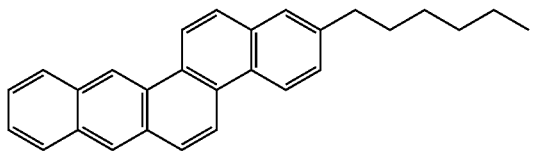 (A6)
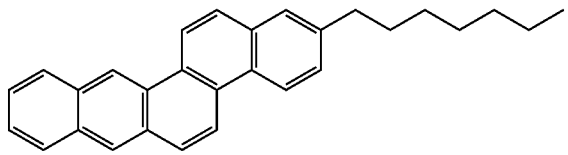 (A7)
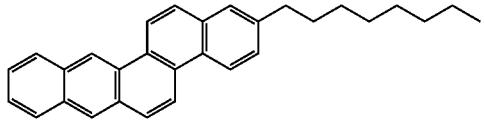 (A8)
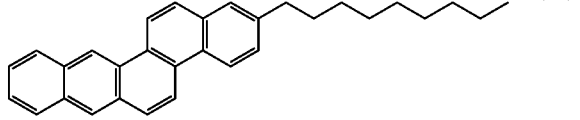 (A9)
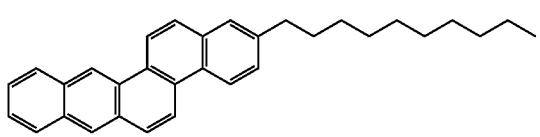 (A10)
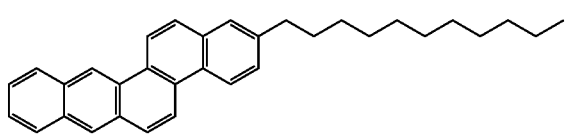 (A11)
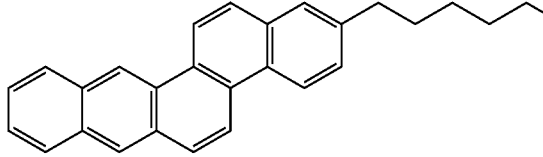 (A12)
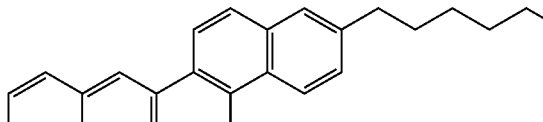 (A13)
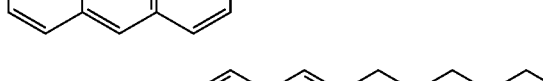 (A14)
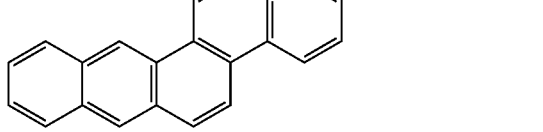 (A15)
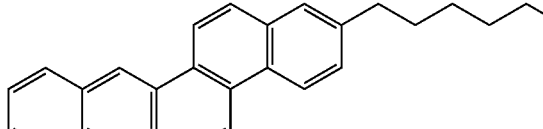 (A16)
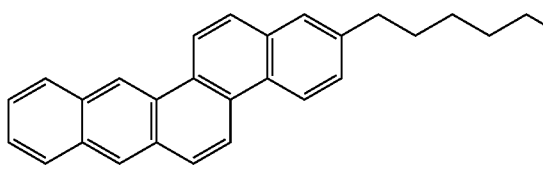

-continued
(A17)
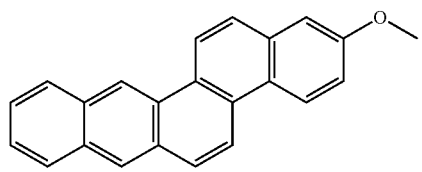
(A18)
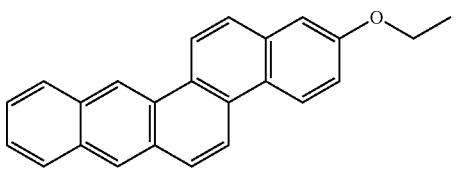
(A19)
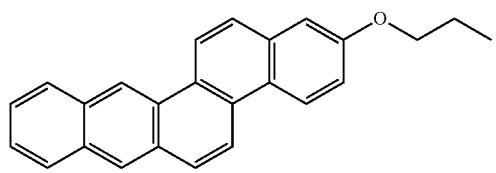
(A20)
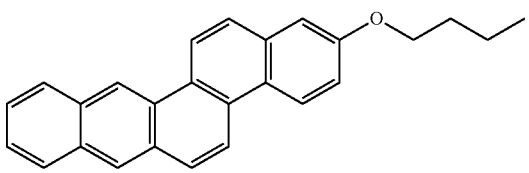
(A21)
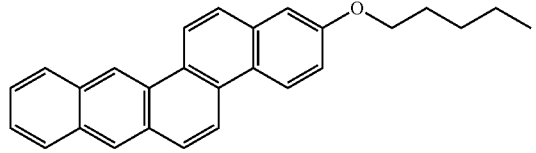
(A22)
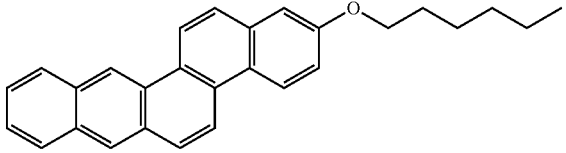
(A23)
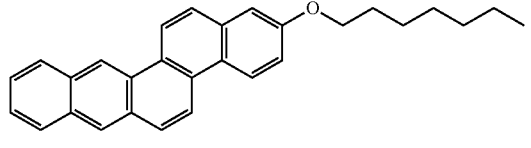
(A24)
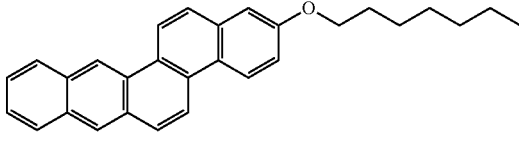
(A25)
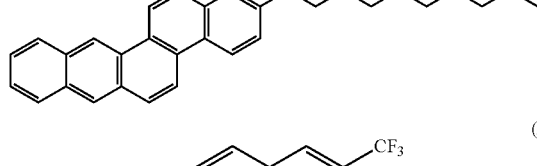
(A26)
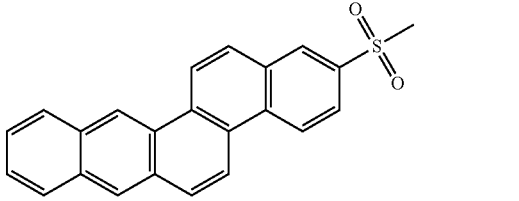
(A27)
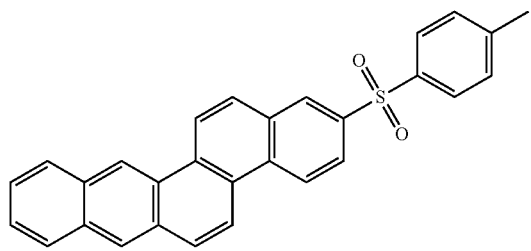
(A28)
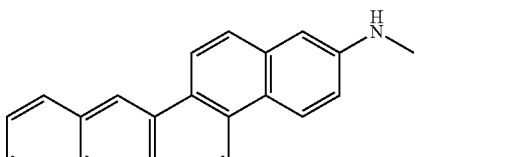
(A29)
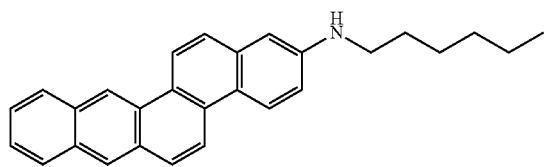
(A30)
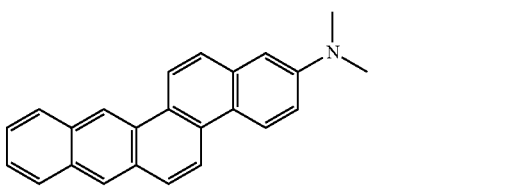
(A31)
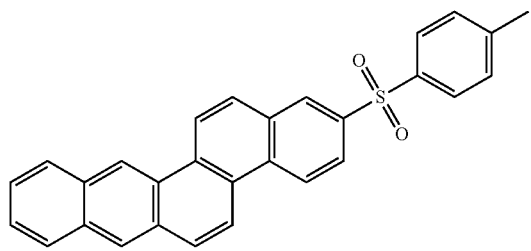
(A32)
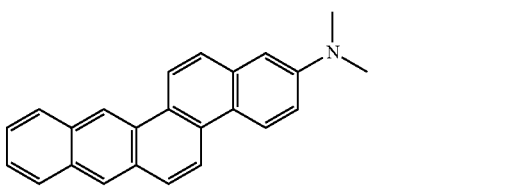

-continued
(A33)
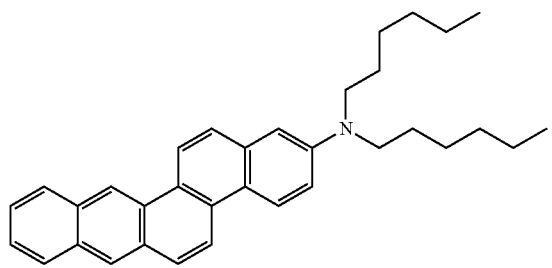
(A34)
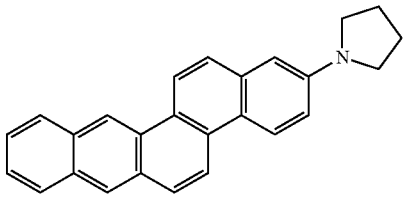
(A35)
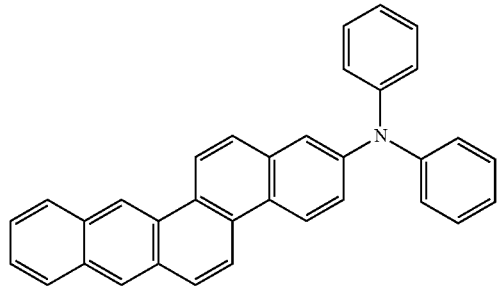
(A36)
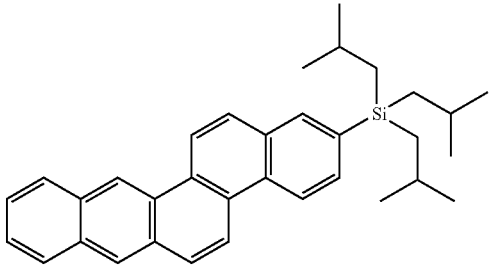
(A37)
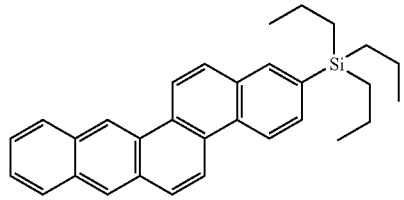
(A38)
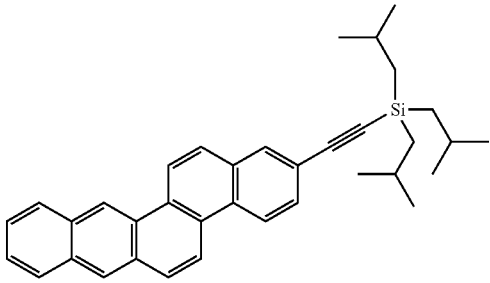
(A39)
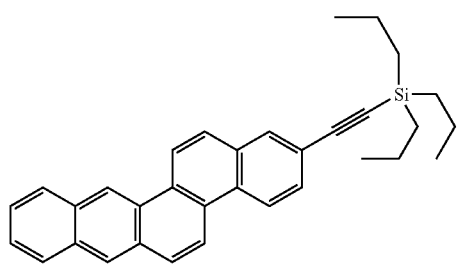
(A40)
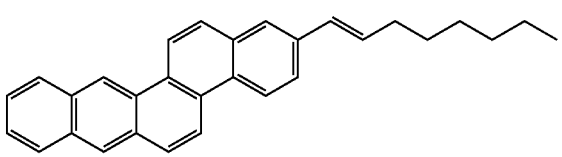
(A41)
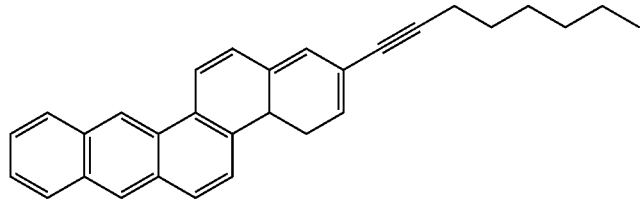

The first compound of the invention can be synthesized by the following synthesis route, for example.

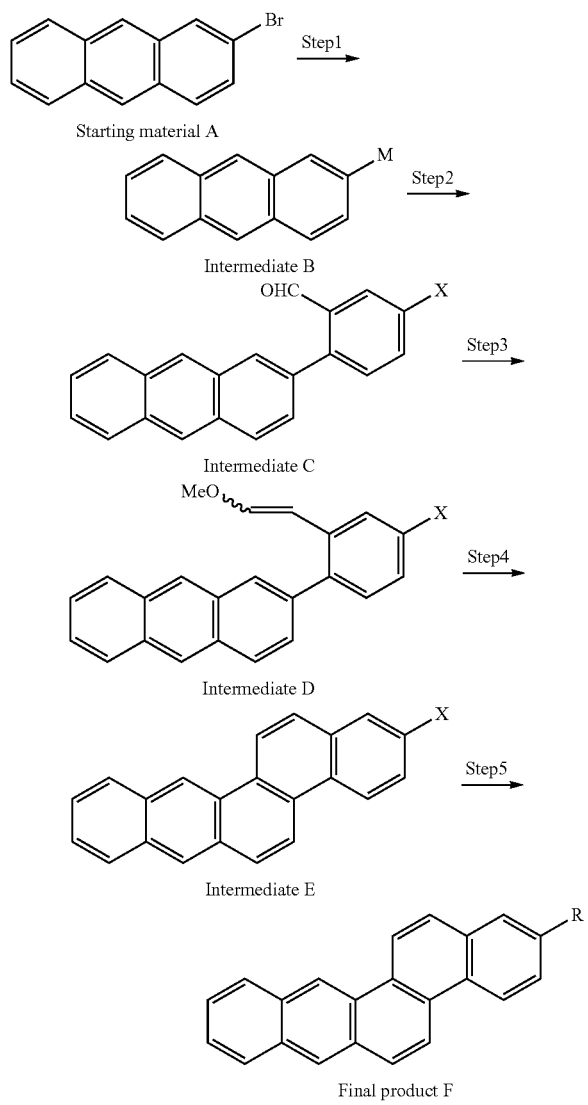

(R is a substituent and X is a halogen atom)

In the step 1, halogenated aromatic compound as the starting material A is metalized or boronated to synthesize the intermediate B. As the reaction used in the step 1, Miyaura-Ishiyama borylation, borylation using n-butyllithium and trimethoxyboran, stannylation using n-butyllithium and tin tributyltin chloride, a conversion reaction to an organozinc reagent using tert-butyllithium and zinc chloride or the like can be given. Of these, Miyaura-Ishiyama borylation is preferable due to a preferable yield and a high solubility of a produced compound.

Step 2 is a step in which the intermediate B and a benzaldehyde derivative are connected to synthesize the intermediate C. As the reaction used for the step 2, Suzuki-Miyaura coupling, Stille coupling, Negishi coupling or the like can be given. Of these, in respect of a good yield, Suzuki-Miyaura coupling is preferable.

Step 3 is a step in which a formyl group is converted to methyl enol ether by using a Wittig reagent to synthesize the intermediate D. As the reagent which can be used in the step 3, (methoxymethyl)triphenylphosphonium chloride can be given.

Step 4 is a step in which a cyclization reaction is conducted using an acid to synthesize the intermediate E. In the step 4, various Lews acids, protonic acids can be used. Use of methanesulfonic acid is preferable since it attains a good yield.

Step 5 is a step in which a substituent is introduced into the intermediate E to synthesize the final product F. As the reaction used in the step 5, Suzuki-Miyaura coupling, Stille coupling, Negishi coupling, Hiyama coupling, Kumada coupling, Mizoroki-Heck coupling or the like can be used. Of these, it is preferable to use Kumada coupling since it can attain a good yield.

Herein below, a second aspect of the invention will be explained.

The compound according to the second aspect of the invention is a compound (heterocyclic asymmetric aromatic compound) represented by the following formula (B-1):

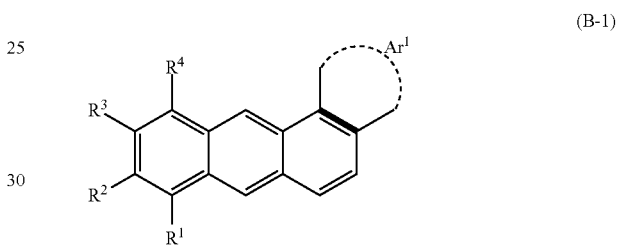

(B-1)

wherein $R^1$ to $R^4$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents;

the two alkyl groups of the above-mentioned dialkylamino group having 2 to 60 carbon atoms may combine with each other to form a ring structure containing a nitrogen atom; and the ring $Ar^1$ is a fused ring which is represented by any of the following formulas (B-2) to (B-5):

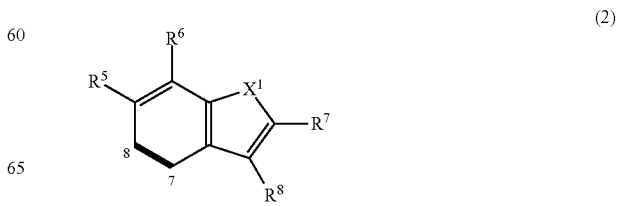

(2)

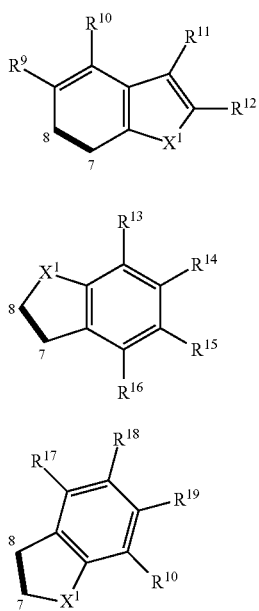

(3)

(4)

(5)

wherein the numerals 7 and 8 in a bold line respectively correspond to the 7th and 8th positions of the anthracene skeleton of the compound represented by the formula (B-1):

$X^1$ is —S—, —O—, or —N($R^{21}$)—;

$R^5$ to $R^{21}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that compounds in which all of $R^{13}$ to $R^{16}$ and all of $R^{17}$ to $R^{20}$ are hydrogen atoms are excluded.

As for the compound represented by the formula (B-1) (hereinafter simply referred to as a second compound of the invention), when used as the material for an organic thin film transistor, intermolecular interaction is enhanced by the extension of the π-electron conjugated system in the entire compound or between molecules and the heavy atom effect of the hetero atom, and hence a higher mobility can be obtained.

Further, as for the second compound of the invention, by causing the structure thereof to be asymmetric and/or by introducing a substituent, solubility in an organic solvent can be improved.

In addition, unlike linear polyacene in which benzene rings, the representative example of which is pentacene, are arranged in a straight line, in the compound of the invention, part of benzene rings are arranged in a bent manner. Accordingly, it has a structure equivalent to phenacene, and hence has excellent stability to oxidization.

In the compound represented by the formula (B-1), in respect of mobility, solubility and stability to oxidization, the ring $Ar^1$ is preferably a fused ring represented by the formula (B-2), (B-3) or (B-4). It is more preferred that the ring $Ar^1$ be a fused ring represented by the formula (B-2) or (B-4).

The second compound of the invention is preferably a compound represented by the following formula (B-6):

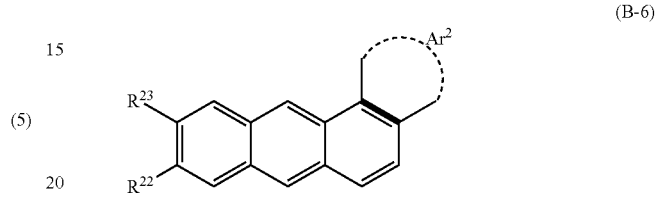

(B-6)

wherein $R^{22}$ and $R^{23}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, which groups may further have one or more substituents;

the two alkyl groups of the above-mentioned dialkylamino group having 2 to 60 carbon atoms may combine with each other to form a ring structure containing a nitrogen atom; and the ring $Ar^2$ is a fused ring represented by any of the following formulas (B-7) to (B-10):

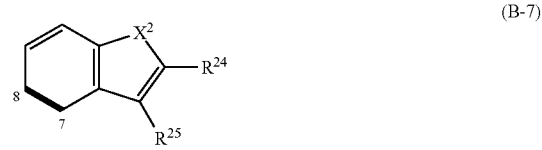

(B-7)

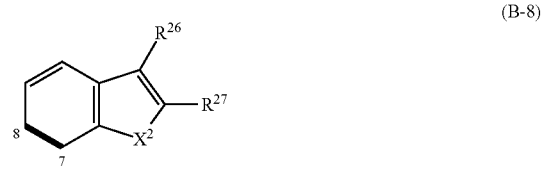

(B-8)

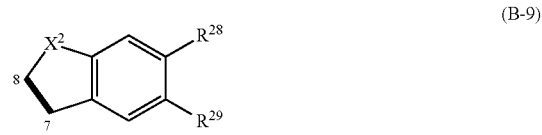

(B-9)

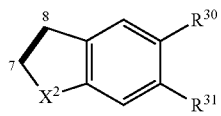

(B-10)

wherein the numerals 7 and 8 in a bold line respectively correspond to the 7$^{th}$ and 8$^{th}$ positions of the anthracene skeleton of the compound represented by the formula (B-6):

X$^2$ is —S—, —O—, or —N(R$^{32}$)—;

R$^{24}$ to R$^{32}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the above-mentioned dialkylamino group having 2 to 60 carbon atoms may combine with each other to form a ring structure containing a nitrogen atom;

provided that compounds in which all of R$^{28}$ to R$^{29}$ and all of R$^{30}$ to R$^{31}$ are hydrogen atoms are excluded.

The compound represented by the formula (B-6) is a compound represented by the formula (B-1) in which R$^1$, R$^4$, R$^5$, R$^6$, R$^9$, R$^{10}$, R$^{13}$, R$^{16}$, R$^{17}$ and R$^{20}$ are hydrogen atoms and shows a strong intermolecular interaction. Therefore, when used in an organic thin film transistor, a high mobility can be expected.

In the compound represented by, the formula (B-6), the ring Ar$^2$ is preferably a fused ring represented by the formula (B-7), (B-8) or (B-9) in respect of mobility, solubility and stability to oxidization. It is more preferred that the ring Ar$^2$ be a fused ring represented by the formula (B-7) or (B-9).

The position numbers of the anthracene skeleton are as follows.

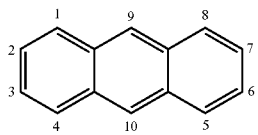

Hereinbelow, each substituent of the second compound of the invention will be explained.

X$^1$ and X$^2$ are preferably —S—. The reason therefor is that hetero atoms (O, N and S) have an interaction called the heavy atom effect, and of these hetero atoms, S has a strong interaction.

In addition, when X$^1$ and X$^2$ are —N(R$^{21}$)— and —N(R$^{32}$)—, in respect of easiness in synthesis of the compound of the invention and generation of a small amount of bi-products, R$^{21}$ and R$^{32}$ are preferably a substituent other than a hydrogen atom. R$^{21}$ and R$^{32}$ are more preferably an alkyl group having 1 to 30 carbon atoms, further preferably an alkyl group having 1 to 6 carbon atoms, with a methyl group being particularly preferable. If R$^{21}$ and R$^{32}$ are a substituent other than a hydrogen atom, a high mobility can be expected.

It is preferred that R$^1$, R$^4$, R$^5$, R$^6$, R$^9$, R$^{10}$, R$^{13}$, R$^{16}$, R$^{17}$ and R$^{20}$ be a hydrogen atom. Further, one of R$^2$ and R$^3$, one of R$^7$ and R$^8$, one of R$^{11}$ and R$^{12}$, one of R$^{19}$ and R$^{20}$, one of R$^{22}$ and R$^{23}$, one of R$^{24}$ and R$^{25}$, one of R$^{26}$ and R$^{27}$, one of R$^{28}$ and R$^{29}$ and one of R$^{30}$ and R$^{31}$ be a hydrogen atoms in respect of easiness of the synthesis of the compound of the invention.

If adjacent groups are both substituents other than a hydrogen atom, a non-bulky substituent such as a short-chain alkyl group is preferable.

As the halogen atom represented by R$^1$ to R$^{32}$, a fluorine atom, a chlorine atom, a bromine atom and an iodine atom can be given.

If the halogen atom is directly bonded to the aromatic ring or the heterocyclic ring, the bonding position thereof is preferably one of R$^2$ and R$^3$, one of R$^7$ and R$^8$, one of R$^{11}$ and R$^{12}$, one of R$^{19}$ and R$^{20}$, one of R$^{22}$ and R$^{23}$, one of R$^{24}$ and R$^{25}$, one of R$^{26}$ and R$^{27}$ and one of R$^{28}$ and R$^{29}$ and one of R$^{30}$ and R$^{31}$.

As the alkyl group having 1 to 30 carbon atoms represented by R$^1$ to R$^{32}$, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group and an n-octadecyl group can be given.

Of these alkyl groups, in respect of mobility and solubility, an alkyl group having 1 to 20 carbon atoms is preferable, with an alkyl group having 1 to 10 carbon atoms being more preferable.

If adjacent groups are both alkyl groups such as R$^2$ and R$^3$, and R$^7$ and R$^8$, it is preferred that R$^2$ and R$^3$ and R$^7$ and R$^8$ be respectively a short-chain alkyl group such as an alkyl group having 1 to 5 carbon atoms since the compound of the invention can be synthesized easily.

As the alkenyl group having 2 to 30 carbon atoms represented by R$^1$ to R$^{32}$, an ethenyl group, a propenyl group, a butenyl group, a pentenyl group, a pentadienyl group, a hexenyl group, a hexadienyl group, a heptenyl group, an octenyl group, an octadienyl group, a 2-ethylhexenyl group and a decenyl group can be given. An alkenyl group having 2 to 10 carbon atoms is preferable.

If the alkenyl group is directly bonded to the aromatic ring or the heterocyclic ring, the bonding position thereof is preferably one of R$^2$ and R$^3$, one of W and R$^8$, one of R$^{11}$ and R$^{12}$, one of R$^{19}$ and R$^{20}$, one of R$^{22}$ and R$^{23}$, one of R$^{24}$ and R$^{25}$, one of R$^{26}$, R$^{27}$ and one of R$^{28}$ and R$^{29}$ and one of R$^{30}$ and R$^{31}$.

As the substituent to be added to an alkenyl group, a phenyl group and/or a phenyl group substituted by an alkyl group can be given. In this case, it is preferred that the substituent be added to the terminal of the straight-chain alkenyl group. Further, as the alkyl group to be added to the alkenyl group, a straight-chain alkyl group is preferable.

As the alkynyl group having 2 to 30 carbon atoms represented by R$^1$ to R$^{32}$, an ethynyl group, a propinyl group, a 2-phenylethynyl group, an n-butynyl group, an n-pentynyl group, an n-hexynyl group, an n-heptyny group, an n-octynyl group, an n-undecynyl group and an n-dodecynyl group can be given. An alkynyl group having 2 to 12 carbon atoms is preferable.

It is preferred that the triple bond of the alkynyl group be bonded to the aromatic ring or the heterocyclic ring of the compound of the invention not through an alkylene group.

As the substituent to be added to the alkynyl group, a phenyl group and/or a phenyl group which is substituted by an alkyl group can be given. In this case, it is preferred that the substituent be added to the terminal of the straight-chain alkynyl group. Moreover, as the alkyl group to be added to the alkynyl group, a straight-chain alkyl group is preferable.

As other substituents to be added to the alkynyl group, a trialkylsilyl group can be given. As the alkyl group to be bonded to the silyl group, a short-chain alkyl group such as a methyl group, an ethyl group and an isopropyl group is preferable.

Specific examples of the haloalkyl group having 1 to 30 carbon atoms represented by $R^1$ to $R^{32}$ include a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bormoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a fluoromethyl group, a 1-fluoroethyl group, a 2-fluoroethyl group, a 2-fluoroisobutyl group, a 1,2-difluoroethyl group, a difluoromethyl group, a trifluoromethyl group, a pentafluoroethyl group, a perfluoroisopropyl group, a perfluorobutyl group and a perfluorocyclohexyl group. A 1-haloalkyl group having 1 to 10 carbon atoms is preferable.

The alkoxy group having 1 to 30 carbon atoms represented by $R^1$ to $R^{32}$ is a group represented by $-OY^1$, and the examples of $Y^1$ include the same groups as those exemplified in the above-mentioned alkyl group. The haloalkoxy group having 1 to 30 carbon atoms represented by $R^1$ to $R^{32}$ is a group represented by $-OY^2$, and the examples of $Y^2$ include the same groups as those exemplified in the above-mentioned haloalkyl group.

The alkylthio group having 1 to 30 carbon atoms represented by $R^1$ to $R^{32}$ is a group represented by $-SY^1$, and the examples of $Y^1$ include the same groups as those exemplified in the above-mentioned alkyl group. The haloalkylthio group having 1 to 30 carbon atoms represented by $R^1$ to $R^{32}$ is a group represented by $-SY^2$, and the examples of $Y^2$ include the same groups as those exemplified in the above-mentioned haloalkyl group.

The alkylamino group having 1 to 30 carbon atoms represented by $R^1$ to $R^{32}$ is a group represented by $-NHY^1$, and is preferably an alkylamino group having 1 to 10 carbon atoms. The dialkylamino group having 2 to 60 carbon atoms represented by $R^1$ to $R^{32}$ is a group represented by $-NY^1Y^3$, and is preferably a dialkylamino group in which the alkyl groups are respectively an alkyl group having 1 to 10 carbon atoms. The examples of $Y^1$ and $Y^3$ include the same groups as those exemplified in the above-mentioned alkyl group.

The alkyl groups of the dialkylamino group having 2 to 60 carbon atoms may combine with each other to form a ring structure containing a nitrogen atom. Examples of the ring structure include pyrrolidine, piperidine, or the like.

In the second compound of the invention, it is preferred that $R^7$ in the formula (B-2), $R^{12}$ in the formula (B-3), $R^{14}$ or $R^{15}$ in the formula (B-4), $R^{18}$ or $R^{19}$ in the formula (B-5), $R^{24}$ in the formula (B-7), $R^{27}$ in the formula (B-8), $R^{28}$ or $R^{29}$ in the formula (B-9) and $R^{30}$ or $R^{31}$ in the formula (B-10) be an alkylamino group or a dialkylamino group.

As the arylamino group having 6 to 60 carbon atoms represented by $R^1$ to $R^{32}$, it suffices that at least one of the substituents bonding to the amino group be an aryl group. Specific examples include a phenylamino group, a methyl phenylamino group, a diphenylamino group, a di-p-tolylamino group, a di-m-tolylamino group, a phenyl-m-tolyl amino group, a phenyl-1-naphthyl amino group, a phenyl-2-naphthylamino group, a phenyl(sec-butylphenyl)amino group, a phenyl-t-butyl amino group; a bis(4-methoxyphenyl)amino group, and a phenyl-4-carbazolylphenylamino group.

In the second compound of the invention, it is preferred that $R^7$ in the formula (B-2), $R^{12}$ in the formula (B-3), $R^{14}$ or $R^{15}$ in the formula (B-4), $R^{18}$ or $R^{19}$ in the formula (B-5), $R^{24}$ in the formula (B-7), $R^{27}$ in the formula (B-8), $R^{28}$ or $R^{29}$ in the formula (B-9), and $R^{30}$ or $R^{31}$ in the formula (B-10) be an arylamino group.

The alkylsulfonyl group having 1 to 30 carbon atoms represented by $R^1$ to $R^{32}$ is a group represented by $-SO_2Y^1$. The examples of $Y^1$ include the same groups as those exemplified in the above-mentioned alkyl group. The haloalkylsulfonyl group having 1 to 30 carbon atoms represented by $R^1$ to $R^{32}$ is a group represented by $-SO_2Y^2$. The examples of $Y^2$ include the same groups as exemplified in the above-mentioned haloalkyl group.

As the aromatic hydrocarbon group having 6 to 60 carbon atoms represented by $R^1$ to $R^{32}$, a phenyl group, a naphthyl group, an anthryl group, a phenanthryl group, a fluorenyl group, a perylenyl group, a tetracenyl group and a pentacenyl group or the like can be given.

As the aromatic heterocyclic group having 3 to 60 carbon atoms represented by $R^1$ to $R^{32}$, a thiophenyl group, a dithienophenyl group, a benzofuranyl group, a benzothiophenyl group, a quinolyl group, a carbazolyl group, a dibenzofuranyl group, a dibenzothiophenyl group, a benzothiadiazonyl group or the like can be given.

In the compound of the invention, it is preferred that $R^7$ in the formula (B-2), $R^{12}$ in the formula (B-3), $R^{14}$ or $R^{15}$ in the formula (B-4), $R^{18}$ or $R^{19}$ in the formula (B-5), $R^{24}$ in the formula (B-7), $R^{27}$ in the formula (B-8), $R^{28}$ or $R^{29}$ in the formula (B-9) and $R^{39}$ or $R^{31}$ in the formula (B-10) be an aromatic heterocyclic group.

As the substituent for the aromatic heterocyclic group, the above-mentioned alkyl group can be given.

The alkylsilyl group having 3 to 20 carbon atoms represented by $R^1$ to $R^{32}$ is a group represented by $-SiY^1Y^2Y^3$. The examples of $Y^1$, $Y^2$ and $Y^3$ the alkyl group include the same groups as those exemplified in the above-mentioned alkyl group. As the alkyl group, a short-chain alkyl group such as a methyl group, an ethyl group and an isopropyl group is preferable.

As the alkylsilylethynyl group having 5 to 60 carbon atoms represented by $R^1$ to $R^{32}$, a trimethylsilylethynyl group, a triethylsilylethynyl group, a triisopropylsilylethynyl group, a tert-butyldimethylsilylethynyl group or the like can be given.

It is preferred that $R^1$ to $R^{32}$ be independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, an alkylamino group having 1 to 30 carbon atoms, a dialkylamino group having 2 to 60 carbon atoms, an arylamino group having 6 to 60 carbon atoms, an aromatic heterocyclic group having 3 to 60 carbon atoms, an alkylsilyl group having 3 to 20 carbon atoms or a cyano group. In particular, if the substituent is an alkyl group, improvement in solubility and mobility can be expected.
Specific examples of the second compound of the invention are given below.
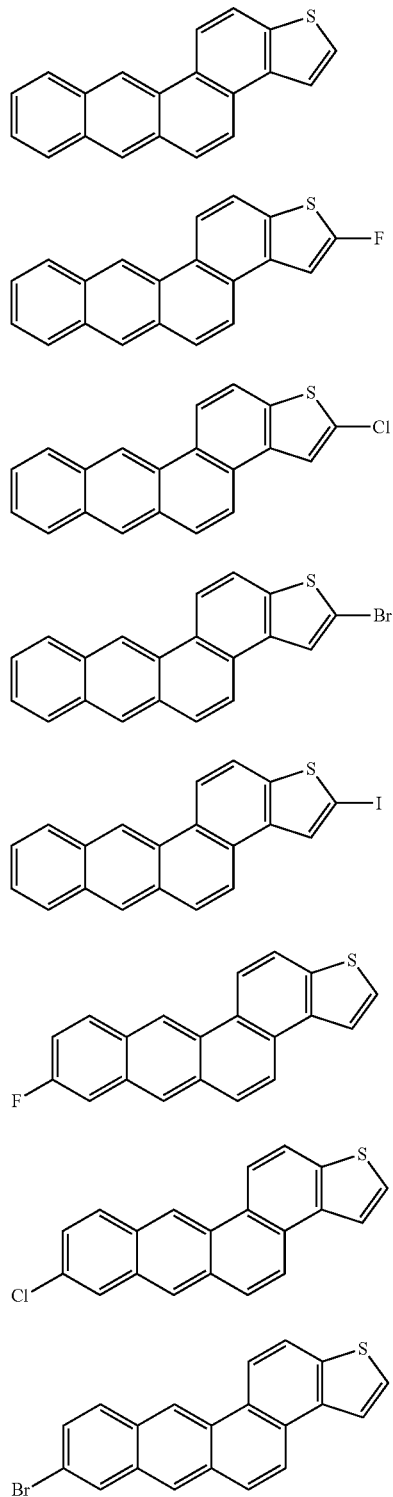
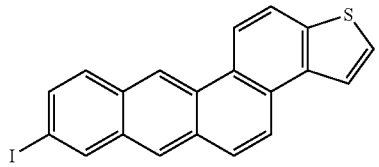
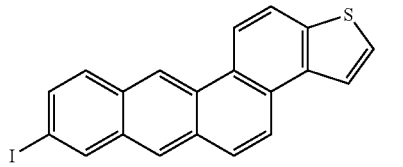
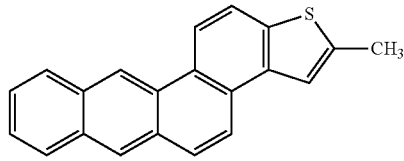
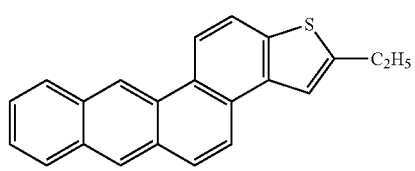
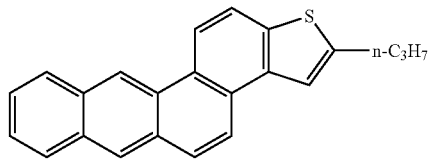
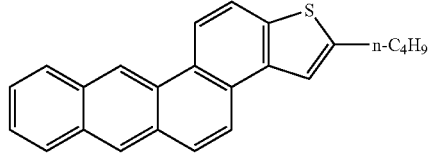
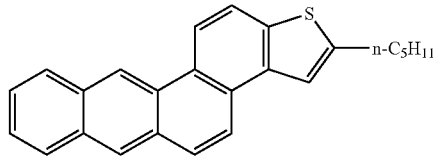
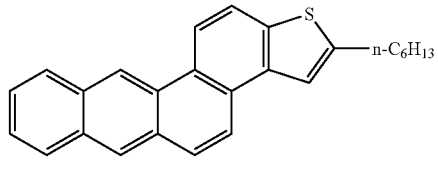
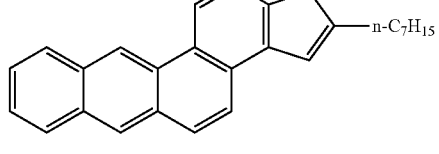
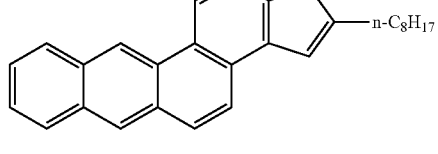

-continued
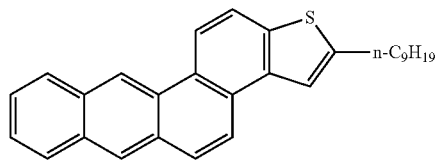 (18)
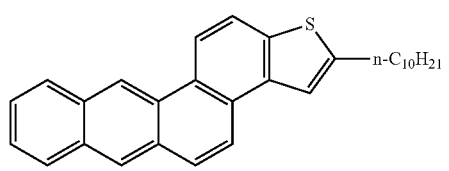 (19)
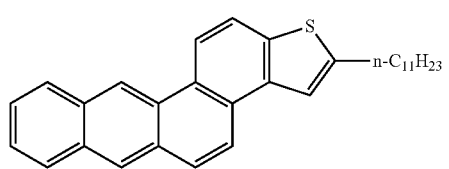 (20)
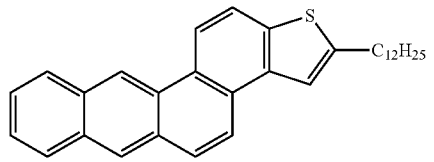 (21)
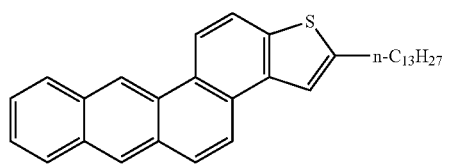 (22)
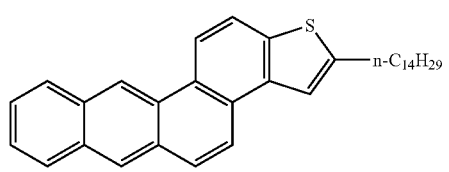 (23)
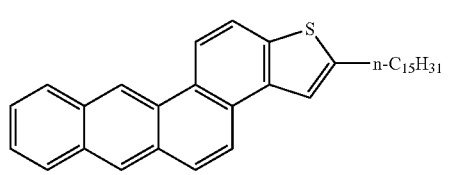 (24)
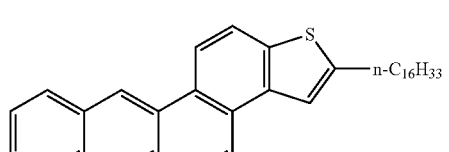 (25)
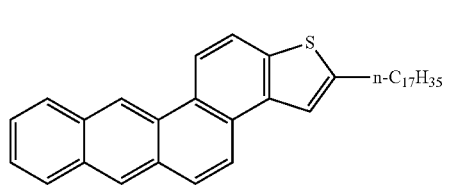 (26)
-continued
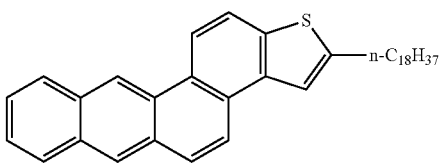 (27)
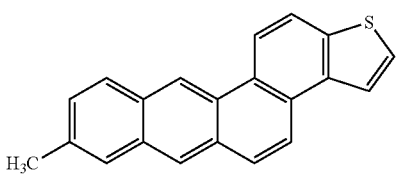 (28)
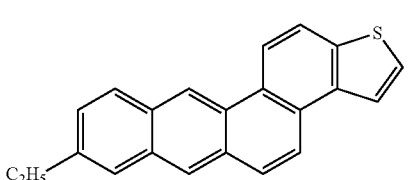 (29)
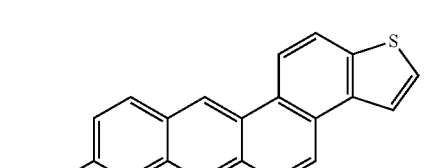 (30)
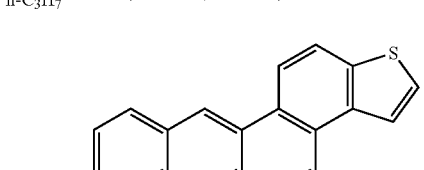 (31)
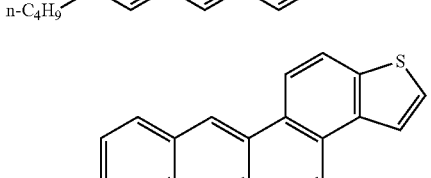 (32)
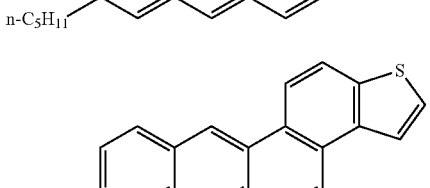 (33)
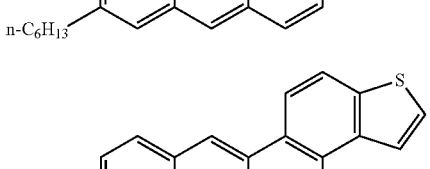 (34)
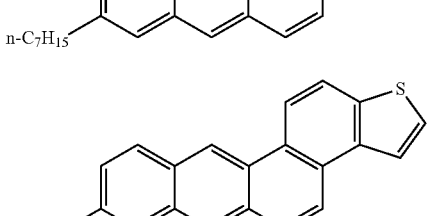 (35)

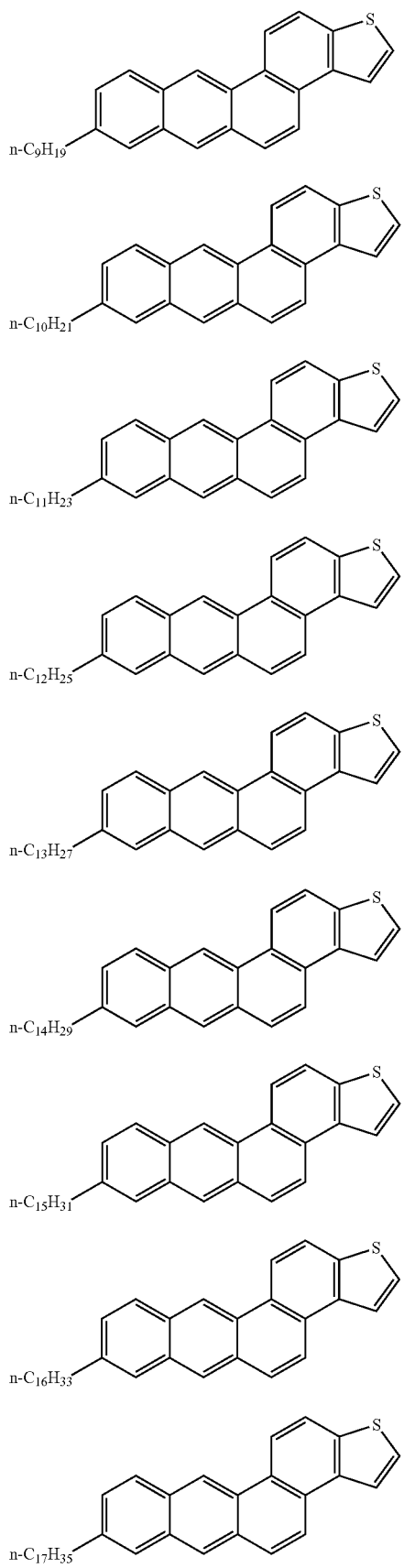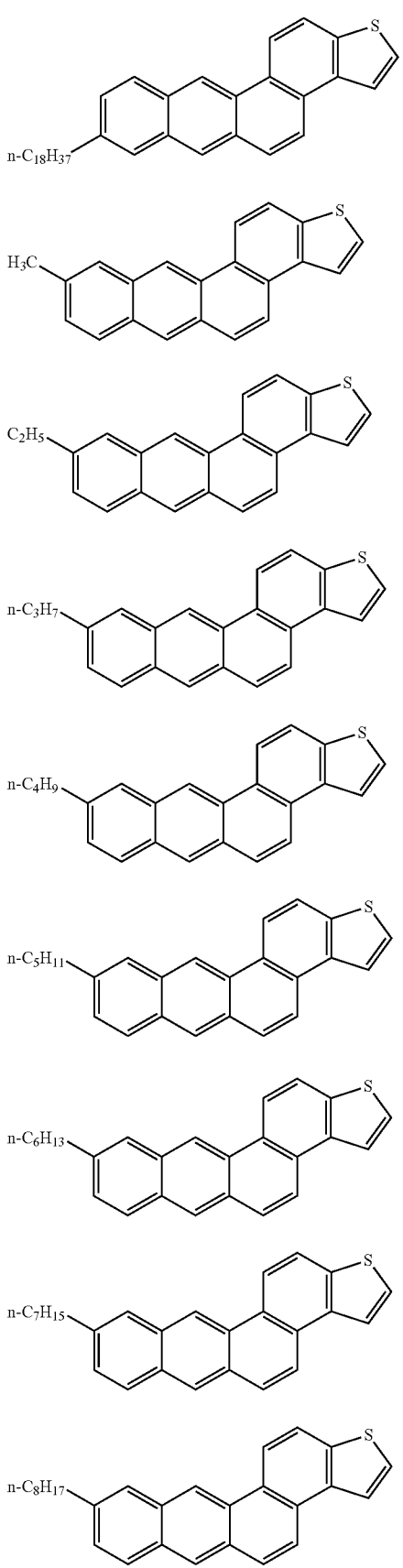

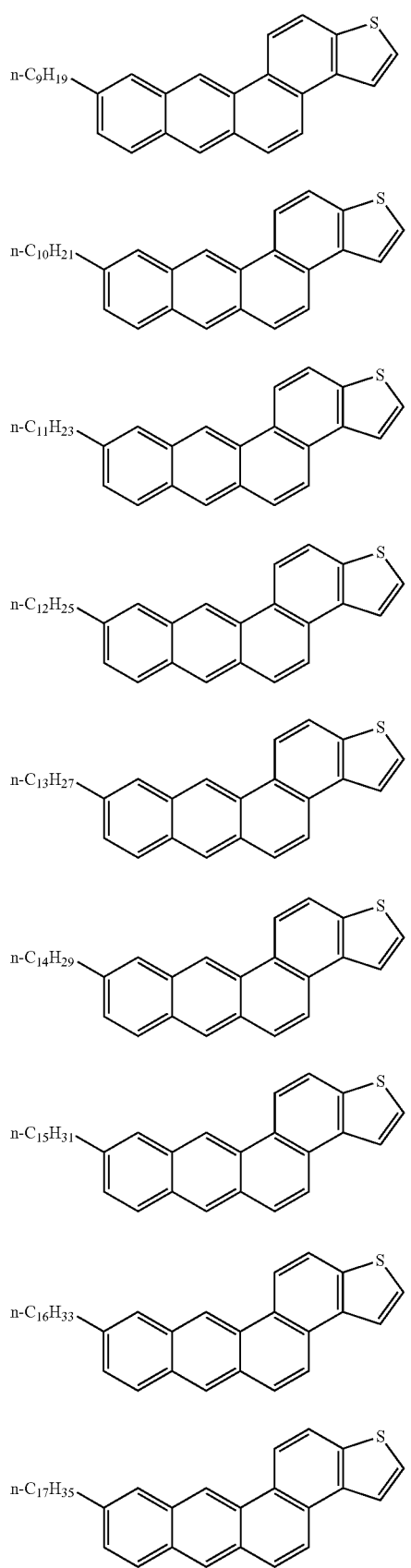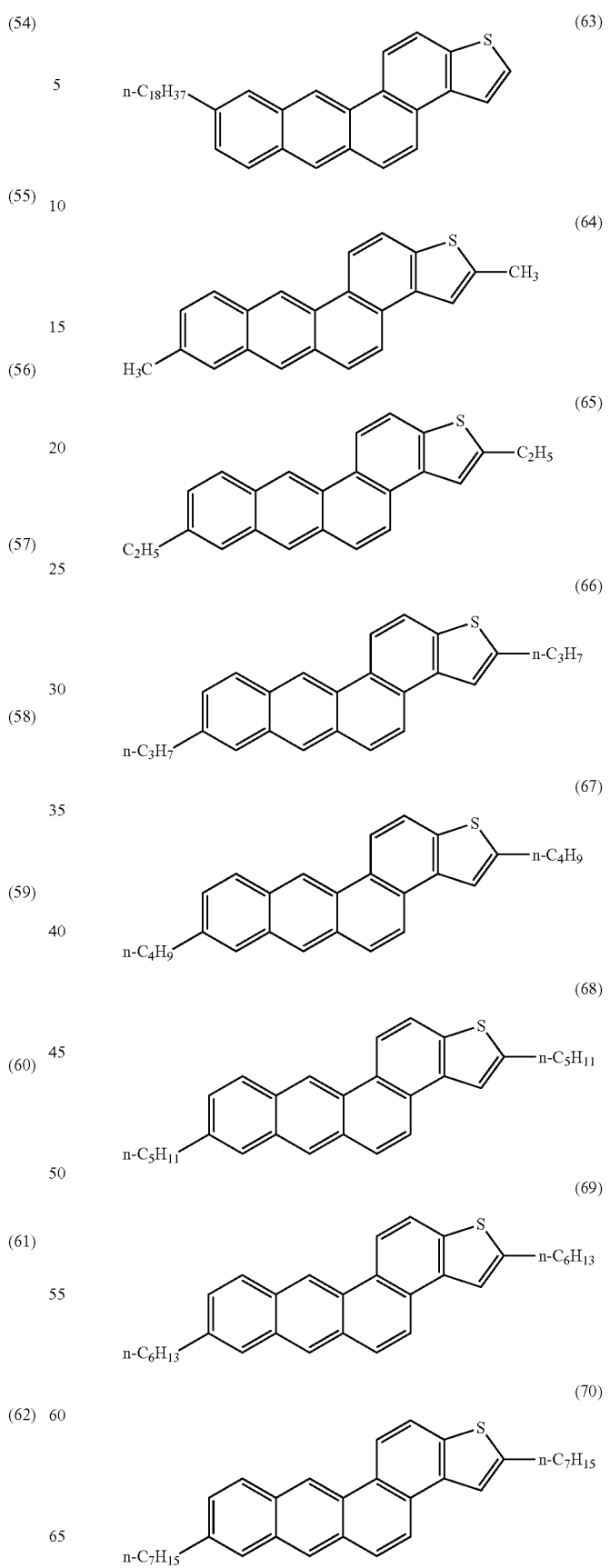

(71)
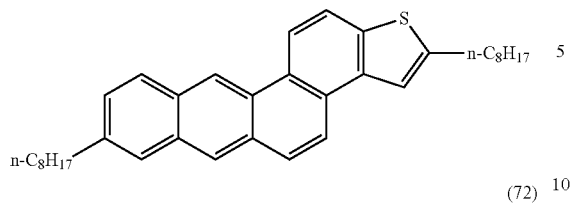
(72)
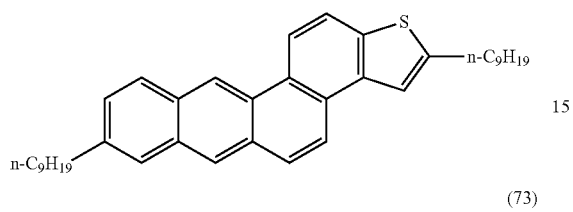
(73)
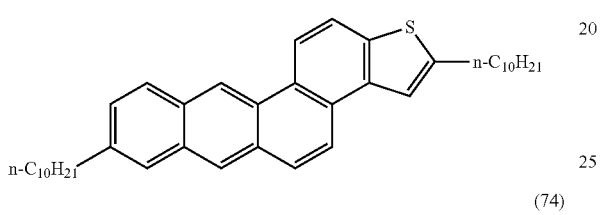
(74)
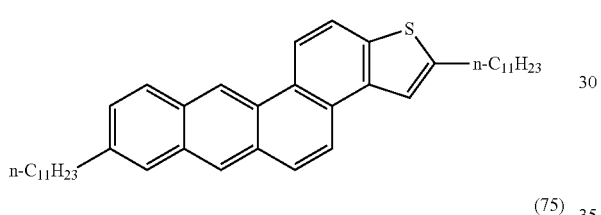
(75)
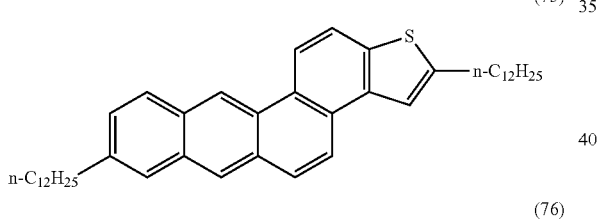
(76)
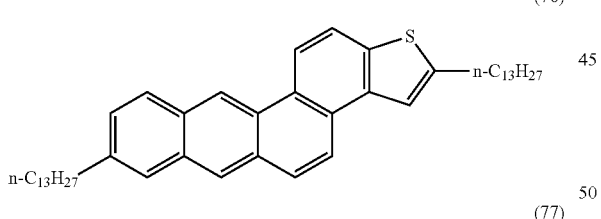
(77)
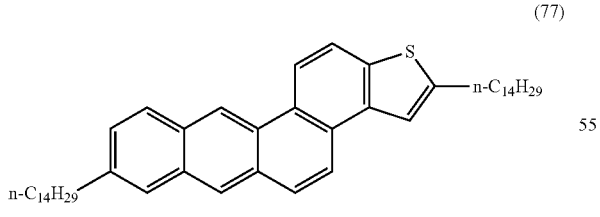
(78)
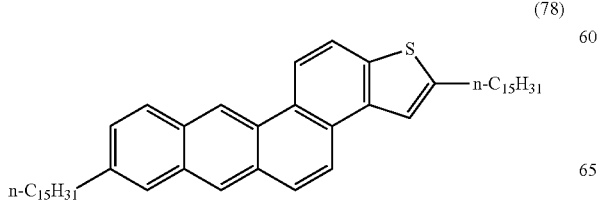
(79)
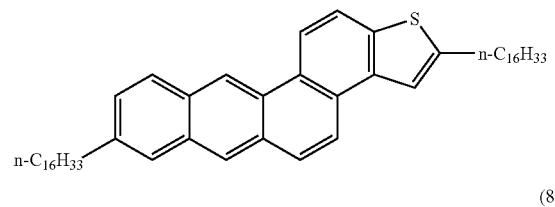
(80)
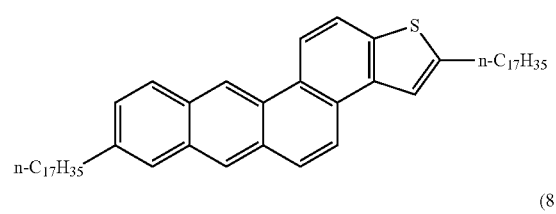
(81)
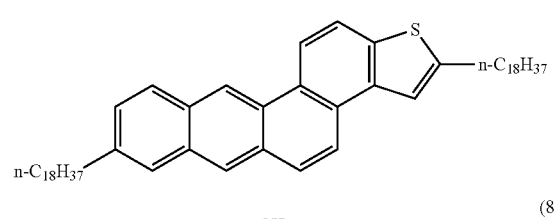
(82)
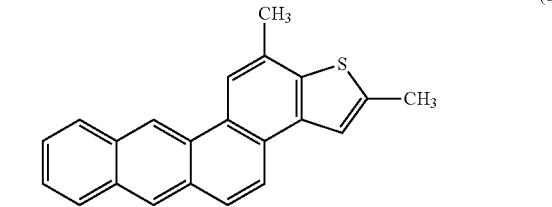
(83)
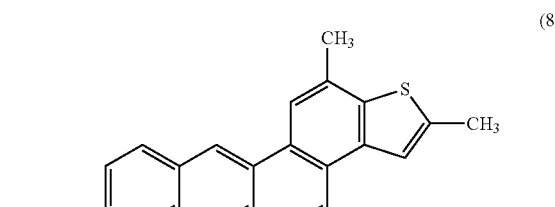
(84)
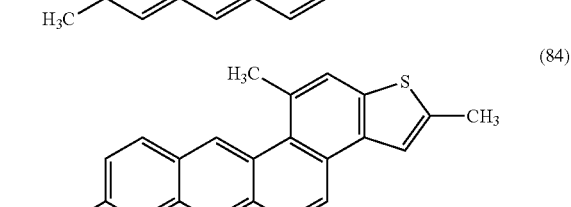
(85)
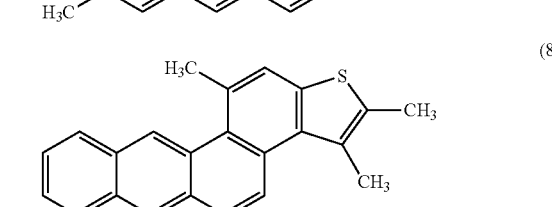
(86)
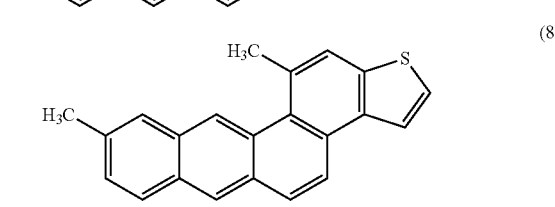

-continued
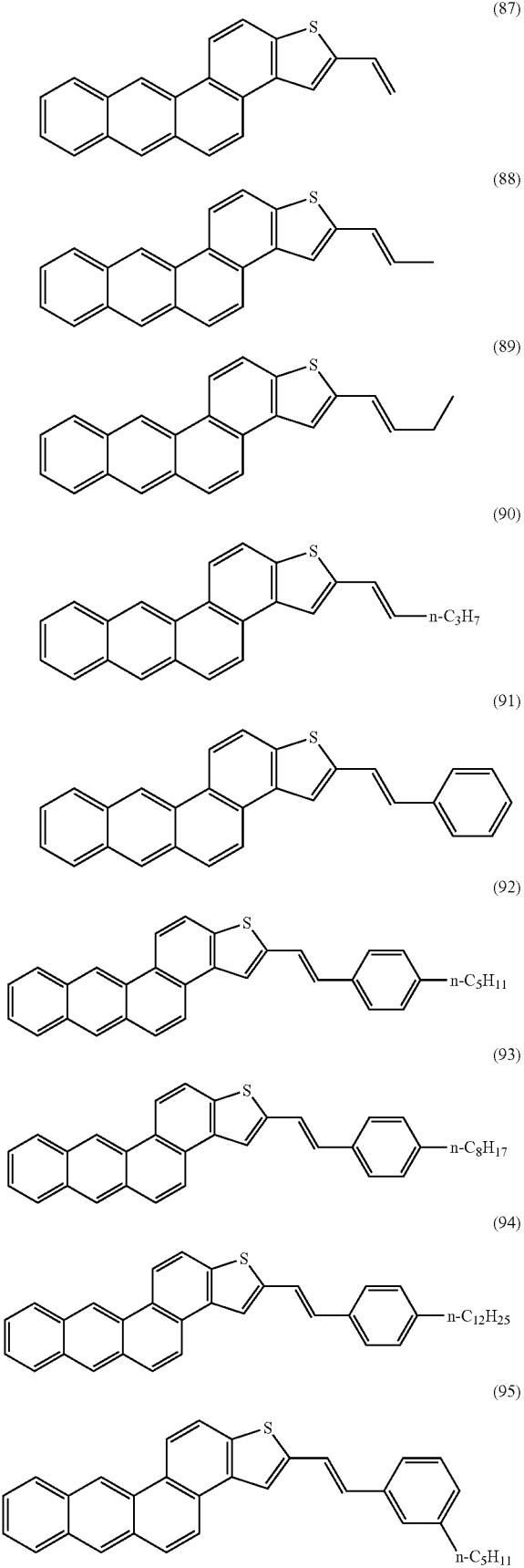
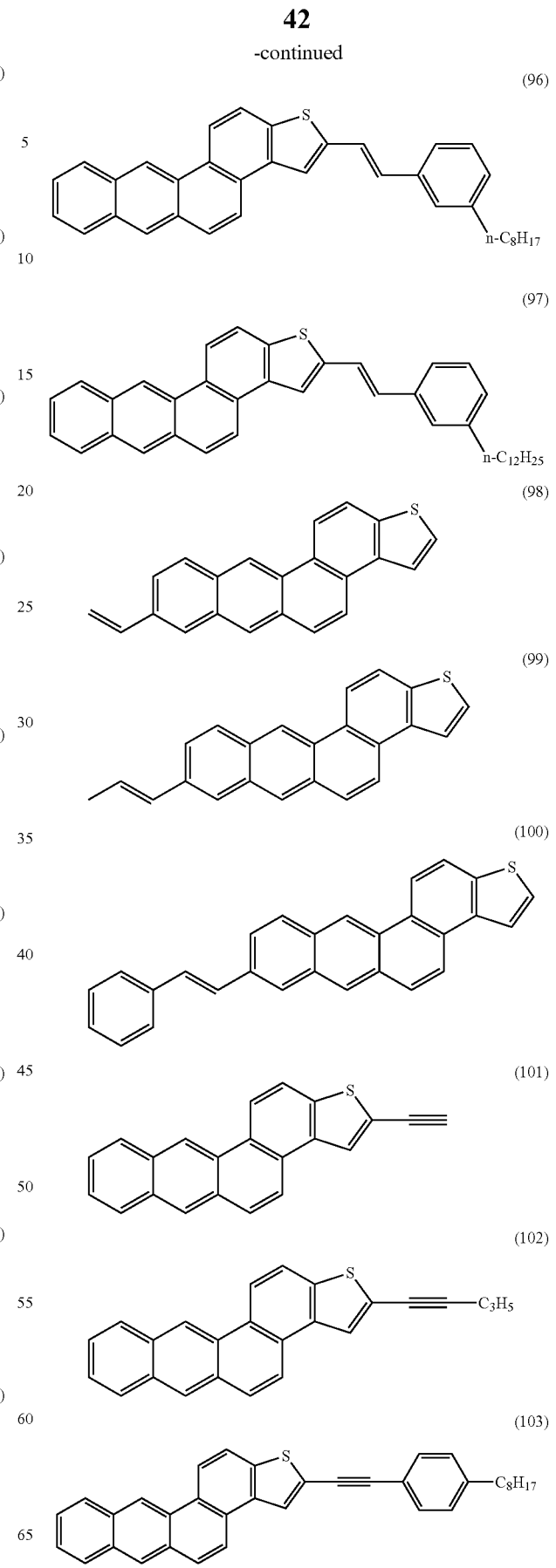

(104) 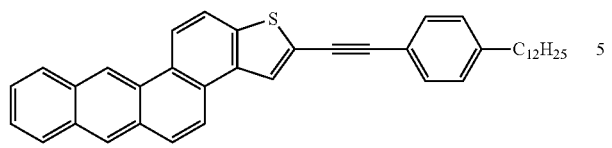
(105) 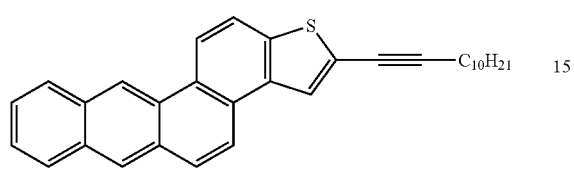
(106) 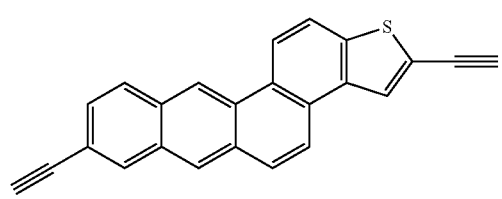
(107) 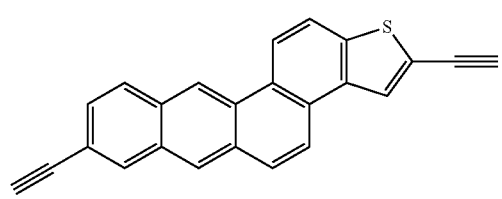
(108) 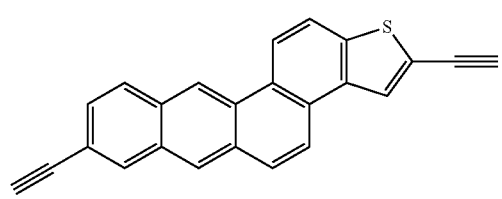
(109) 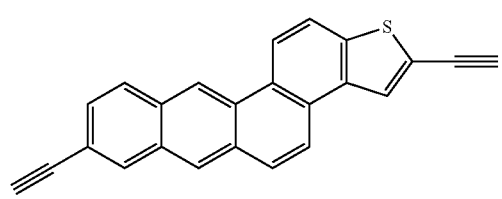
(110) 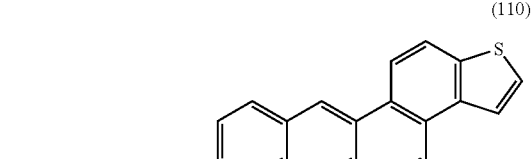
(111) 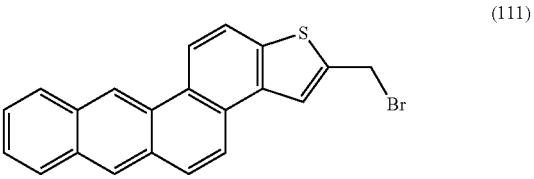 [SMILES: Cc1cc2c(ccc3c4cc5ccccc5cc4ccc23)o1]
(112) 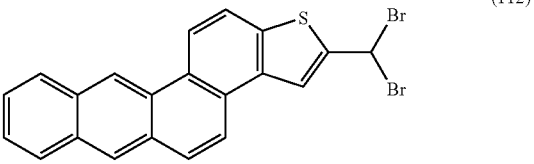
(113) 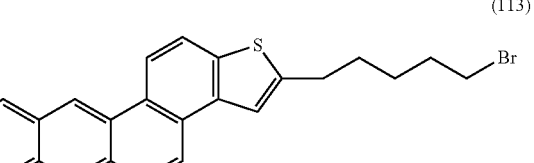
(114) 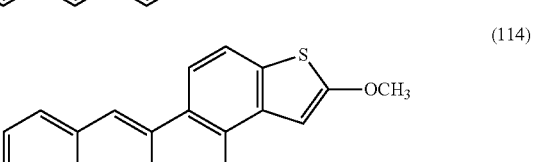
(115) 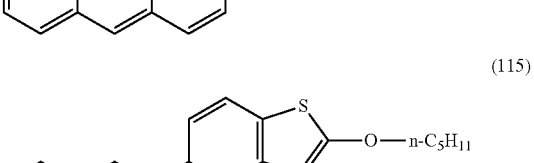
(116) 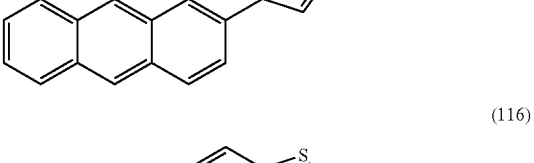
(117) 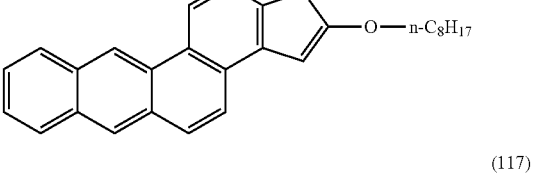

(118) 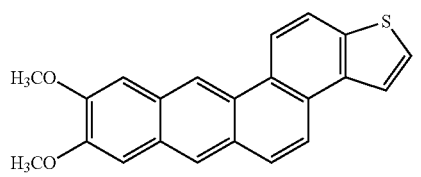
(119) 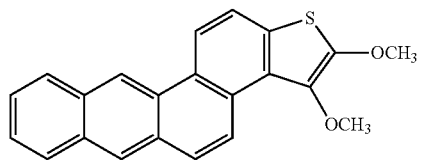
(120) 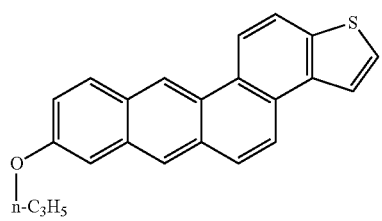
(121) 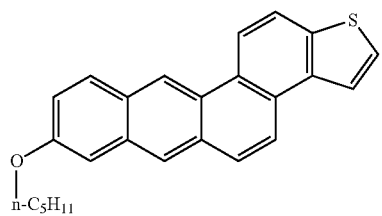
(122) 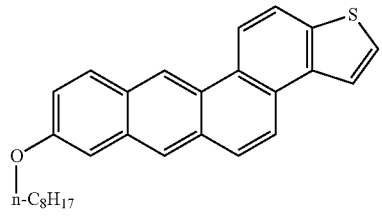
(123) 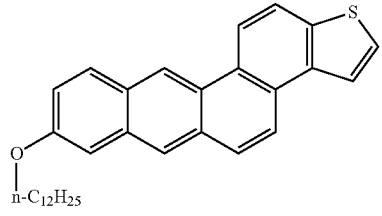
(124) 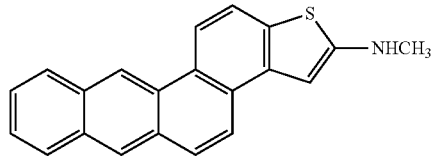
(125) 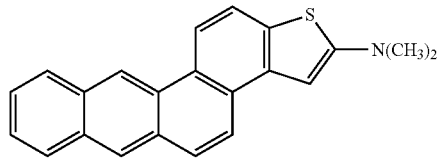
(126) 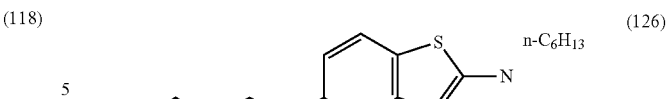
(127) 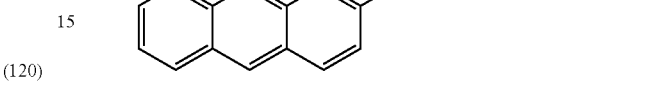
(128) 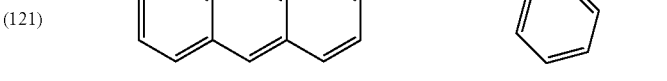
(129) 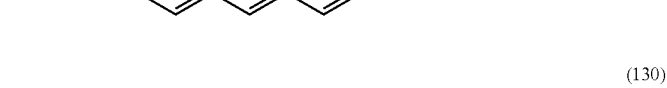
(130) 
(131) 
(132) 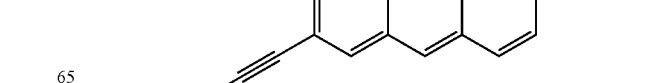

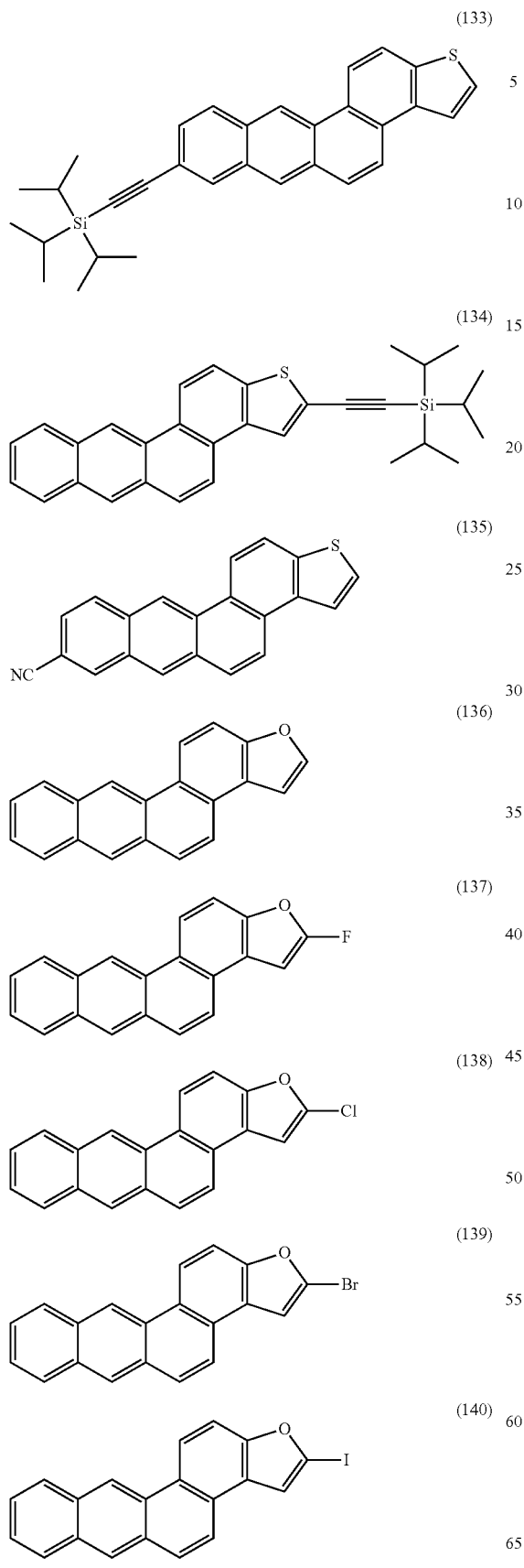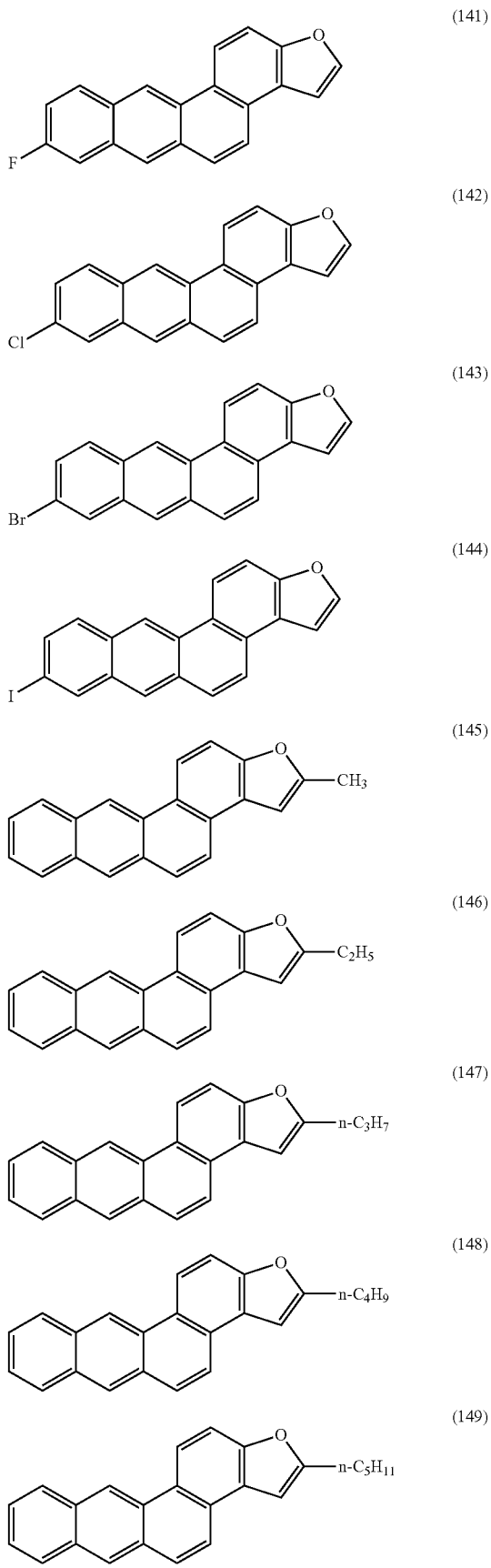

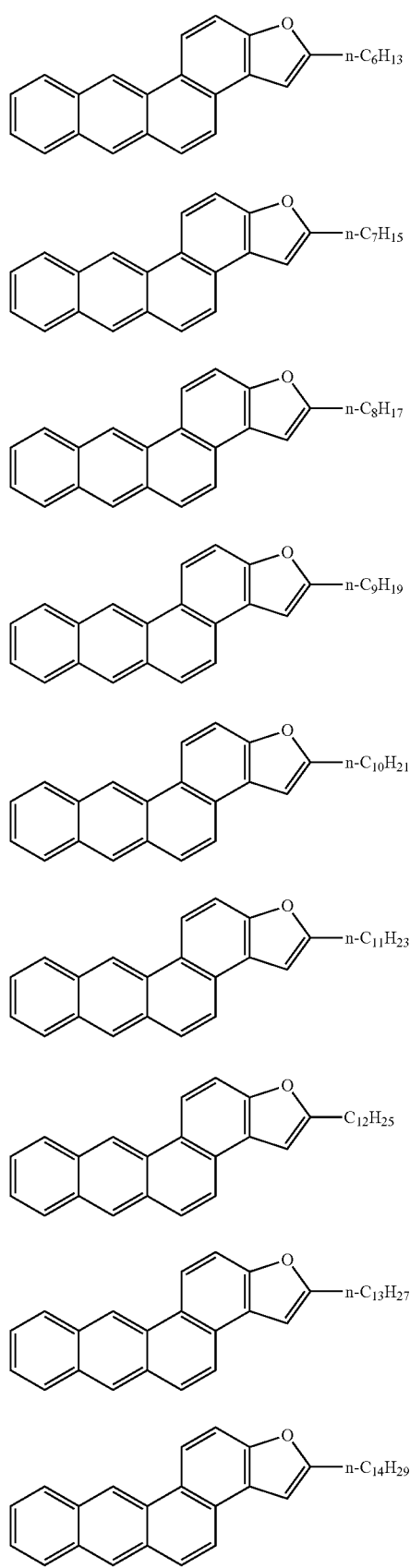
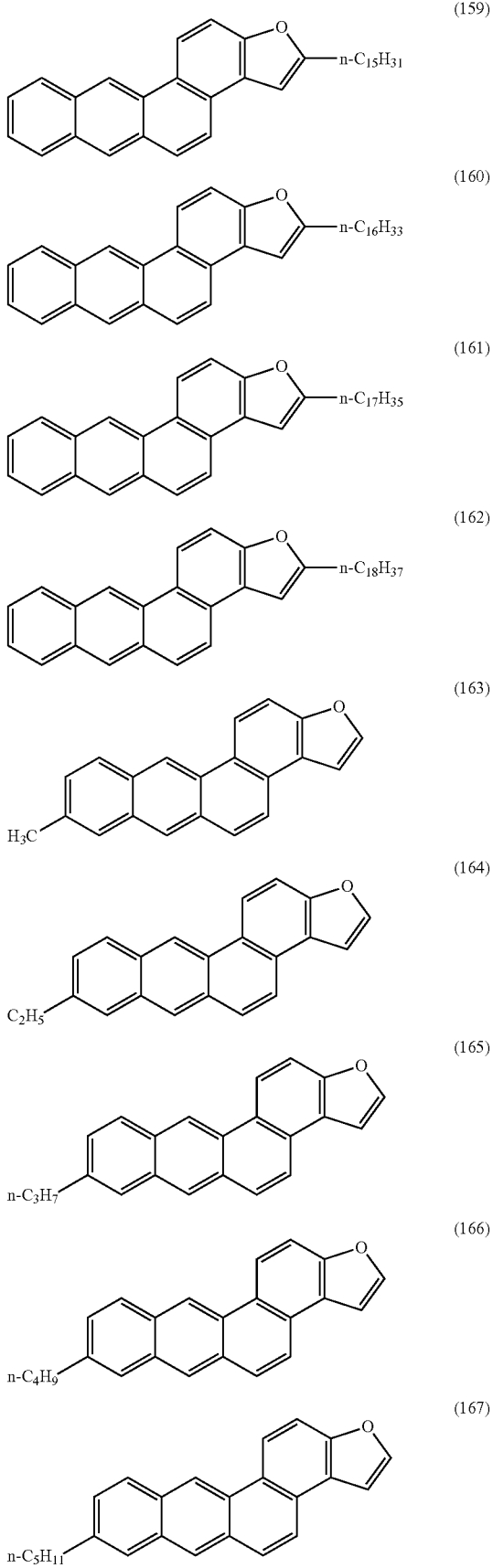

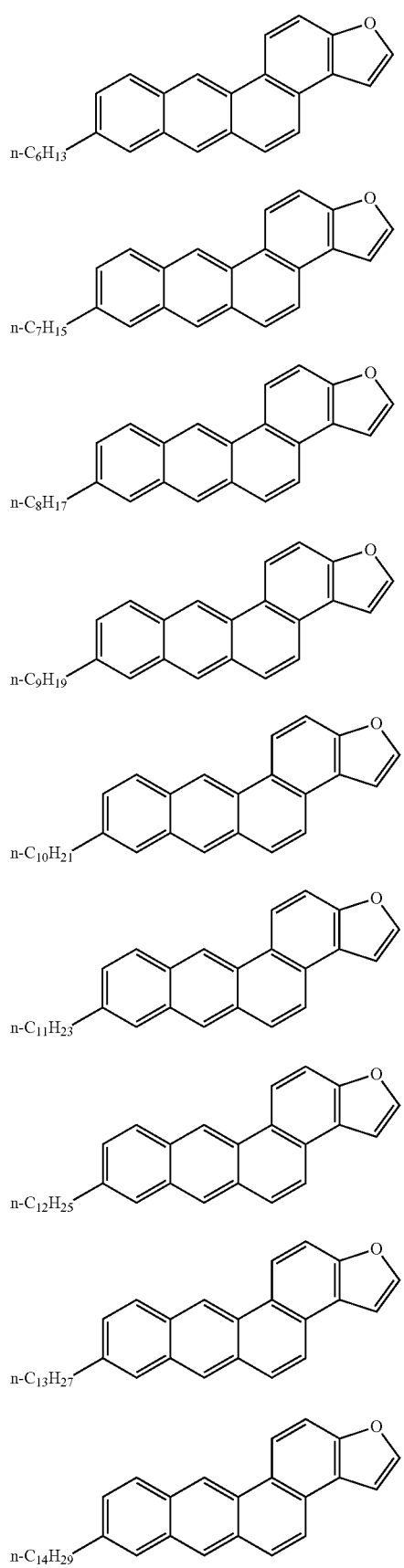
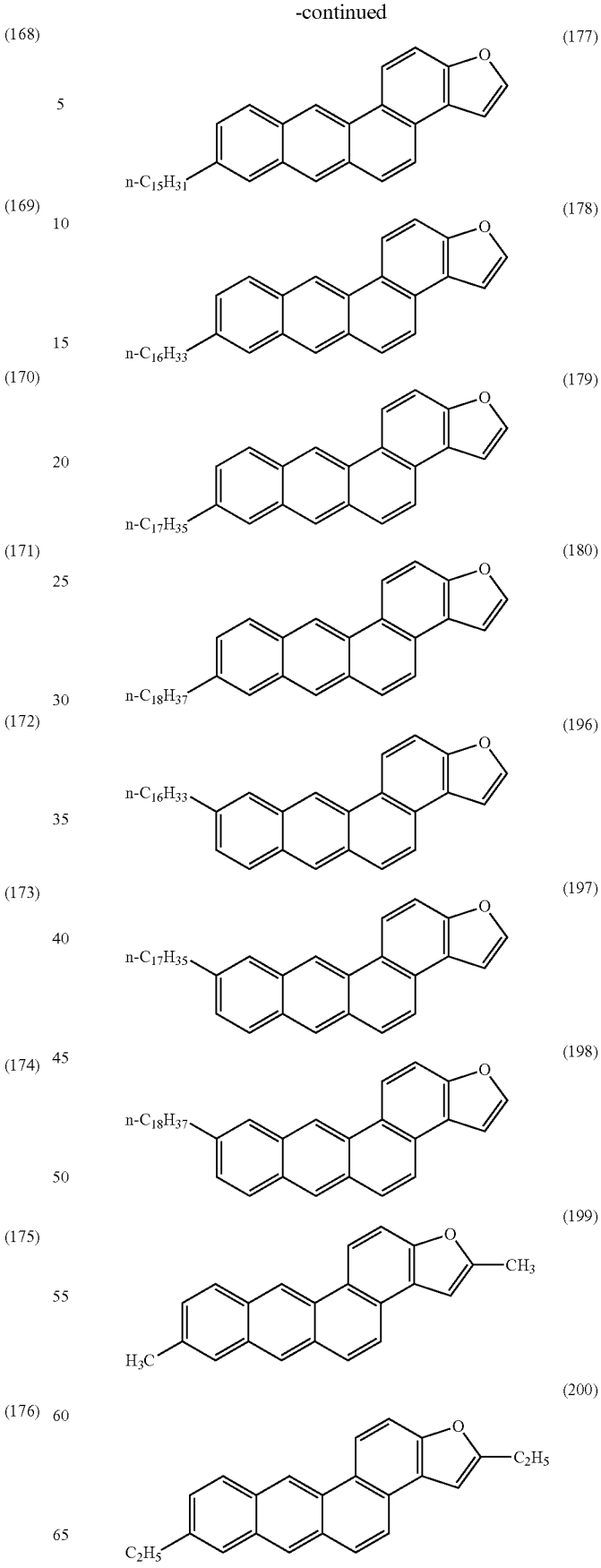

(201)
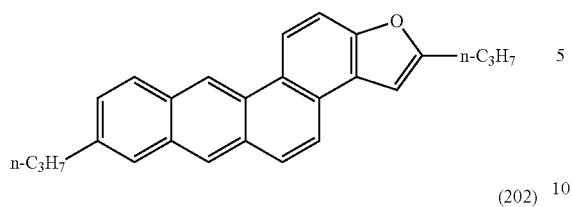
(202)
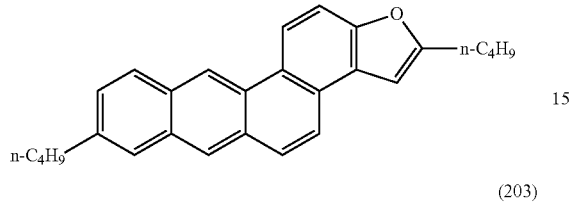
(203)
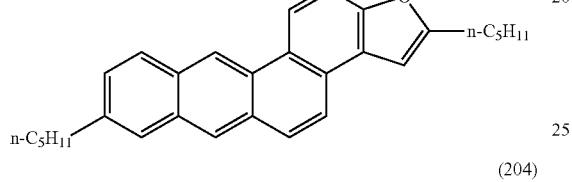
(204)
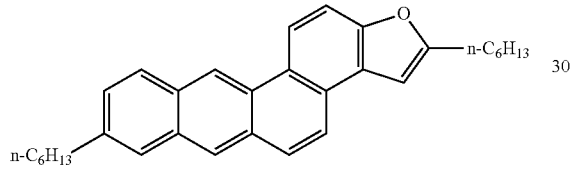
(205)
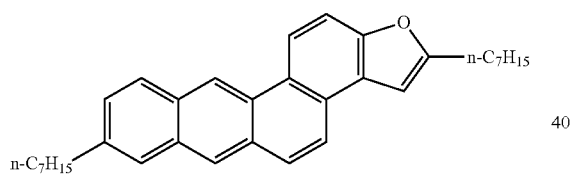
(206)
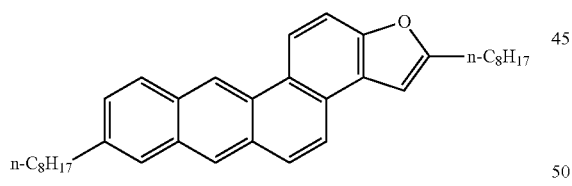
(207)
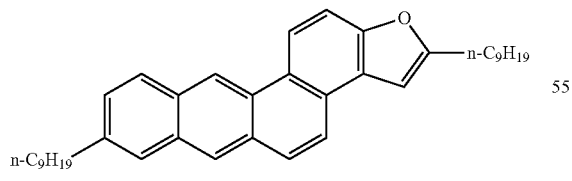
(208)
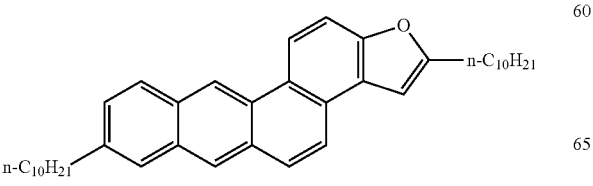
(209)
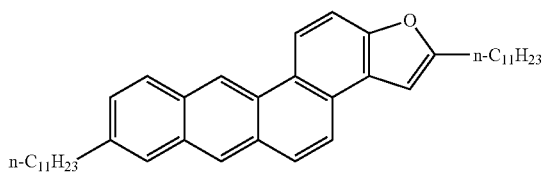
(210)
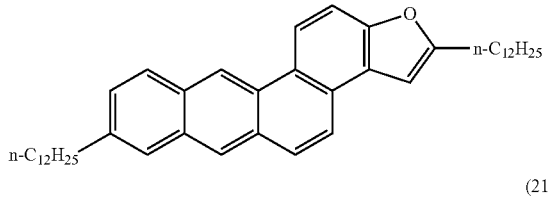
(211)
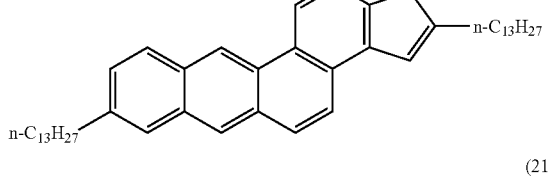
(212)
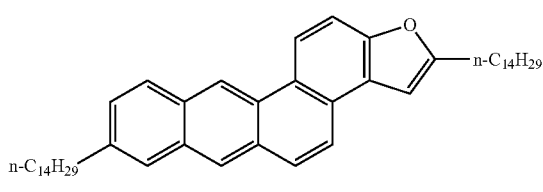
(213)
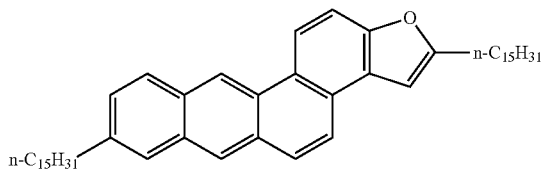
(214)
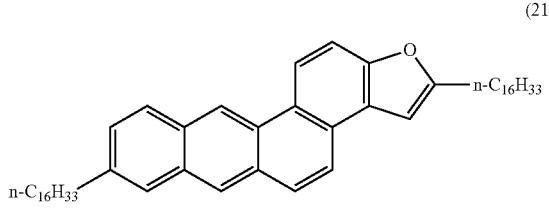
(215)
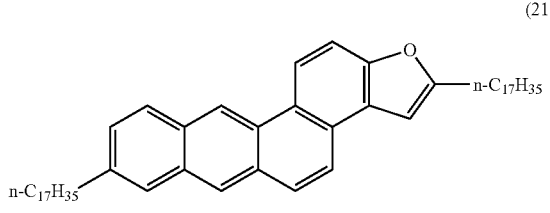
(216)
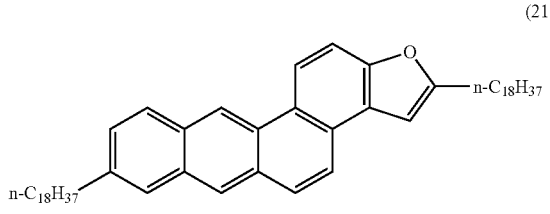

(217) 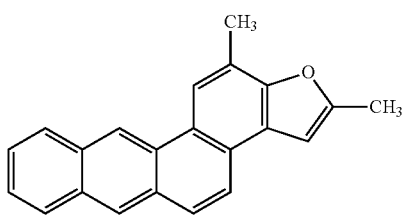
(218) 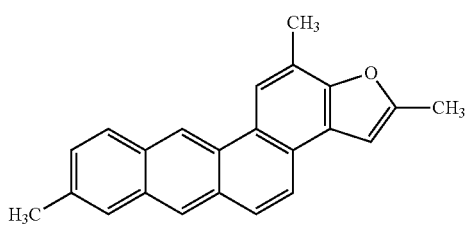
(219) 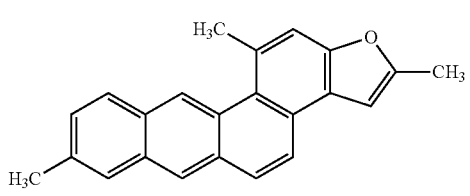
(220) 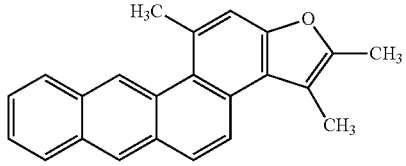
(221) 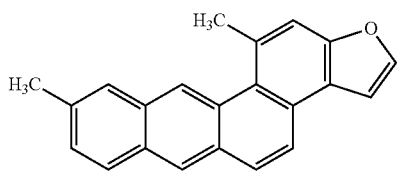
(222) 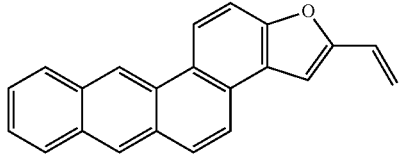
(223) 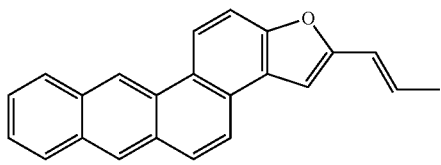
(224) 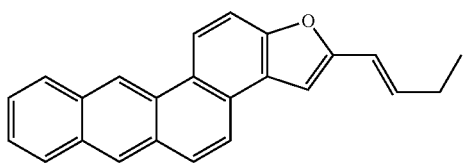
(225) 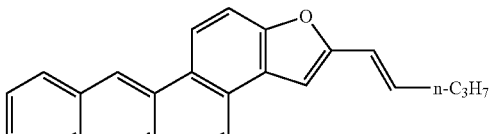
(226) 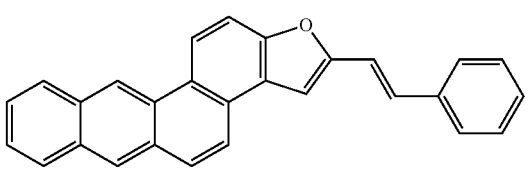
(227) 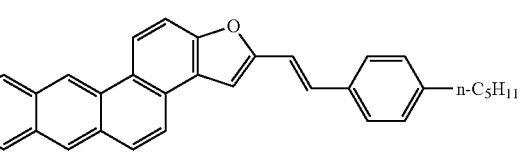
(228) 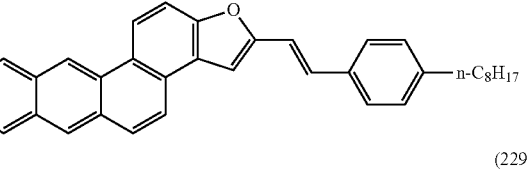
(229) 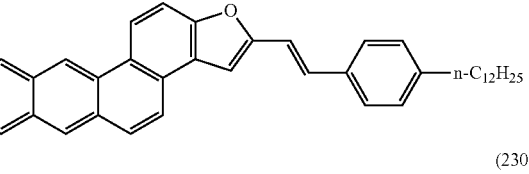
(230) 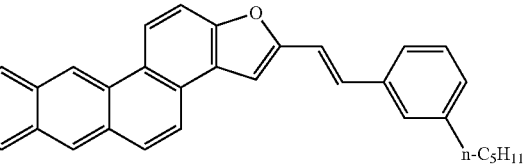
(231) 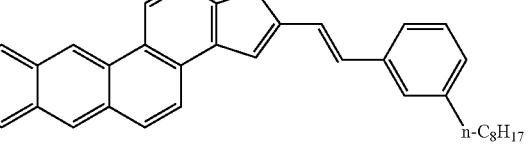
(232) 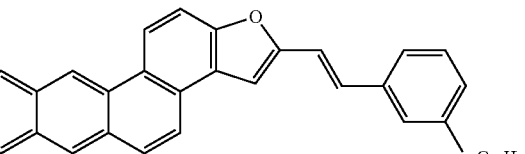

(233) 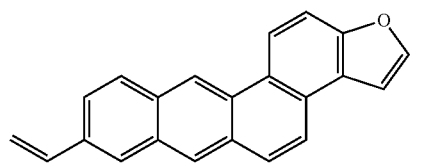
(234) 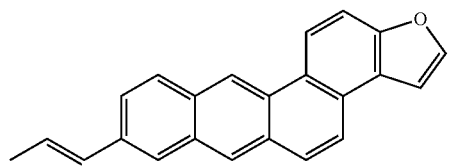
(235) 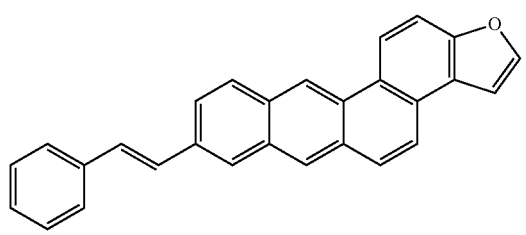
(236) 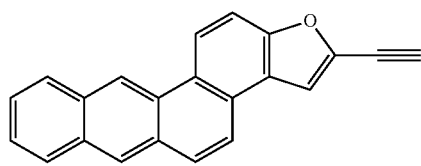
(237) 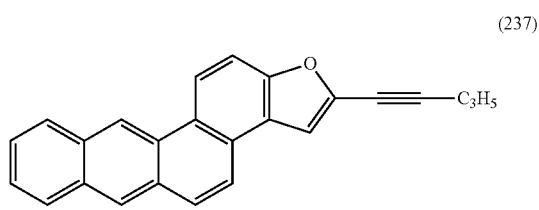
(238) 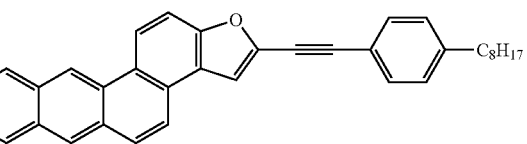
(239) 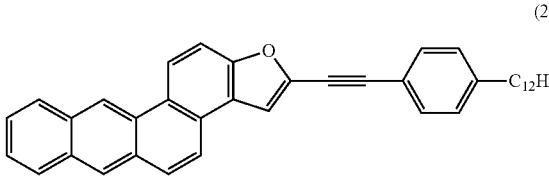
(240) 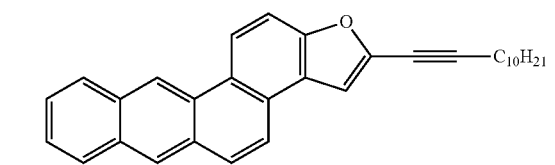
(241) 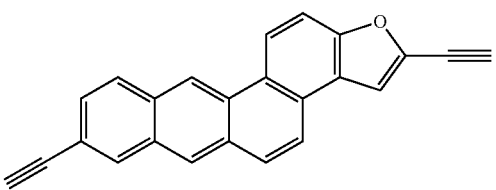
(242) 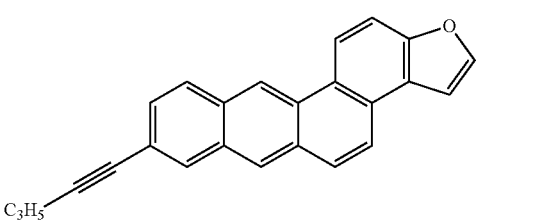
(243) 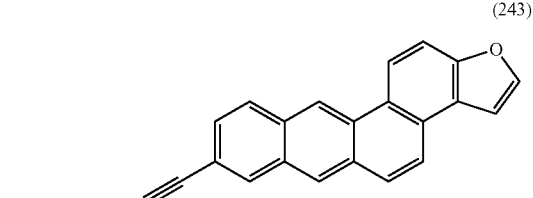
(244) 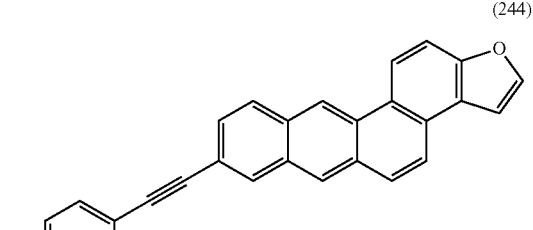
(245) 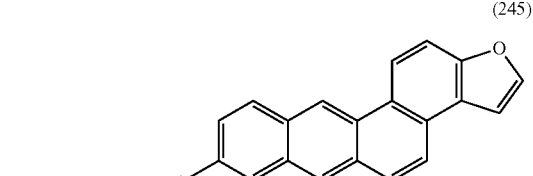
(246) 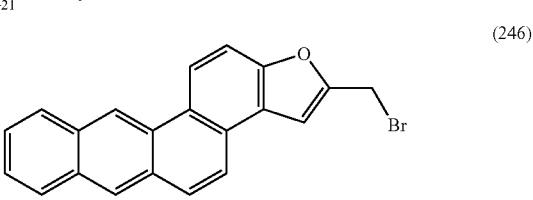

-continued
(247)
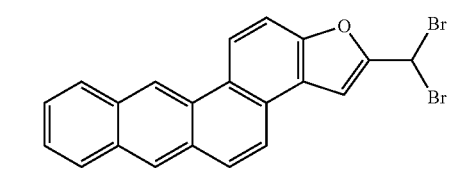
(248)
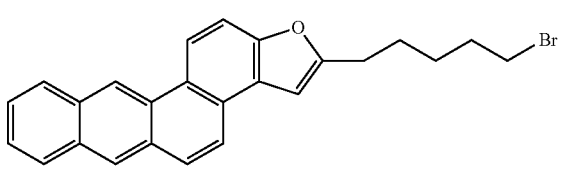
(249)
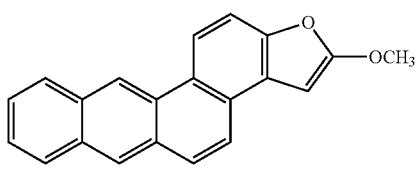
(250)
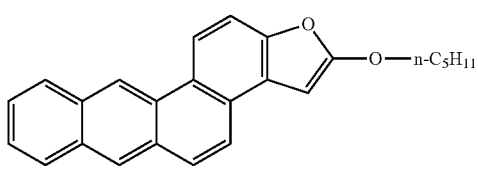
(251)
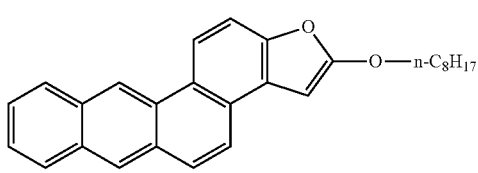
(252)
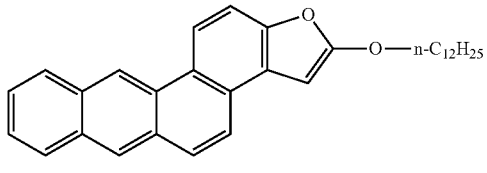
(253)
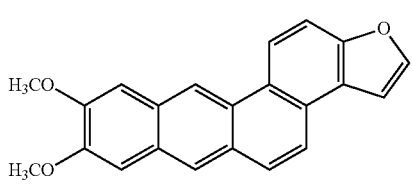
(254)
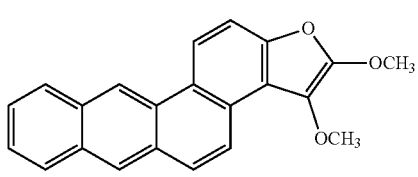
-continued
(255)
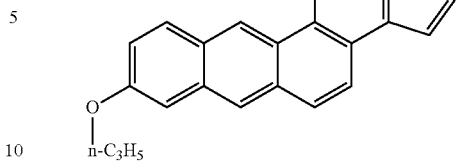
(256)
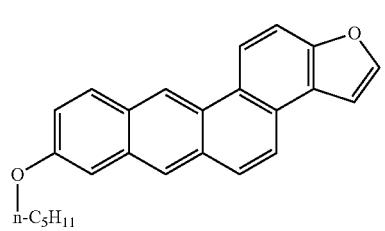
(257)
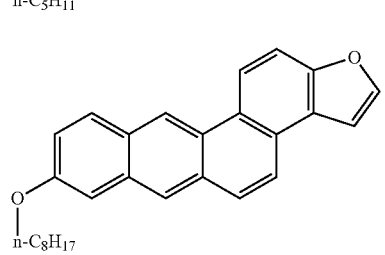
(258)
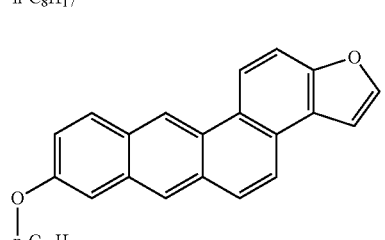
(259)
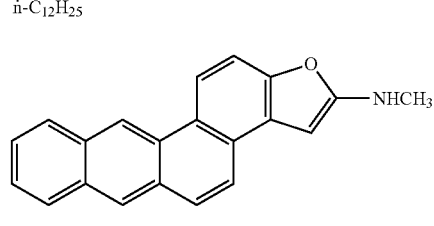
(260)
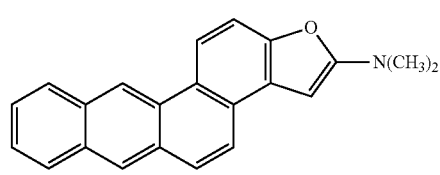
(261)
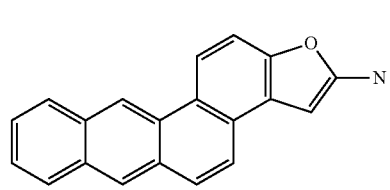
(262)
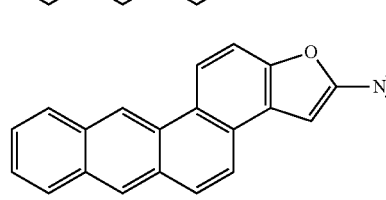

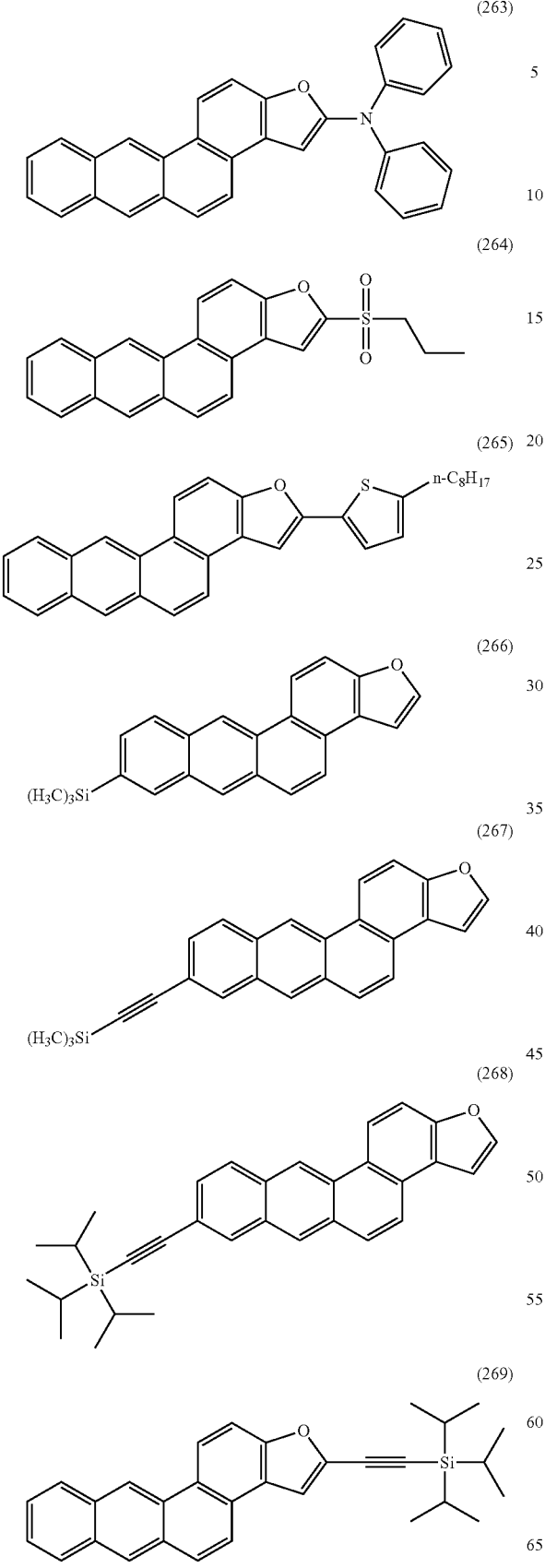
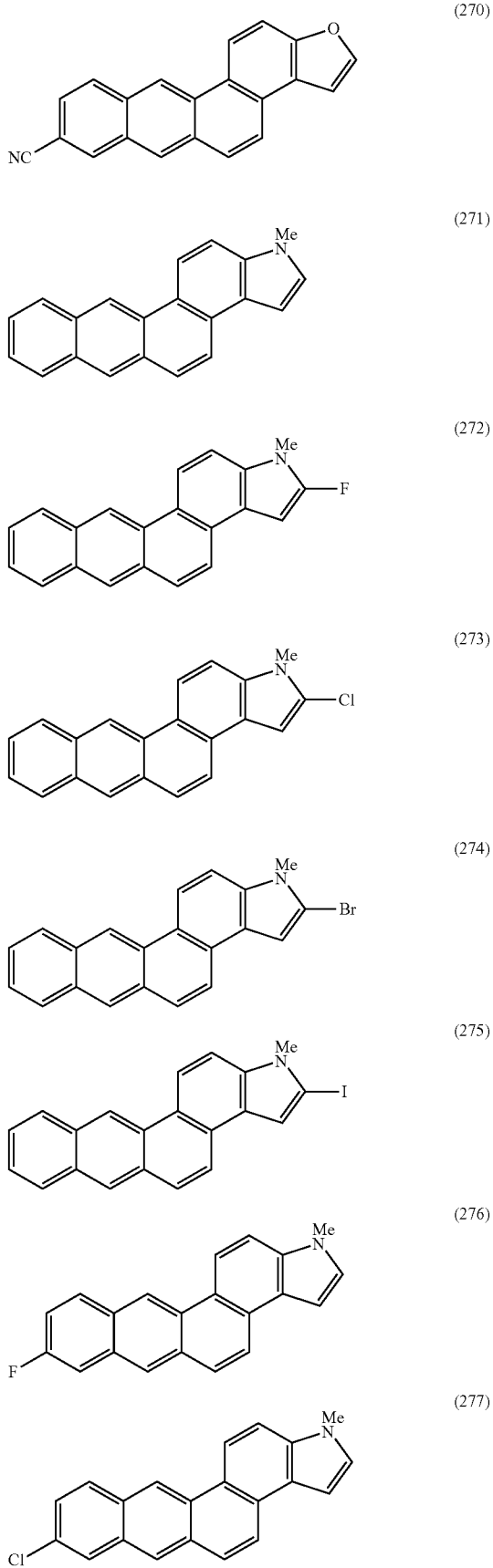

| | |
|---|---|
| (278) 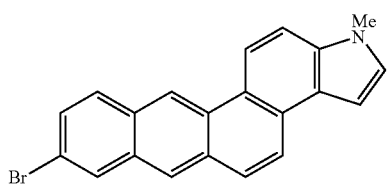 | (286) 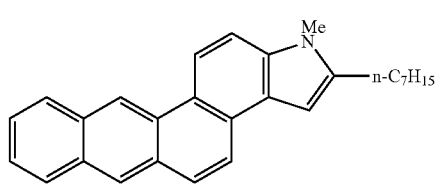 |
| (279) 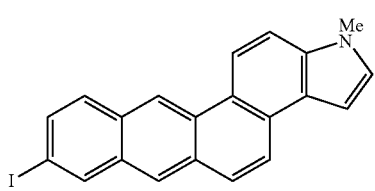 | (287) 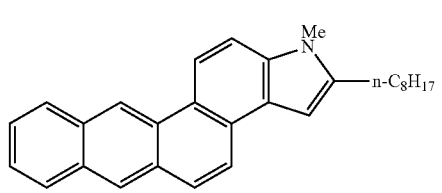 |
| (280) 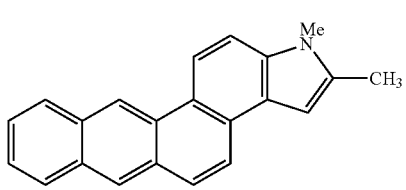 | (288) 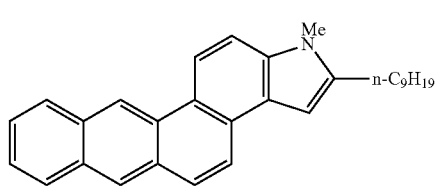 |
| (281) 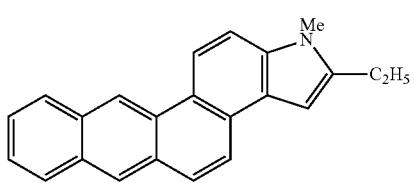 | (289) 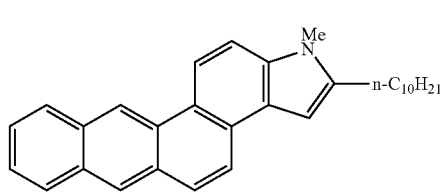 |
| (282) 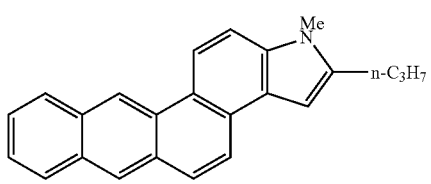 | (290) 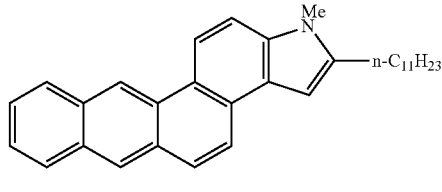 |
| (283) 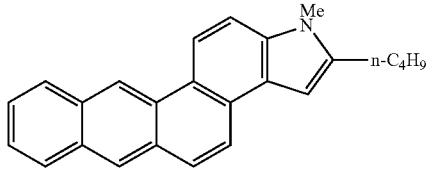 | (291) 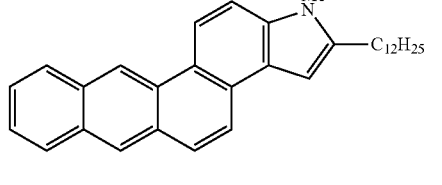 |
| (284) 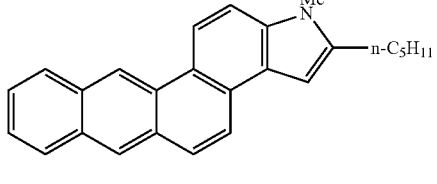 | (292) 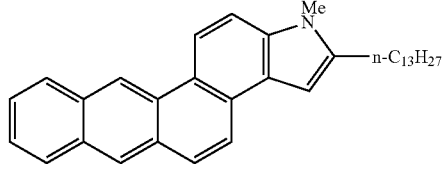 |
| (285) 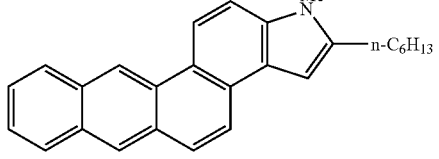 | (293) 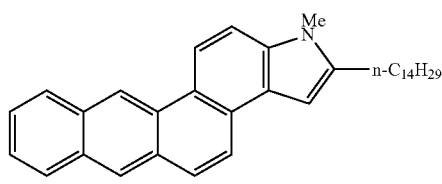 |

-continued
(294)
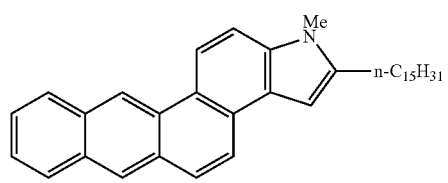
(295)
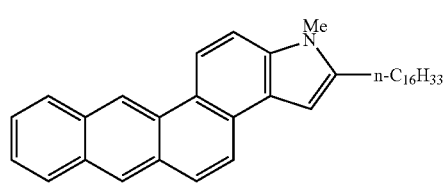
(296)
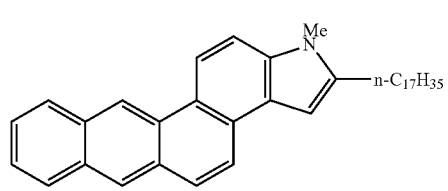
(297)
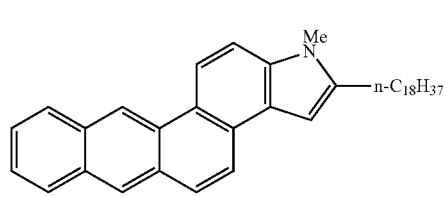
(298)
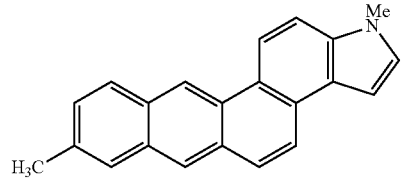
(299)
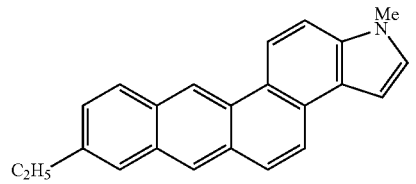
(300)
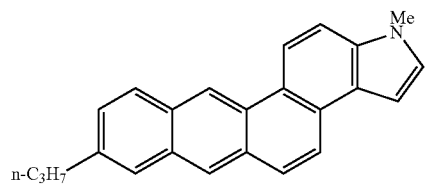
(301)
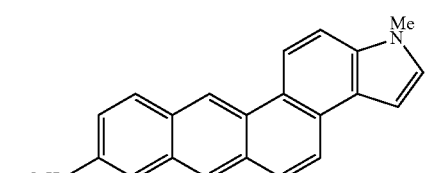
-continued
(302)
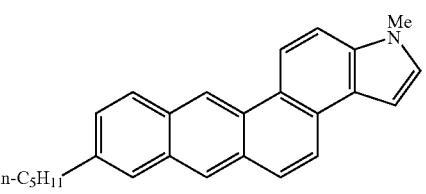
(303)
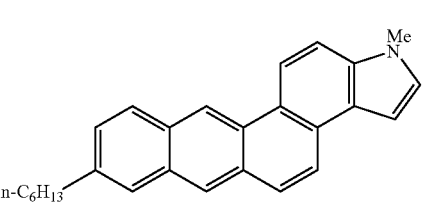
(304)
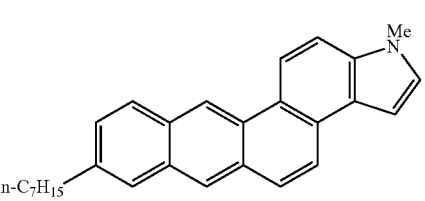
(305)
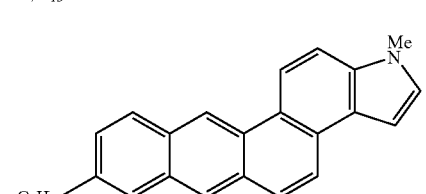
(306)
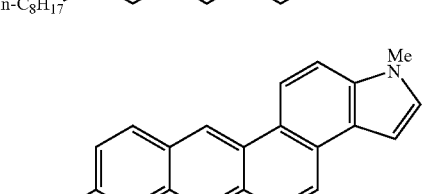
(307)
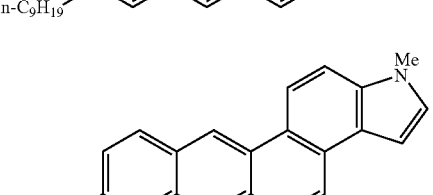
(308)
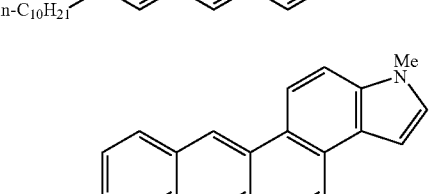
(309)
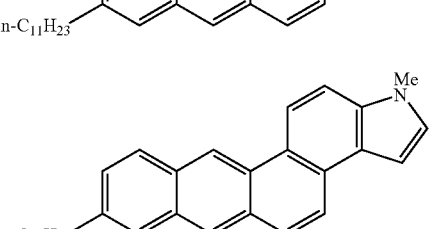

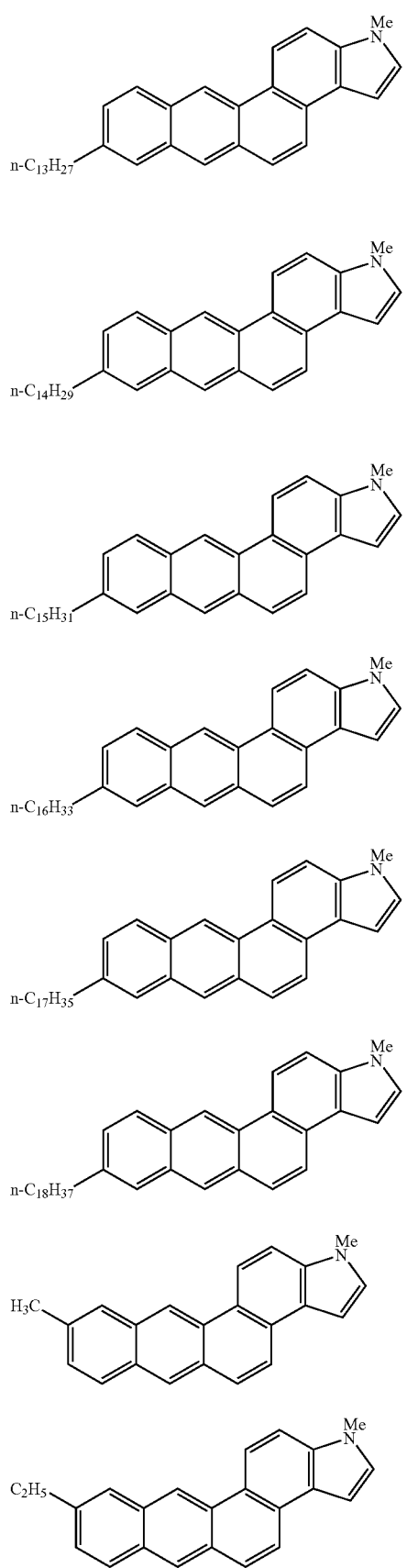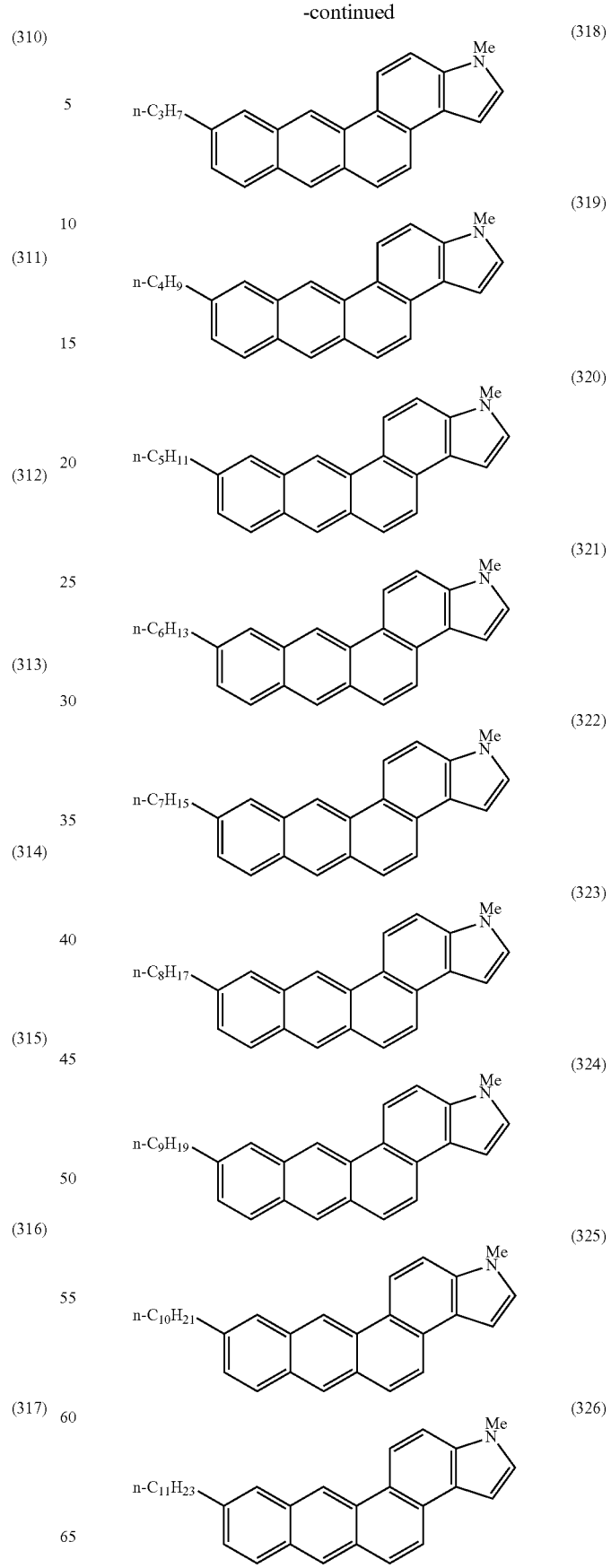

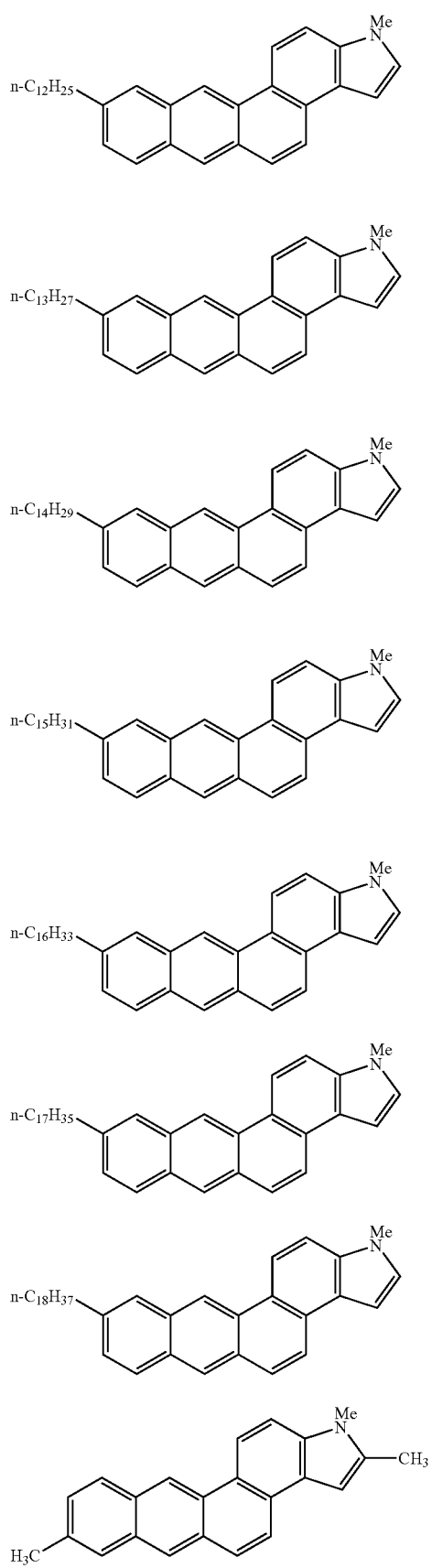
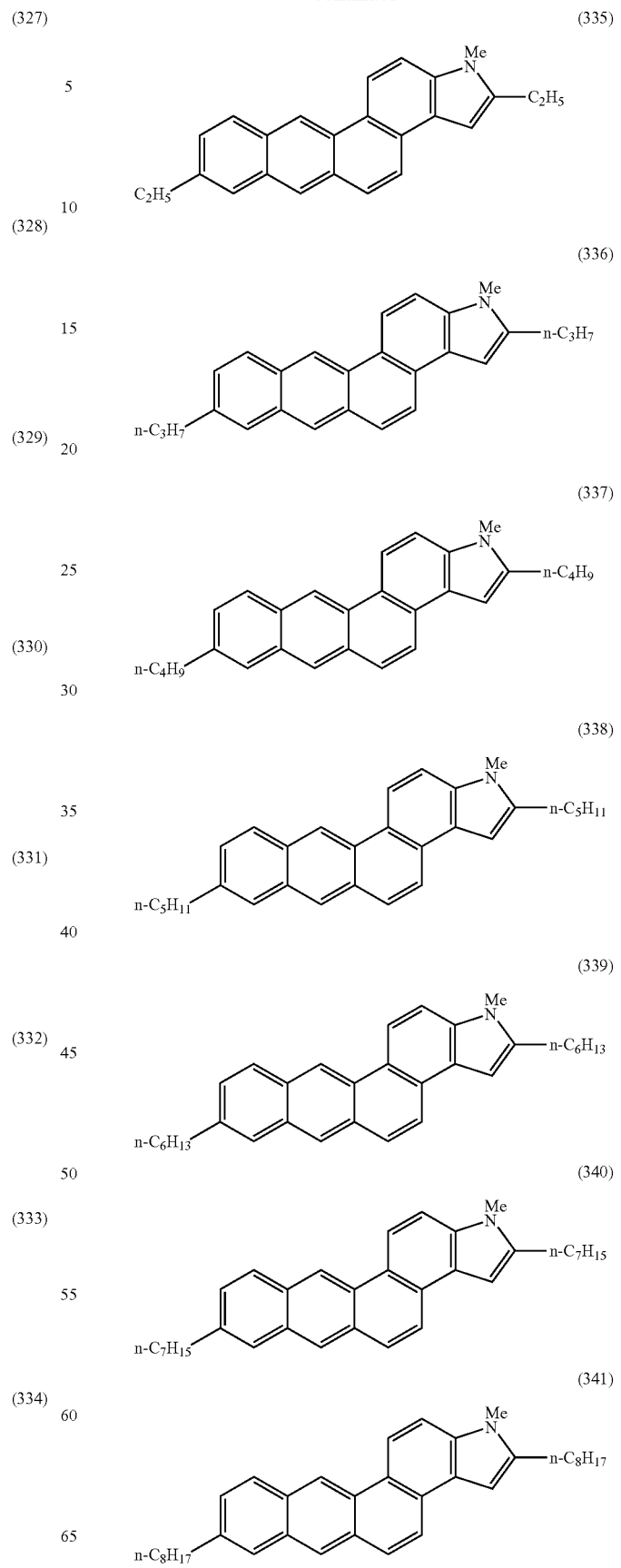

-continued
(342)
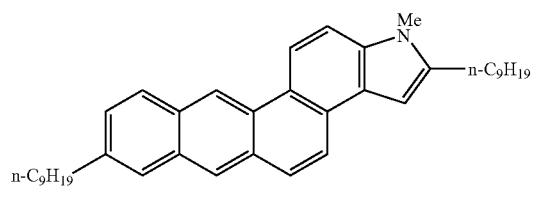
(343)
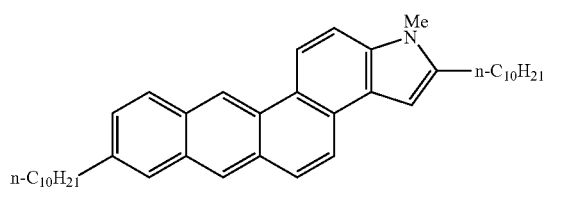
(344)
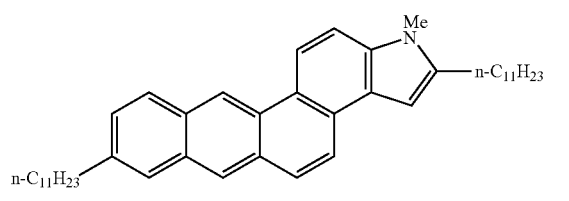
(345)
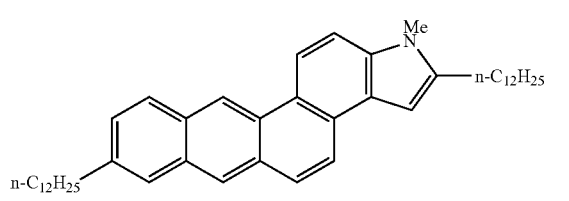
(346)
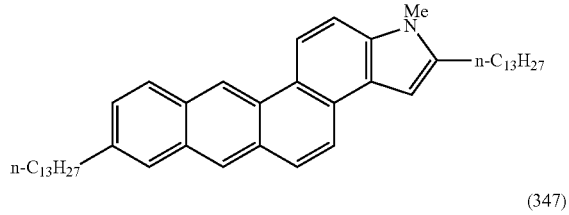
(347)
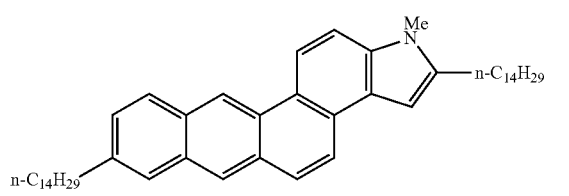
(348)
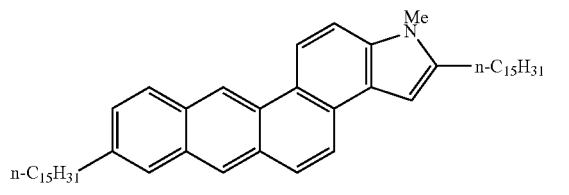
-continued
(349)
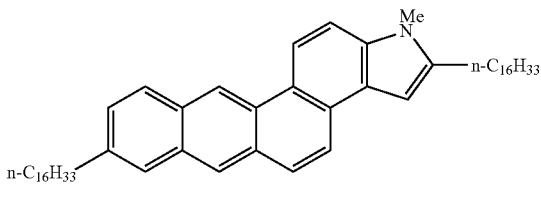
(350)
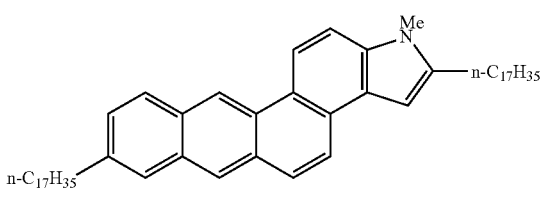
(351)
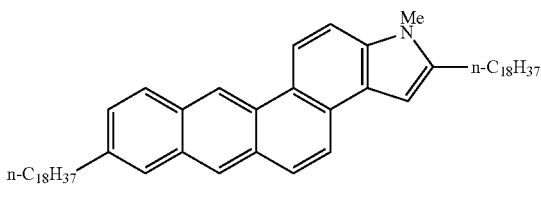
(352)
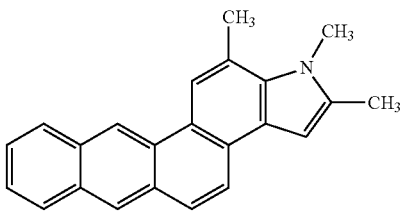
(353)
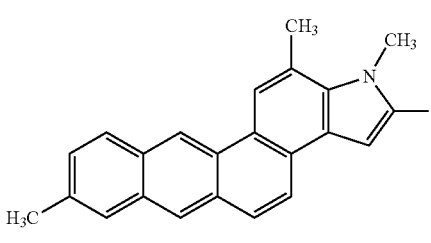
(354)
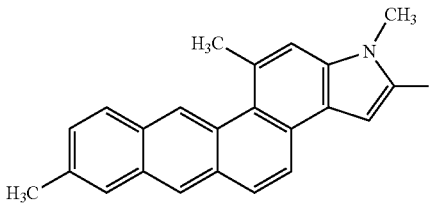
(355)
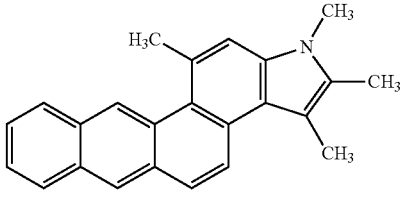

-continued
(356)
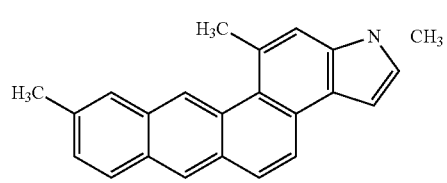
(357)
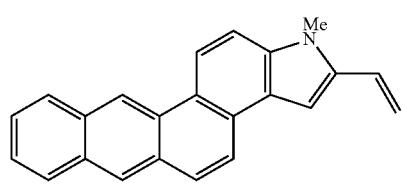
(358)
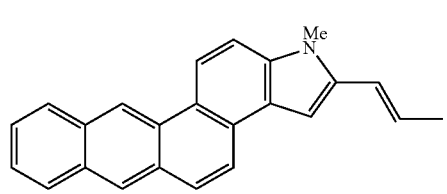
(359)
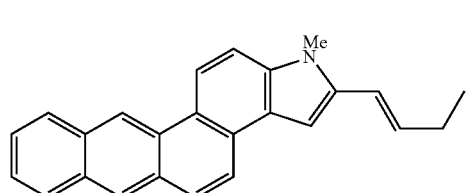
(360)
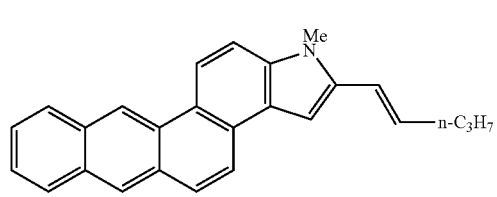
(361)
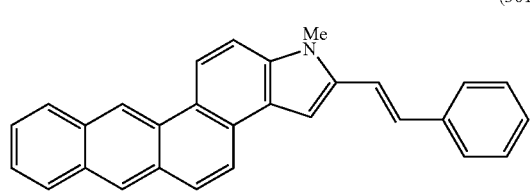
(362)
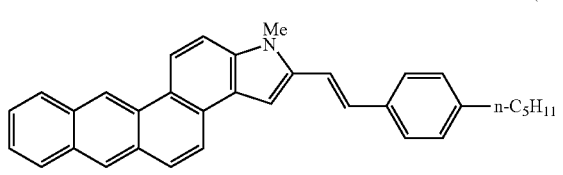
(363)
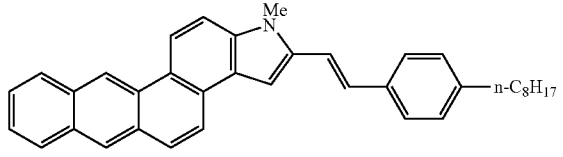
-continued
(364)
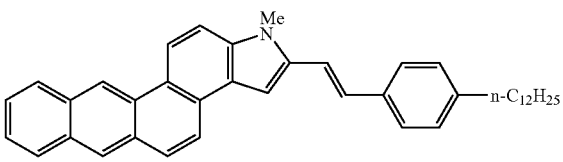
(365)
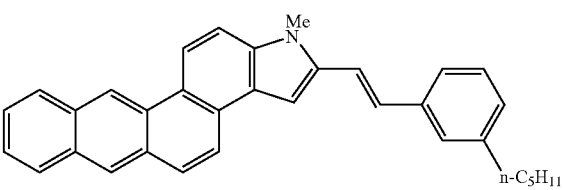
(366)
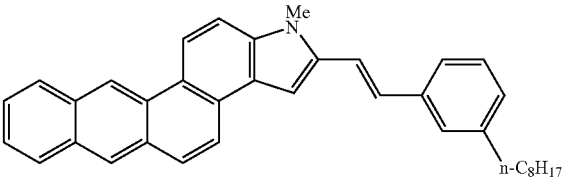
(367)
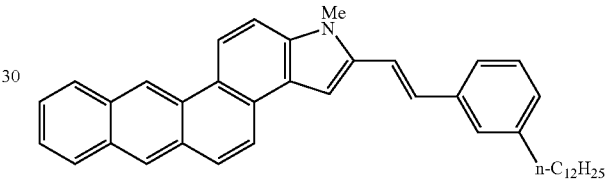
(368)
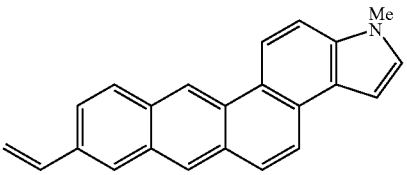
(369)
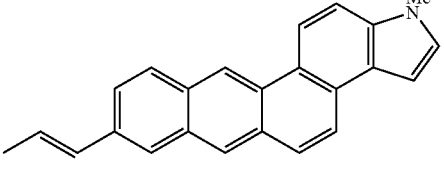
(370)
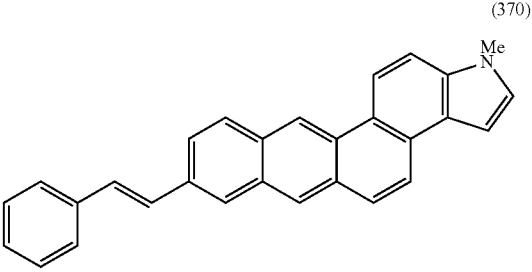
(371)
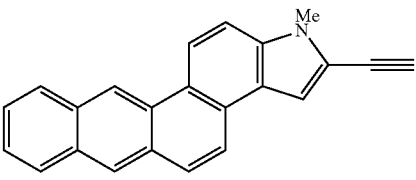

75
-continued
(372)
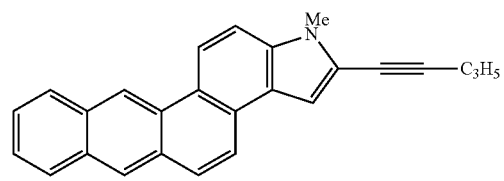
(373)
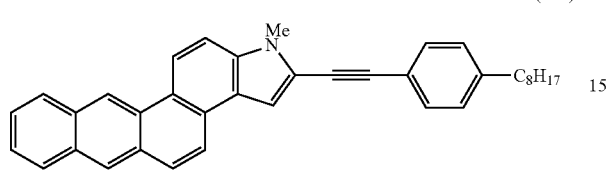
(374)
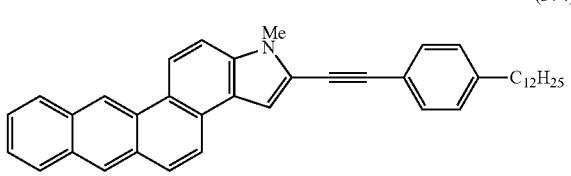
(375)
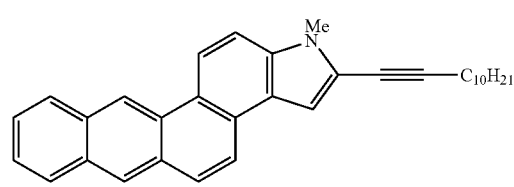
(376)
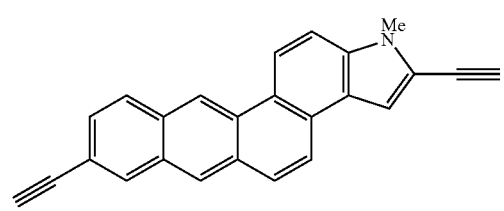
(377)
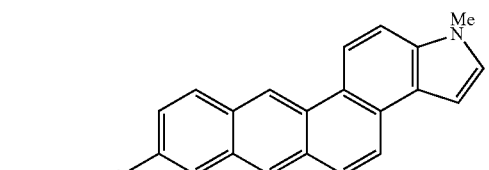
(378)
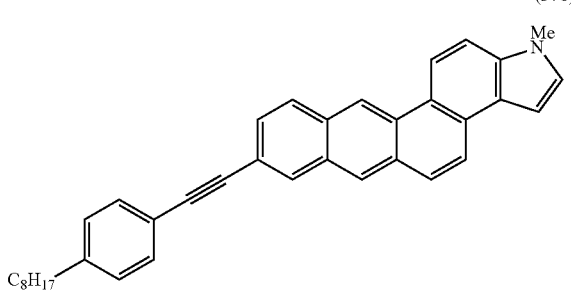
76
-continued
(379)
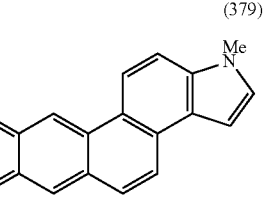
(380)
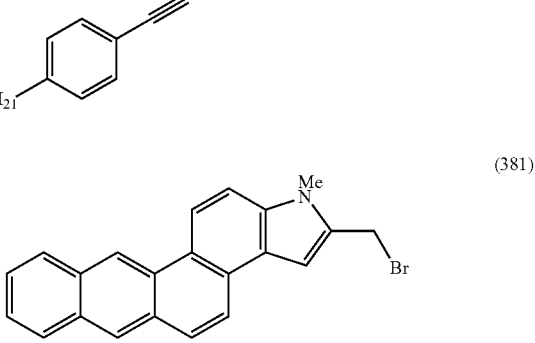
(381)
(382)
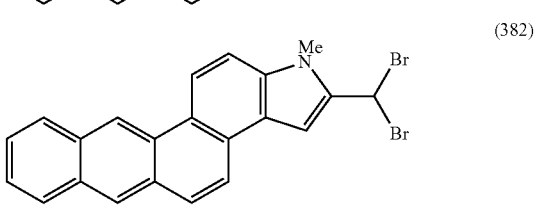
(383)
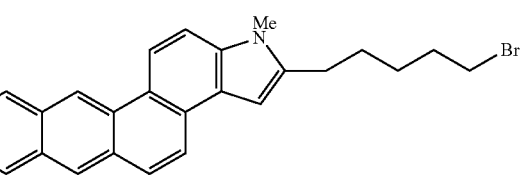
(384)
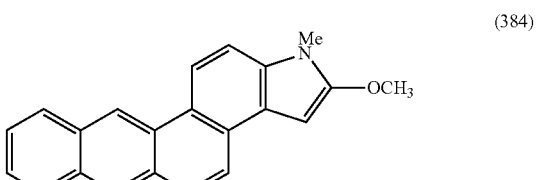
(385)
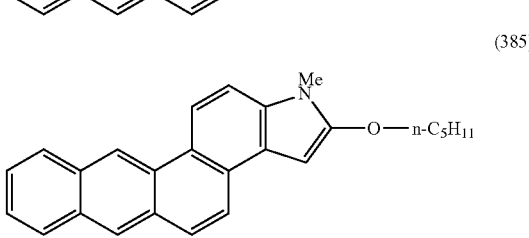

-continued
(386) 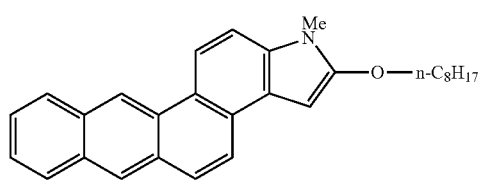
(387) 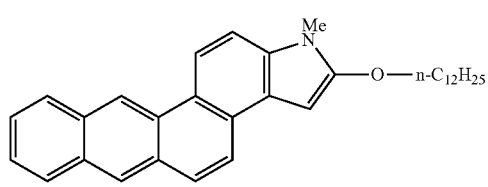
(388) 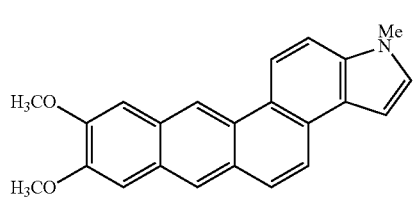
(389) 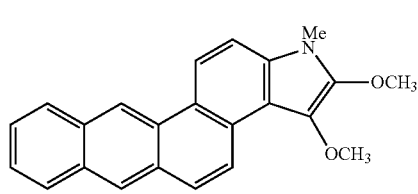
(390) 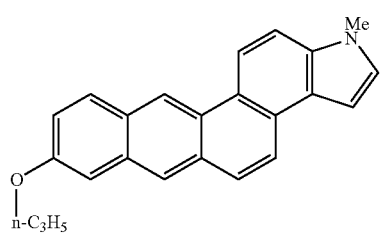
(391) 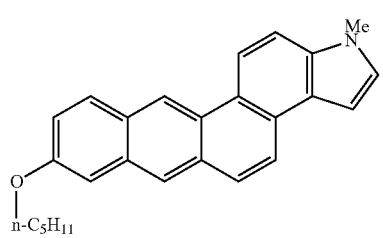
(392) 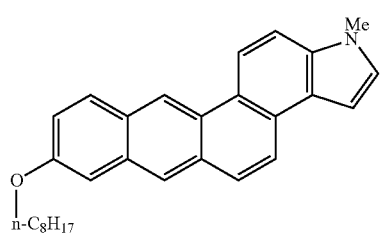
-continued
(393) 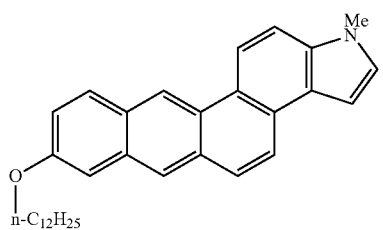
(394) 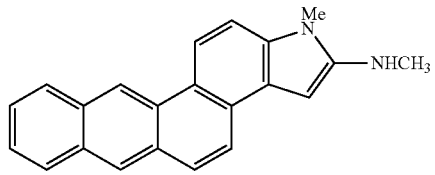
(395) 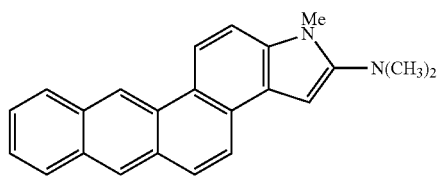
(396) 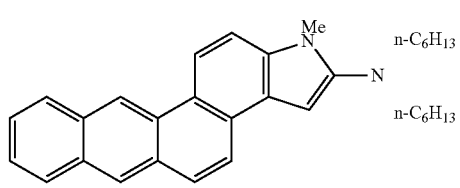
(397) 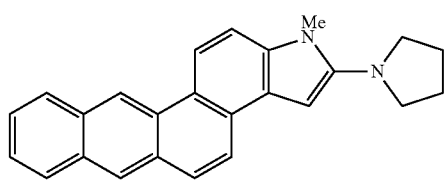
(398) 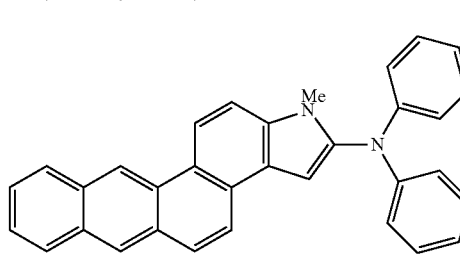
(399) 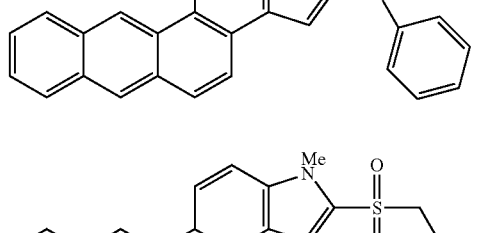
(400) 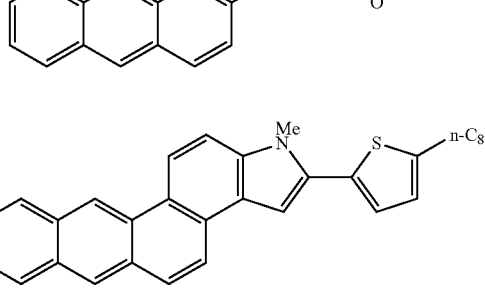

-continued
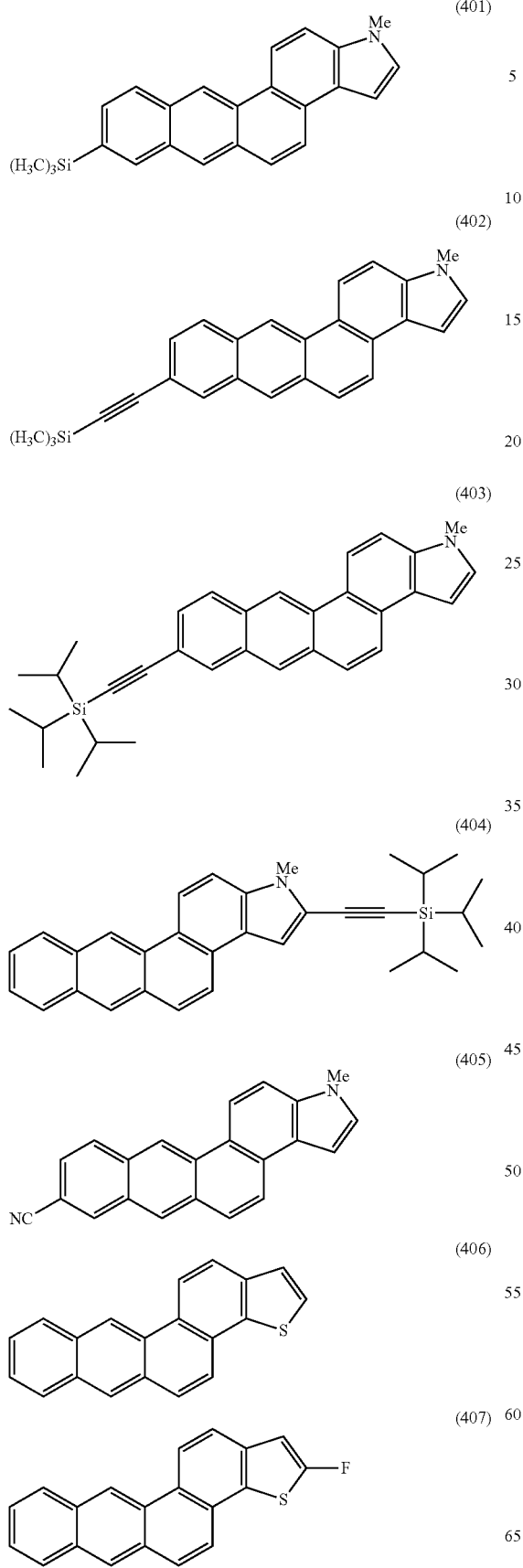
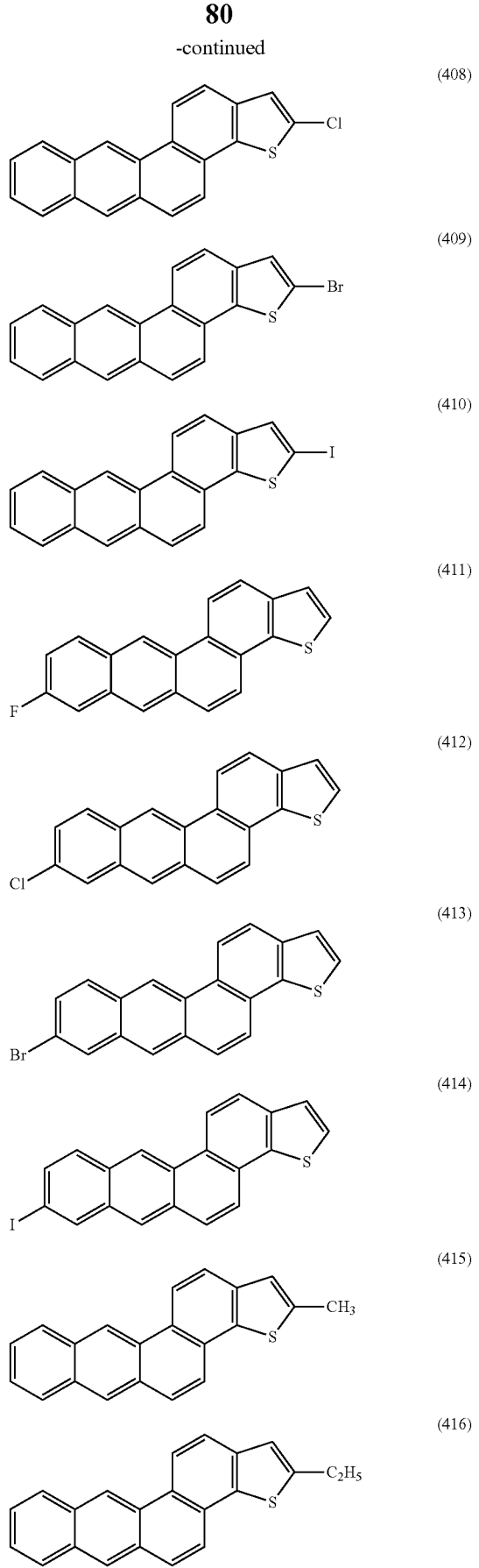

-continued
(417) 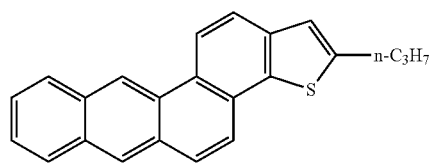
(418) 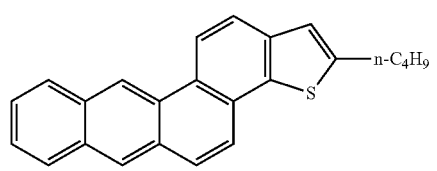
(419) 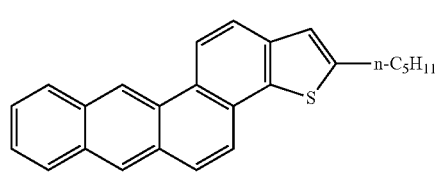
(420) 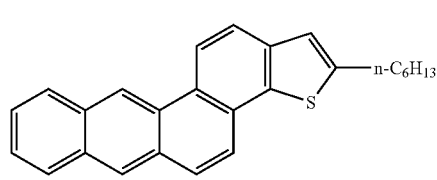
(421) 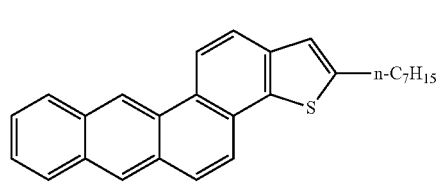
(422) 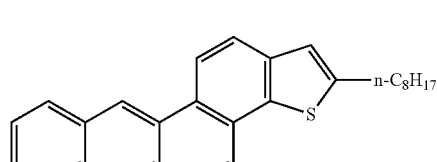
(423) 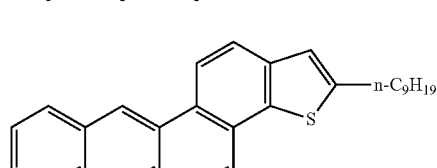
(424) 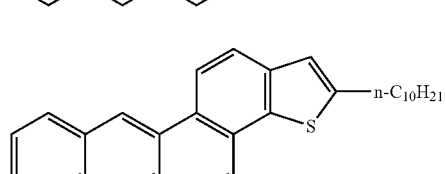
(425) 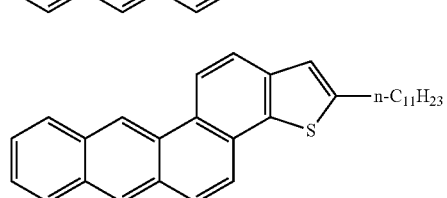
-continued
(426) 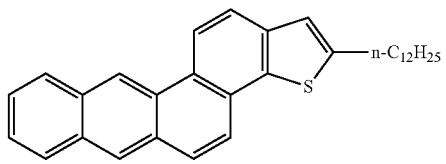
(427) 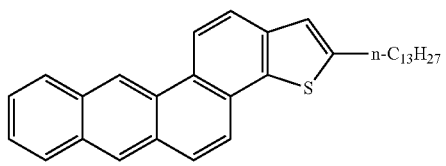
(428) 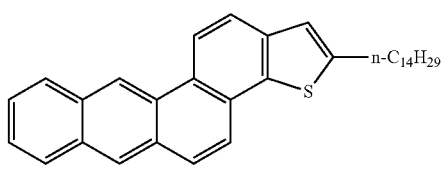
(429) 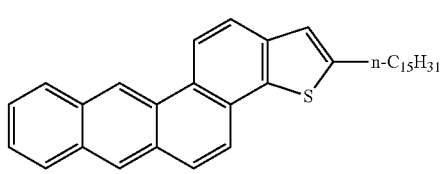
(430) 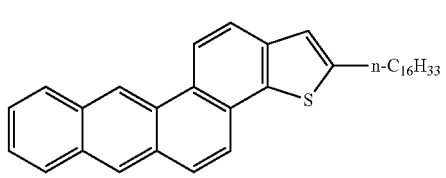
(431) 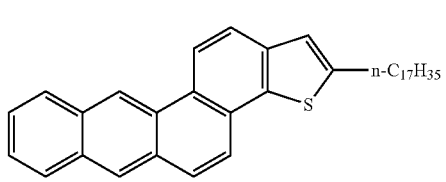
(432) 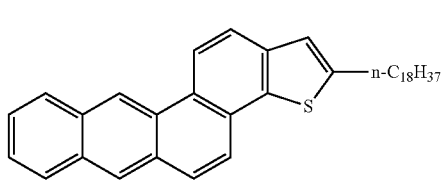
(433) 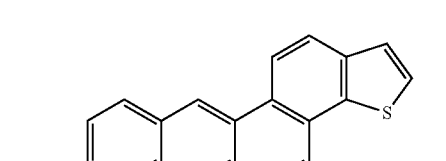
(434) 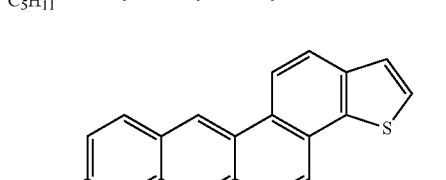

(435)
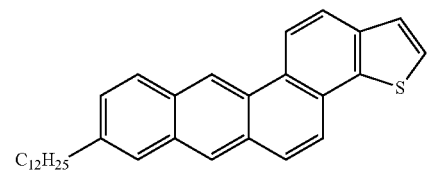
(436)
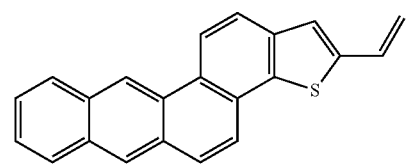
(437)
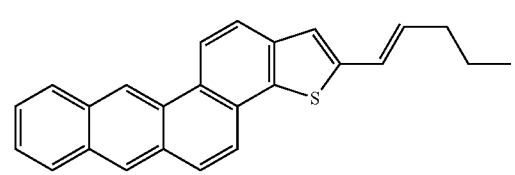
(438)
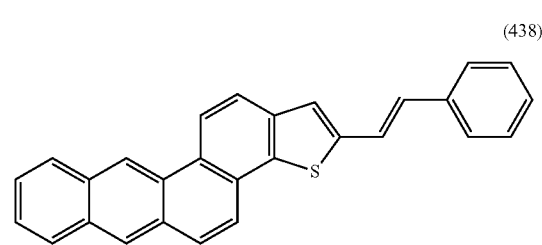
(439)
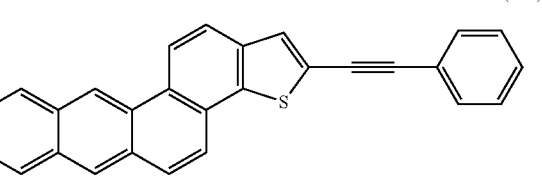
(440)
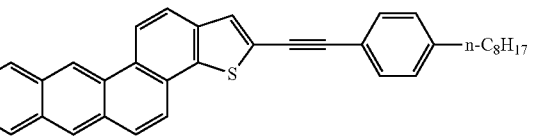
(441)
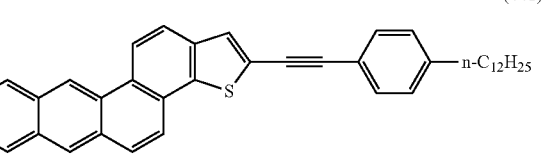
(442)
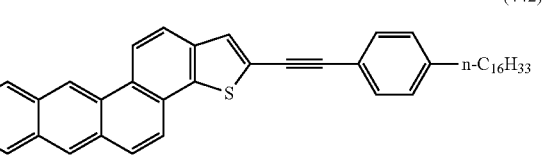
(443)
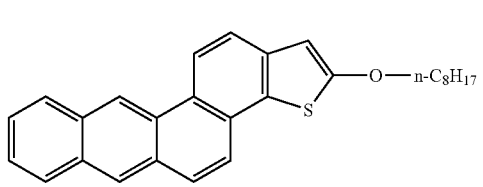
(444)
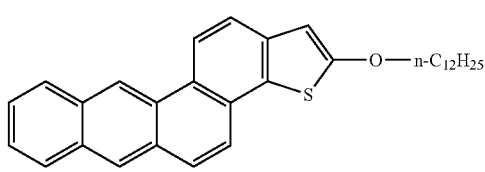
(445)
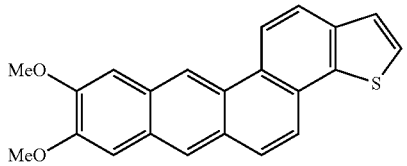
(446)
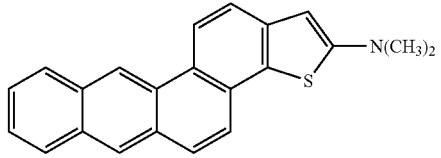
(447)
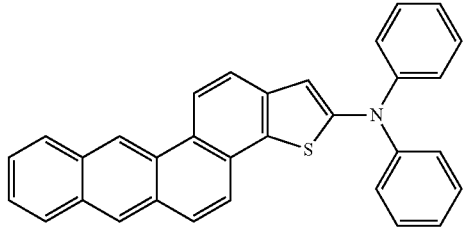
(448)
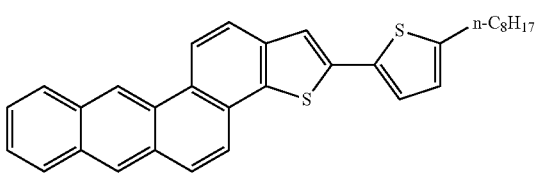
(449)
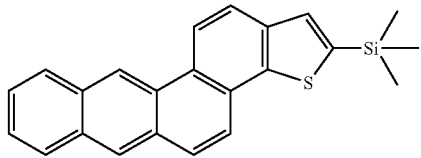
(450)
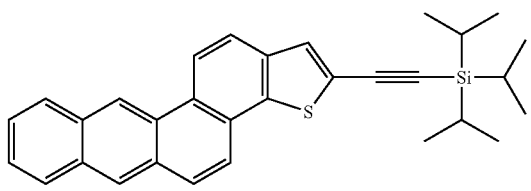

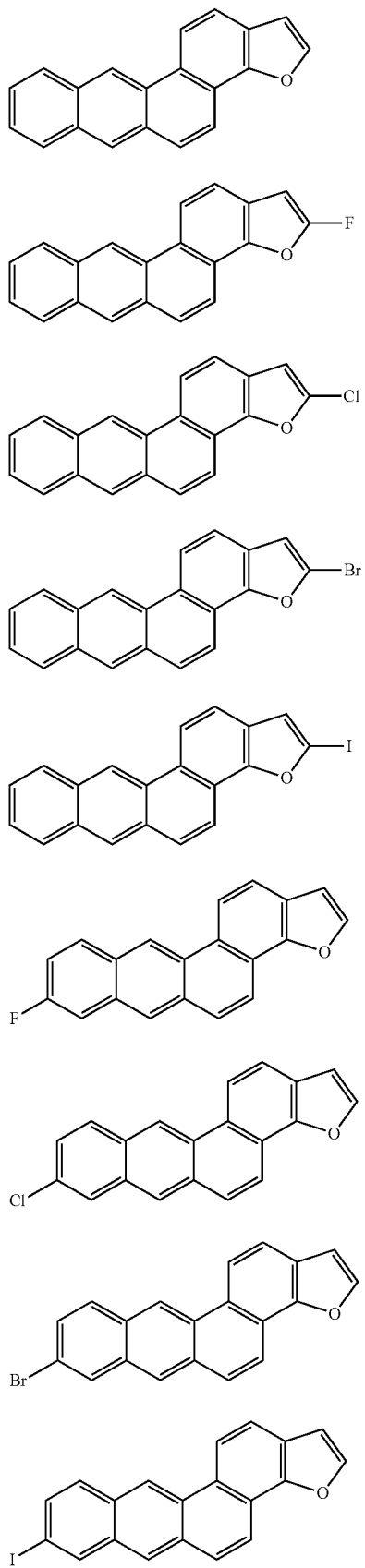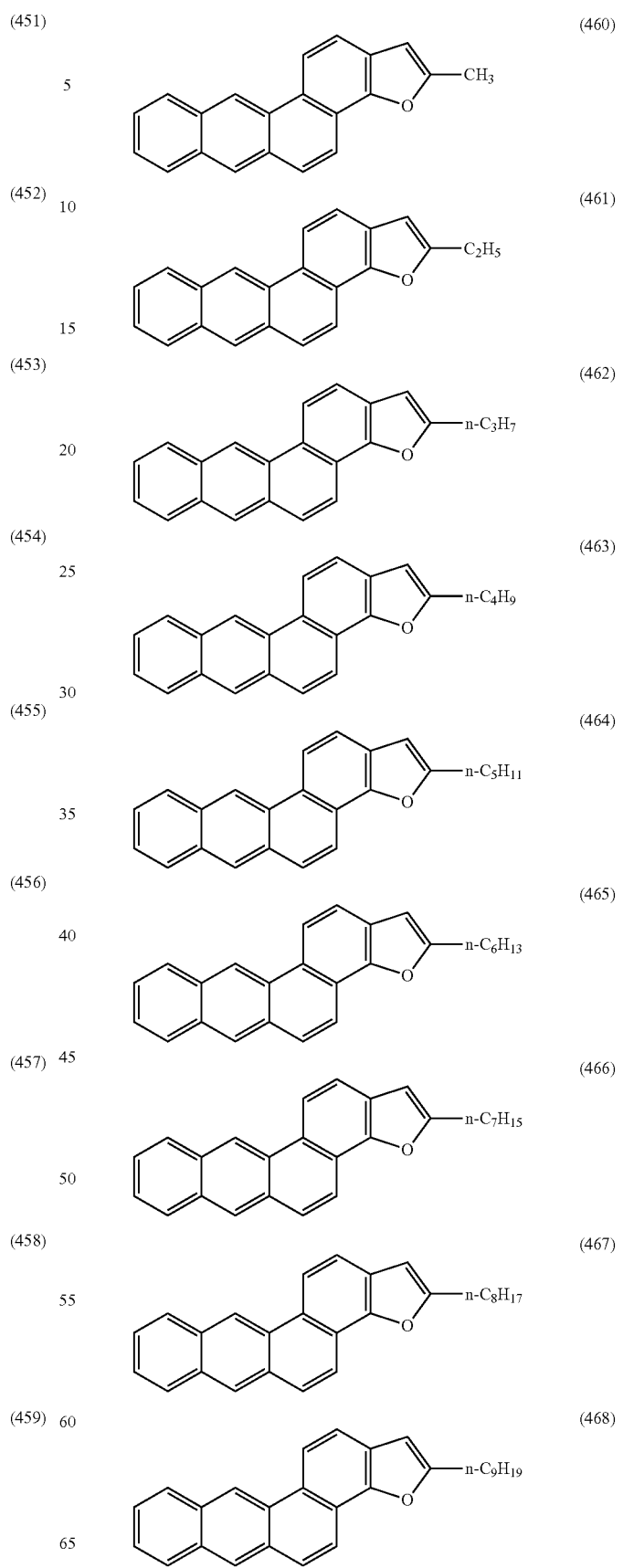

(469) 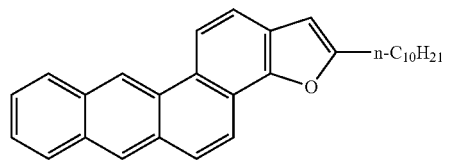 n-C₁₀H₂₁
(470) 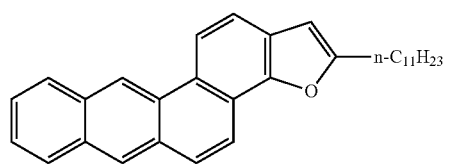 n-C₁₁H₂₃
(471) 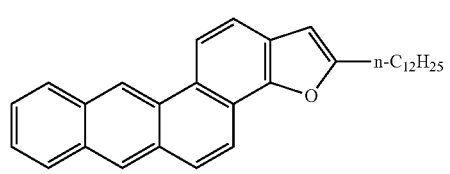 n-C₁₂H₂₅
(472) 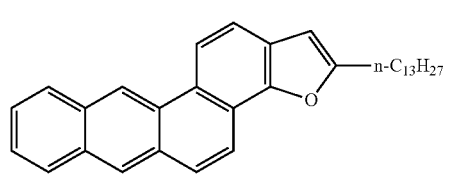 n-C₁₃H₂₇
(473) 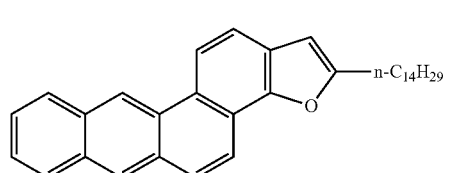 n-C₁₄H₂₉
(474) 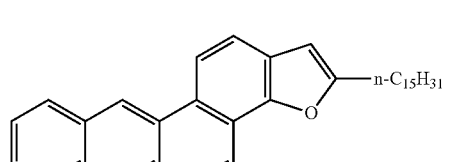 n-C₁₅H₃₁
(475) 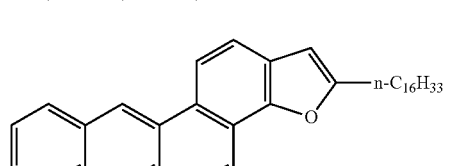 n-C₁₆H₃₃
(476) 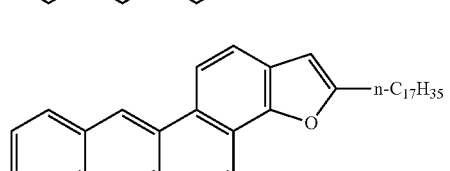 n-C₁₇H₃₅
(477) 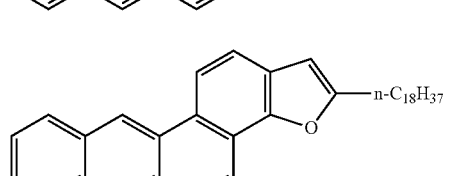 n-C₁₈H₃₇
(478) 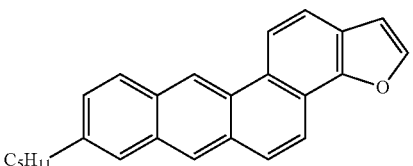
(479) 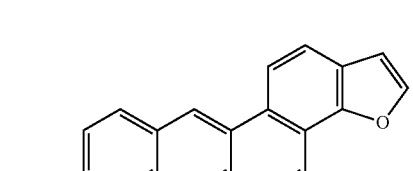
(480) 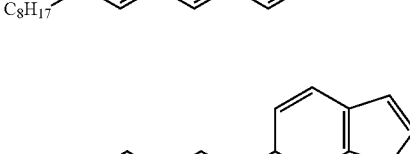
(481) 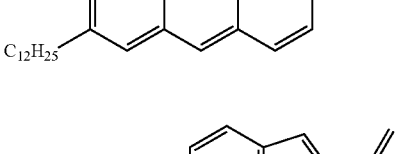
(482) 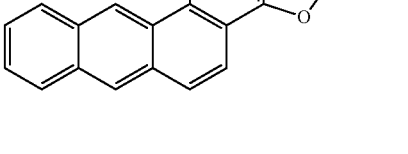
(483) 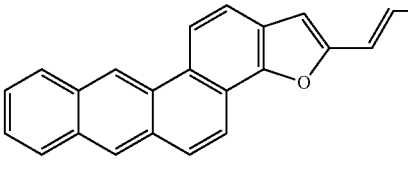
(484) 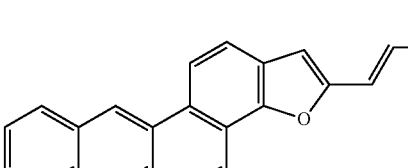
(485) 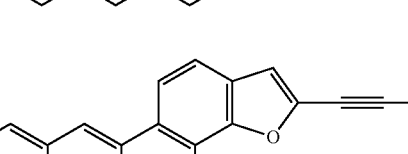
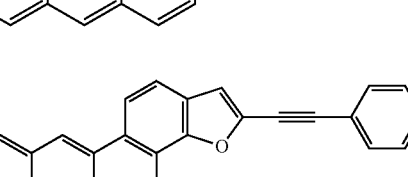

-continued
(486)
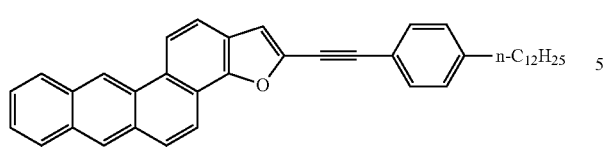
(487)
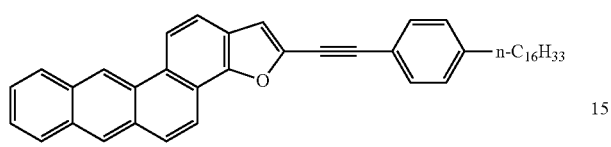
(488)
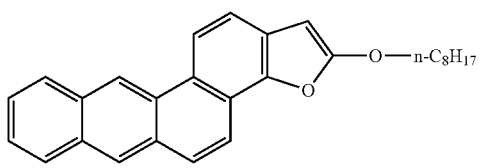
(489)
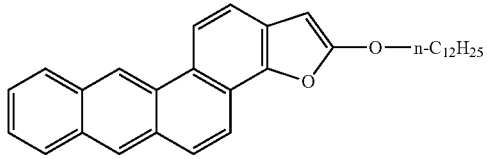
(490)
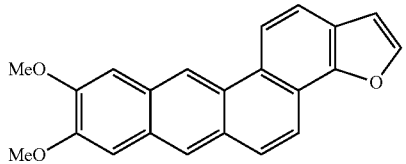
(491)
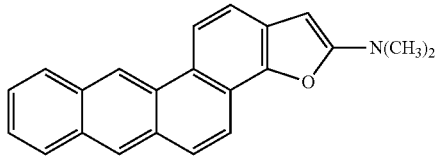
(492)
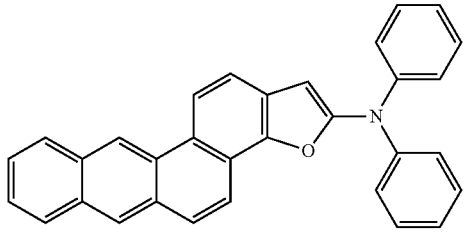
(493)
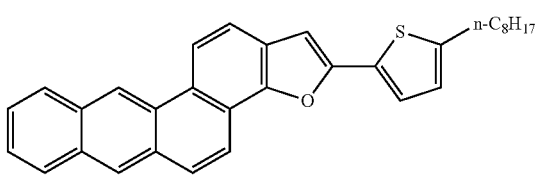
-continued
(494)
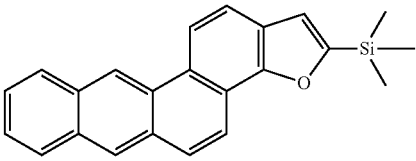
(495)
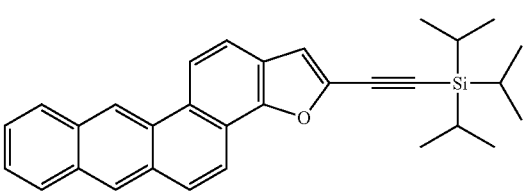
(496)
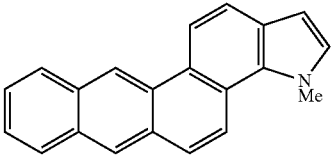
(497)
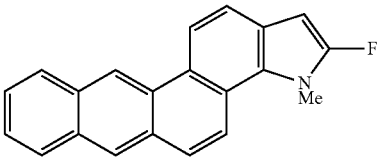
(498)
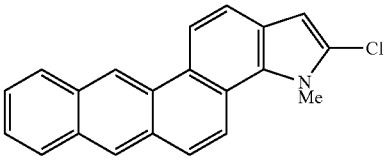
(499)
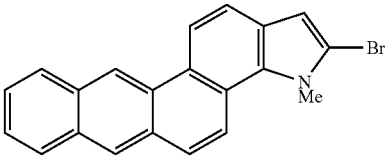
(500)
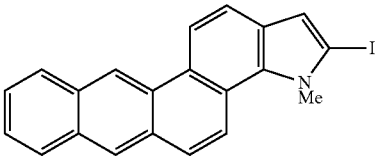
(501)
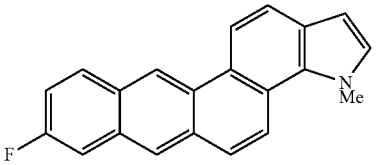
(502)
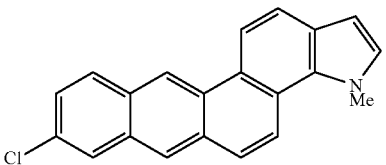

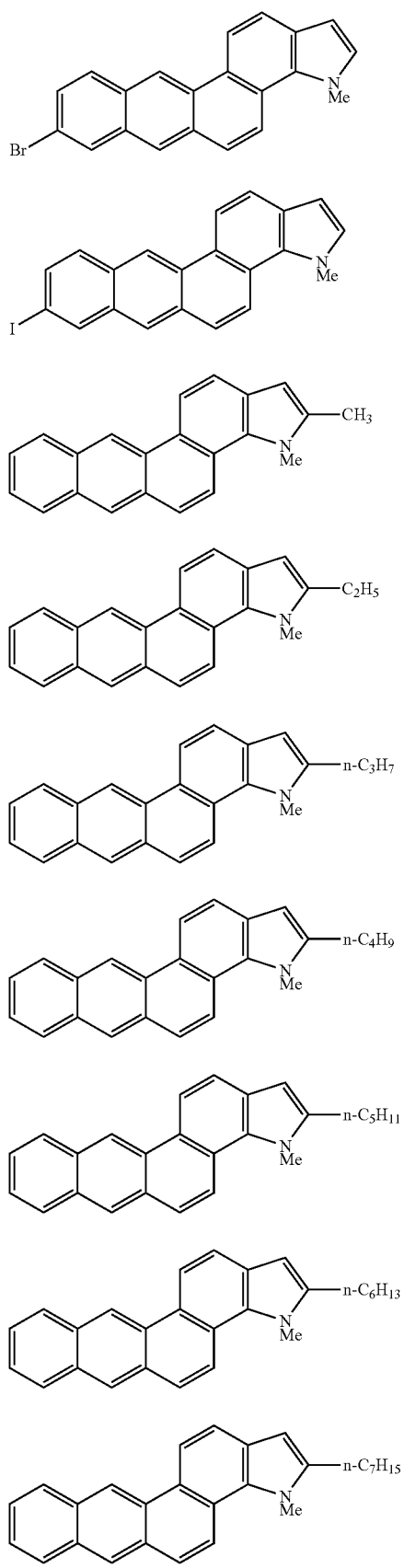
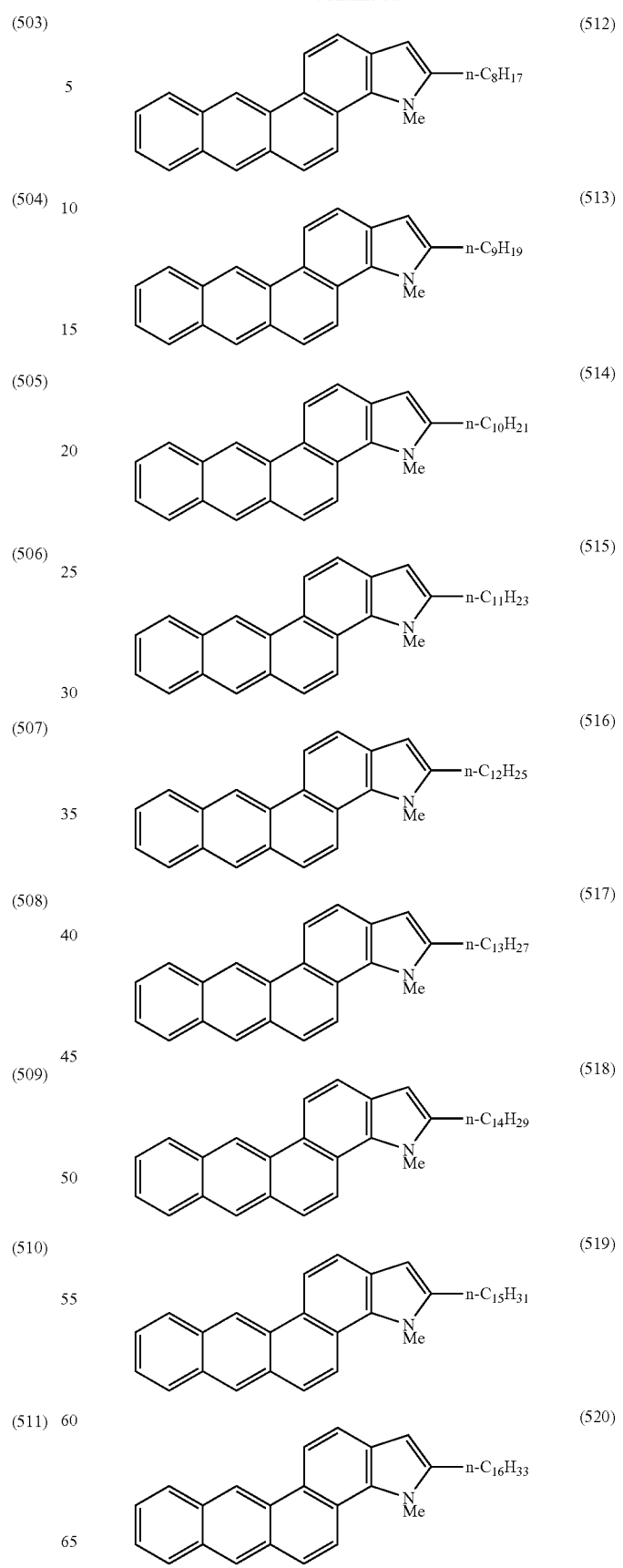

-continued
(521) 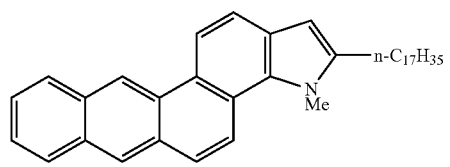
(522) 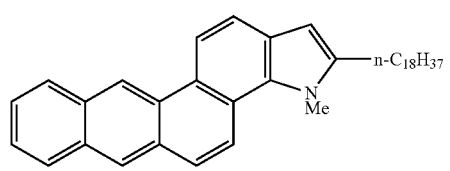
(523) 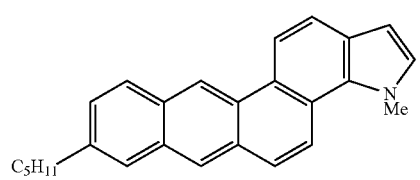
(524) 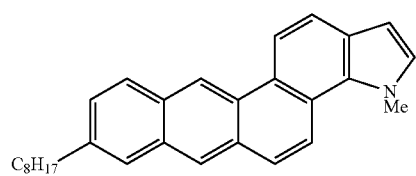
(525) 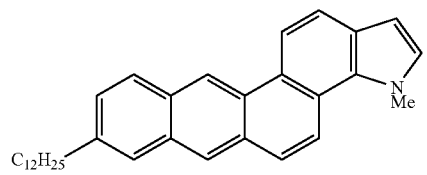
(526) 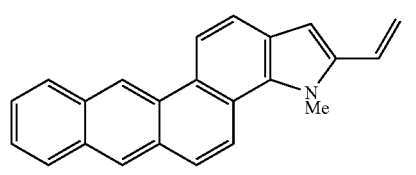
(527) 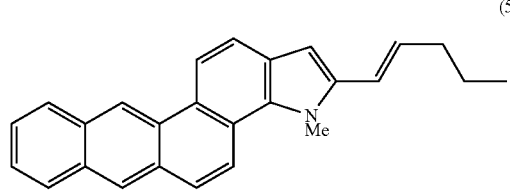
(528) 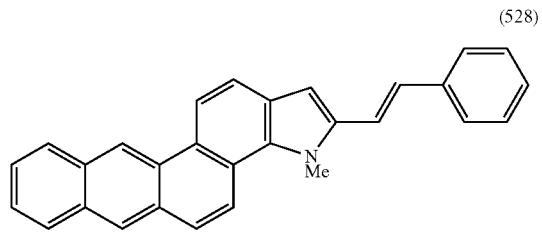
-continued
(529) 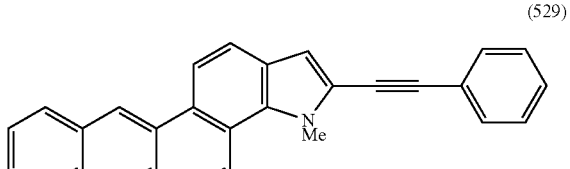
(530) 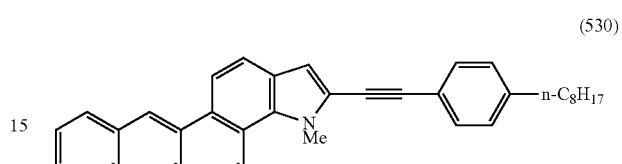
(531) 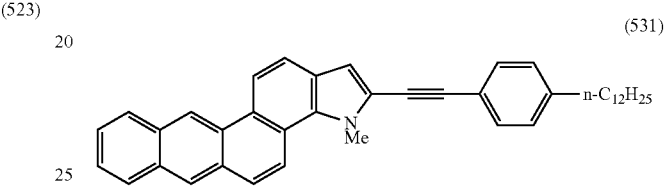
(532) 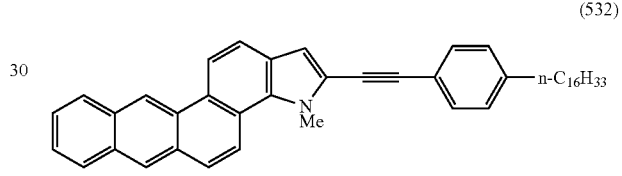
(533) 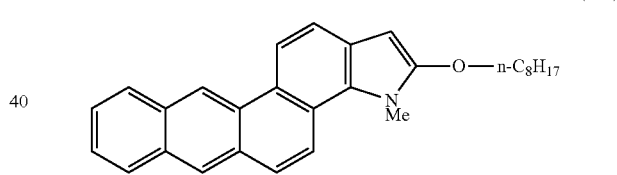
(534) 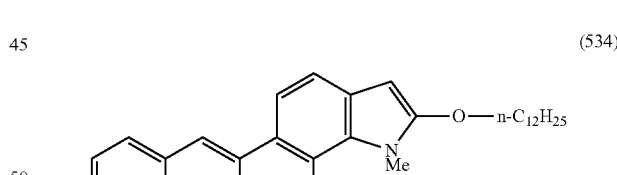
(535) 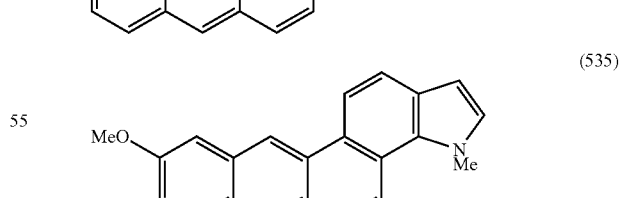
(536) 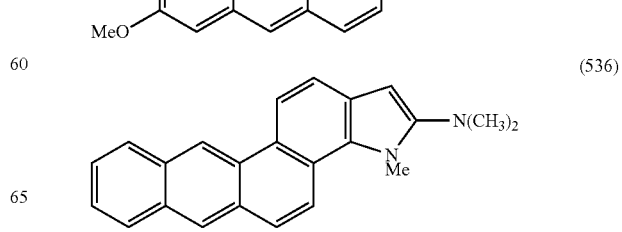

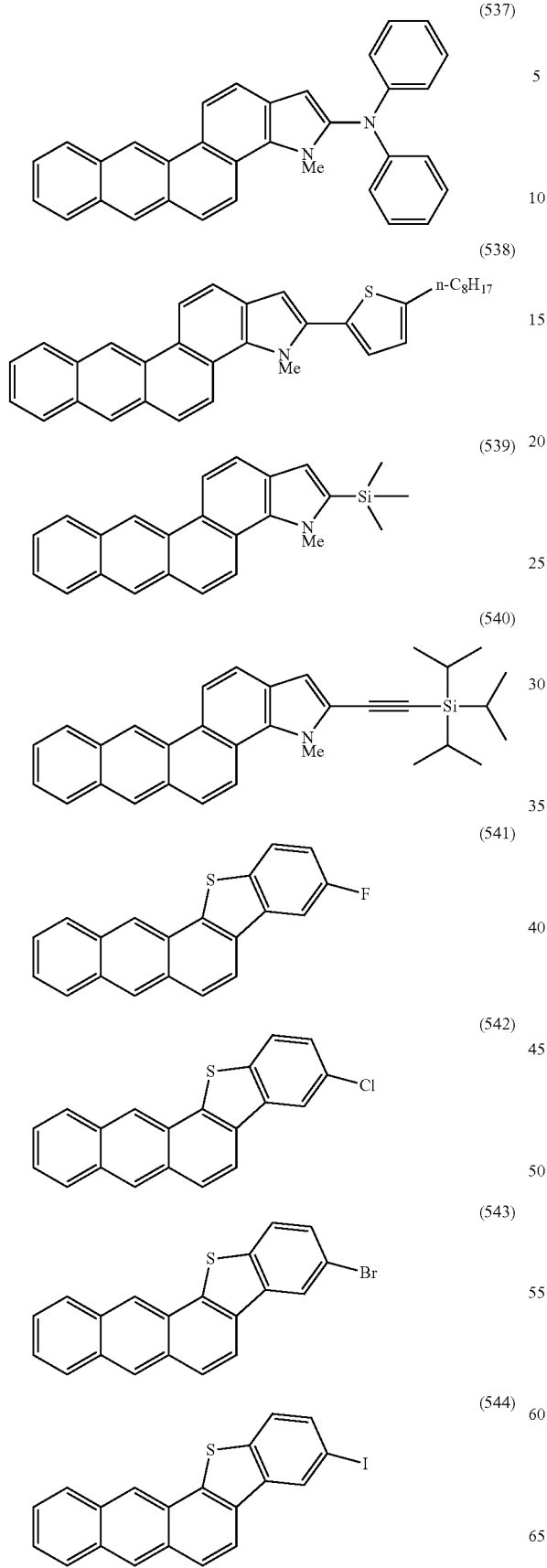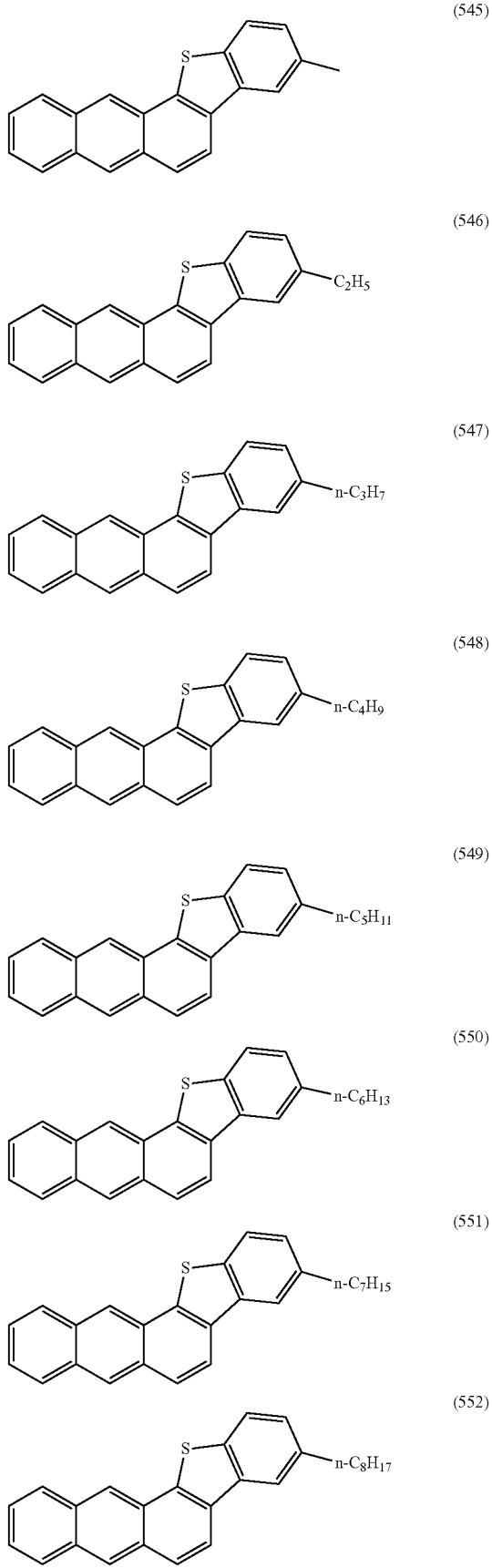

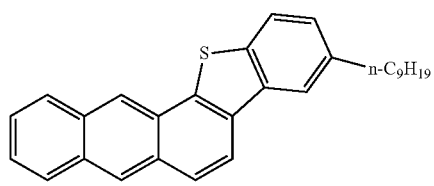 (553)
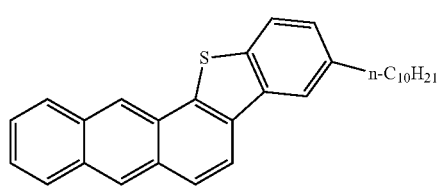 (554)
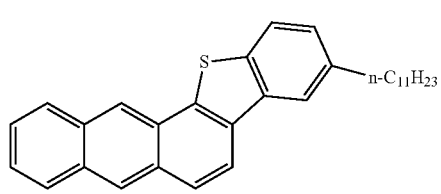 (555)
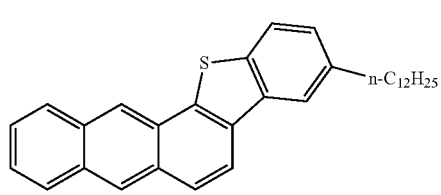 (556)
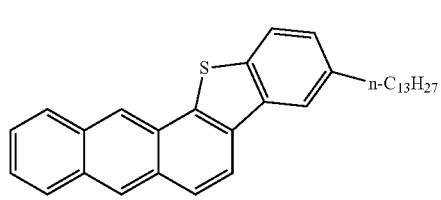 (557)
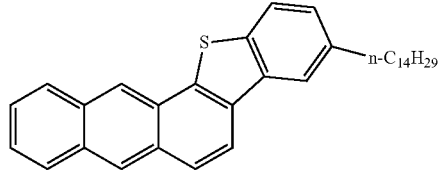 (558)
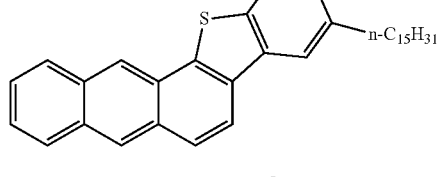 (559)
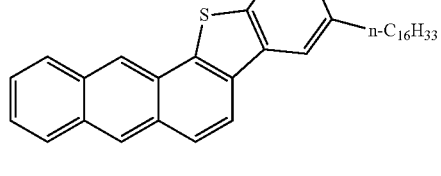 (560)
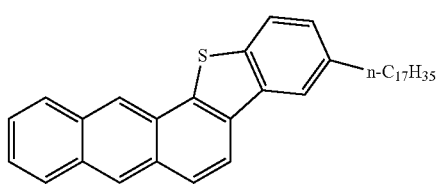 (561)
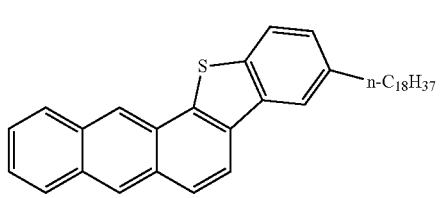 (562)
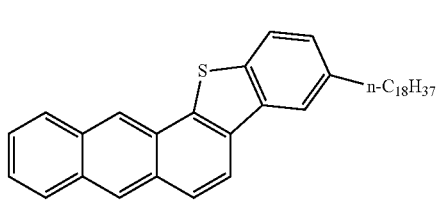 (563)
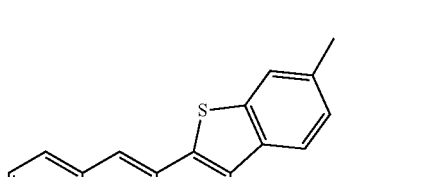 (564)
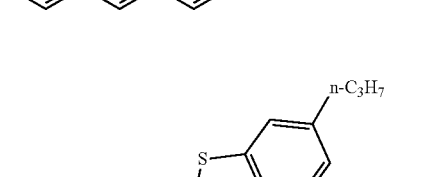 (565)
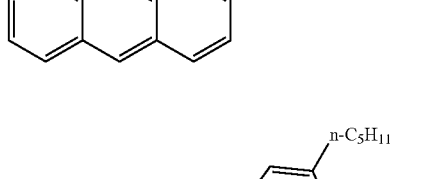 (566)
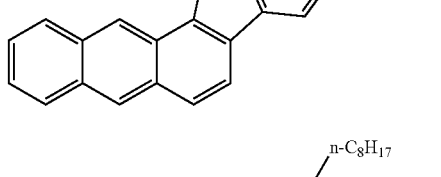 (567)

99
-continued
(568)
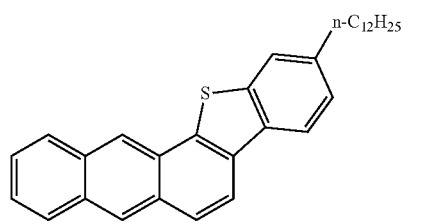
(569)
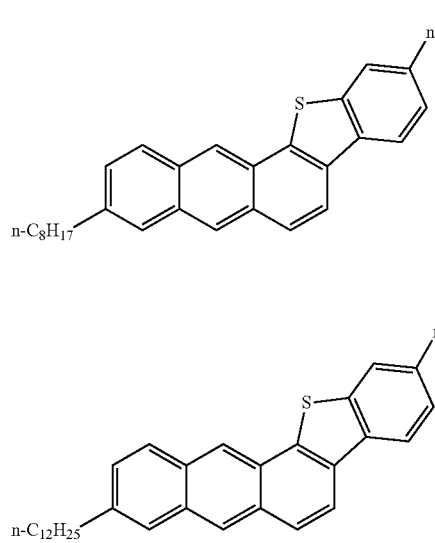
(570)
(571)
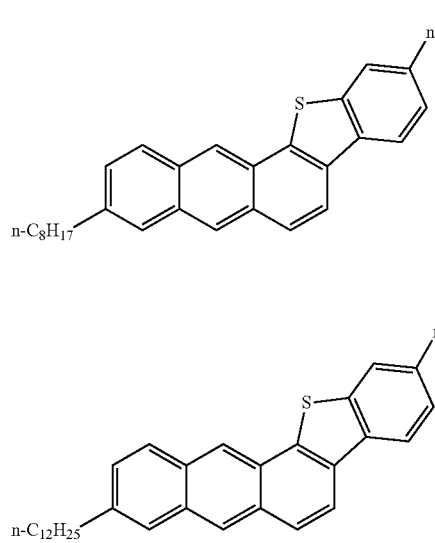
(572)
(573)
(574)
100
-continued
(575)
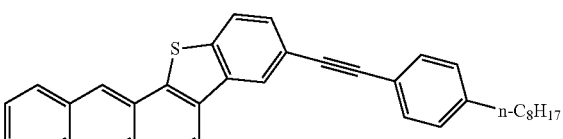
(576)
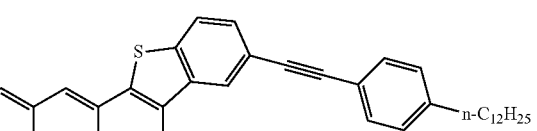
(577)
(578)
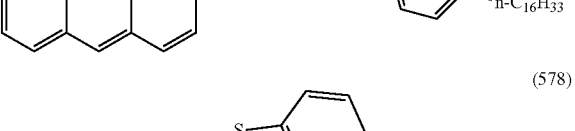
(579)
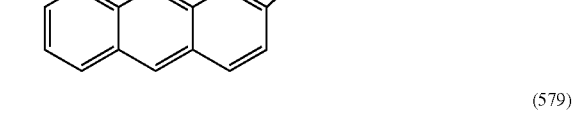
(580)
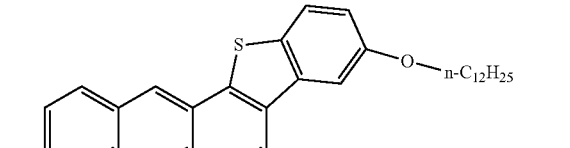
(581)
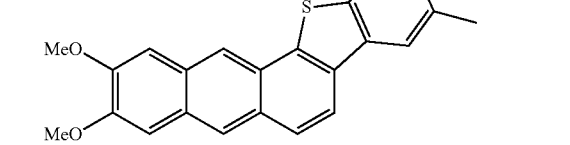
(582)
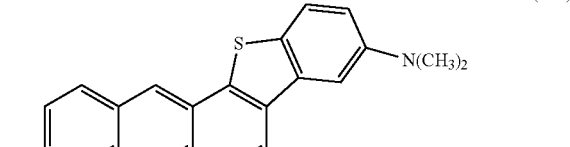

-continued
(583) 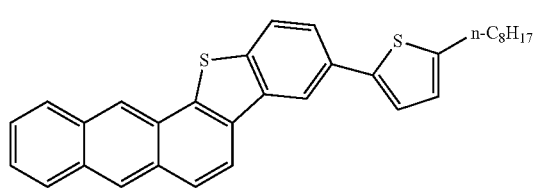
(584) 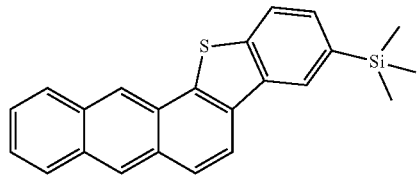
(585) 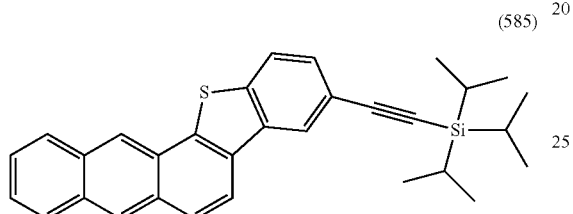
(586) 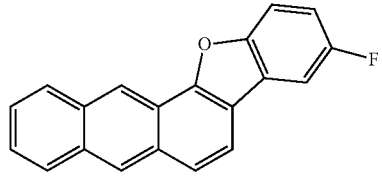
(587) 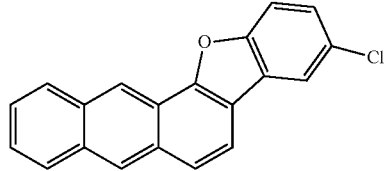
(588) 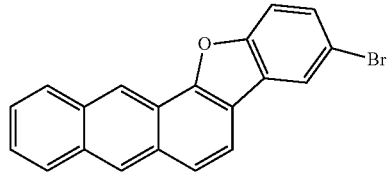
(589) 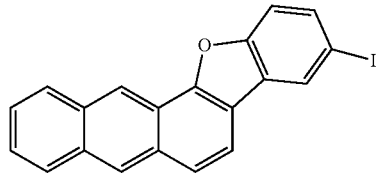
(590) 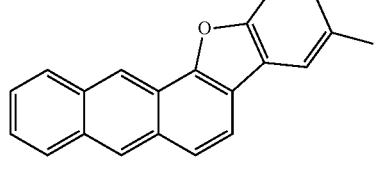
-continued
(591) 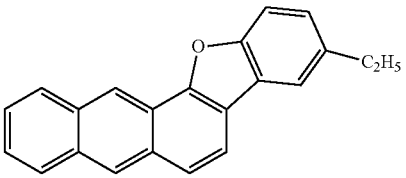
(592) 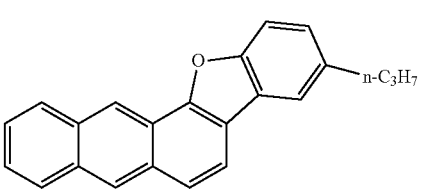
(593) 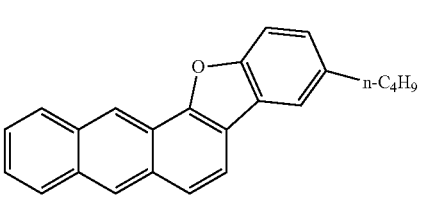
(594) 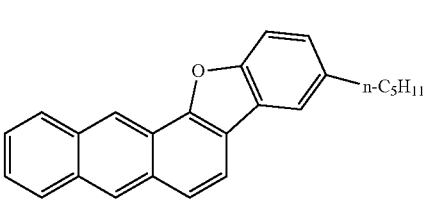
(595) 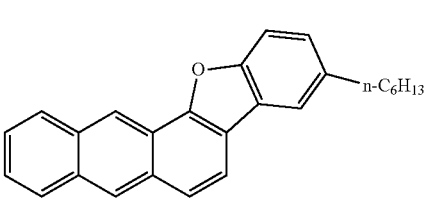
(596) 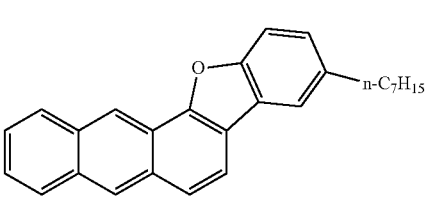
(597) 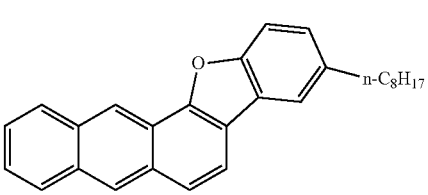
(598) 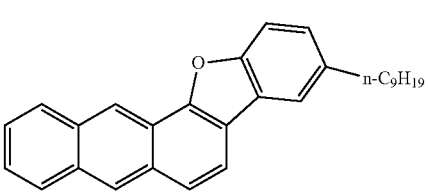

(599) 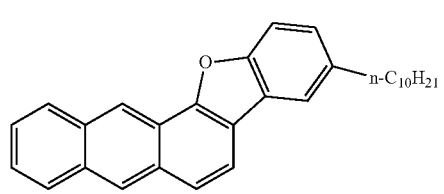
(600) 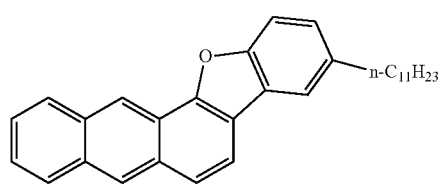
(601) 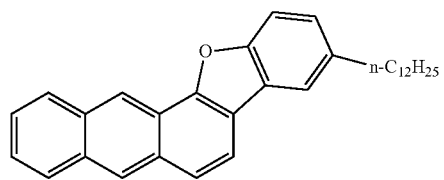
(602) 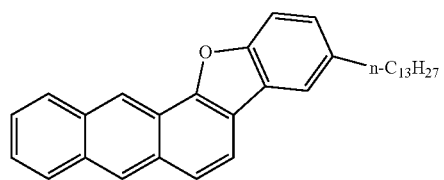
(603) 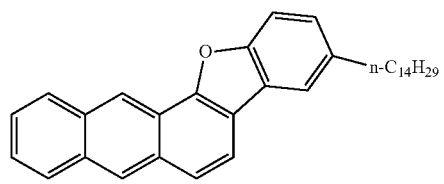
(604) 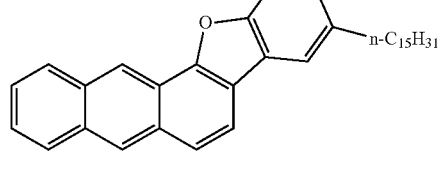
(605) 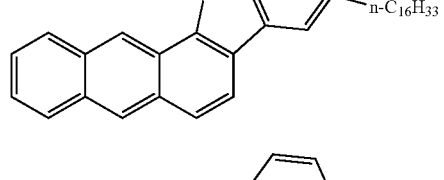
(606) 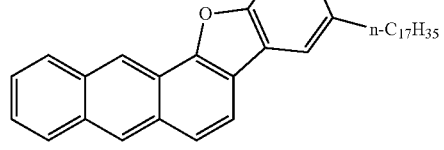
(607) 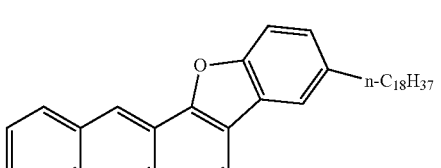
(608) 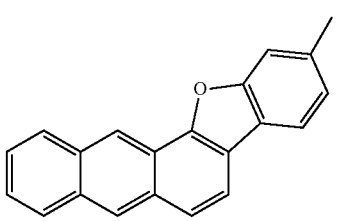
(609) 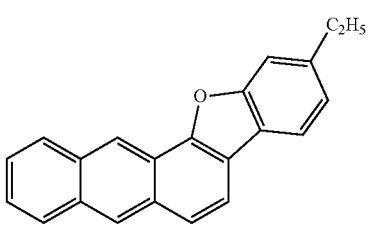
(610) 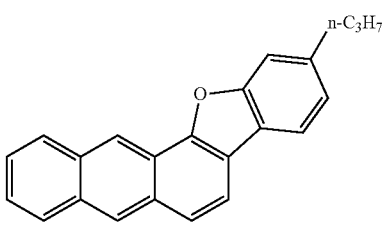
(611) 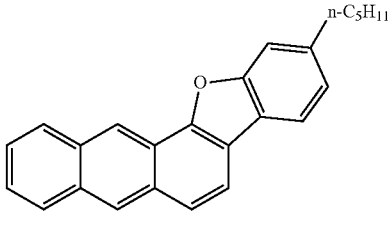
(612) 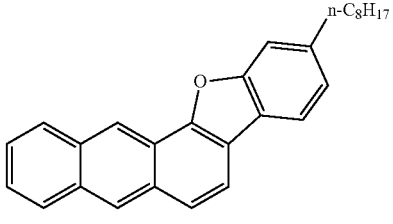
(613) 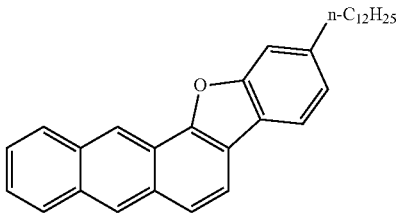

(614)
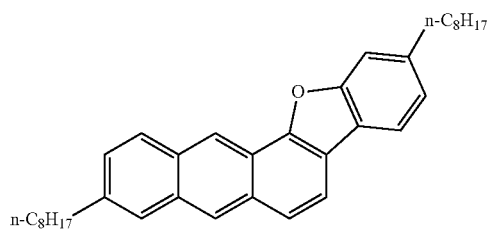
(615)
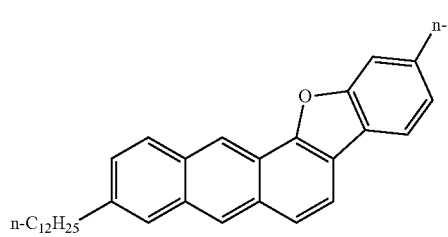
(616)
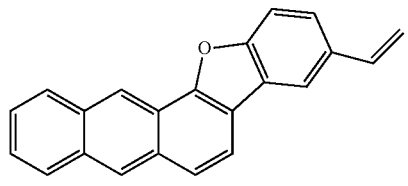
(617)
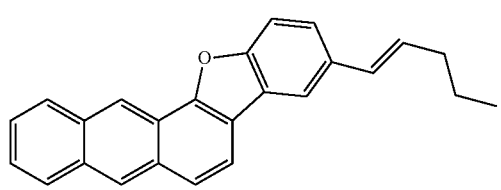
(618)
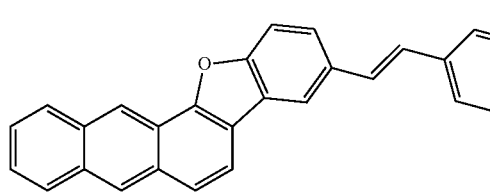
(619)
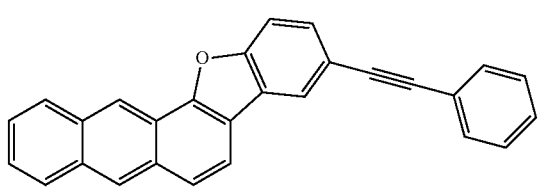
(620)
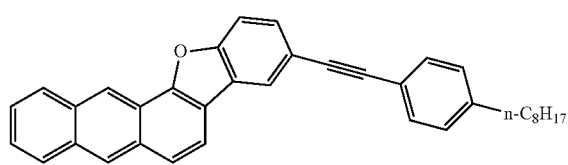
(621)
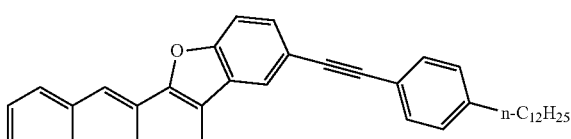
(622)
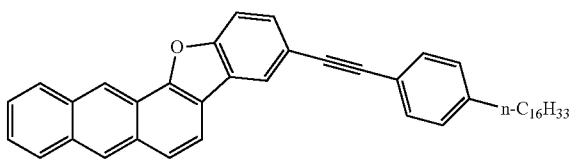
(623)
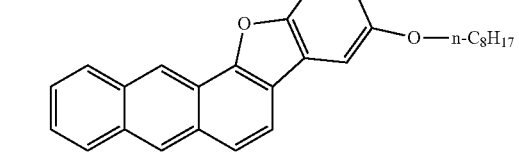
(624)
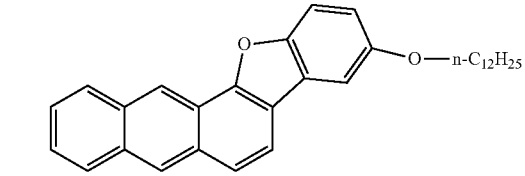
(625)
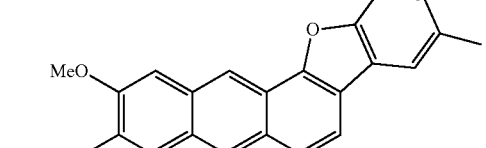
(626)
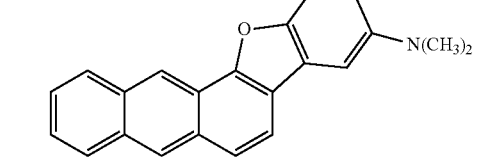
(627)
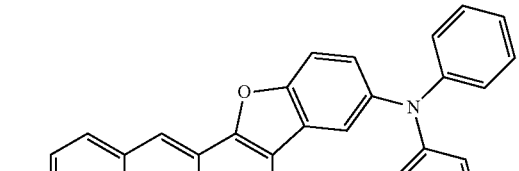
(628)
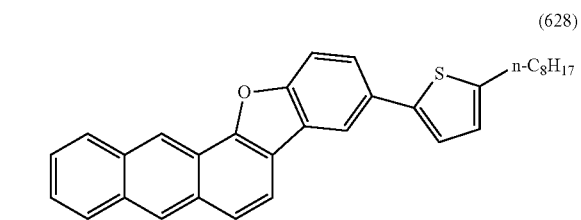

(629) 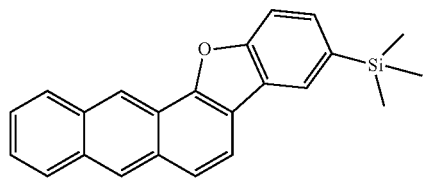
(630) 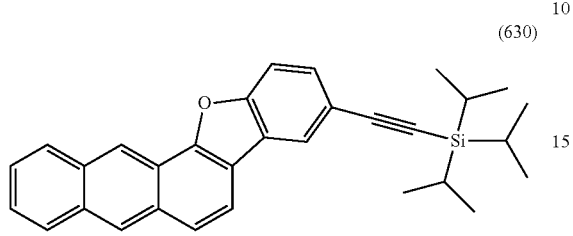
(631) 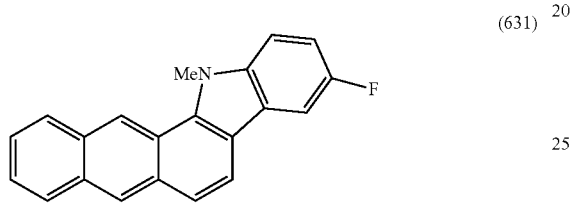
(632) 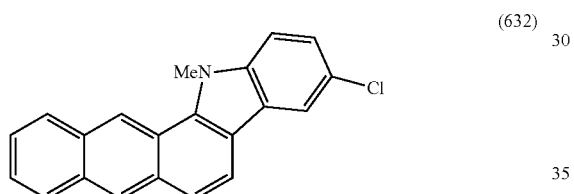
(633) 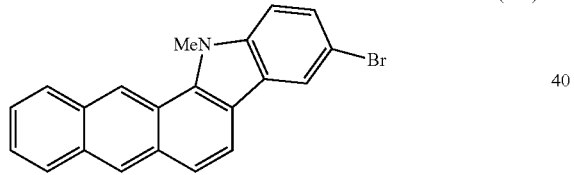
(634) 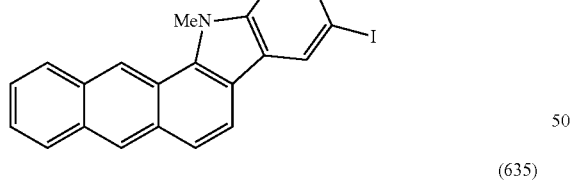
(635) 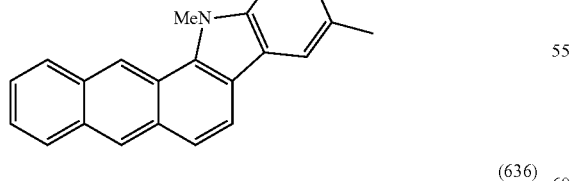
(636) 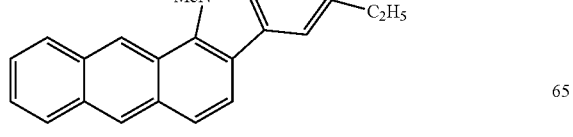
(637) 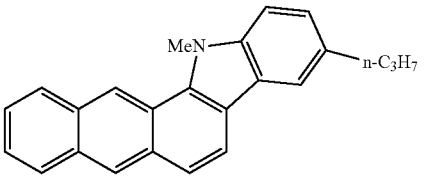
(638) 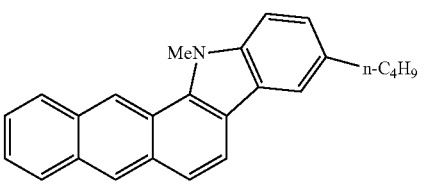
(639) 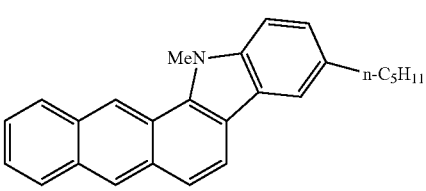
(640) 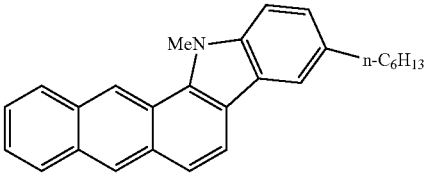
(641) 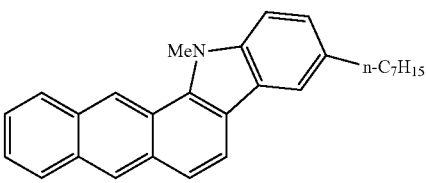
(642) 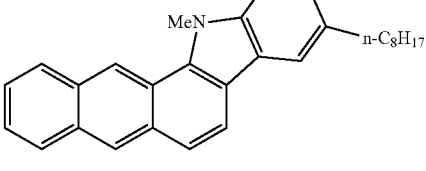
(643) 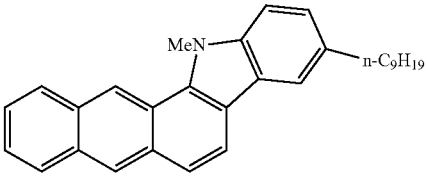
(644) 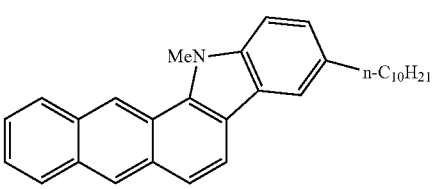

(645) 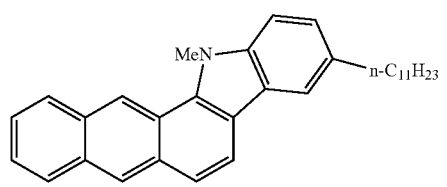
(646) 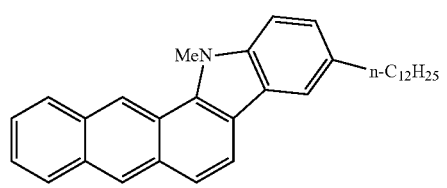
(647) 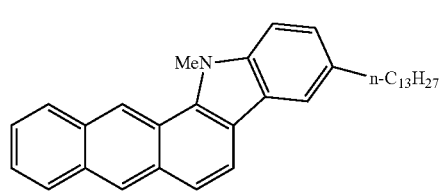
(648) 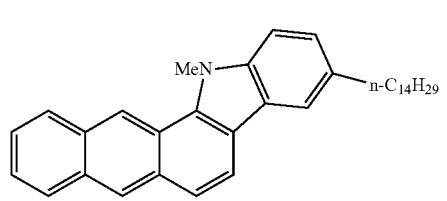
(649) 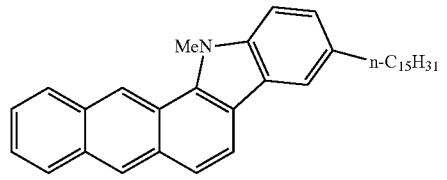
(650) 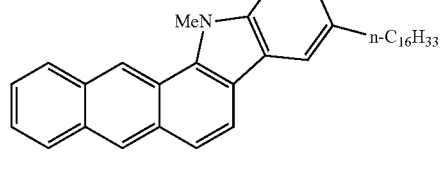
(651) 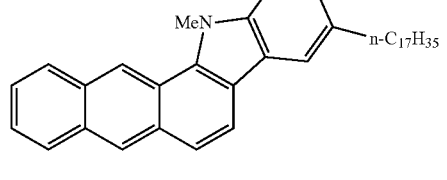
(652) 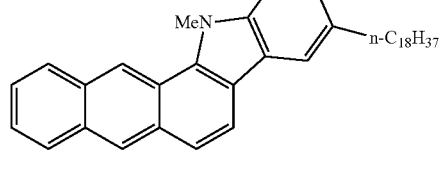
(653) 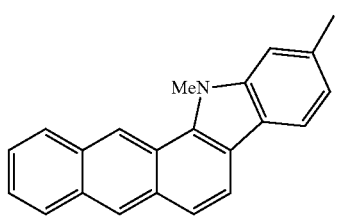
(654) 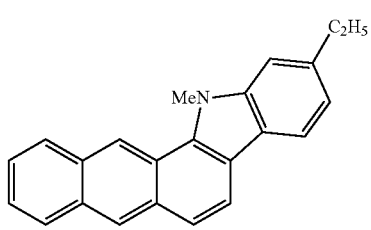
(655) 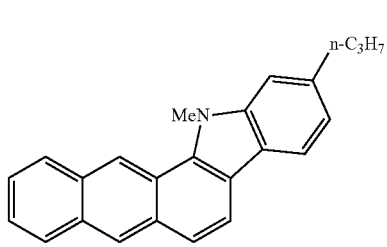
(656) 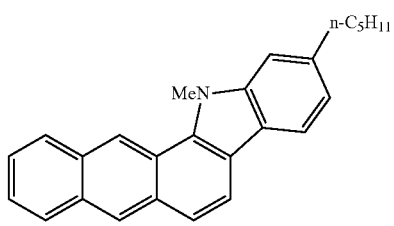
(657) 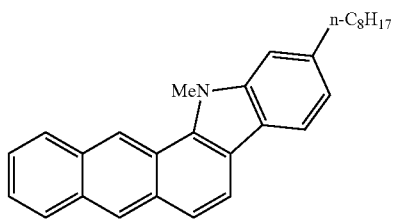
(658) 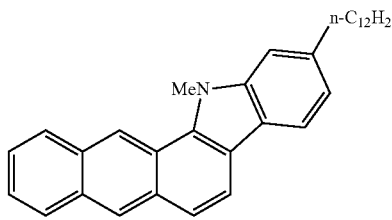
(659) 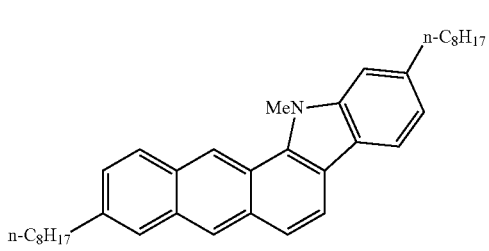

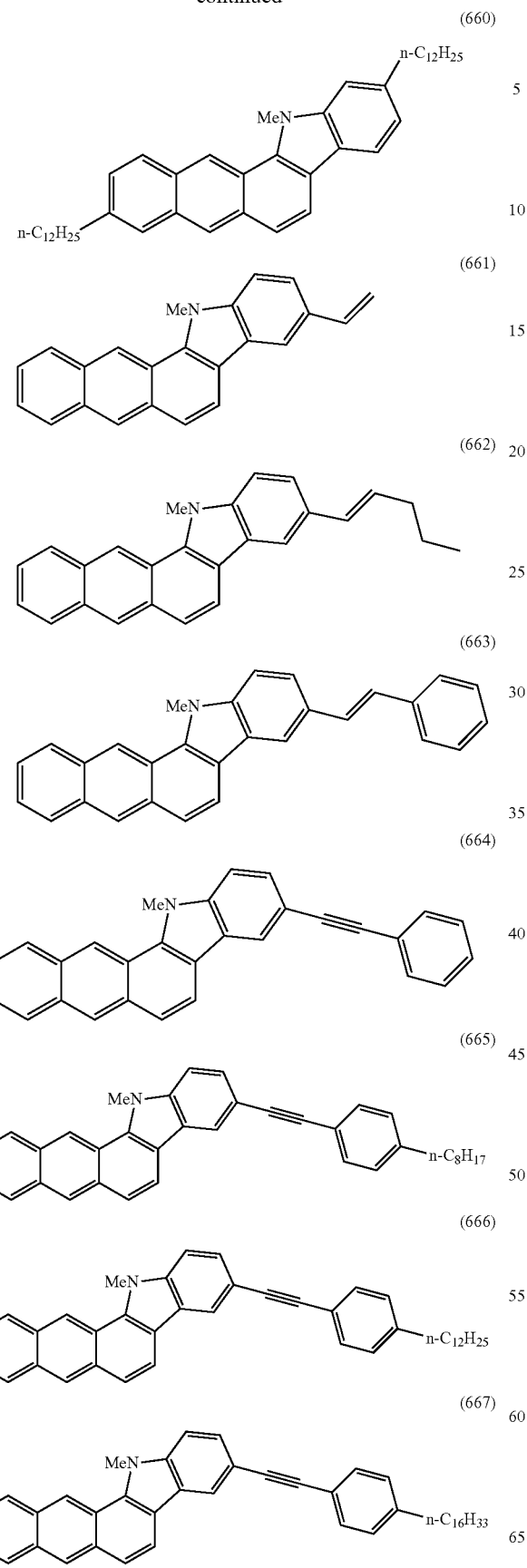
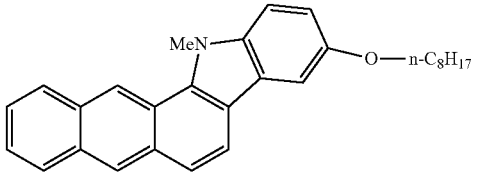
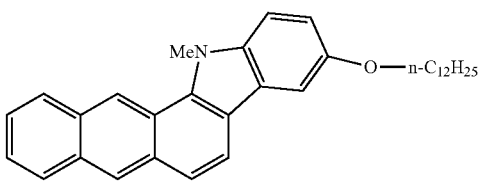
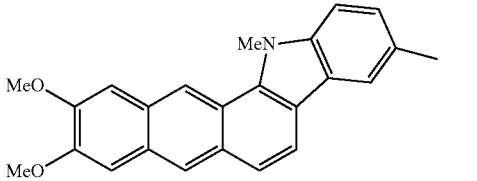
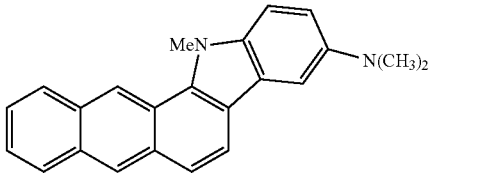
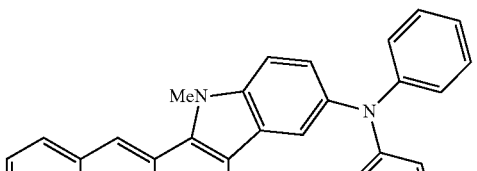
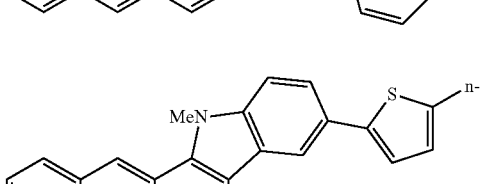
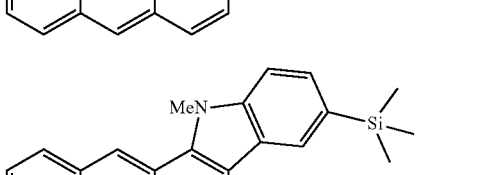
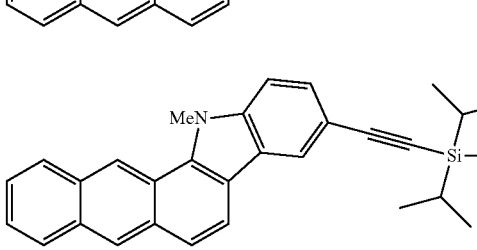

(676) 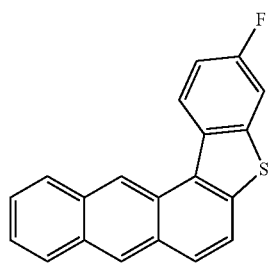
(677) 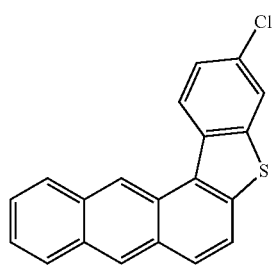
(678) 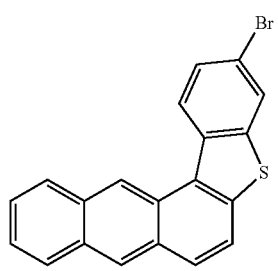
(679) 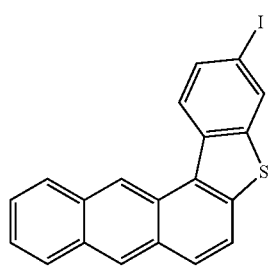
(680) 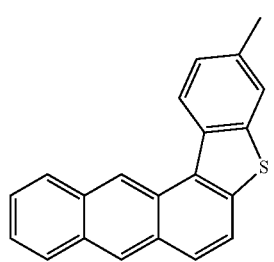
(681) 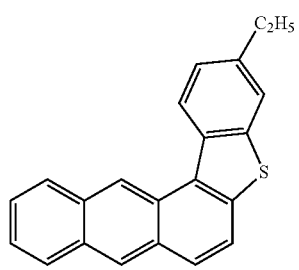
(682) 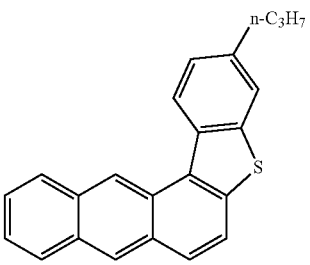
(683) 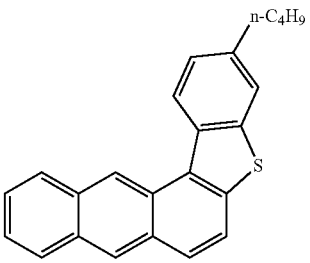
(684) 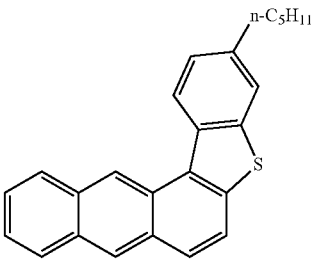
(685) 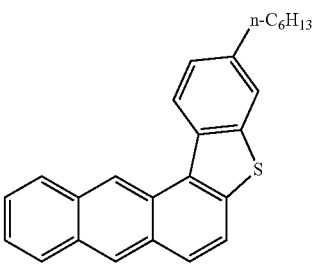
(686) 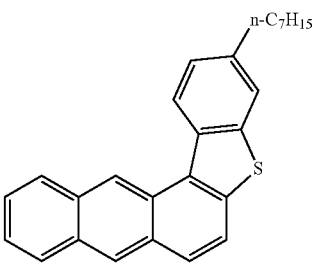
(687) 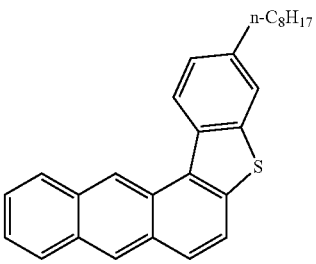

(688) 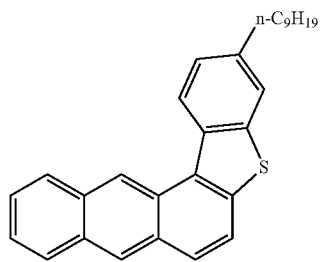
(689) 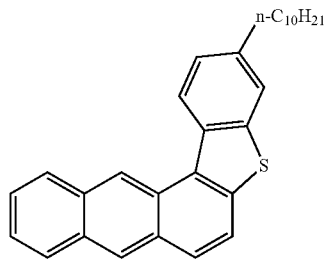
(690) 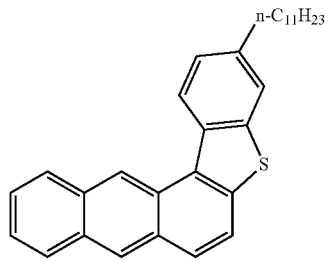
(691) 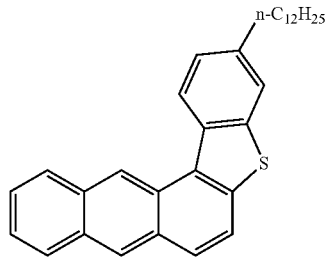
(692) 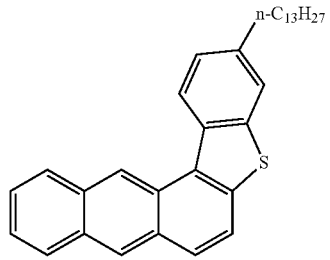
(693) 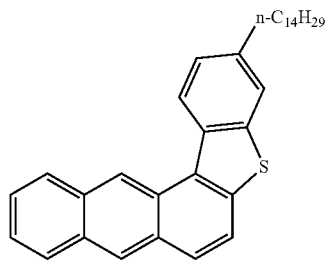
(694) 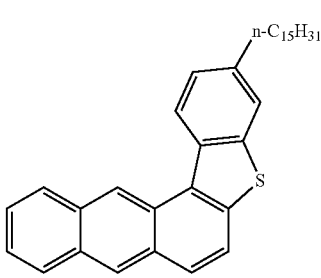
(695) 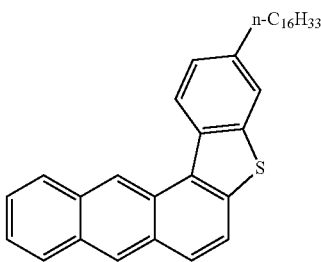
(696) 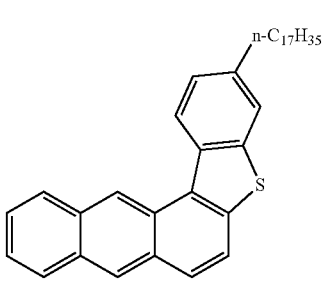
(697) 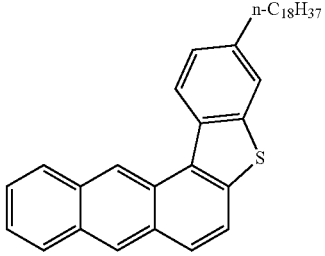
(698) 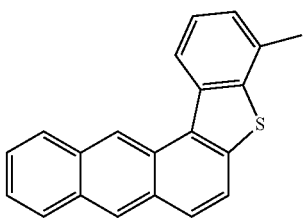
(699) 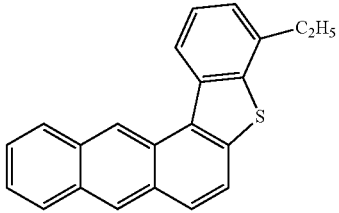

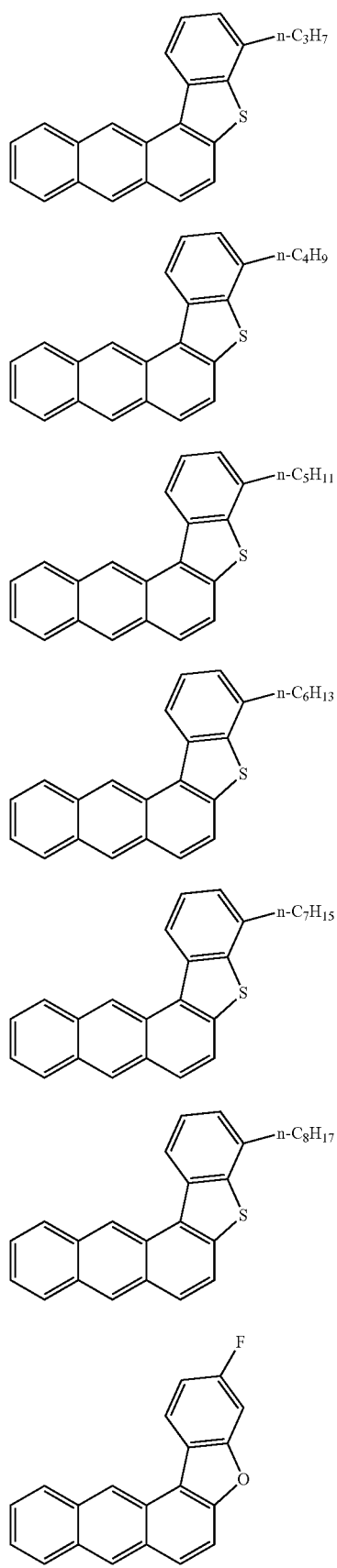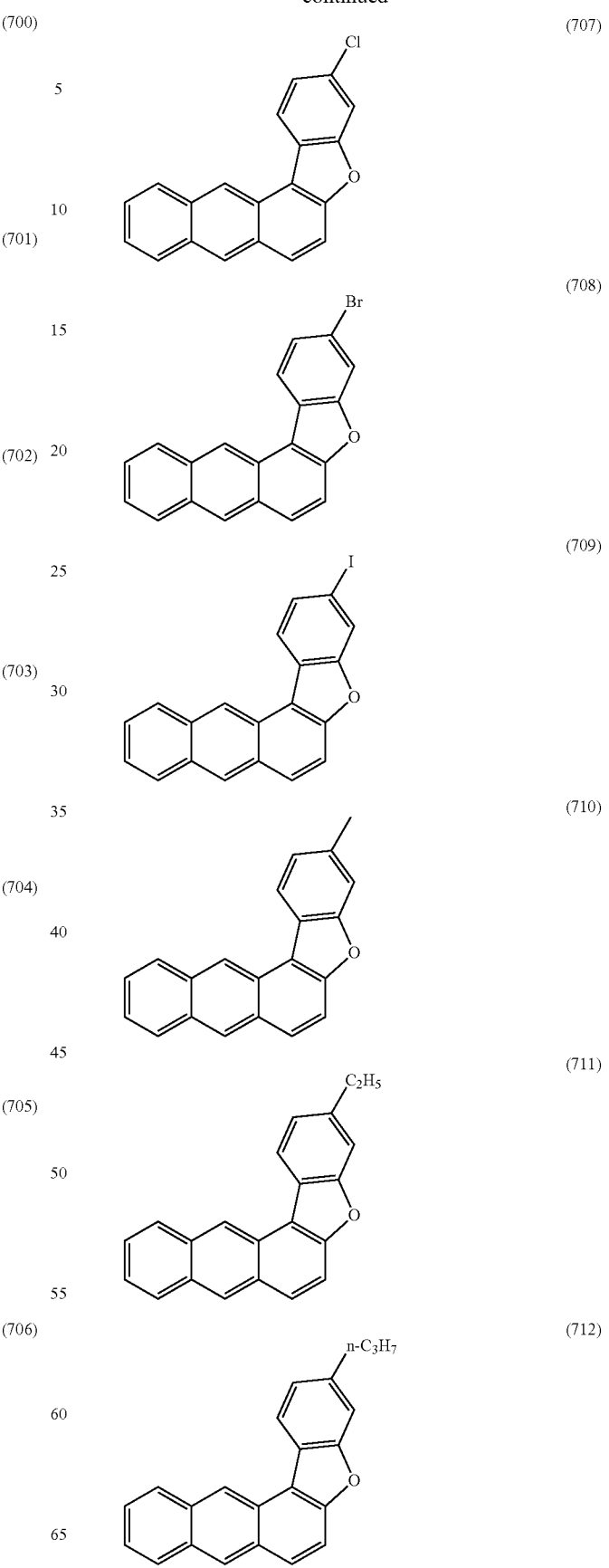

-continued
(713)
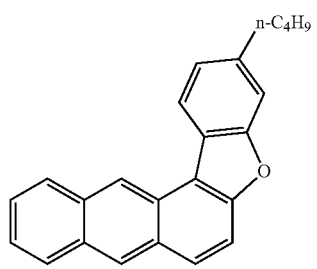
(714)
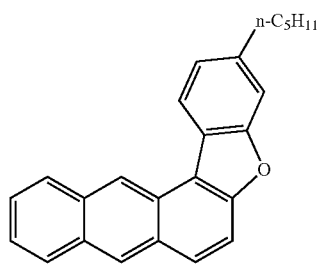
(715)
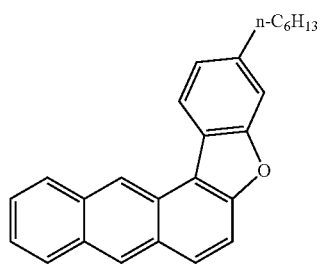
(716)
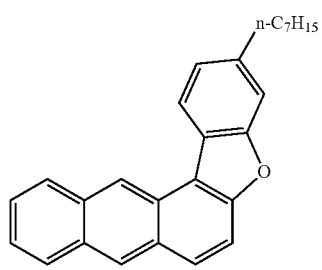
(717)
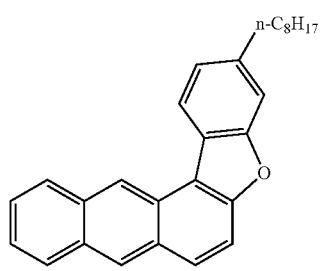
(718)
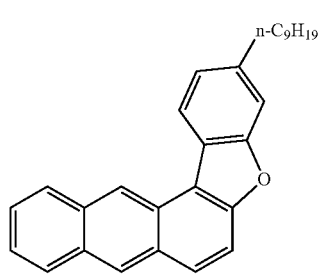
-continued
(719)
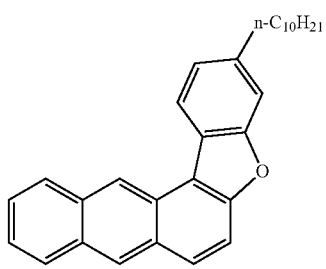
(720)
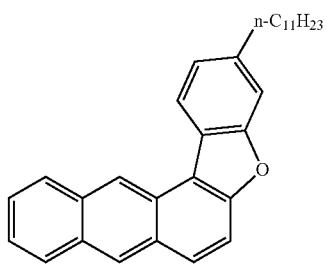
(721)
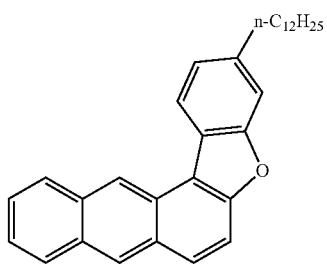
(722)
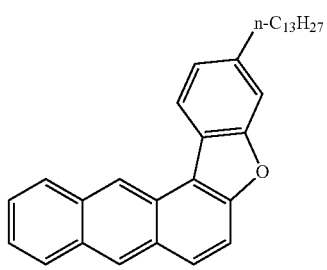
(723)
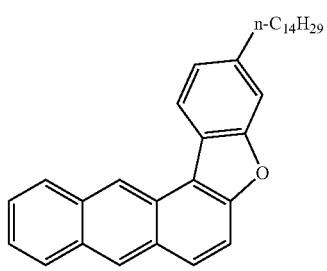
(724)
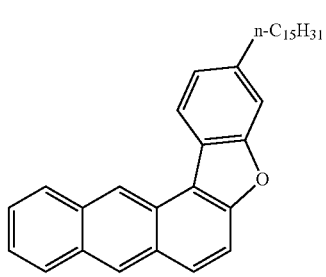

(725)
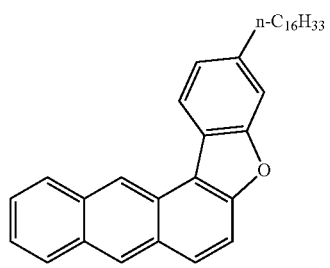
(726)
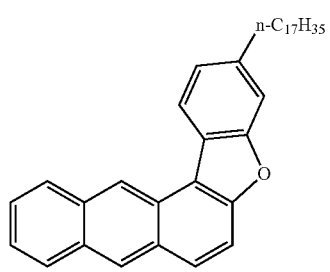
(727)
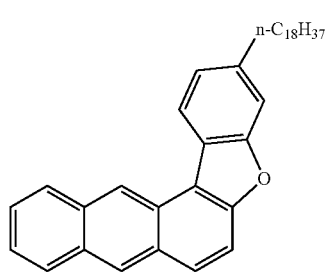
(728)
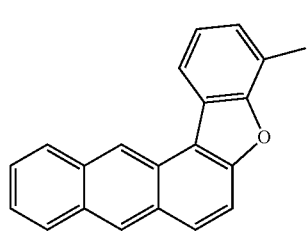
(729)
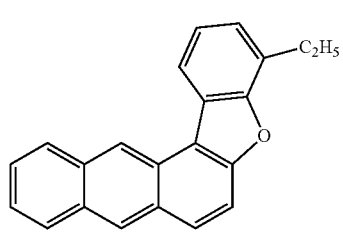
(730)
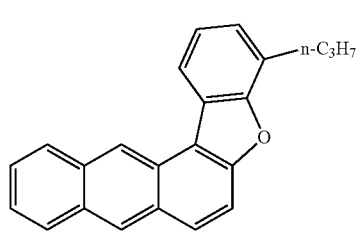
(731)
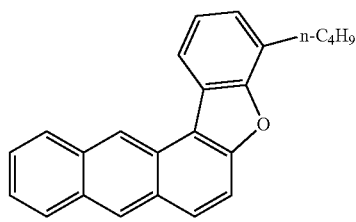
(732)
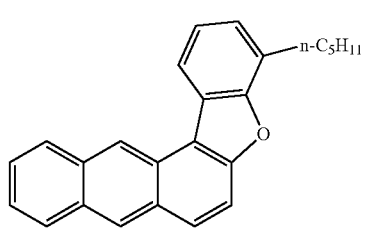
(733)
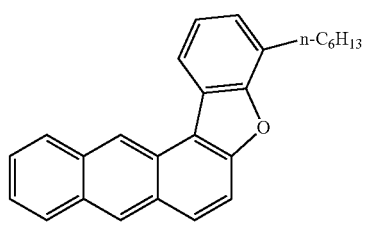
(734)
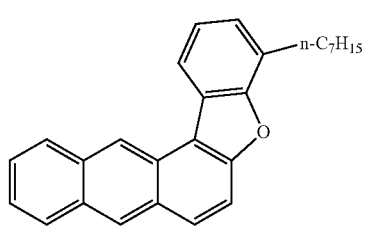
(735)
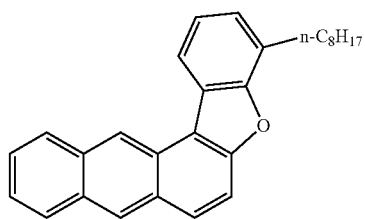
(736)
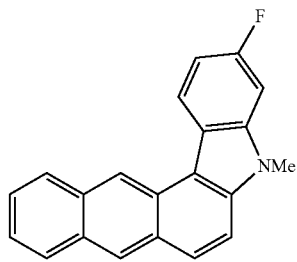

(737)
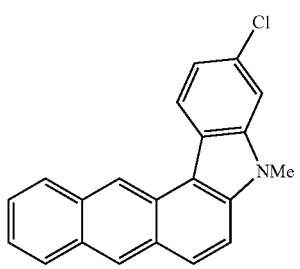
(738)
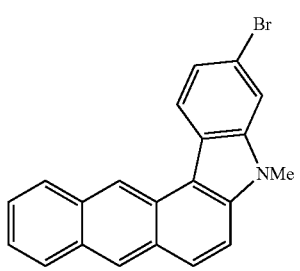
(739)
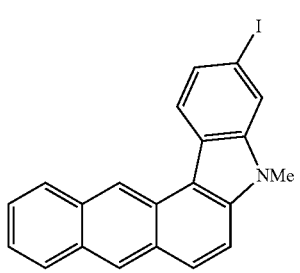
(740)
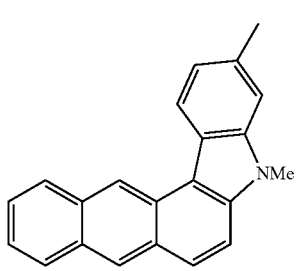
(741)
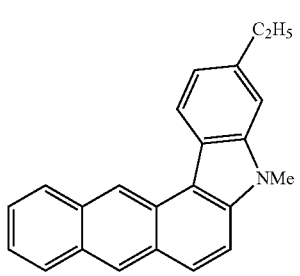
(742)
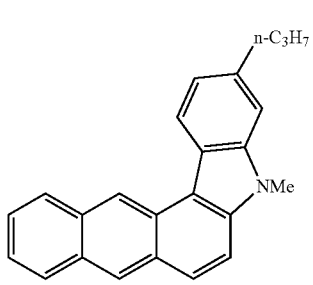
(743)
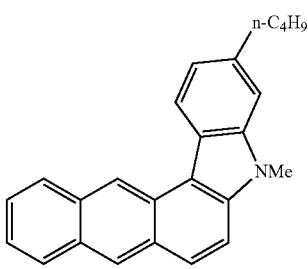
(744)
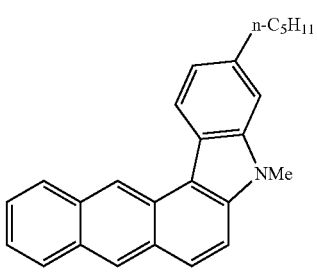
(745)
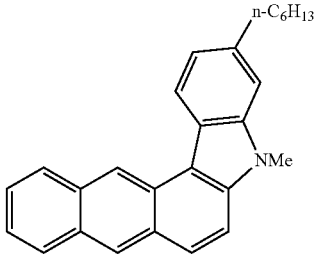
(746)
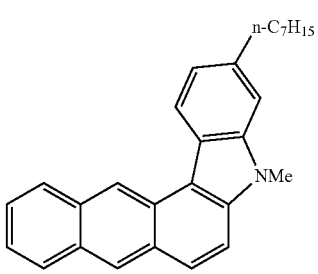
(747)
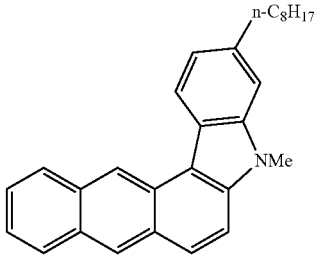
(748)
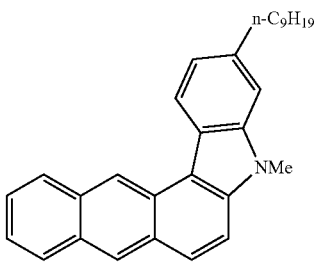

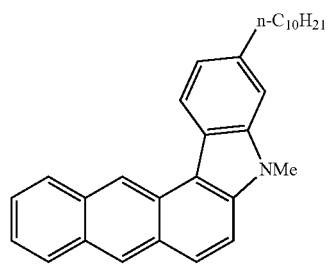
(749)
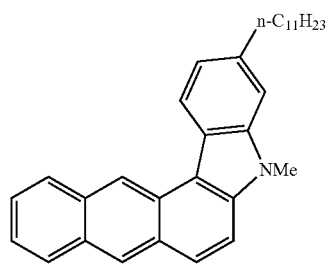
(750)
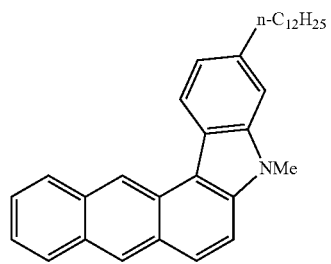
(751)
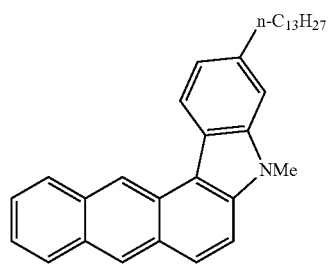
(752)
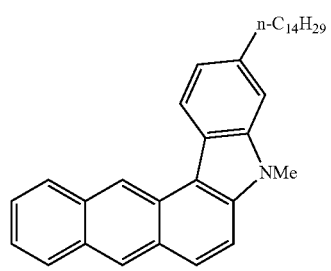
(753)
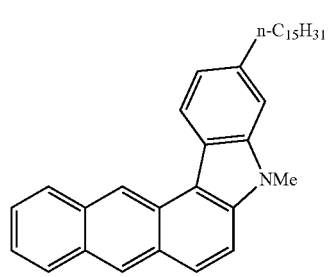
(754)
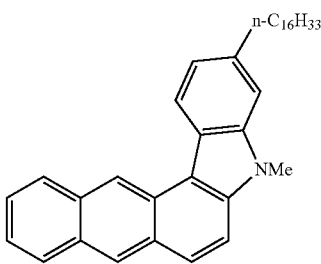
(755)
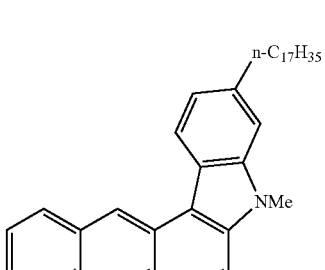
(756)
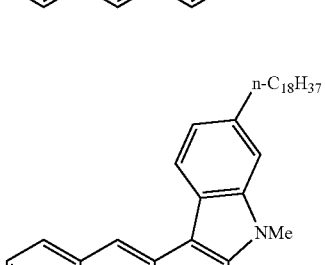
(748)
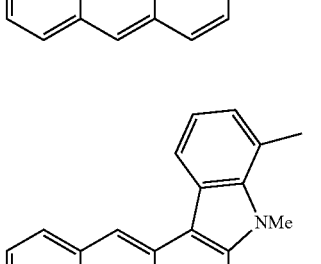
(773)
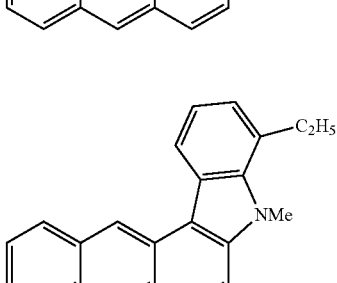
(774)
(775)

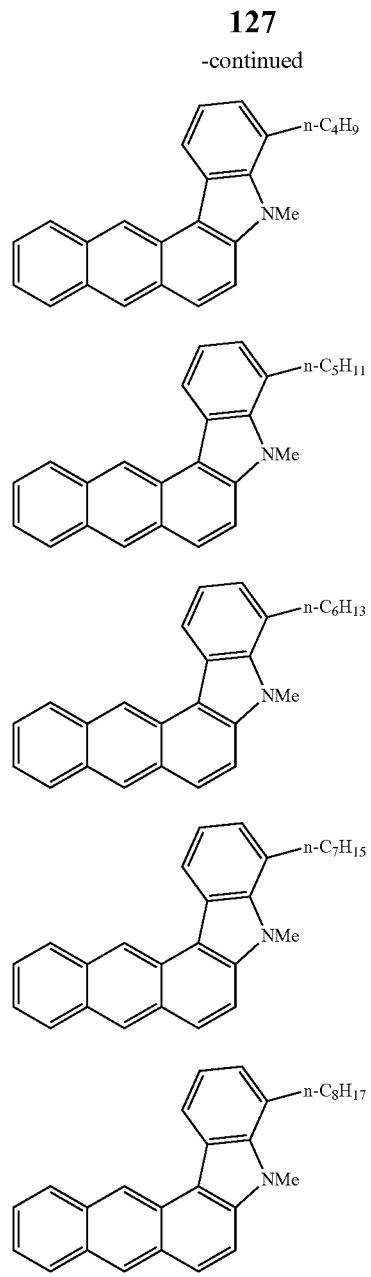

The second compound of the invention can be produced by the following synthesis route (Synthesis method I, Synthesis method II and Synthesis method III).

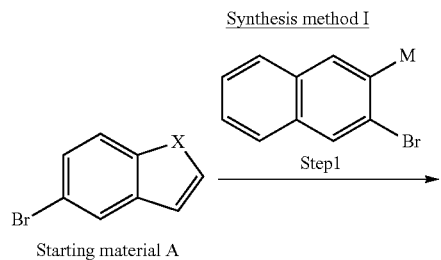

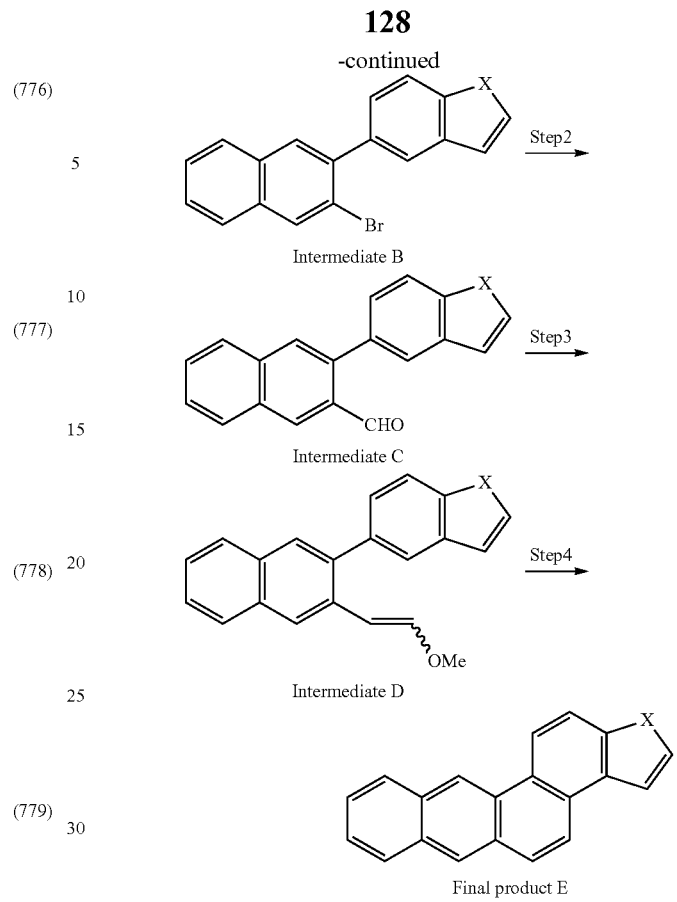

(X is the same as $X^1$ and $X^2$ in the second compound of the invention)

In the step 1, a halogenated benzoheterocyclic compound as the starting material A and 3-bromonaphthalene in which the $2^{nd}$ position thereof is metalized or boronized are connected to synthesize the intermediate B. As the reaction used in the step 1, Suzuki-Miyaura coupling, Stille coupling, Negishi coupling, Hiyama coupling or the like can be given. Of these, Suzuki-Miyaura coupling is preferable since a preferable yield can be attained.

As for the starting material A, a commercially available product can be used, or synthesis can be conducted with reference to the following reports.

J. Med. Chem. 2006 4374-4383.

ELI LILLY AND COMPANY; WO2006/107784; (2006); (A1)

In the step 2, the intermediate B is formylated to produce the intermediate C. As the reaction used in the step 2, a Stille carbonylation reaction, a formylation reaction using BuLi/DMF or Mg/DMF or the like can be given. Of these, a formylation reaction using BuLi/DMF is preferable due to easiness in handling.

In the step 3, a formyl group is converted to methyl enol ether by using a Wittig reagent to produce the intermediate D. As the reagent used in the step 3, (methoxymethyl)triphenylphosphonium chloride can be given.

In the step 4, a cyclization reaction by using an acid is conducted to produce a final product E. In the step 4, various Lews acids and protonic acids can be used. It is preferable to use a methanesulfonic acid since it attains a good yield.

Synthesis method II

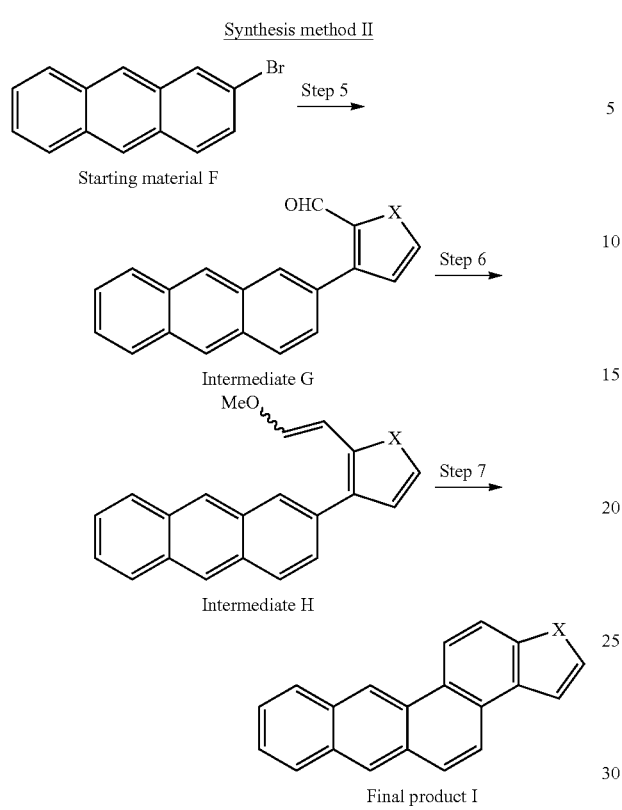

In the step 5, a halogenated aryl as the starting material F is connected to a metalized compound or a boron compound containing a heterocycle to synthesize the intermediate G. As the reaction used in the step 5, Suzuki-Miyaura coupling, Stifle coupling, Negishi coupling, Hiyama coupling or the like can be given. Of these, Suzuki-Miyaura coupling is preferable since it attains a good yield.

In the step 6, a formyl group is converted to methylenolether by using a Wittig reagent to produce the intermediate H. As the reagent used in the step 6, (methoxymethyl)triphenylphosphonium chloride can be given.

In the step 7, a cyclization reaction by using an acid is conducted to produce the final product I, where various Lews acids and protic acids can be used. It is preferable to use a methanesulfonic acid since it attains a good yield.

Synthesis method III

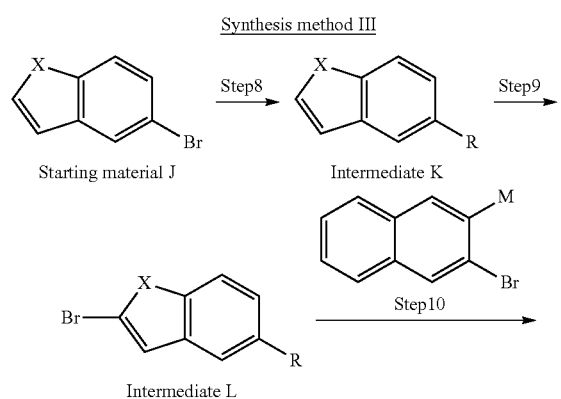

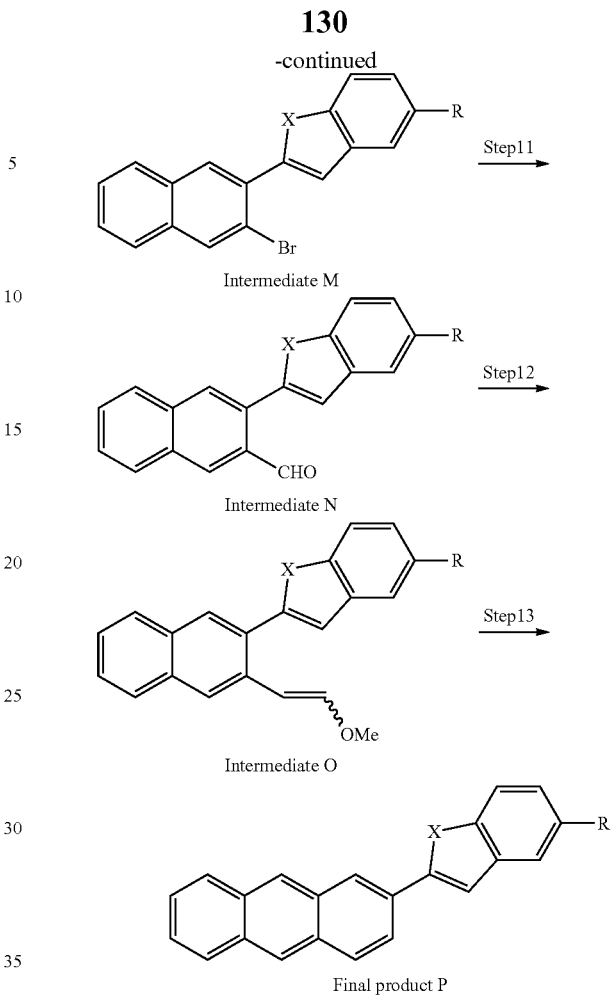

In the step 8, a substituent is introduced into a halogenated benzoheterocyclic compound as the starting material J to synthesize the intermediate K. As the reaction used in the step 8, Suzuki-Miyaura coupling, Stille coupling, Hiyama coupling, Negishi coupling or the like can be given. Of these, Suzuki-Miyaura coupling is preferable since it attains a good yield.

In the step 9, an intermediate K is brominated to synthesize the intermediate L. As the reagent used in the step 9, N-bromosuccinimide, BuLi/$Br_2$ and the like can be given. Of these, it is preferable to use N-bromosuccinimide due to easiness in handling.

In the step 10, 3-bromonaphthalene of which the $2^{nd}$ position thereof is metalized or boronized is bonded to the intermediate M. As the reaction used in the step 10, Suzuki-Miyaura coupling, Stille coupling, Negishi coupling, Hiyamai coupling or the like can be given. Of these, Suzuki-Miyaura coupling is preferable since it attains a good yield.

In the step 11, the intermediate M is formylated to synthesize the intermediate N. As the reaction used in the step 11, a Stille carbonylation reaction, a formylation reaction using BuLi/DMF or Mg/DMF or the like can be given. Of these, a formylation reaction using BuLi/DMF is preferable due to easiness in handling.

In the step 12, a formyl group is converted to methyl enol ether by using a Wittig reagent to produce the intermediate O. As the reagent used in the step 12, (methoxymethyl)triphenylphosphonium chloride can be given.

In the step 13, a cyclization reaction by using an acid is conducted to produce a final product P. In the step 13, various Lews acids and protic acids can be used. It is preferable to use a methanesulfonic acid since it attains a good yield.

Herein below, a third aspect of the invention will be explained.

The compound according to the third aspect of the invention is represented by the following formula (C-1) or (C-2).

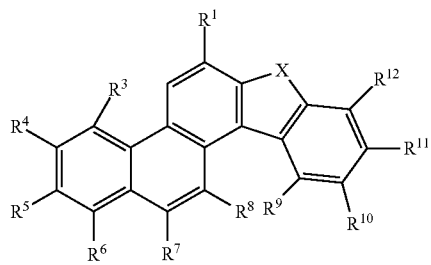

(C-1)

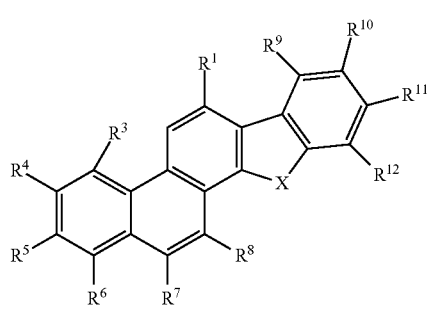

(C-2)

wherein $R^1$ to $R^8$ are independently a hydrogen atom, a halogen atom, an alkyl group having 2 to 30 carbon atoms, an alkenyl group having 2 to 30 carbon atoms, an alkynyl group having 2 to 30 carbon atoms, a haloalkyl group having 1 to 30 carbon atoms, an alkoxy group having 2 to 30 carbon atoms, a haloalkoxy group having 1 to 30 carbon atoms, an alkylthio group having 2 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms or an alkylsilylethynyl group having 5 to 60 carbon atoms, which groups may further have one or more substituents;

the two alkyl groups of the above-mentioned dialkylamino group having 2 to 60 carbon atoms may combine with each other to form a ring structure containing a nitrogen atom;

X is —S—, —O—, or —N($R^{13}$)—;

$R^9$ to $R^{13}$ are independently a hydrogen atom, a halogen atom, an alkyl group having 2 to 30 carbon atoms, an alkenyl group having 2 to 30 carbon atoms, an alkynyl group having 2 to 30 carbon atoms, a haloalkyl group having 1 to 30 carbon atoms, an alkoxy group having 2 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the above-mentioned dialkylamino group having 2 to 60 carbon atoms may combine with each other to form a ring structure containing a nitrogen atom; $R^{13}$ may be a methyl group;

provided that at least one of $R^1$ to $R^{12}$ is a group other than hydrogen.

As for the compound represented by the formulas (C-1) and (C-2) (hereinafter simply referred to as a third compound of the invention), when used as the material for an organic thin film transistor, intermolecular interaction is enhanced by the extension of the π-electron conjugated system in the entire compound or between molecules and the heavy atom effect of the hetero atom, a higher mobility can be obtained.

Further, as for the third compound of the invention, by causing the structure thereof to be asymmetric and/or by introducing a substituent, solubility in an organic solvent can be, improved.

In addition, unlike linear polyacene in which benzene rings, the representative example of which is pentacene, are arranged in a straight line, in the third compound of the invention, part of benzene rings are arranged in a bent manner. Accordingly, it has a structure equivalent to phenacene, and hence has excellent stability to oxidization.

The third compound of the invention is preferably a compound represented by the following formula (C-3) or (C-4):

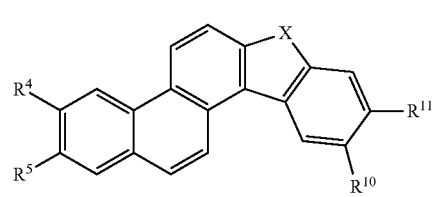

(C-3)

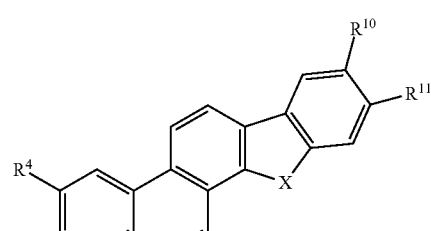

(C-4)

wherein X, $R^4$, $R^5$, $R^{10}$ and $R^{11}$ are the same as those in the formulas (C-1) and (C-2). At least one of $R^4$, $R^5$, $R^{19}$ and $R^{11}$ is a group other than hydrogen.

The compound represented by the formula (C-3) or (C-4) is a compound represented by the formula (C-1) or (C-2) in which $R^1$ to $R^3$, $R^6$ to $R^9$ and $R^{12}$ are hydrogen atoms. This compound has a strong intermolecular action, and hence a high mobility can be expected when used in an organic thin film transistor.

Further, it is preferred that one of $R^4$ and $R^5$ and one of $R^{10}$ and $R^{11}$ be hydrogen atoms, since the third compound of the invention can be synthesized easily.

Each substituent of the third compound of the invention will be explained below.

X is preferably —S—. The reason therefor is that hetero atoms (O, N and S) have an interaction called the heavy atom effect, and of these hetero atoms, S has a strong interaction.

In addition, when X is —N($R^{13}$)—, in respect of easiness in synthesis of the third compound of the invention and generation of a small amount of by-products, $R^{13}$ is preferably a substituent other than a hydrogen atom. $R^{13}$ is more preferably an alkyl group having 1 to 30 carbon atoms, further preferably an alkyl group having 1 to 6 carbon atoms, with a methyl group being particularly preferable. If $R^{13}$ is a substituent other than a hydrogen atom, a high mobility can be expected. Unlike the case of $R^1$ to $R^{12}$, $R^{13}$ may be a methyl group.

As the halogen atom represented by $R^1$ to $R^{13}$, a fluorine atom, a chlorine atom, a bromine atom and an iodine atom can be given.

If the halogen atom is directly bonded to the aromatic ring or the heterocyclic ring constituting the compounds represented by the formulas (C-1) to (C-4), the bonding position thereof is preferably one of $R^4$ and $R^5$ and one of $R^{10}$ and $R^{11}$.

As the alkyl group having 2 to 30 carbon atoms represented by $R^1$ to $R^{13}$, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group and an n-octadecyl group can be given.

Of these alkyl groups, in respect of solubility, a straight-chain alkyl group is preferable. A straight-chain alkyl group having 3 to 18 carbon atoms is preferable, with a straight-chain alkyl group having 5 to 12 carbon atoms being particularly preferable. In the case of a straight-chain alkyl group having 19 or more carbon atoms, heat resistance may be insufficient when used in an organic thin film transistor.

In the case of an alkyl group having 1 carbon atom (methyl group), solubility of the compound is insufficient, making the compound difficult to be used in a coating process. $R^{13}$ may be a methyl group.

If adjacent groups such as $R^4$ and $R^5$ and $R^{10}$ and $R^{11}$ are both alkyl groups, it is preferred that the adjacent groups be respectively a short-chain alkyl group such as an alkyl group having 1 to 5 carbon atoms since the synthesis of the third compound of the invention can be synthesized easily.

As the alkenyl group having 2 to 30 carbon atoms represented by $R^1$ to $R^{13}$, a vinyl group, a propenyl group, a butenyl group, a pentenyl group, a pentadienyl group, a hexenyl group, a hexadienyl group, a heptenyl group, an octenyl group, an octadienyl group, a 2-ethylhexenyl group and a decenyl group can be given. An alkenyl group having 2 to 10 carbon atoms is preferable. As exemplified, the alkenyl group may be a group having two or more double bonds. However, an alkenyl group having one double bond is preferable in respect of easiness in synthesis of an intended product.

If the alkenyl group is directly bonded to the aromatic ring or the heterocyclic ring constituting the compounds represented by the formulas (C-1) to (C-4), the bonding position thereof is preferably one of $R^4$ and $R^5$ and one of $R^{10}$ and $R^{11}$.

As the alkynyl group having 2 to 30 carbon atoms represented by $R^1$ to $R^{13}$, an ethynyl group, a propinyl group, a 2-phenylethynyl group, an n-butynyl group, an n-pentynyl group, an n-hexynyl group, an n-heptyny group, an n-octynyl group, an n-undecynyl group and an n-dedecynyl group can be given. An alkynyl group having 2 to 12 carbon atoms is preferable.

It is preferred that the triple bond of the alkynyl group be bonded to the aromatic ring or the heterocyclic ring constituting the third compound of the invention represented by the formulas (C-1) to (C-4) not though an alkylene group. The bonding position of the alkynyl group is preferably one of $R^4$ and $R^5$ and one of $R^{10}$ and $R^{11}$.

As the substituent to be added to the alkynyl group, a phenyl group and/or a phenyl group which is substituted by an alkyl group can be given. As the alkyl group in this case, the above-mentioned alkyl group having 2 to 30 carbon atoms can be given. However, the alkyl group may be a methyl group. The preferable range is also the same.

Specific examples of the haloalkyl group having 1 to 30 carbon atoms represented by $R^1$ to $R^{13}$, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a fluoromethyl group, a 1-fluoroethyl group, a 2-fluoroethyl group, a 2-fluoroisobutyl group, a 1,2-difluoroethyl group, a difluoromethyl group, a trifluoromethyl group, a pentafluoroethyl group, a perfluoroisopropyl group, a perfluorobutyl group and a perfluorocyclohexyl group can be given. A 1-haloalkyl group having 1 to 10 carbon atoms is preferable.

The alkoxy group having 2 to 30 carbon atoms represented by $R^1$ to $R^{13}$ is a group represented by —$OY^1$, and the examples of $Y^1$ include the same groups as exemplified in the above-mentioned alkyl group. The haloalkoxy group having 1 to 30 carbon atoms represented by $R^1$ to $R^{13}$ is a group represented by —$OY^2$, and the examples of $Y^2$ include the same groups as those exemplified in the above-mentioned haloalkyl group.

The alkylthio group having 2 to 30 carbon atoms represented by $R^1$ to $R^5$ is a group represented by —$SY^1$, and the examples of $Y^1$ include the same groups as exemplified in the above-mentioned alkyl group.

The alkylthio group having 1 to 30 carbon atoms represented by $R^9$ to $R^{13}$ is a group represented by —$SY^1$, and the examples of $Y^1$ include the same groups as exemplified in the above-mentioned alkyl group and a methyl group.

The haloalkylthio group having 1 to 30 carbon atoms represented by $R^1$ to $R^{13}$ is a group represented by —$SY^2$, and the examples of $Y^2$ include the same groups as those exemplified in the above-mentioned haloalkyl group.

The alkylamino group having 1 to 30 carbon atoms represented by $R^1$ to $R^{13}$ is a group represented by —$NHY^1$, and is preferably an alkylamino group having 1 to 10 carbon atoms. The dialkylamino group having 2 to 60 carbon atoms represented by $R^1$ to $R^{13}$ is a group represented by —$NY^1Y^3$, and is preferably a dialkylamino group in which the alkyl groups are respectively an alkyl group having 1 to 10 carbon atoms. The examples of $Y^1$ and $Y^3$ include the same groups as exemplified in the above-mentioned alkyl group and a methyl group.

The alkyl groups of the dialkylamino group having 2 to 60 carbon atoms may combine with each other to form a ring structure containing a nitrogen atom. Examples of the ring structure include pyrrolidine, piperidine, or the like.

In the third compound of the invention, the bonding position of the alkylamino group or the dialkylamino group is preferably one of $R^4$ and $R^5$ and one of $R^{19}$ and $R^{11}$.

As the arylamino group having 6 to 60 carbon atoms represented by $R^1$ to $R^{13}$, it suffices that at least one of the substituent(s) bonding to the amino group be an aryl group. Specific examples include a phenylamino group, a methylphenylamino group, a diphenylamino group, a di-p-tolylamino group, a di-m-tolylamino group, a phenyl-m-tolylamino group, a phenyl-1-naphthylamino group, a phenyl-2-naphthylamino group, a phenyl(sec-butylphenyl)amino group, a phenyl-t-butylamino group, a bis(4-methoxyphenyl) amino group, and a phenyl-4-carbazolylphenylamino group.

In the compound of the invention, the bonding position of the arylamino group is preferably one of $R^4$ and $R^5$ and one of $R^{19}$ and $R^{11}$.

The alkylsulfonyl group having 1 to 30 carbon atoms represented by $R^1$ to $R^{13}$ is a group represented by $—SO_2Y^1$, and the examples of $Y^1$ include the same groups as those mentioned in the alkyl group and a methyl group. The haloalkylsulfonyl group having 1 to 30 carbon atoms represented by $R^1$ to $R^{13}$ is a group represented by $—SO_2Y^2$, and the examples of $Y^2$ include the same groups as those mentioned in the haloalkyl group.

As the aromatic hydrocarbon group having 6 to 60 carbon atoms represented by $R^1$ to $R^{13}$, a phenyl group, a naphthyl group, an anthryl group, a phenanthryl group, a fluorenyl group, a perylenyl group, a tetracenyl group and a pentacenyl group or the like can be given.

In the third compound of the invention, the bonding position of the aromatic hydrocarbon group is preferably one of $R^4$ and $R^5$ and one of $R^{19}$ and $R^{11}$.

As the aromatic heterocyclic ring having 3 to 60 carbon atoms represented by $R^1$ to $R^{13}$, a thiophenyl group, a dithienophenyl group, a benzofuranyl group, a benzothiophenyl group, a quinolyl group, a carbazolyl group, a dibenzofuranyl group, a dibenzothiophenyl group, a benzothiazonyl group or the like can be given.

In the third compound of the invention, the bonding position of the aromatic heterocyclic group is preferably one of $R^4$ and $R^5$ and one of $R^{10}$ and $R^{11}$.

As the substituent for the aromatic heterocyclic group, a methyl group and the above-mentioned alkyl group can be given.

The alkylsilyl group having 3 to 20 carbon atoms represented by $R^1$ to $R^{13}$ is a group represented by $—SiY^1Y^2Y^3$. As the examples of $Y^1$, $Y^2$ and $Y^3$, the same groups as those mentioned in the above-mentioned alkyl group and a methyl group can be given. As the alkyl group, a short-chain alkyl group such as a methyl group, an ethyl group and an isopropyl group is preferable.

As the alkylsilylethynyl group having 5 to 60 carbon atoms represented by $R^1$ to $R^{13}$, a trimethylsilylethynyl group, a triethylsilylethynyl group, a triisopropylsilylethynyl group, a tert-butyldimethylsilylethynyl group or the like can be given.

$R^9$ to $R^{13}$ may be a cyano group.

It is preferred that $R^1$ to $R^{13}$ be independently a hydrogen atom, a halogen atom, an alkyl group having 2 to 30 carbon atoms, an alkenyl group having 2 to 30 carbon atoms, an alkynyl group having 2 to 30 carbon atoms or an alkoxy group having 2 to 30 carbon atoms. In particular, if the substituent is an alkyl group, improvement in solubility and mobility can be expected.

Specific examples of the third compound of the invention will be given below.

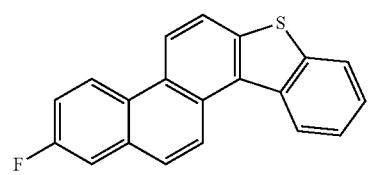

(1)

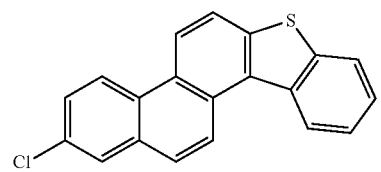

(2)

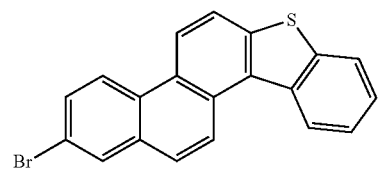

(3)

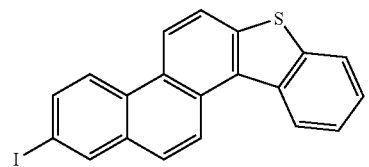

(4)

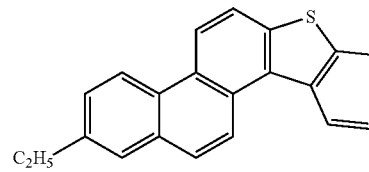

(5)

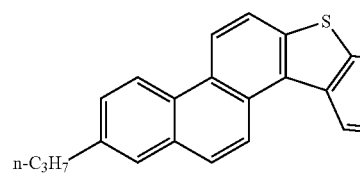

(6)

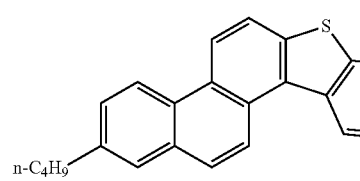

(7)

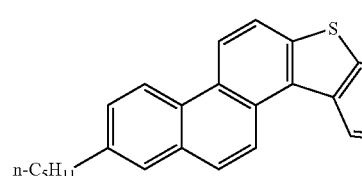

(8)

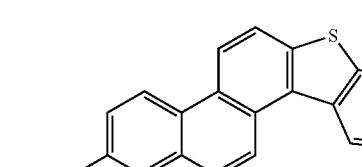

(9)

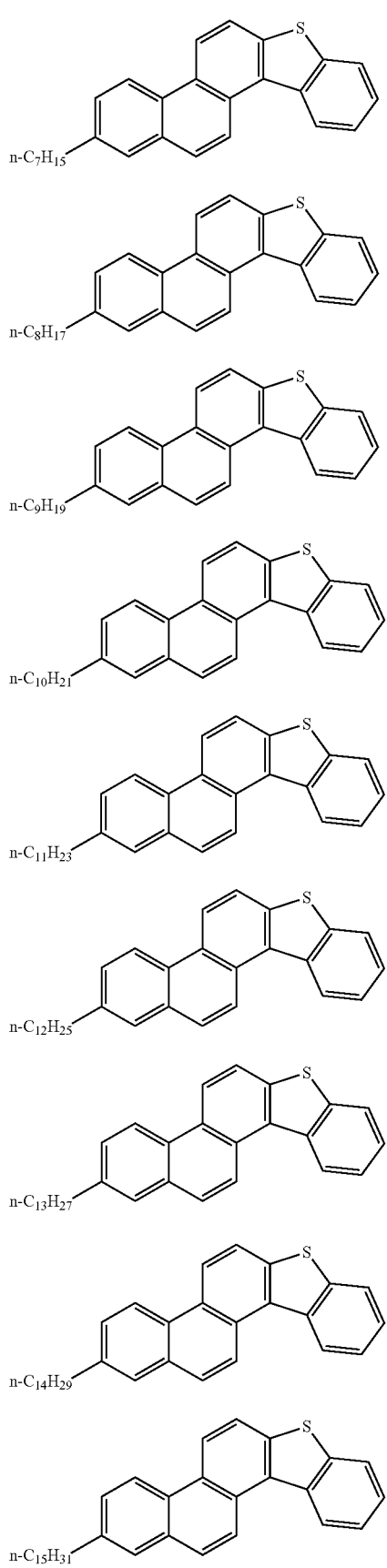
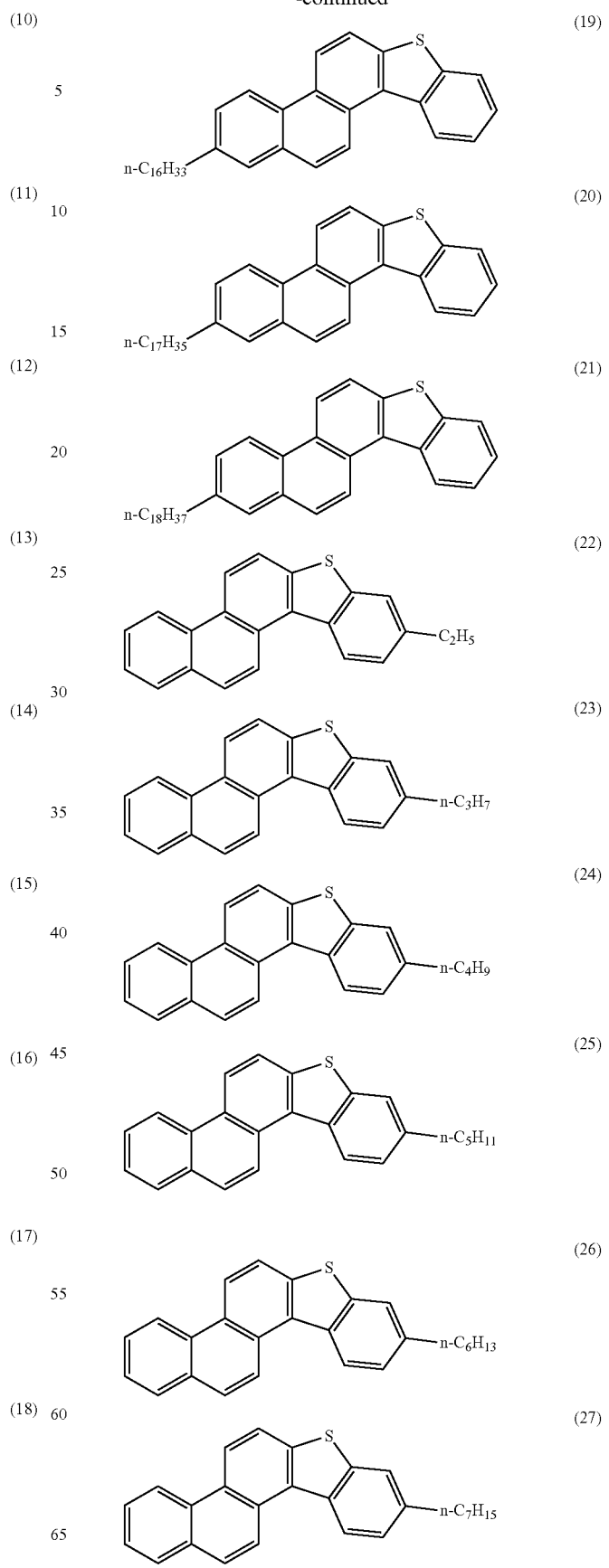

-continued
(28) 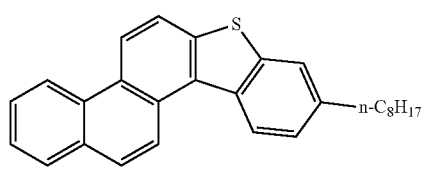
(29) 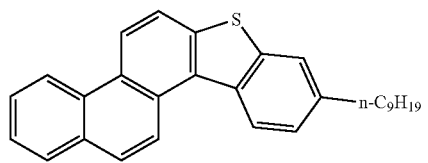
(30) 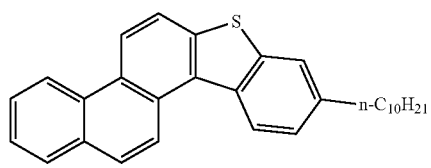
(31) 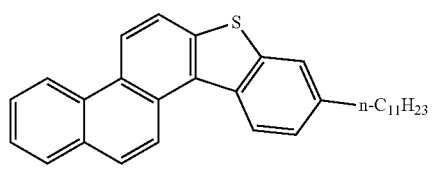
(32) 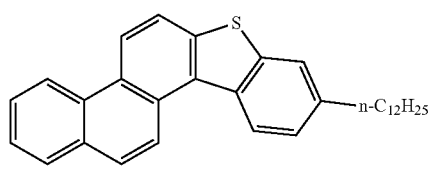
(33) 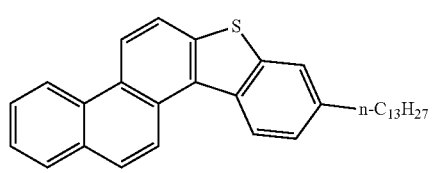
(34) 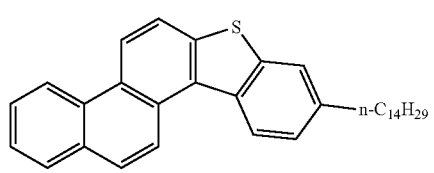
(35) 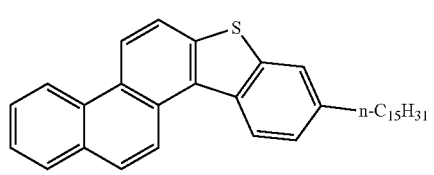
(36) 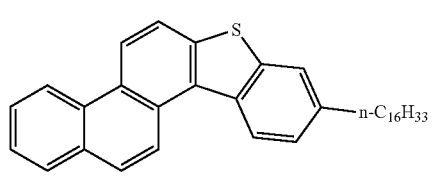
-continued
(37) 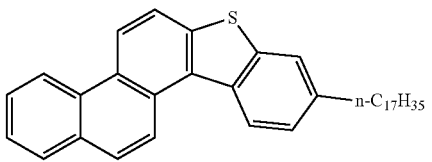
(38) 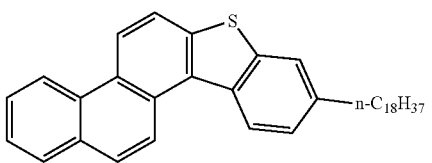
(39) 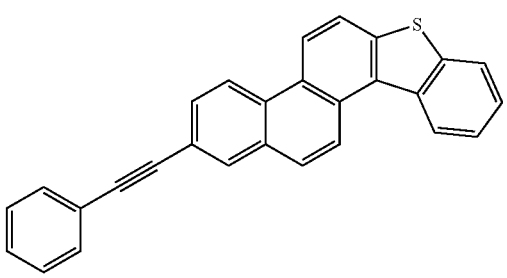
(40) 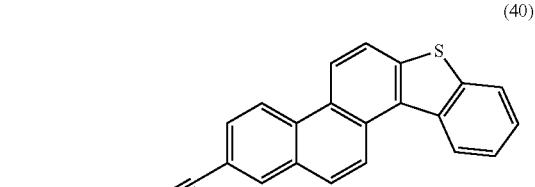
(41) 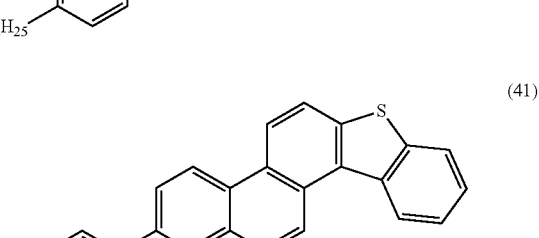
(42) 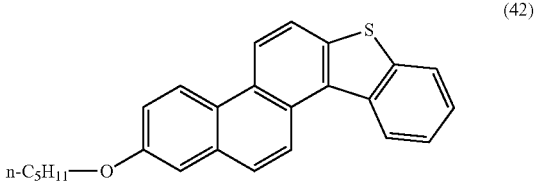
(43) 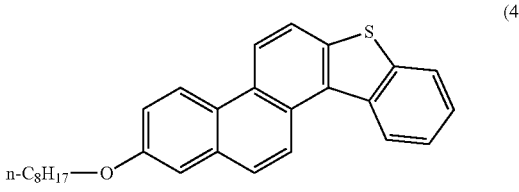

-continued
(44)
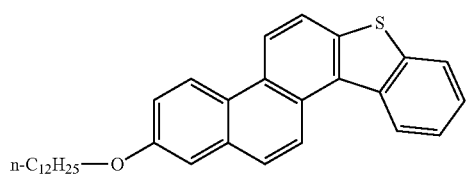
n-C₁₂H₂₅—O
(45)
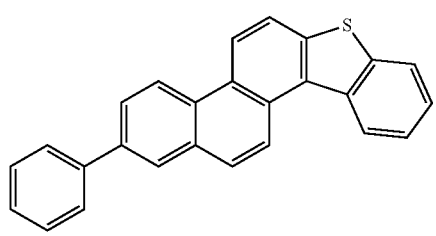
(46)
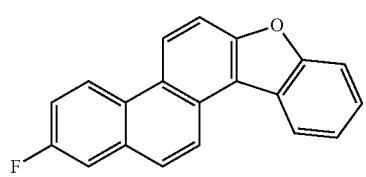
F
(47)
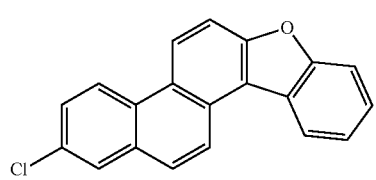
Cl
(48)
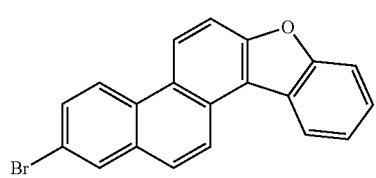
Br
(49)
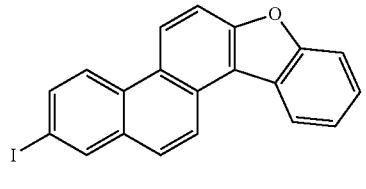
I
(50)
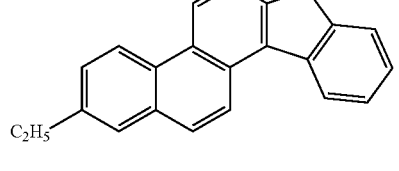
C₂H₅
(51)
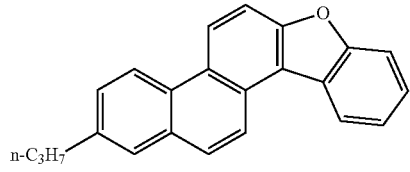
n-C₃H₇
-continued
(52)
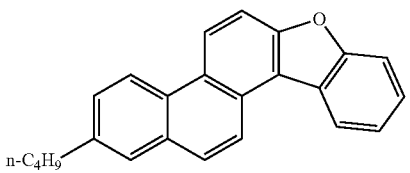
n-C₄H₉
(53)
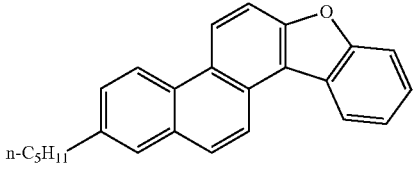
n-C₅H₁₁
(54)
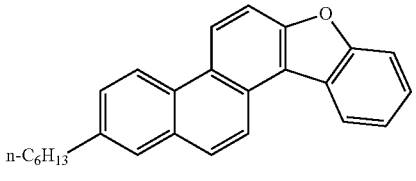
n-C₆H₁₃
(55)
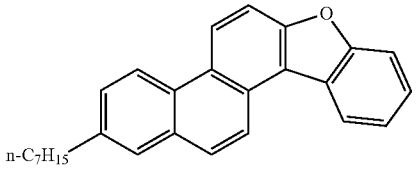
n-C₇H₁₅
(56)
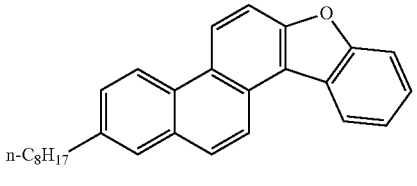
n-C₈H₁₇
(57)
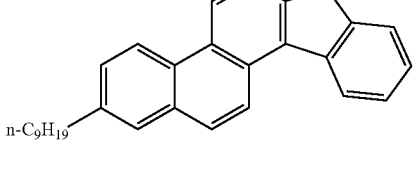
n-C₉H₁₉
(58)
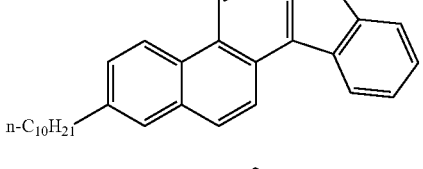
n-C₁₀H₂₁
(59)
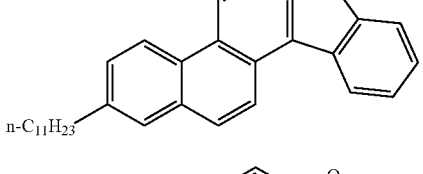
n-C₁₁H₂₃
(60)
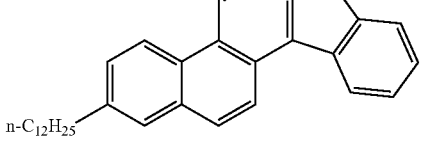
n-C₁₂H₂₅

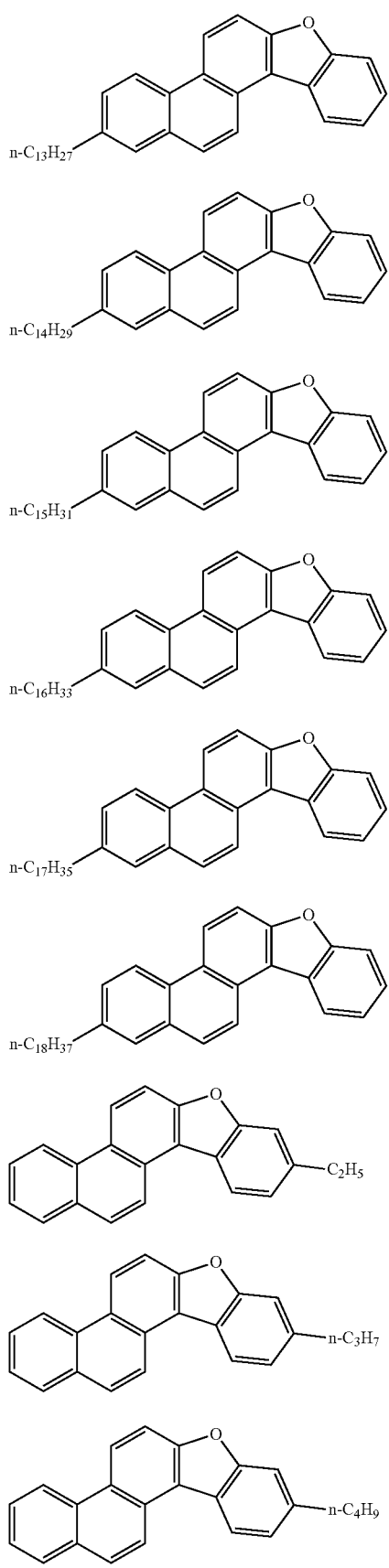
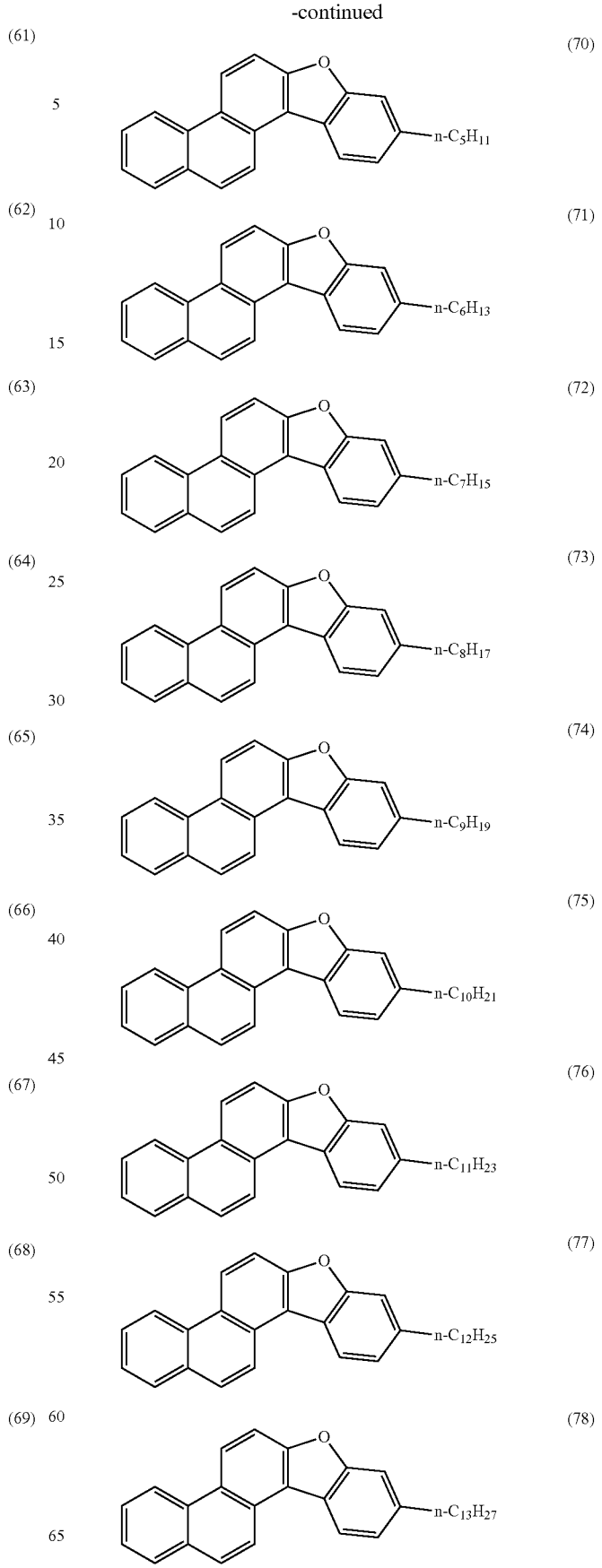

-continued
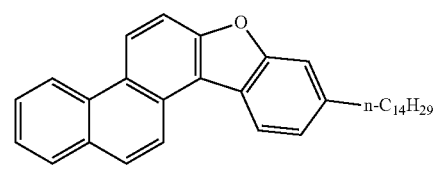 (79)
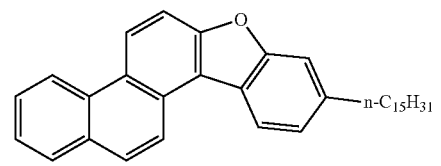 (80)
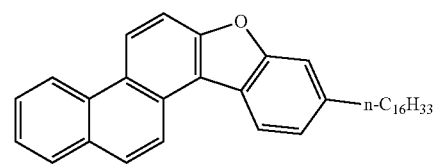 (81)
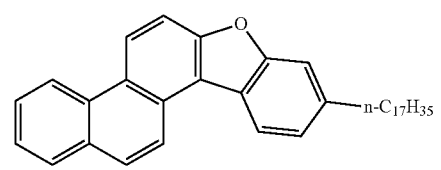 (82)
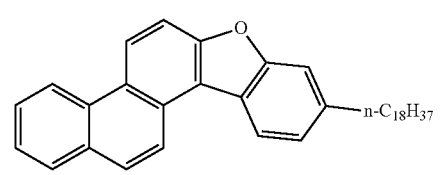 (83)
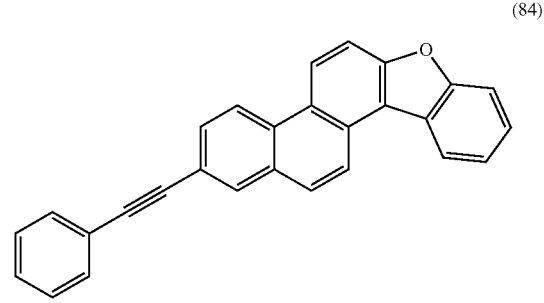 (84)
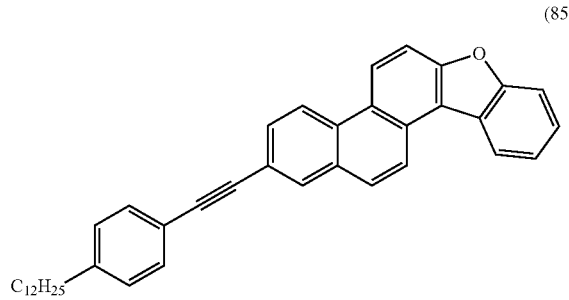 (85)
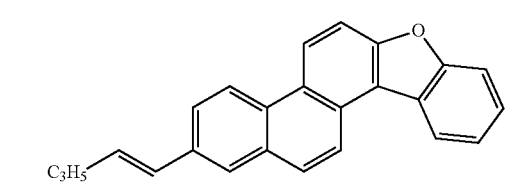 (86)
-continued
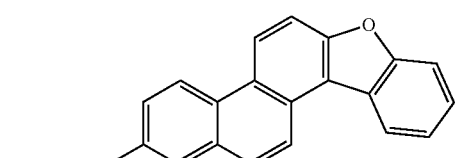 (87)
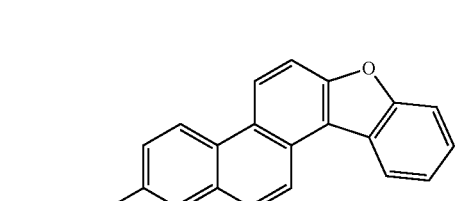 (88)
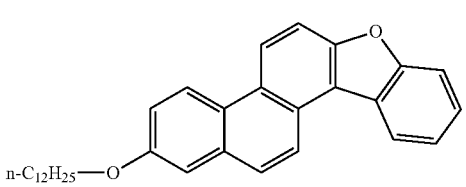 (89)
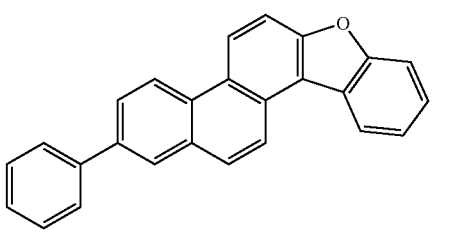 (90)
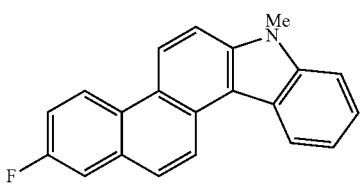 (91)
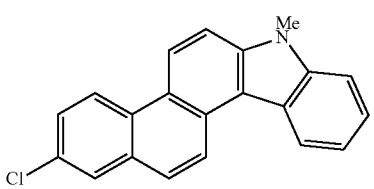 (92)
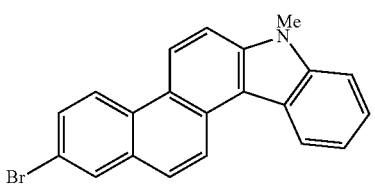 (93)
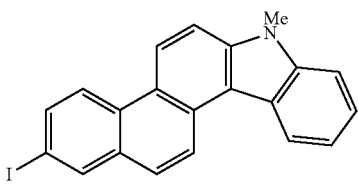 (94)

147
-continued
(95)
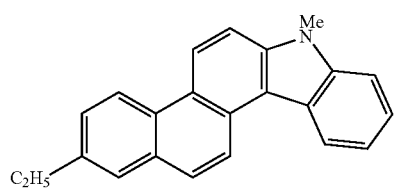
C₂H₅
(96)
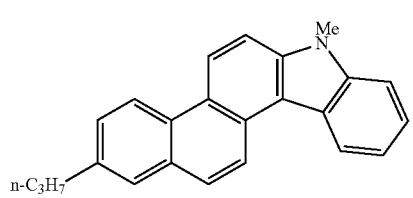
n-C₃H₇
(97)
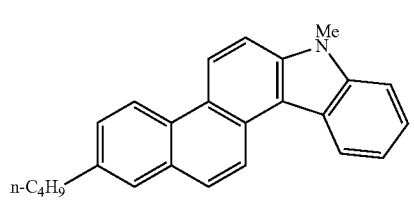
n-C₄H₉
(98)
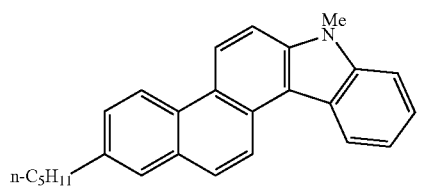
n-C₅H₁₁
(99)
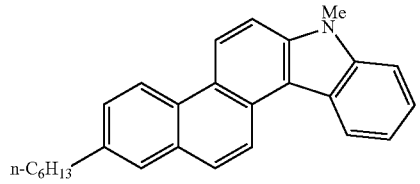
n-C₆H₁₃
(100)
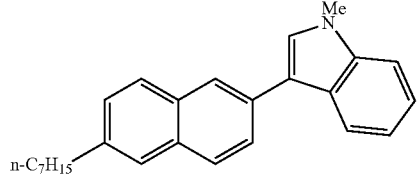
n-C₇H₁₅
(101)
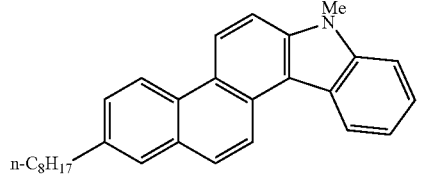
n-C₈H₁₇
(102)
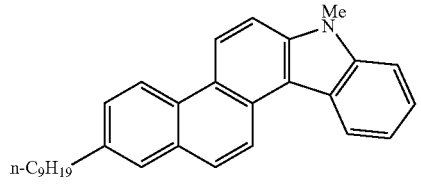
n-C₉H₁₉
148
-continued
(103)
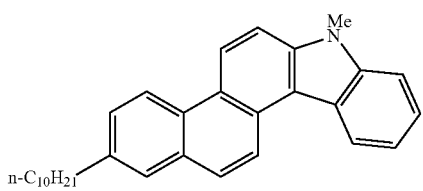
n-C₁₀H₂₁
(104)
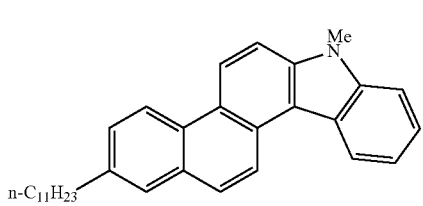
n-C₁₁H₂₃
(105)
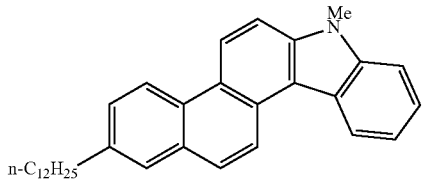
n-C₁₂H₂₅
(106)
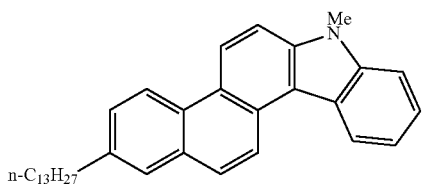
n-C₁₃H₂₇
(107)
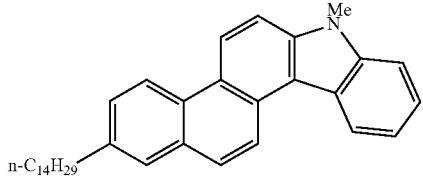
n-C₁₄H₂₉
(108)
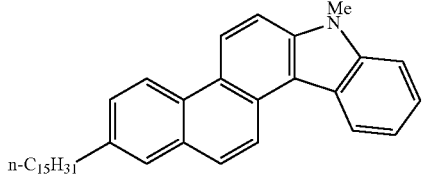
n-C₁₅H₃₁
(109)
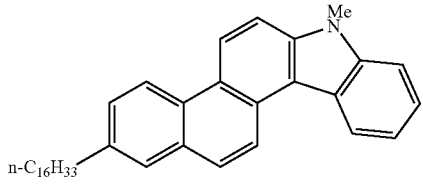
n-C₁₆H₃₃
(110)
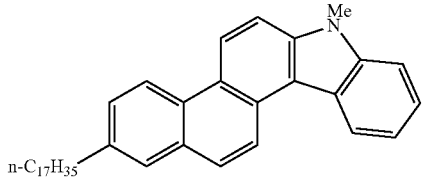
n-C₁₇H₃₅

-continued
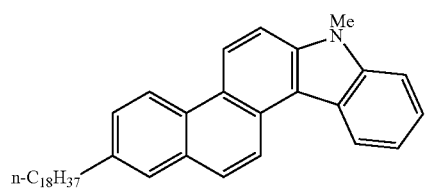 (111)
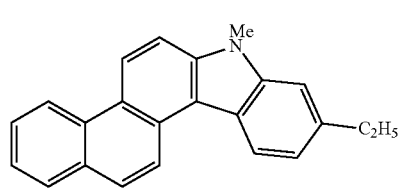 (112)
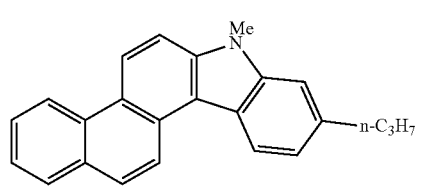 (113)
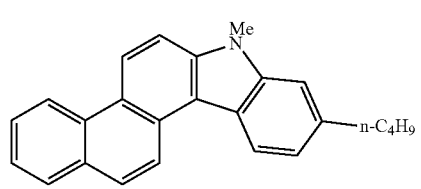 (114)
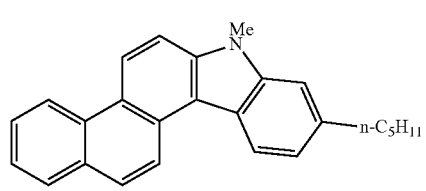 (115)
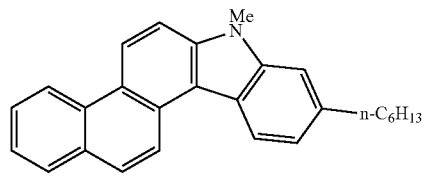 (116)
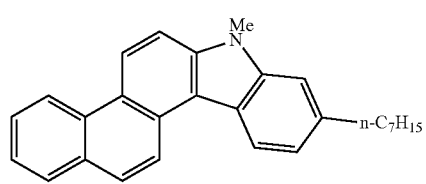 (117)
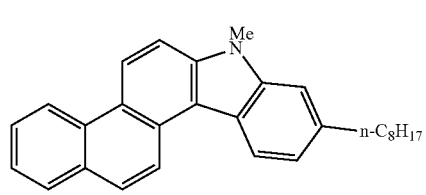 (118)
-continued
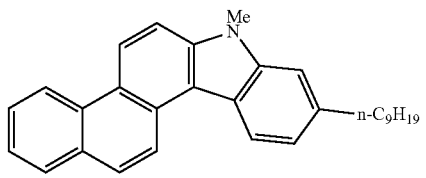 (119)
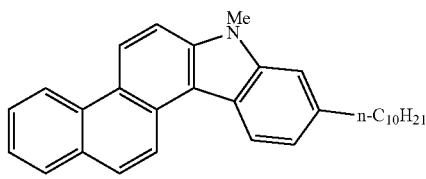 (120)
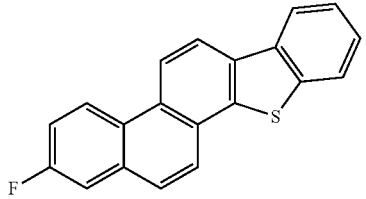 (136)
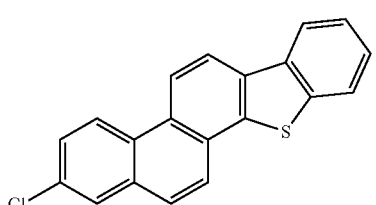 (137)
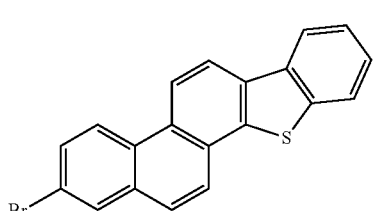 (138)
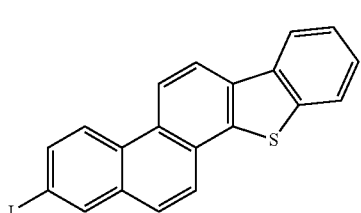 (139)
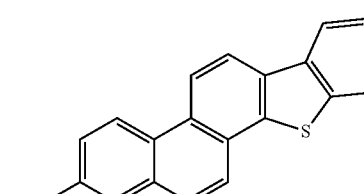 (140)
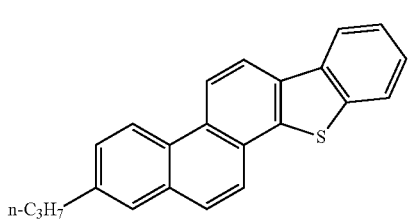 (141)

-continued
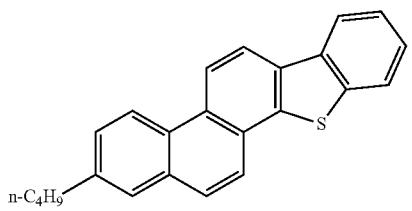
(142)
n-C$_4$H$_9$
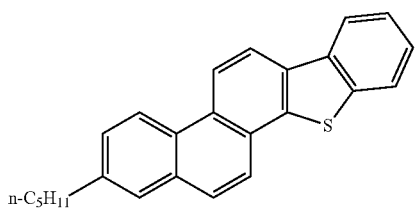
(143)
n-C$_5$H$_{11}$
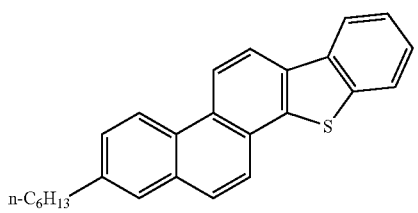
(144)
n-C$_6$H$_{13}$
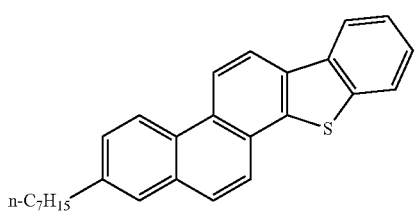
(145)
n-C$_7$H$_{15}$
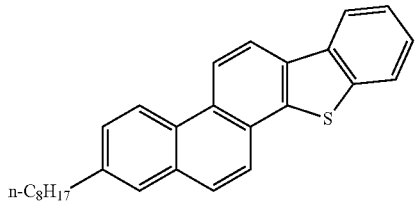
(146)
n-C$_8$H$_{17}$
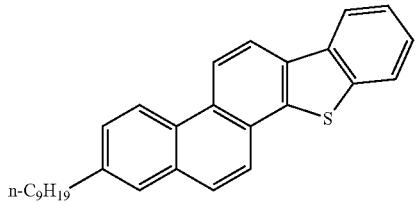
(147)
n-C$_9$H$_{19}$
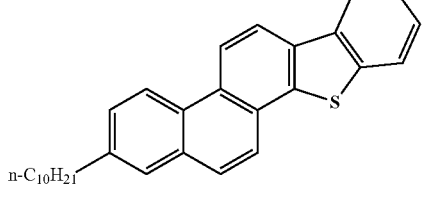
(148)
n-C$_{10}$H$_{21}$
-continued
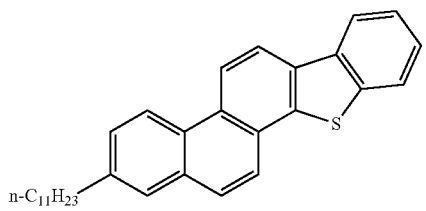
(149)
n-C$_{11}$H$_{23}$
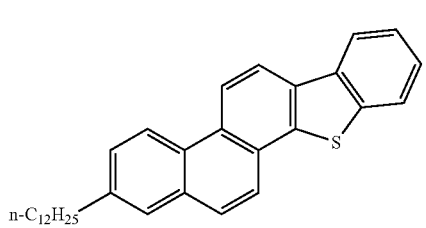
(150)
n-C$_{12}$H$_{25}$
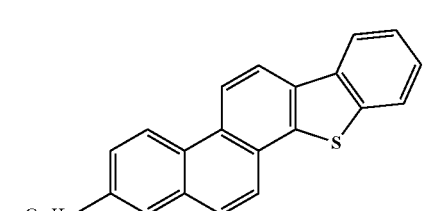
(151)
n-C$_{13}$H$_{26}$
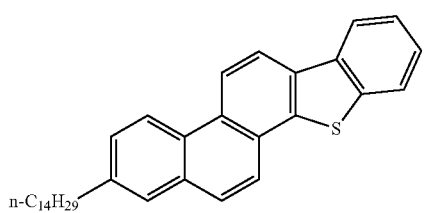
(152)
n-C$_{14}$H$_{29}$
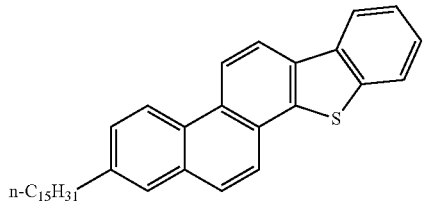
(153)
n-C$_{15}$H$_{31}$
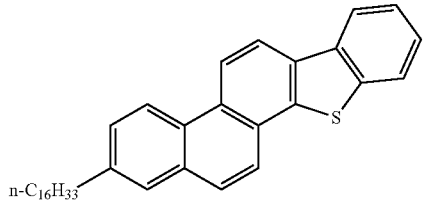
(154)
n-C$_{16}$H$_{33}$
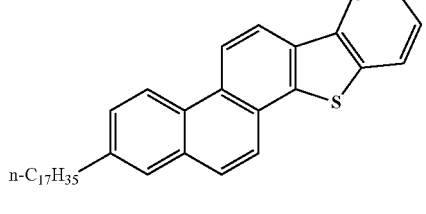
(155)
n-C$_{17}$H$_{35}$ (156)
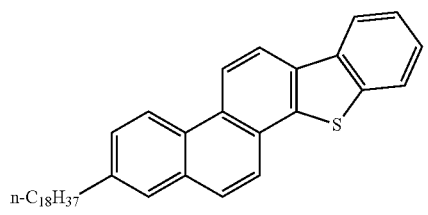
(157)
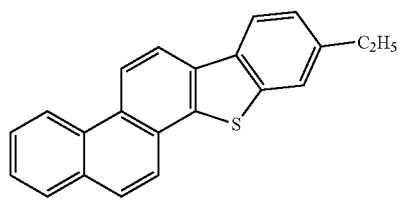
(158)
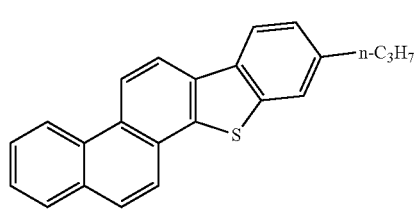
(159)
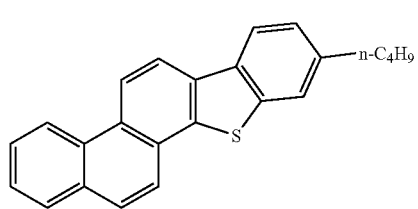
(160)
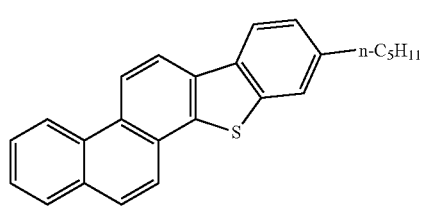
(161)
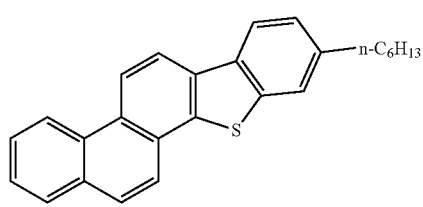
(162)
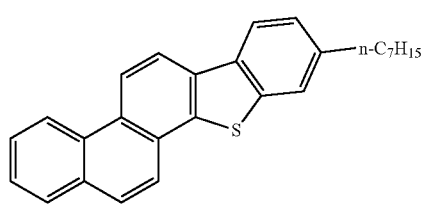
(163)
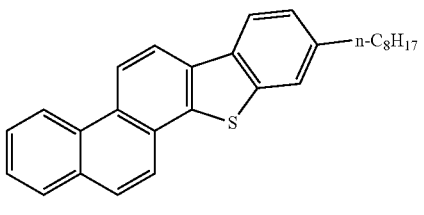
(164)
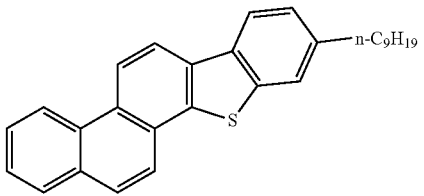
(165)
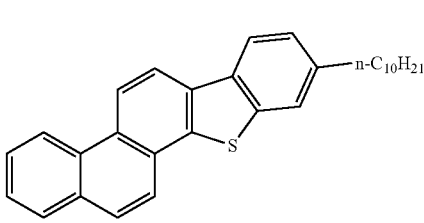
(166)
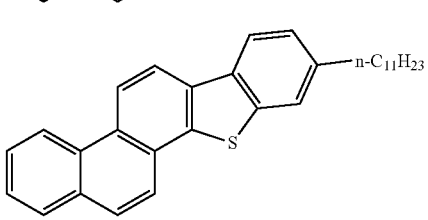
(167)
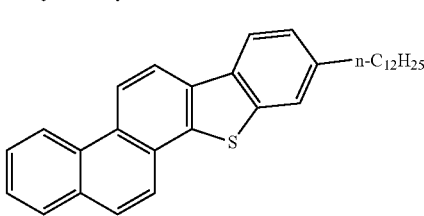
(168)
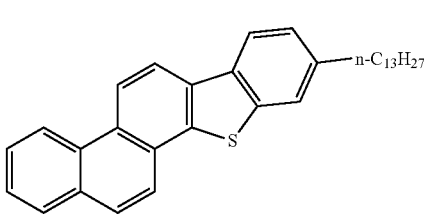
(169)
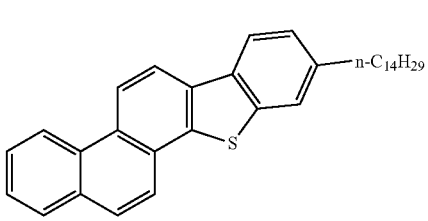
(170)
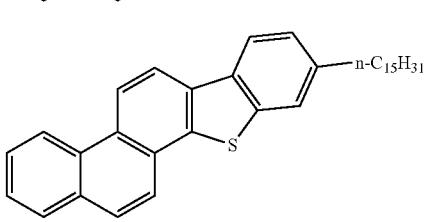

-continued
(171)
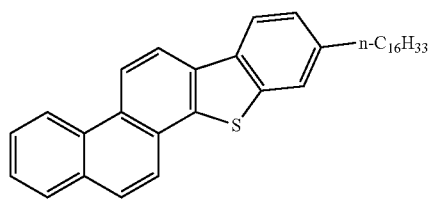
(172)
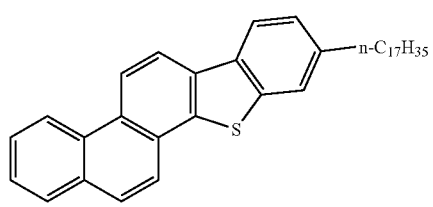
(173)
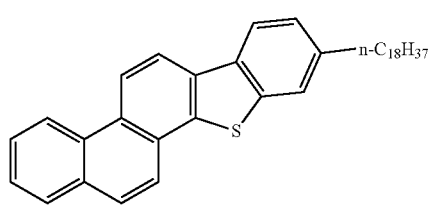
(174)
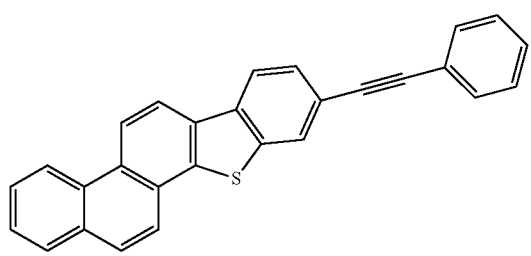
(175)
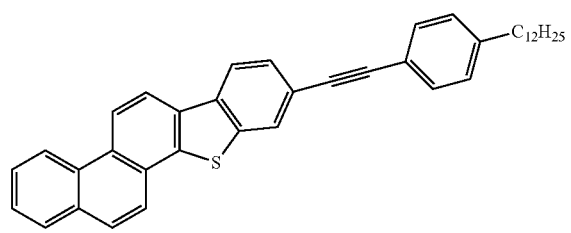
(176)
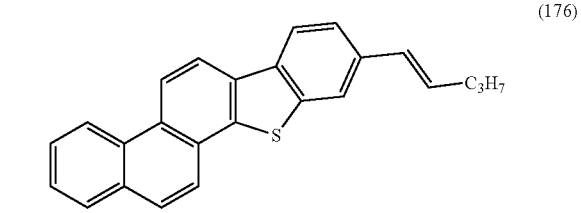
(177)
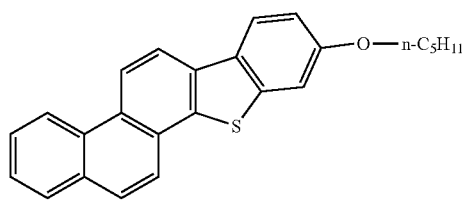
-continued
(178)
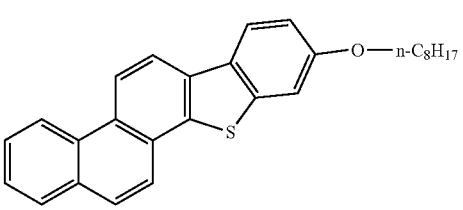
(179)
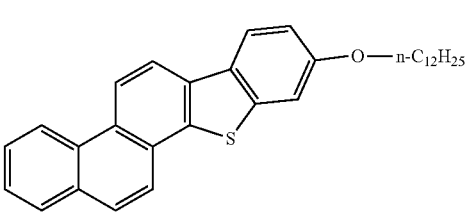
(180)
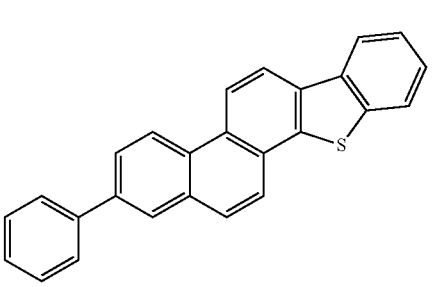
(181)
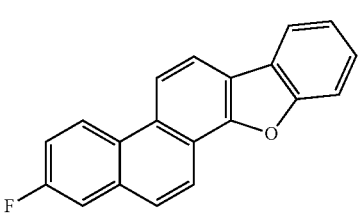
(182)
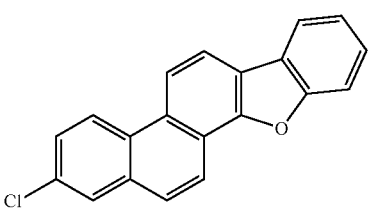
(183)
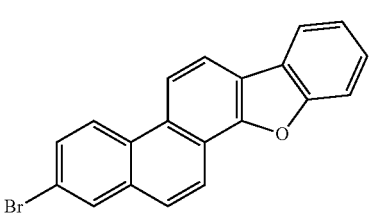
(184)
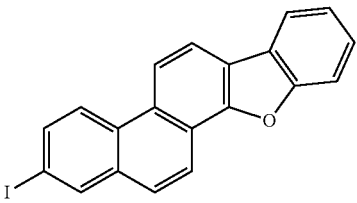

-continued
(185) 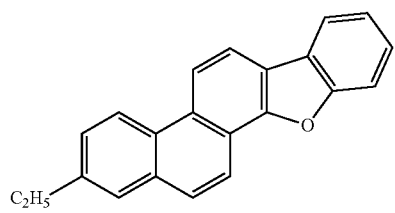
C₂H₅
(186) 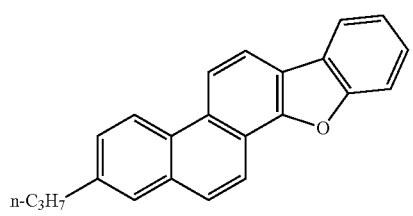
n-C₃H₇
(187) 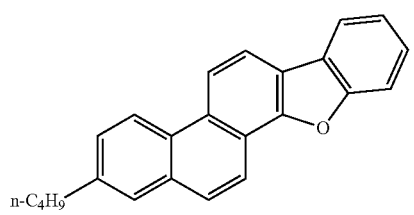
n-C₄H₉
(188) 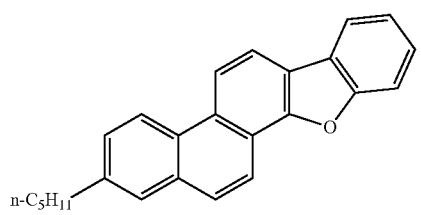
n-C₅H₁₁
(189) 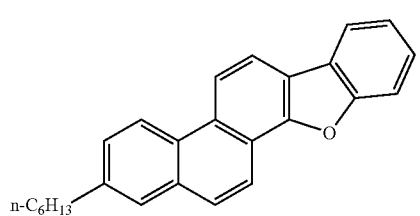
n-C₆H₁₃
(190) 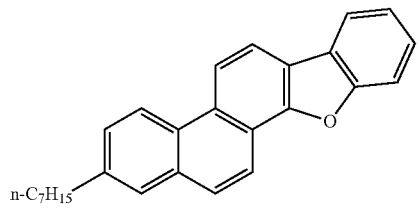
n-C₇H₁₅
(191) 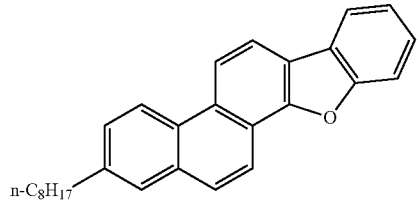
n-C₈H₁₇
-continued
(192) 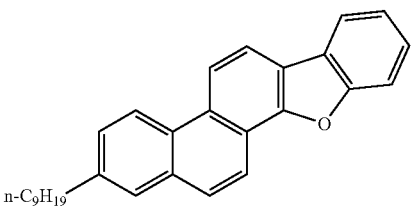
n-C₉H₁₉
(193) 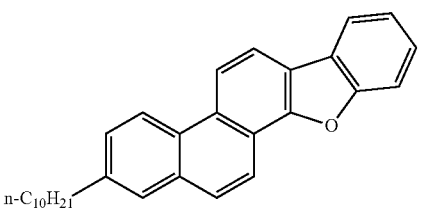
n-C₁₀H₂₁
(194) 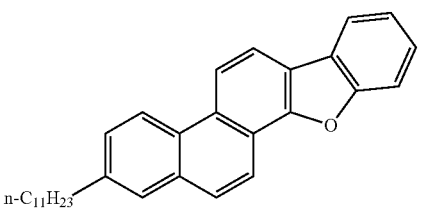
n-C₁₁H₂₃
(195) 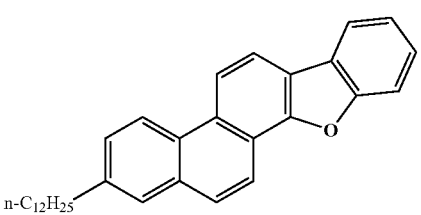
n-C₁₂H₂₅
(196) 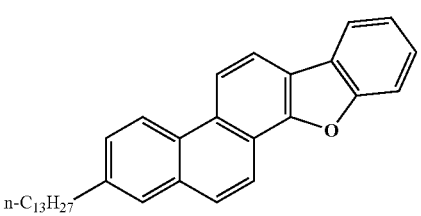
n-C₁₃H₂₇
(197) 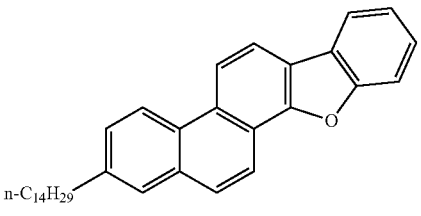
n-C₁₄H₂₉
(198) 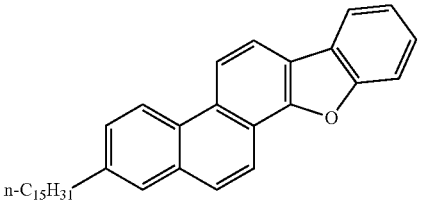
n-C₁₅H₃₁

(199) 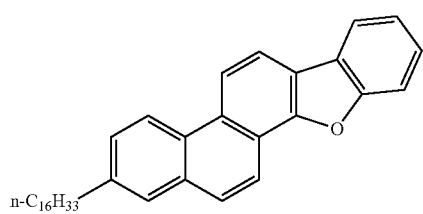
(200) 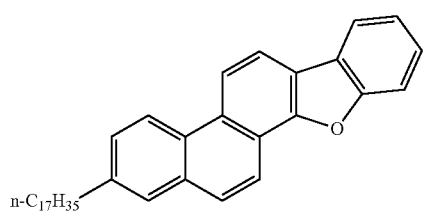
(201) 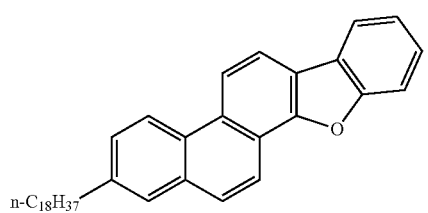
(202) 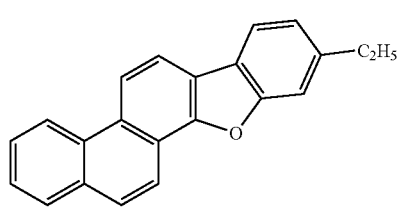
(203) 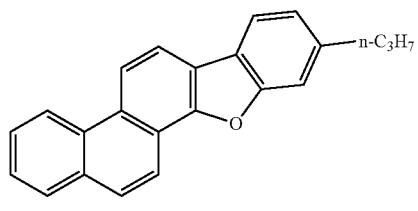
(204) 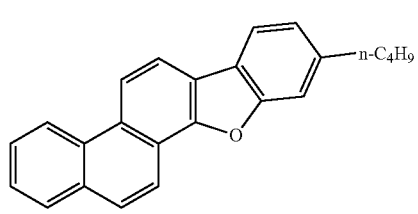
(205) 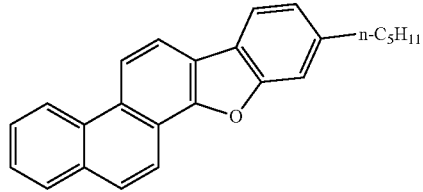
(206) 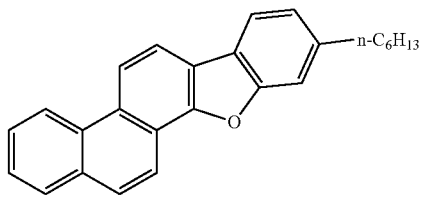
(207) 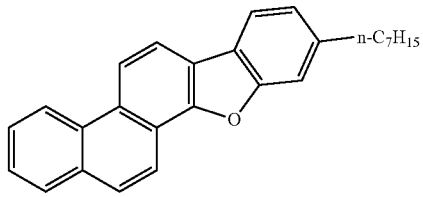
(208) 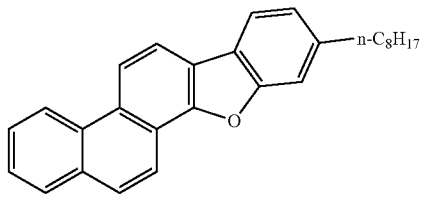
(209) 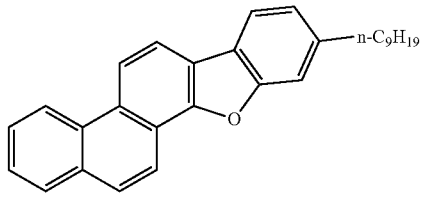
(210) 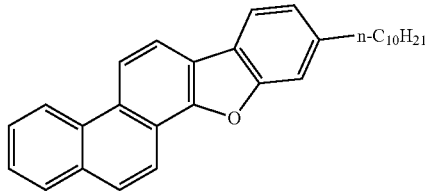
(211) 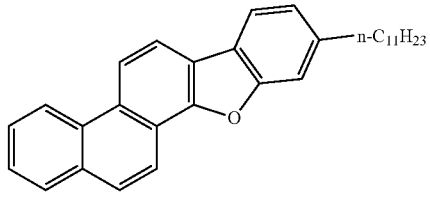
(212) 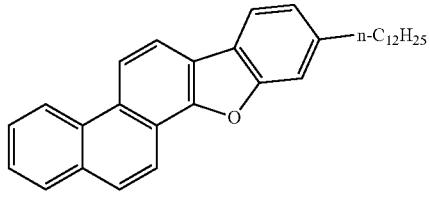
(213) 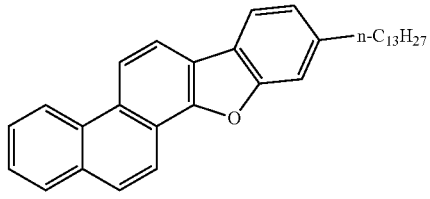

(214)
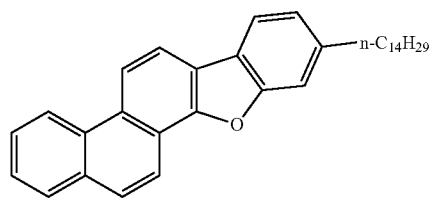
(215)
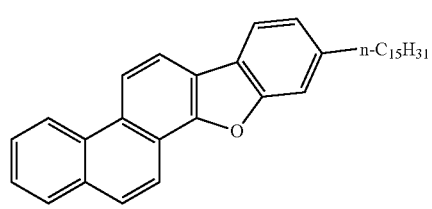
(216)
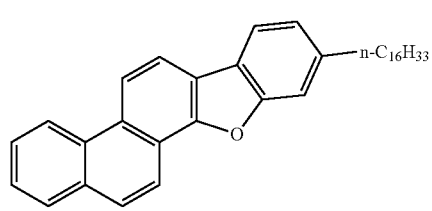
(217)
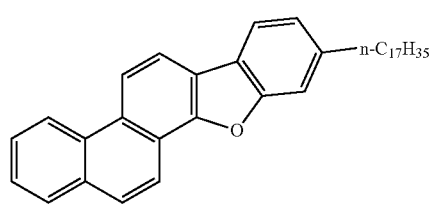
(218)
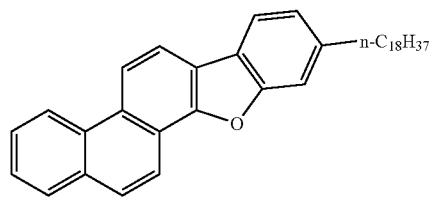
(219)
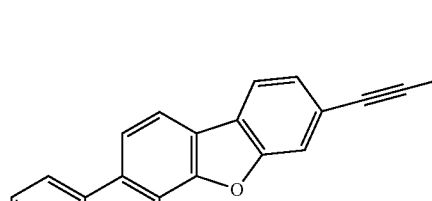
(220)
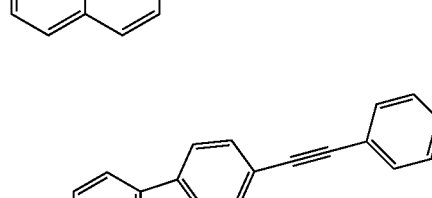
(221)
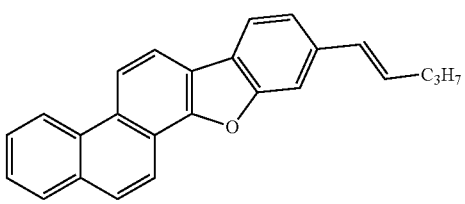
(222)
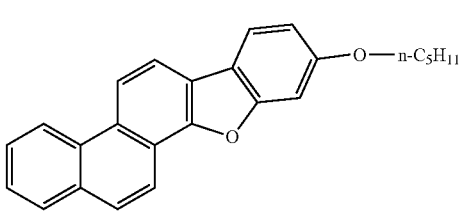
(223)
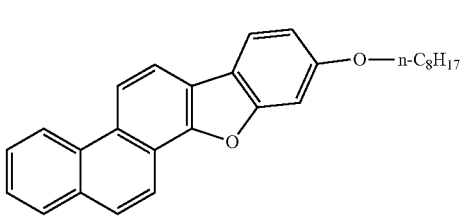
(224)
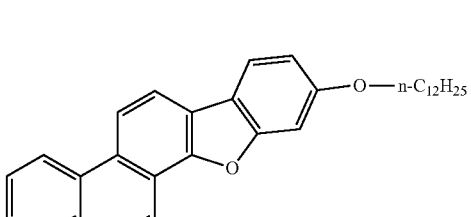
(225)
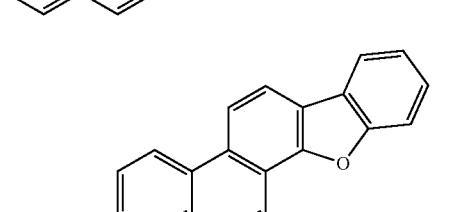
(226)
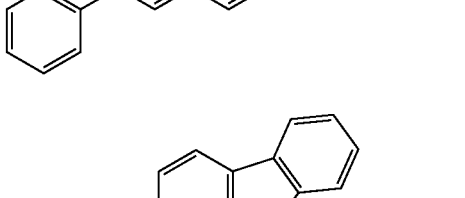
(227)
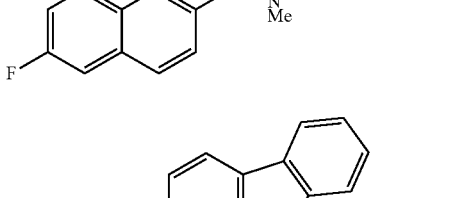

-continued
(228)
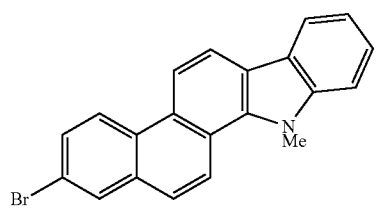
(229)
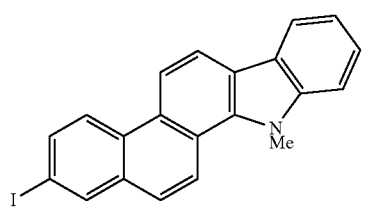
(230)
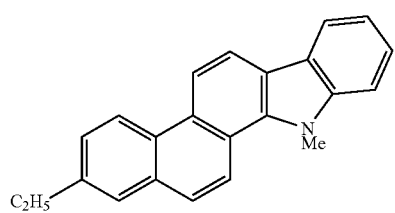
(231)
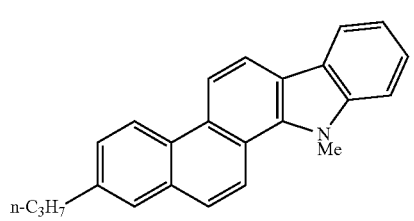
(232)
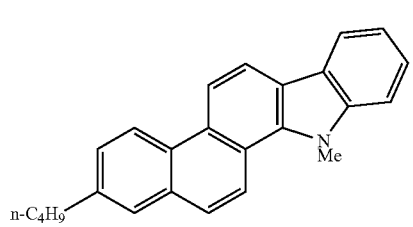
(233)
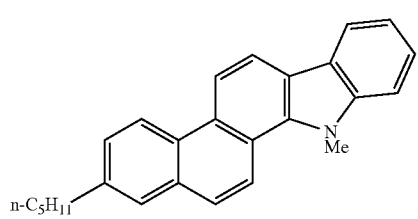
(234)
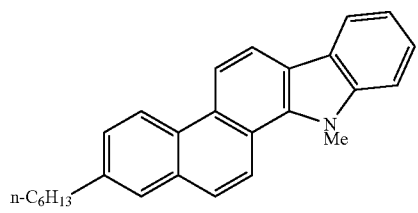
-continued
(235)
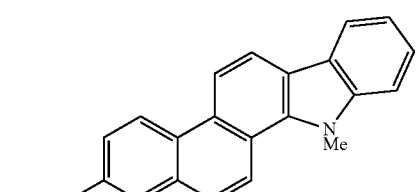
(236)
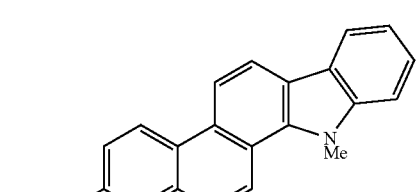
(237)
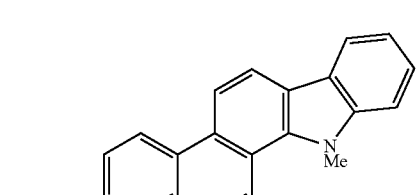
(238)
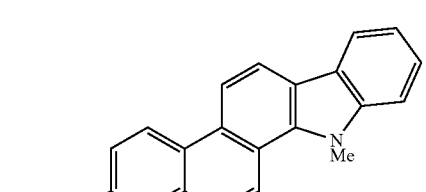
(239)
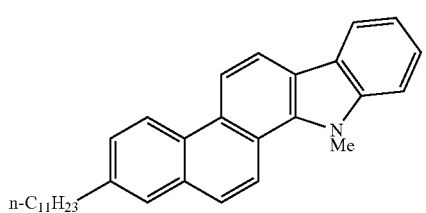
(240)
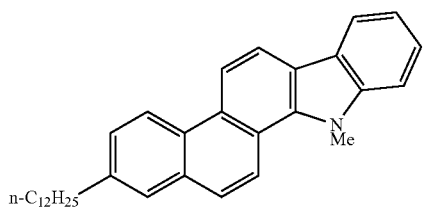
(241)
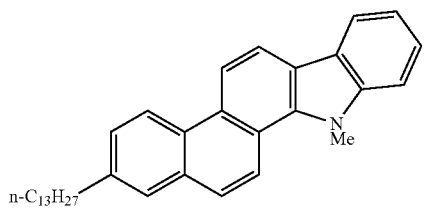

-continued
(242) 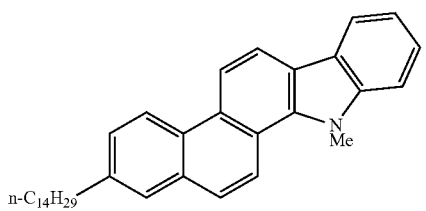
(243) 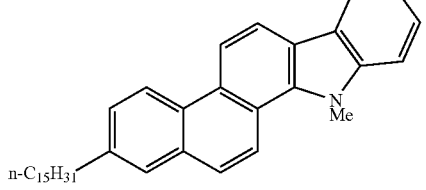
(244) 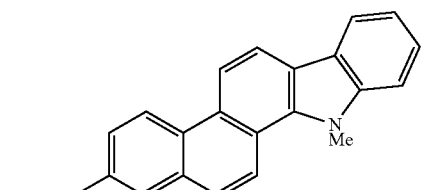
(245) 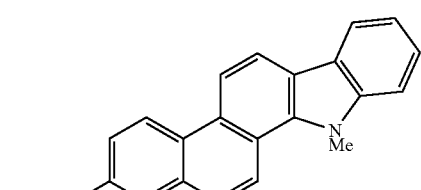
(246) 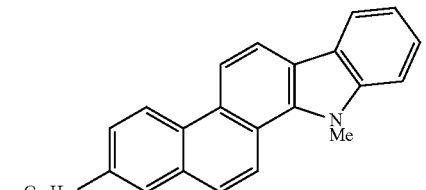
(247) 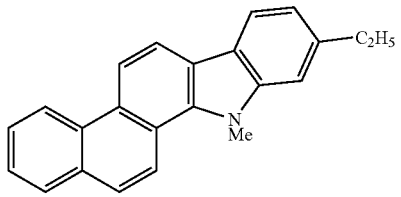
(248) 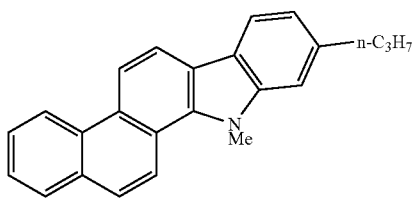
-continued
(249) 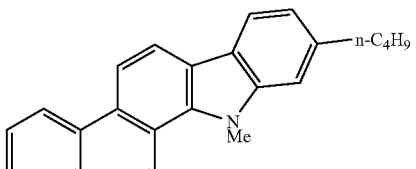
(250) 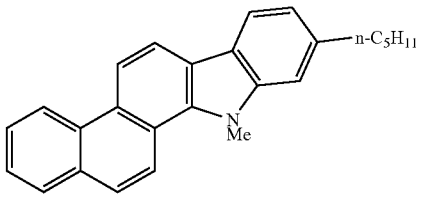
(251) 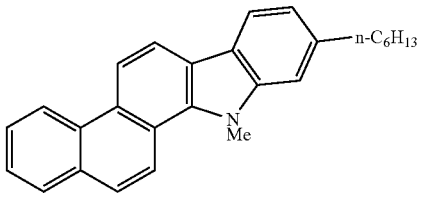
(252) 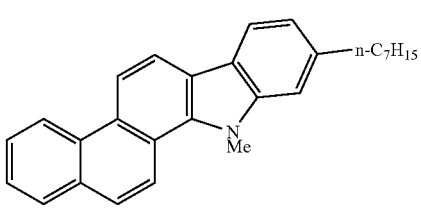
(253) 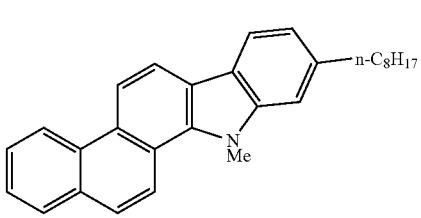
(254) 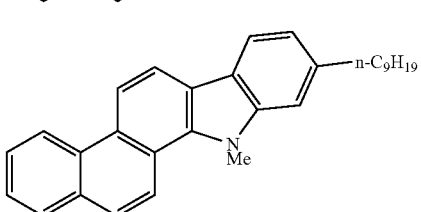
(255) 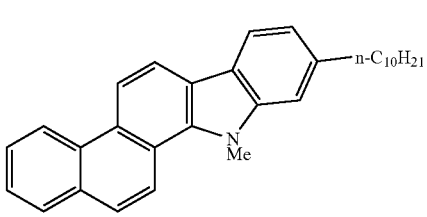
(256) 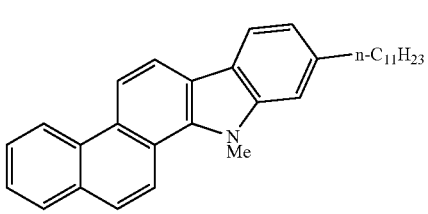

-continued
(257) 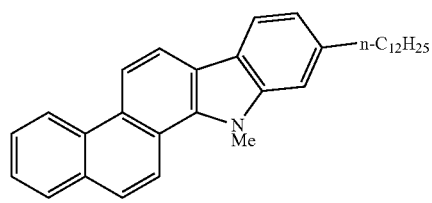
(258) 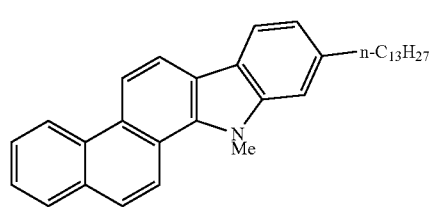
(259) 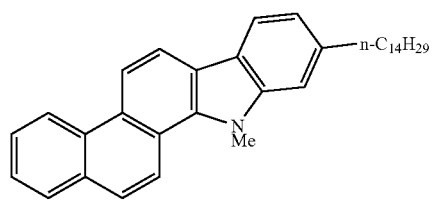
(260) 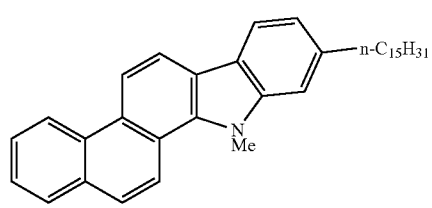
(261) 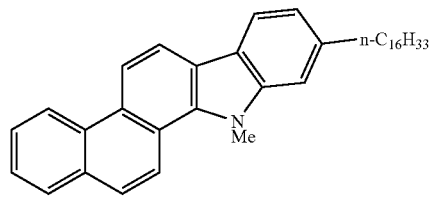
(262) 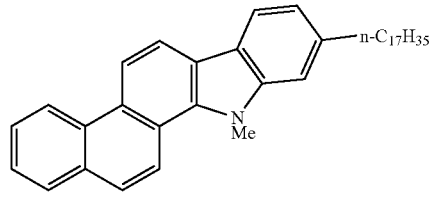
(263) 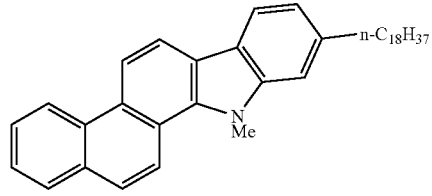
-continued
(264) 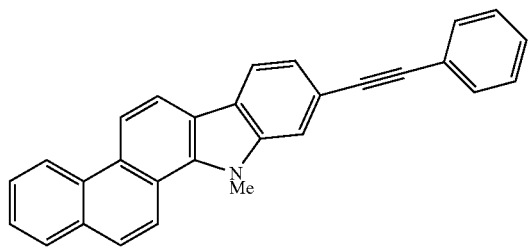
(265) 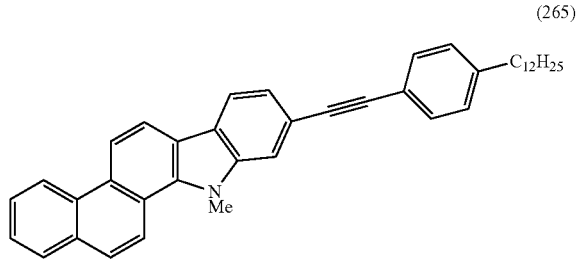
(266) 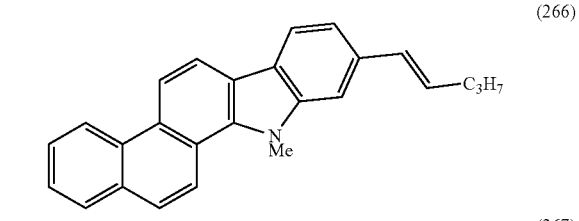
(267) 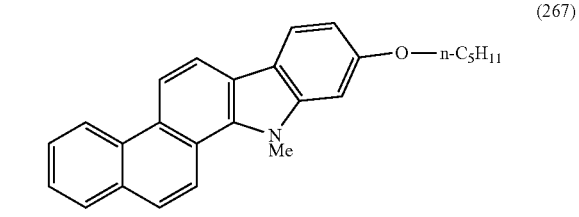
(268) 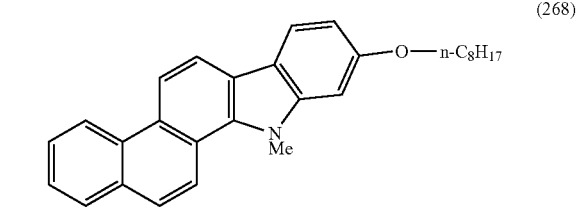
(269) 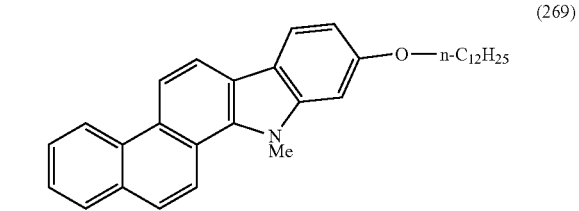
(270) 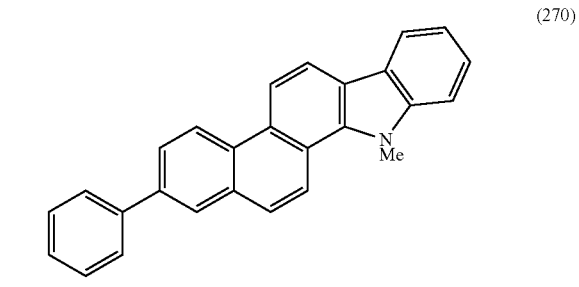

These third compounds can provide a high mobility when used as a material for an organic thin film transistor due to enhanced intermolecular interaction by expanding the π-conjugated system and by the heavy metal effect of hetero atoms. Further, by allowing the structure to be asymmetric and/or introducing a substituent, the compound of the invention can have improved solubility.

In addition, unlike a linear polyacene, the representative example of which is pentacene, in which benzene rings are arranged like a straight line, the compound of the invention has a phenacene-like structure in which some of the benzene rings are arranged in a zig-zag manner, and hence has excellent stability to oxidization.

The third compound of the invention can be synthesized by the following synthesis method A or B, for example.

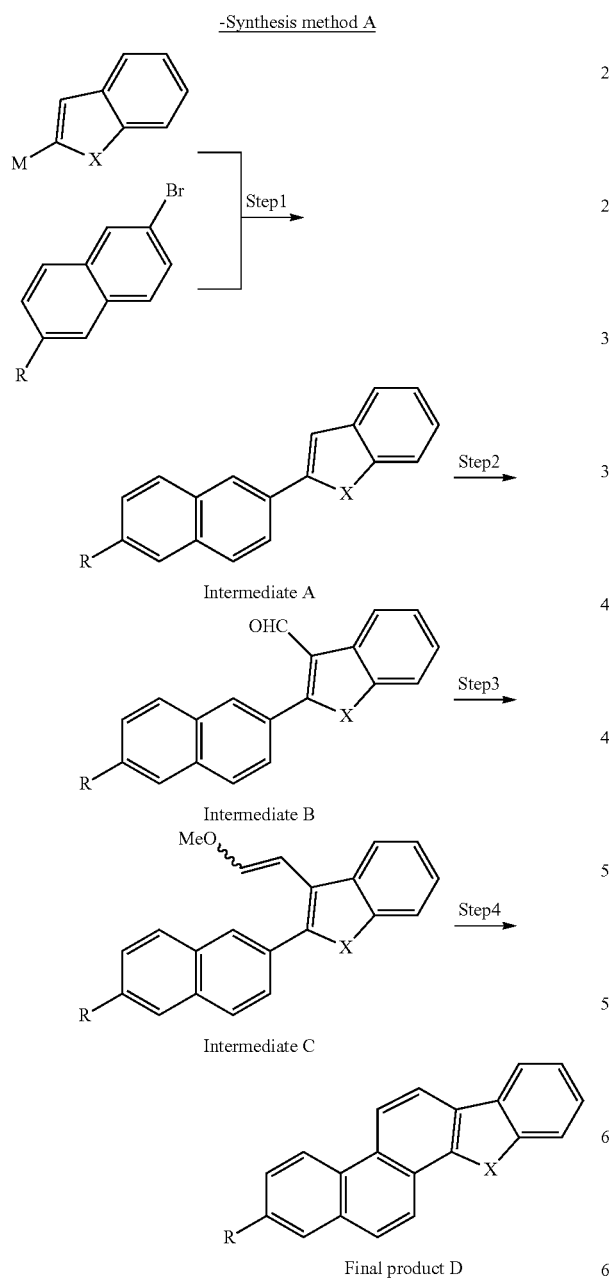

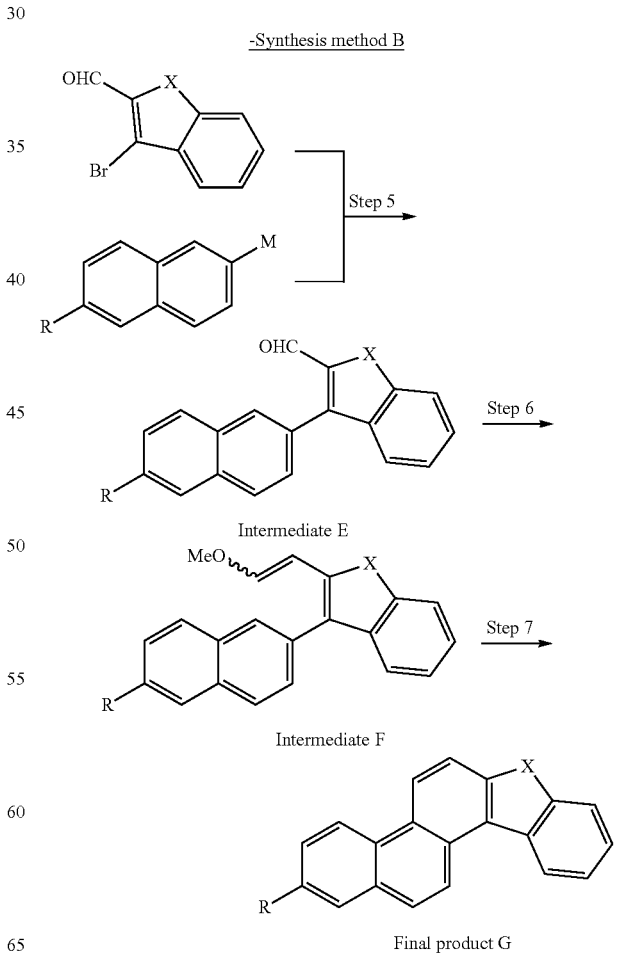

(X is the same groups as those in the above-mentioned formula (C-1); R is the same groups as $R^1$ in the formula (C-1) or the like; M is a boronic acid or the like and Me is a methyl group)

In the step 1, a derivative of a benzoheterocyclic compound of which the $2^{nd}$ position is boronated or metalized as the starting material is bonded to a naphthalene derivative to synthesize the intermediate A. As the reaction used in the step 1, Suzuki-Miyaura coupling, Stille coupling, Negishi coupling, Hiyama coupling or the like can be given. Of these, Suzuki-Miyaura coupling is preferable since it can attain a preferable yield.

The starting materials can be commercially available or be synthesized in any known method.

In the step 2, the intermediate A is formylated to produce the intermediate B. As the reaction used in the step 2, a formylation reaction using BuLi/DMF, a Friedel-Crafts reaction using CH$_2$ClOMe or the like can be given. Of these, a formylation reaction using BuLi/DMF is preferable due to easiness in handling.

In the step 3, a formyl group is converted to methyl enol ether by using a Wittig reagent to synthesize the intermediate C. As the reagent used in the step 3, (methoxymethyl)triphenylphosphonium chloride can be given.

In the step 4, a cyclization reaction by using an acid is conducted to produce the final product D where, various Lews acids and protonic acids can be used. It is preferable to use a methanesulfonic acid since it attains a good yield.

(X is the same groups as those in the above-mentioned formula (C-1); R is the same groups as $R^1$ in the formula (C-1) or the like; M is a boronic acid or the like and Me is a methyl group)

In the step 5, 3-bromo-2-formylbenzoheterocyclic compound is connected to a naphthalene derivative of which the $2^{nd}$ position is boronated or metalized to synthesize the intermediate E. As the reaction used in the step 5, Suzuki-Miyaura coupling, Stille coupling, Hiyama coupling or the like can be given. Of these, Suzuki-Miyaura coupling is preferable since it can attain a preferable yield.

As for the starting material, a commercially-available product can be used or synthesis can be conducted by a known method.

In the step 6, a formyl group is converted to methyl enol ether by using a Wittig reagent to synthesize the intermediate F. As the reagent which can be used in the step 6, (methoxymethyl)triphenylphosphonium chloride can be given.

In the step 7, a cyclization reaction using an acid to synthesize the final product G where, various Lews acids, protonic acids can be used. Use of methanesulfonic acid is preferable since it attains a good yield.

In an electric device like a transistor, the field effect mobility or the on/off ratio can be enhanced by using a material having a high purity. Therefore, according to need, it is desired that the first, second and third compounds of the invention thus produced (hereinafter these compounds may be comprehensively referred to as the compound of the invention) can be purified by techniques such as column chromatography, recrystallization, distillation, sublimation or the like. Preferably, by using these purification methods repeatedly or by combining a some of these methods, the purity of the compound of the invention is improved. Further, it is desired that the sublimation should be repeated at least twice or more as the final step of the purification. By using these techniques, it is preferable to allow the compound to have a purity of 90% or more. By allowing the purity to be further preferably 95% or more and particularly preferably 98.5% or more, the field effect mobility or the on-off ratio of an organic thin film transistor can be enhanced, and at the same time, performance intrinsic to the material can be brought out.

The compound of the invention is a material for an organic thin film transistor which can be preferably used in an organic thin film transistor. The compound of the invention can be particularly preferably used in an organic semiconductor layer of an organic thin film transistor.

The compound of the invention has a high solubility in an organic solvent, and hence, an applying process can be extended to various methods when producing an organic thin film transistor. Further, since the compound of the invention has excellent stability against oxidization, in an organic thin film transistor using the compound of the invention, the deterioration with time of the transistor properties thereof can be suppressed.

When an organic thin film transistor is produced by an applying wet process by using the compound of the invention, the solvent for the compound of the invention, aromatic solvents such as toluene and xylene; a halogenated solvents such as dichloromethane, chloroform and chlorobenzene, ether solvents such as diethylether, tetrahydrofuran, dimethoxyethane and anisol; hydrocarbon solvents such as hexane and heptane; lactams such as N-methylpyrrolidone, or the like can be given. Further, these solvents may be mixed in an arbitrary amount ratio. In an applying wet process, it is preferable to select a solvent which enables a preferable film property such as flatness.

When wet process is applied, where an organic semiconductor layer having a film thickness of 0.5 nm to 2 μm is obtained, the concentration of the compound of the invention is preferably 0.05 to 2.0 wt %.

The device configuration of the organic thin film transistor of the invention is explained as follows.

The organic thin film transistor of the invention has a configuration in which it comprises, on a substrate, at least three terminals of a gate electrode, a source electrode and a drain electrode, an insulator layer and an organic semiconductor layer, and current flowing between the source electrode and the drain electrode is controlled by applying a voltage to the gate electrode. It is preferred that the organic semiconductor layer of the organic thin film transistor of the invention contain the compound of the invention.

No specific restrictions are imposed on the structure of the transistor, and it may have a known device configuration except for the component of the organic semiconductor layer.

Specific examples of the device configuration of the organic thin film transistor is explained with reference to the drawings.

FIGS. 1 to 4 are typical drawings each showing one example of the device configuration of the organic thin film transistor of the invention.

In an organic thin film transistor 1 shown in FIG. 1, on a substrate 10, a source electrode 11 and a drain electrode 12 are provided which are formed such that they are opposed with a predetermined distance there between. Further, an organic semiconductor layer 13 is formed so as to cover the source electrode 11, the drain electrode 12 and the gap there between. Further, an insulator layer 14 is stacked thereon. A gate electrode 15 is formed on the insulator layer 14 and above the gap between the source electrode 11 and the drain electrode 12.

Figure 2:
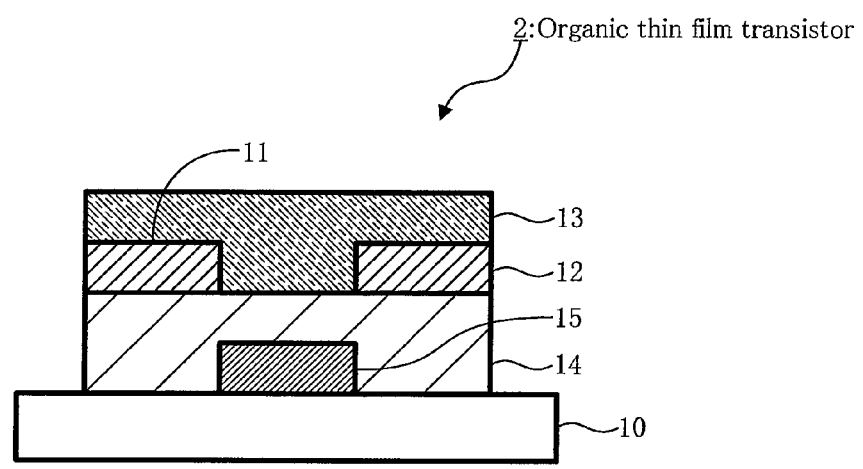
FIG. 2 is a view showing another embodiment of the thin film transistor of the invention.

In an organic thin film transistor 2 shown in FIG. 2, on the substrate 10, the gate electrode 15 and the insulator layer 14 are provided in this sequence. On the insulating layer 14, a pair of the source electrode 11 and the drain electrode 12 is provided which are formed with a predetermined distance there between. The organic semiconductor layer 13 is formed thereon. The organic semiconductor layer 13 constitutes a channel region. The on-off operation is conducted by controlling current flowing between the source electrode 11 and the drain electrode 12 with a voltage applied to the gate electrode 15.

Figure 3:
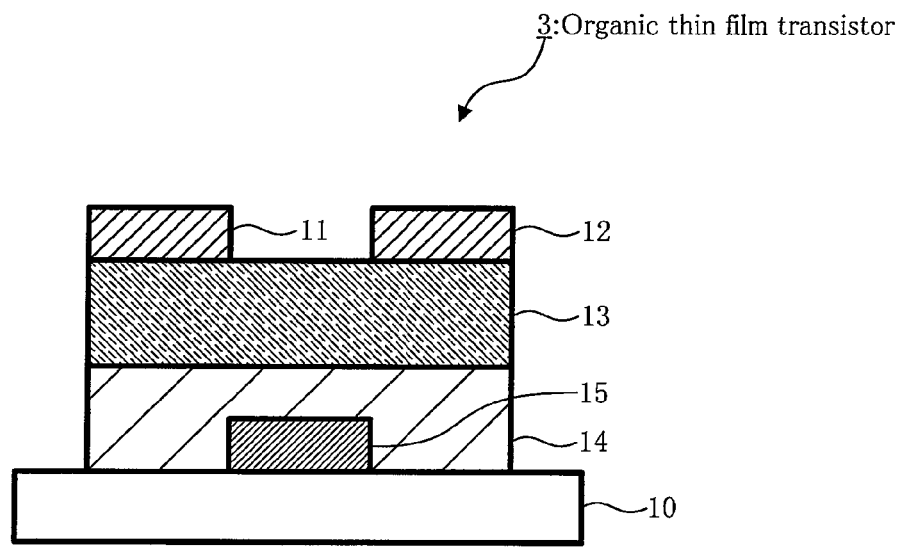
FIG. 3 is a view showing another embodiment of the thin film transistor of the invention.

In an organic thin film transistor 3 shown in FIG. 3, on the substrate 10, the gate electrode 15, the insulator layer 14 and the organic semiconductor layer 13 are provided in this sequence. On the organic semiconductor layer 13, a pair of the source electrode 11 and the drain electrode 12 is provided which are formed with a predetermined distance there between.

Figure 4:
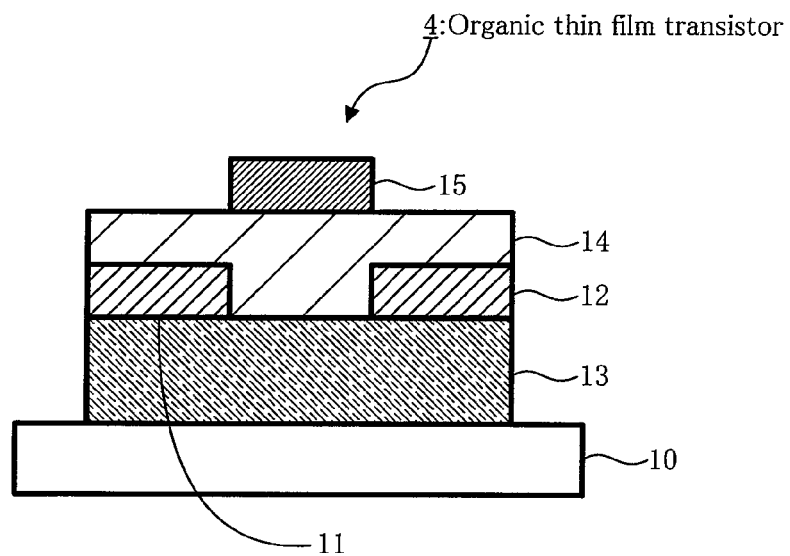
FIG. 4 is a view showing another embodiment of the thin film transistor of the invention.

In an organic thin film transistor 4 shown in FIG. 4, on the substrate 10, the organic semiconductor layer 13 is provided. On the organic semiconductor layer 13, a pair of the source electrode 11 and the drain electrode 12 is provided which are formed with a predetermined distance there between. Further, the insulator layer 14 and the gate electrode 15 are provided in this sequence.

The organic thin film transistor of the invention has a field effect transistor structure. As mentioned above, there are some configurations different in the position of the electrodes, the stacking order of the layers or the like. The organic thin film transistor has an organic semiconductor layer (organic compound layer), a source electrode and a drain electrode which are formed such that they are opposed with a predetermined distance there between, and a gate electrode which is formed with a predetermined distance from the source electrode and the drain electrode. Current flowing between the source electrode and the drain electrode is controlled by applying a voltage to the gate electrode. The distance between the source electrode and the drain electrode is determined according to the application in which the organic thin film transistor of the invention is used, but it is normally 0.1 µm to 1 mm, preferably 1 µm to 100 µm, and further preferably 5 µm to 100 µm.

In addition to the above-mentioned configurations, various configurations have been proposed for organic thin film transistors. The configuration of the organic thin film transistor of the invention is not restricted to the configuration as mentioned above as long as the on-off operation is conducted by controlling current flowing between the source electrode and the drain electrode with an applied voltage to the gate electrode.

Figure 5:
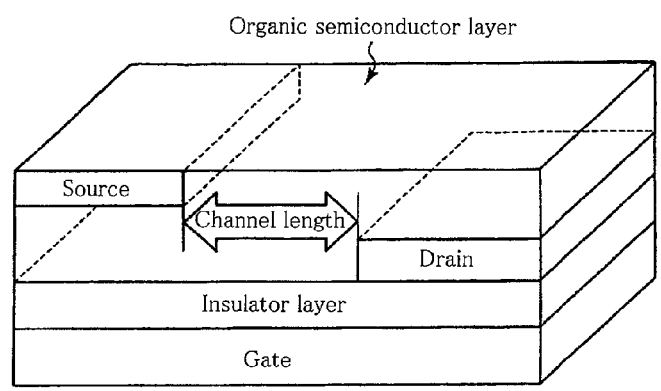
FIG. 5 is a view showing another embodiment of the thin film transistor of the invention.
Figure 6:
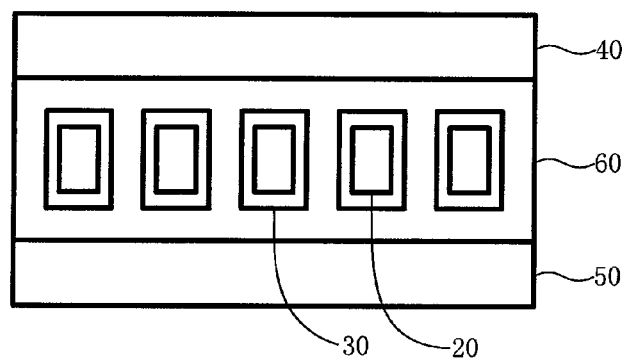
FIG. 6 is a view showing another embodiment of the thin film transistor of the invention.

For example, it may have a device configuration like the top and bottom contact type organic thin film transistor (see FIG. 5) proposed by Yoshida et al. of the National Institute of the Advanced Industrial Science and Technology in 27a-M-3 (March, 2002) of the preprints of the 49$^{th}$ Japanese Journal Applied Physics or a vertical organic thin film transistor (see FIG. 6) proposed by Kudo et al. of Chiba University in page 1440 of the Journals of the Institute of Electrical Engineers of Japan 118-A (1998). Herein below, each constitutional element of the organic thin film transistor is explained.

(Organic Semiconductor Layer)

The organic semiconductor layer in the organic thin film transistor of the invention preferably comprises the compound for an organic thin film transistor of the invention.

The organic semiconductor layer may comprise the compound of the invention singly or in combination of two or more. Further, the organic semiconductor layer may contain a known semiconductor such as pentacene and a thiophene oligomer as long as the object of the invention can be attained. It may be a thin film comprising a mixture of a plurality of compounds or a stacked body.

Although the film thickness of the organic semiconductor layer is not particularly restricted, it is normally 0.5 nm to 1 µm, and preferably 2 nm to 250 nm.

Further, the method for forming the organic semiconductor layer is not particularly restricted and it can be formed by a known method. For example, printing or coating method such as the molecular beam epitaxy method (the MBE method), the vacuum vapor deposition method, the chemical vapor deposition, the dipping method of a solution in which a material is dissolved in a solvent, the spin coating method, the casting method, the bar coat method, the roll coat method, and the ink-jet method, baking, electro-polymerization, self-assembly from a solution, and combination thereof.

Since the field effect mobility can be improved by improving the crystallinity of the organic semiconductor layer, in order to obtain a high performance device, it is preferable to be annealed after film formation irrespective of the film formation method. It is preferable to be annealed at a temperature of 50 to 200° C., further preferably 70 to 200° C. The annealing time is preferable 10 minutes to 12 hours, with 1 to 10 hours being further preferable.

(Substrate)

The substrate in the organic thin film transistor of the invention has a function of supporting the structure of the organic thin film transistor. As the material for the substrate, in addition to glass, inorganic compounds such as metal oxides or nitrides, plastic films (PET, PES, PC) or a metal substrate or a composite or a stacked body of these or the like can be used. Further, if the structure of the organic thin film transistor can be fully supported by other constitutional elements than the substrate, the substrate may not be used. As the material for the substrate, silicon (Si) wafer may frequently be used. However, it is possible to use Si itself as the substrate which also functions as the gate electrode. Further, it is possible to oxidize the surface of Si to form $SiO_2$ to use it as an insulating layer. In this case, a layer of a metal such as Au may be formed on the Si substrate which also functions as the gate electrode as the electrode for connecting a lead wire.

(Electrode)

No specific restrictions are imposed on the material for the gate electrode, the source electrode and the drain electrode in the organic thin film transistor of the invention as long as they are conductive materials. Platinum, gold, silver, nickel, chromium, copper, iron, tin, antimony, lead, tantalum, indium, palladium, tellurium, rhenium, iridium, aluminum, ruthenium, germanium, molybdenum, tungsten, tin oxide antimony, indium tin oxide (ITO), fluoride-doped zinc oxide, zinc, carbon, graphite, glassy carbon, silver paste and carbon paste, lithium, beryllium, sodium, magnesium, potassium, calcium, scandium, titanium, manganese, zirconium, gallium, niobium, sodium potassium alloy, a magnesium/copper mixture, a magnesium/silver mixture, a magnesium/aluminum mixture, a magnesium/indium mixture, an aluminum/aluminum oxide mixture, a lithium/aluminum mixture, or the like can be used.

As the method for forming the electrode, deposition, electron beam deposition, sputtering, the atmospheric plasma method, ion plating, chemical vapor deposition, electrodeposition, electroless plating, spin coating, printing or ink jet or the like can be given. Further, as the method of patterning which is conducted according to need, a method in which a conductive thin film formed by the above-mentioned method is formed into electrodes by a known photolithographic method or a lift-off method, a method in which the conductive thin film formed by the above-mentioned method is heat-transferred to metal foil such as aluminum or copper, and then a resist is formed by the ink jet method or the like, followed by etching.

The film thickness of the thus formed electrode is not particularly restricted as long as it passes electric current. The film thickness is preferably 0.2 nm to 10 µm, further preferably 4 nm to 300 nm. As long as the thickness of the electrode is within this range, a drop in voltage does is not caused by an increase in resistance due to a small film thickness. In the above-mentioned film thickness range, since it is not too large, film formation does not take time, and hence, stacking of layers can be conducted smoothly without causing steps when a protective layer, an organic semiconductor layer or other layers are stacked.

In the organic thin film transistor of the invention, as the other method for forming the source electrode, the drain electrode and the gate electrode, it is possible to form by using a fluidic electrode material such as a solution, a paste, ink, a dispersion liquid or the like, each containing the above-mentioned conductive material. In this case, in particular, a method in which a fluidic electrode material containing a conductive polymer or metal fine particles containing platinum, gold, silver or copper is used is preferable.

As the solvent or the dispersion medium, in order to suppress damage on an organic semiconductor, a solvent or a dispersion medium containing 60 mass % or more, preferably 90 mass % or more of water is preferable. As the dispersion containing metal fine particles, a known conductive paste or the like can be used, for example. Normally, a dispersion containing metal fine particles having a particle size of 0.5 nm to 50 nm or 1 nm to 10 nm is preferable.

As the material for metal fine particles, platinum, gold, silver, nickel, chromium, copper, iron, tin, lead antimony, tantalum, indium, palladium, tellurium, rhenium, iridium, aluminum, ruthenium, germanium, molybdenum, tungsten, zinc, or the like can be used. It is preferable to form electrodes using a dispersion in which these metal fine particles are dispersed in a dispersion medium such as water or an arbitral organic solvent by using a dispersion stabilizer formed mainly of an organic material.

As the method for producing a dispersion of metal fine particles, a physical forming method such as the gas evaporation method, the sputtering method and the metal vapor synthesis method or a chemical forming method such as the colloidal method and the co-precipitation method, in which metal ions are reduced in a liquid phase to form metal fine particles. Preferably, a dispersion of metal fine particles produced by the colloidal method disclosed in JP-A-H11-76800, JP-A-H11-80647, JP-A-H11-319538, JP-A-2000-239853 or the gas evaporation method disclosed in JP-A-2001-254185, JP-A-2001-53028, JP-A-2001-35255, JP-A-2000-124157 and JP-A-2000-123634.

The electrode may be formed by directly performing patterning according to the ink-jet method by using the above-mentioned dispersion containing fine metal particles, or may be formed from a coating film by lithography, laser ablation or the like. Further, it is possible to use a method for patterning according to the printing method such as relief printing, intaglio printing, planographic printing or screen printing. The electrode is shaped, and the solvent is dried. Thereafter, according to need, the electrode is heated along with the shape thereof at a temperature of 100° C. to 300° C., preferably 150° C. to 200° C., whereby fine metal particles are thermally bonded, thus making it possible to form an electrode pattern having an intended shape.

As other materials for the gate electrode, the source electrode and the drain electrode, it is also preferable to use known conductive polymers of which the conductivity is improved by doping or the like as the material. For example, a complex of polyaniline, polypyrrole, polythiophene, polyethylene dioxythiophene (PEDOT) and polystyrene sulfonic acid can be preferably used. These materials can reduce contact resistance between the source electrode and the drain electrodes, and the organic semiconductor layer. To form the electrode, patterning may be performed according to the ink-jet method, and the electrode may be formed from the coating film by lithography, laser ablation, or the like. Further, it is possible to use a method for patterning according to the printing method such as relief printing, intaglio printing, planographic printing or screen printing.

In particular, as the material for forming the source electrode and the drain electrode, of the above-mentioned materials, materials having a low electric resistance in a surface being in contact with the organic semiconductor layer, are preferable. That is, this electric resistance corresponds to a field effect mobility when an electric-current control device is manufactured, and, in order to obtain a high mobility, resistance is required to be as small as possible. Generally, this depends on the magnitude relationship between the work function of electrode materials and the energy level of the organic semiconductor layer.

It is preferred that the following relationship be satisfied, in which a is the work function (W) of materials for the electrodes, b is the ionization potential (Ip) of the organic semiconductor layer, and c is the electron affinity (Af) of the organic semiconductor layer. Herein, a, b, and c are all positive values relative to the vacuum level.

In the case of a p-type organic thin film transistor, it is preferred that the relationship $b-a<1.5$ eV (formula (I)) be satisfied, further preferably $b-a<1.0$ eV. If this relationship is kept in the relationship with the organic semiconductor layer, a high-performance device can be obtained. It is preferable to select as large a work function as possible especially for the work function of the electrode materials. It is preferred that the work function of the electrode material be 4.0 eV or more, further preferably 4.2 eV or more.

The value of the work function of the metal may be selected from the list of effective metals having a work function of 4.0 eV or more stated in Chemistry Manual Basic Edition II, page 493 (Revised third edition, edited by Chemical Society of Japan, issued by Maruzen Co., Ltd., 1983).

Examples of such metals having a large work function include Ag (4.26, 4.52, 4.64, 4.74 eV), Al (4.06, 4.24, 4.41 eV), Au (5.1, 5.37, 5.47 eV), Be (4.98 eV), Bi (4.34 eV), Cd (4.08 eV), Co (5.0 eV), Cu (4.65 eV), Fe (4.5, 4.67, 4.81 eV), Ga (4.3 eV), Hg (4.4 eV), Ir (5.42, 5.76 eV), Mn (4.1 eV), Mo (4.53, 4.55, 4.95 eV), Nb (4.02, 4.36, 4.87 eV), Ni (5.04, 5.22, 5.35 eV), Os (5.93 eV), Pb (4.25 eV), Pt (5.64 eV), Pd (5.55 eV), Re (4.72 eV), Ru (4.71 eV), Sb (4.55, 4.7 eV), Sn (4.42 eV), Ta (4.0, 4.15, 4.8 eV), Ti (4.33 eV), V (4.3 eV), W (4.47, 4.63, 5.25 eV) and Zr (4.05 eV).

Of these, noble metals (Ag, Au, Cu, Pt), and other transition metals (Ni, Co, Os, Fe, Ga, Ir, Mn, Mo, Pd, Re, Ru, V and W) are preferable. In addition to metals, ITO, conductive polymers such as polyanilline and PEDOT:PSS and carbon are preferable. No particular restrictions are imposed on the electrode materials as long as the work function satisfies the formula (I) even if the material contains one or more kinds of the above-mentioned substances having a large work function.

In the case of an n-type organic thin film transistor, it is preferred that the relationship $a-c<1.5$ eV (formula (II)) be satisfied, further preferably $a-c<1.0$ eV. If this relationship is kept, in the relationship with the organic semiconductor layer, a high-performance device can be obtained. It is preferable to select as small a work function as possible especially for the work function of the electrode material. It is preferable to select a work function of the electrode material of 4.3 eV or less, further preferably 3.7 eV or less.

As for the specific examples of such metals having a small work function, selection may be made from the list of effective metals having a work function of 4.3 eV or less described in Chemistry Manual Basic Edition II, page 493 (Revised third edition, edited by Chemical Society of Japan, issued by Maruzen Co., Ltd., 1983). Specific examples include Ag (4.26 eV), Al (4.06, 4.28 eV), Ba (2.52 eV), Ca (2.9 eV), Ce (2.9 eV), Cs (1.95 eV), Er (2.97 eV), Eu (2.5 eV), Gd (3.1 eV), Hf (3.9 eV), In (4.09 eV), K (2.28 eV), La (3.5 eV), Li (2.93 eV), Mg (3.66 eV), Na (2.36 eV), Nd (3.2 eV), Rb (4.25 eV), Sc (3.5 eV), Sm (2.7 eV), Ta (4.0, 4.15 eV), Y (3.1 eV), Yb (2.6 eV), and Zn (3.63 eV). Among these metals, preferred metals are Ba, Ca, Cs, Er, Eu, Gd, Hf, K, La, Li, Mg, Na, Nd, Rb, Y, Yb, and Zn.

No particular restrictions are imposed on the electrode material as long as the work function thereof satisfies the formula (II) even if the material contains one or a plurality of the above-mentioned substances having a small work function. However, metals having a small work function easily deteriorate when they are brought into contact with moisture or oxygen in the atmosphere, and hence, it is preferable to coat these small-work-function metals with metals, such as Ag or Au, which are stable in the air, if necessary. The film thickness necessary for coating is 10 nm or more, and metals can be more surely protected from oxygen and water in proportion to an increase in film thickness. However, in practical use, it is preferable to set the film thickness to be 1 µm or less from the viewpoint of productivity enhancement or the like.

In the organic thin film transistor according to the invention, a buffer layer may be provided between the organic semiconductor layer and the source and drain electrodes in order to improve carrier-injection efficiency, for example. As the buffer layer, for an n-type organic thin film transistor, compounds having an alkaline metal, or alkaline earth metal ionic bonds such as LiF, $Li_2O$, CsF, $Na_2CO_3$, KCl, Mg $F_2$, or $CaCO_3$ used for a cathode of an organic EL device are preferable. In addition, a compound, such as $Alq_3$, which is used as an electron-injecting layer or as an electron-transporting layer in an organic EL device may be inserted as the buffer layer.

For a p-type organic thin film transistor, it is desirable to use $FeCl_3$, a cyano compound such as, TCNQ, $F_4$-TCNQ and HAT, CFx, metal oxides other than oxides of alkaline metals and alkaline earth metals such as $GeO_2$, $MoO_3$, $V_2O_5$, $VO_2$, $V_2O_3$, MnO, $Mn_3O_4$, $ZrO_2$, $WO_3$, $TiO_2$, $In_2O_3$, ZnO, NiO, $HfO_2$, $Ta_2O_5$, $ReO_3$, and $PbO_2$, or an inorganic compound such as ZnS or ZnSe.

In many cases, these oxides cause oxygen deficiency, and hence are suitable for hole injection. Further, this buffer layer may be made of an amine-based compound, such as TPD or NPD, or a compound, such as CuPc, which is used as a hole-injecting layer or as a hole-transporting layer in an organic EL device. Further, two or more of the above-mentioned compounds may preferably be used in combination.

It is known that the buffer layer has the effect of lowering a threshold voltage by lowering the injection barrier of carriers and the effect of driving the transistor at a low voltage. The buffer layer exhibits the effect of low voltage driving for the compounds of the invention.

It suffices that the buffer layer be present as a thin film between the electrodes and the organic semiconductor layer, and the thickness thereof is 0.1 nm to 30 nm, and, preferably 0.3 nm to 20 nm.

(Insulator Layer)

No particular restrictions are imposed on materials used for an insulator layer in the organic thin film transistor of the invention as long as these materials have electric insulating properties and can be formed as thin films. It is possible to use materials, such as metallic oxides (including oxides of silicon), metal nitrides (including nitrides of silicon), polymers, or organic low molecules, whose electrical resistivity is 10 $\Omega$cm or more at room temperature. Especially, an inorganic oxide film having a high relative dielectric constant is preferable.

Examples of inorganic oxides include silicon oxide, aluminum oxide, tantalum oxide, titanium oxide, tin oxide, vanadium oxide, barium strontium titanate, barium zirconate titanate, lead zirconate titanate, lead lanthanum titanate, strontium titanate, barium titanate, lanthanum oxide, fluorine oxide, magnesium oxide, bismuth oxide, bismuth titanate, niobium oxide, strontium bismuth titanate, strontium bismuth tantalate, tantalum pentoxide, bismuth tantalate niobate, trioxide yttrium, and combinations of these compounds. Silicon oxide, aluminum oxide, tantalum oxide and titanium oxide are preferable.

Further, inorganic nitrides, such as silicon nitride ($Si_3N_4$, SixNy (x, y>0)) and aluminum nitride, can be preferably used.

The insulator layer may be made of a precursor containing a metal alkoxide. In this case, for example, the substrate is covered with a solution of the precursor, and is subjected to a chemical solution process including a heat treatment, and, as a result, an insulator layer is formed.

The metals forming the metal alkoxide are selected from transition metals, lanthanides or main group elements. Specific examples of such metals include barium (Ba), strontium (Sr), titanium (Ti), bismuth (Bi), tantalum (Ta), zirconium (Zr), iron (Fe), nickel (Ni), manganese (Mn), lead (Pb), lanthanum (La), lithium (Li), sodium (Na), potassium (K), rubidium (Rb), cesium (Cs), francium (Fr), beryllium (Be), magnesium (Mg), calcium (Ca), niobium (Nb), thallium (T1), mercury (Hg), copper (Cu), cobalt (Co), rhodium (Rh), scandium (Sc) and yttrium (Y). Examples of alkoxides forming the metal alkoxide include those derived from alcohols including methanol, ethanol, propanol, isopropanol, butanol and isobutanol, and those derived from alkoxy alcohols including methoxyethanol, ethoxyethanol, propoxyethanol, butoxyethanol, pentoxyethanol, heptoxyethanol, methoxypropanol, ethoxypropanol, propoxypropanol, butoxypropanol, pentoxypropanol and heptoxypropanol.

In the invention, if the insulator layer is made of the above-mentioned materials, polarization tends to occur easily in the insulator layer, and the threshold voltage of transistor operation can be reduced.

Examples of materials for the insulator layer using organic compounds include polyimide, polyamide, polyester, polyacrylate, a photo-curable resin such as a photoradical polymerization resin and a photocationic polymerization resin, a copolymer containing acrylonitrile components, polyvinylphenol, polyvinylalcohol, novolac resin and cyanoethylpullulan.

Other examples thereof include wax, polyethylene, polychloropyrene, polyethylene terephthalate, polyoxymethylene, polyvinyl chloride, polyvinylidene fluoride, polysulfone, polyimidecyanoethyl pullulan, poly(vinylphenol) (PVP), poly(methylmethacrylate) (PMMA), polycarbonate (PC), polystyrene (PS), polyolefin, polyacrylamide, poly(acrylic acid), a novolac resin, a resol resin, polyimide, polyxylylene, and an epoxy resin. In addition to these resins, polymer materials having a high dielectric constant such as pullulan can be used.

A particularly suitable organic compound material or polymer material for the insulator layer is a material having water repellency. The use of a material having such water repellency makes it possible to control interaction between the insulator layer and the organic semiconductor layer, and makes it possible to enhance the crystallinity of the organic semiconductor layer by utilizing cohesive properties intrinsic to an organic semiconductor, whereby device performance can be improved. A polyparaxylylene derivative described in Yasuda et al., Jpn. J. Appl. Phys. Vol. 42 (2003) pp. 6614-6618 or a compound described in Janos Veres et al., Chem. Mater., Vol. 16 (2004) pp. 4543-4555 can be mentioned as an example of the organic compound.

When the top gate structure shown in FIG. 1 and FIG. 4 is used, the use of the above-mentioned organic compound as the material for the insulator layer is an effective method, since it makes it possible to form a film while lessening damage exerted on the organic semiconductor layer.

The insulator layer may be a mixed layer in which the above-mentioned inorganic or organic compound materials are used in combination, and may be a stacked layer composed of these materials. In this case, device performance can also be controlled by mixing or stacking a material having a high dielectric constant and a material having water repellency, according to need.

Further, the insulator layer may be formed of an anodic oxidized film, or this anodic oxidized film may be used as a part of the structure of the insulator layer. Preferably, the anodic oxidized film is subjected to a sealing process. The anodic oxidized film is formed by anodizing a metal, which can be anodized, by a known method. Aluminum or tantalum can be mentioned as a metal which can be anodized. No particular restrictions are imposed on the anodizing method, and a known method can be used. An oxidized film is formed by performing an anodizing process. Any type of solution can be used as the electrolytic solution used for the anodizing process as long as a porous oxidized film can be formed. In general, sulfuric acid, phosphoric acid, oxalic acid, chromic acid, boric acid, sulfamic acid, benzenesulfonic acid, or a mixed acid produced by combining two or more kinds of the above-mentioned acids, or salts of the above-mentioned acids are used.

Anodizing process conditions cannot be absolutely specified because they variously change depending on an electrolytic solution to be used. In general, appropriate conditions are an electrolyte concentration of 1 to 80 mass %, an electrolyte temperature of 5 to 70° C., an electric current density of 0.5 to 60 A/cm$^2$, a voltage of 1 to 100 volts, and an electrolysis time of 10 seconds to 5 minutes. A preferred anodizing process is to use an aqueous solution of sulfuric acid, phosphoric acid or boric acid as the electrolytic solution and to perform the process by using direct current. Alternating current can also be used instead of direct current. Preferably, the concentration of these acids is 5 to 45 mass %, and the electrolytic process is performed for 20 to 250 seconds under the conditions of an electrolyte temperature of 20 to 50° C. and an electric current density of 0.5 to 20 A/cm$^2$.

As for the thickness of the insulator layer, if the thickness is small, an effective voltage to be applied to the organic semiconductor will be increased, and hence, the driving voltage and threshold voltage of the device itself can be lowered. However, since current leakage between the source electrode and the gate electrode is increased if the thickness is too small, an appropriate film thickness is required to be selected. Normally, the thickness of the insulator layer is 10 nm to 5 μm, and, preferably 50 nm to 2 μm, and more preferably 100 nm to 1 μm.

An arbitrary orientation process may be applied between the insulator layer and the organic semiconductor layer. A preferred example thereof is a method of applying a water-repellent process or the like to the surface of the insulator layer to reduce the interaction between the insulator layer and the organic semiconductor layer, thereby improving the crystallinity of the organic semiconductor layer. Specifically, a method in which a silylating coupling agent such as hexamethyldisilazane, octadecyltrichlorosilane and trichloromethylsilazane, or a material for a self-assembled oriented film such as alkanephosphoric acid, alkanesulfonic acid and alkanecarboxylic acid is brought into contact with the surface of the insulating film in the liquid phase state or the vapor phase state to form a self-assembled film, followed by an appropriate dry process. A method is also preferable in which a film made of, for example, polyimide is formed on the surface of the insulating film as in case of the orientation of liquid crystals, and the surface of the film is subjected to a rubbing process.

Examples of methods employed for forming the insulator layer include dry processes, e.g., the vacuum vapor deposition method, the molecular beam epitaxial growth method, the ion cluster beam method, the low energy ion beam method, the ion plating method, the CVD method, the sputtering method and the atmospheric-pressure plasma method disclosed in JP-A-H11-61406, JP-A-H11-133205, JP-A-2000-121804, JP-A-2000-147209 and JP-A-2000-185362, and wet processes, e.g., the coating method, such as the spray coating method, the spin coating method, the blade coating method, the dip coating method, the casting method, the roll coating method, the bar coating method and the die coating method, and the patterning method such as printing and ink-jetting. An adequate process may be used in accordance with materials. For example, as for the wet process, a method of applying and drying a liquid obtained by dispersing fine particles of an inorganic oxide into an arbitrary organic solvent or water by using a dispersion assisting agent, such as a surfactant, as necessary, or the so-called sol-gel method in which an oxide precursor, for example, an alkoxide solution, is applied and dried, are used.

No particular restrictions are imposed on the method for forming the organic thin film transistor of the invention, and a known method can be used. It is preferred that a series of device forming steps consisting of substrate mounting, gate electrode formation, insulator layer formation, organic semiconductor layer formation, source electrode formation, and drain electrode formation be carried out while completely avoiding contact with the atmosphere according to a desired device structure, because device performance can be prevented from being impaired by moisture or oxygen in the atmosphere as a result of contact with the atmosphere. Even when the device must be formed by being unavoidably brought into contact with the atmosphere once, steps subsequent to the step of organic semiconductor layer formation are performed while completely avoiding contact with the atmosphere, and, immediately before the step of organic semiconductor layer formation, a surface on which the organic semiconductor layer is stacked is purified and activated by, for example, ultraviolet light irradiation, ultraviolet light/ozone irradiation, oxygen plasma, argon plasma or the like, and then the organic semiconductor layer is stacked thereon. Some of the materials for a p-type organic thin film transistor can improve the performance thereof by being brought into contact with the atmosphere once so as to absorb oxygen and other gases. Accordingly, contact with the atmosphere is conducted appropriately depending on materials to be used.

Further, a gas barrier layer may be formed on the entire or part of the outer peripheral surface of the organic transistor device, for example, taking into consideration an influence exerted on the organic semiconductor layer by oxygen or water contained in the atmosphere. Materials normally used in this field can be used for forming the gas barrier layer. Examples of such materials include polyvinyl alcohol, an ethylene-vinyl alcohol copolymer, polyvinyl chloride, polyvinylidene chloride and polychlorotrifluoroethylene. Further, inorganic substances having insulation properties exemplified regarding the above-mentioned insulator layer can also be used.

In the invention, it is possible to provide an organic thin film transistor which can emit light by using current flowing between the source electrode and the drain electrode, and of which light emission is controlled by applying a voltage to the gate electrode. That is, the organic thin film transistor can be used as a light-emitting device (organic EL device). Since the transistor for controlling light emission and the light-emitting device can be integrated, cost can be reduced by increasing the aperture ratio of a display and by simplifying the manufacturing process, and as a result, a practically great advantage can be brought about. When the organic thin film transistor is used as an organic light-emitting transistor, a hole is required to be injected from one of the source electrode and the drain electrode whereas an electron is required to be injected from the remaining electrode, and the following conditions are satisfied to improve light-emission performance.

In order to improve hole-injecting properties, in the organic thin film light-emitting transistor it is preferred that at least one of the source electrode and the drain electrode serve as a hole-injecting electrode. The hole-injecting electrode means an electrode containing a material having a work function of 4.2 eV or more as mentioned above.

In order to improve electron-injection properties, in the organic thin film light-emitting transistor, it is preferred that at least one of the source electrode and the drain electrode be an electron-injecting electrode. An organic thin film light-emitting transistor in which one of the electrodes is a hole-injecting electrode and the other is an electron-injecting electrode is further preferable.

The electron-injecting electrode means an electrode containing a material having a work function of 4.3 eV or less as mentioned above.

In order to improve hole-injection properties, it is preferred that a hole-injecting layer be inserted between at least one of the source and drain electrodes and the organic semiconductor layer. For example, an amine-based material, which is used as a hole-injecting material or a hole-transporting material in an organic EL device, can be used in the hole-injecting layer.

In order to improve electron-injecting properties, it is preferred that an electron-injecting layer be inserted between at least one of the source electrode and the drain electrode, and the organic semiconductor layer. It is further preferred that a hole-injecting layer be between one of the electrodes and the organic semiconductor layer, and an electron-injecting layer be between the remaining electrode and the organic semiconductor layer. As in the case of the hole, an electron-injecting material used in an organic EL device can be used in the electron-injecting layer.

An apparatus using the organic thin film transistor of the invention may be an apparatus which uses the organic thin film transistor of the invention. Examples thereof include a circuit, a personal computer, a display, a mobile phone and electric paper.

EXAMPLES

The invention will be described in detail with reference to the following examples which should not be construed as limiting the scope of the invention.

Example 1

Compound (A-8) was synthesized according to the following scheme:

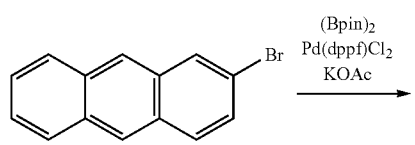

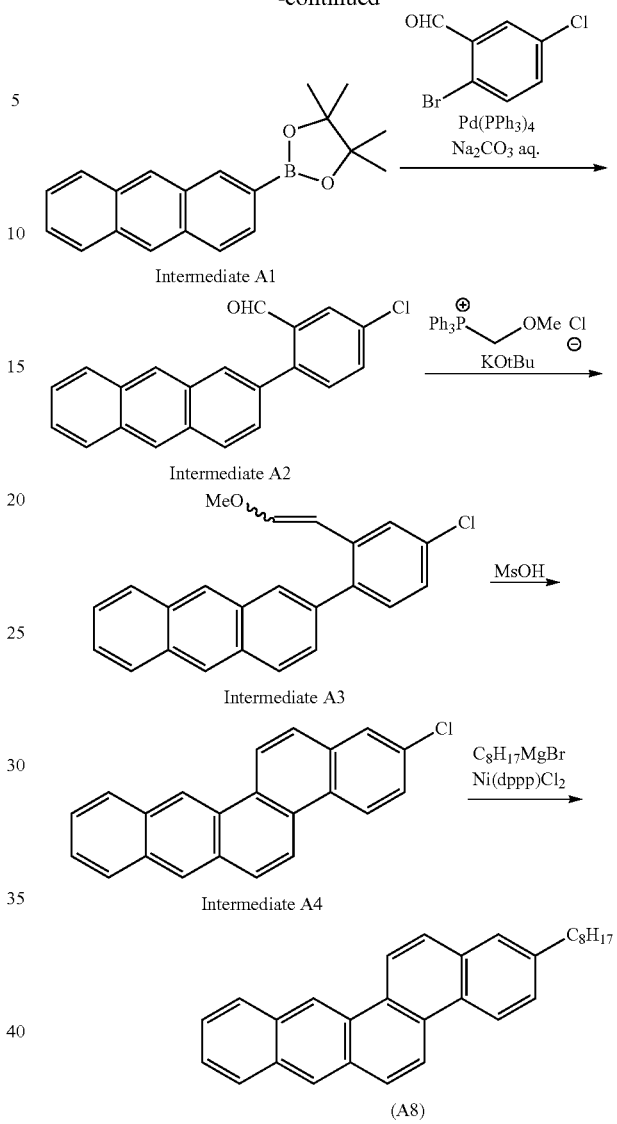

[Synthesis of Intermediate A1]

In a four-necked 200 mL round bottomed flask, 2-bromoanthracene (2.2 g, 8.2 mmol), bis(pinacolato)diboron (2.3 g, 9.0 mmol), (diphenylphosphino)ferrocene dichloropalladium/dichloromethane complex (0.2 g, 0.24 mmol) and potassium acetate (2.6 g, 27 mmol) were placed, and dissolved in anhydrous dimethyl sulfoxide (30 mL). The reaction mixture was stirred at 80° C. for 10 hours. After completion of the reaction, toluene and water were added. An organic phase was extracted with toluene, dried over magnesium sulfate, followed by concentration under reduced pressure. The resulting crude product was purified by column chromatography, whereby intermediate A1 was obtained (1.7 g, yield 68%).

The intermediate A1 was identified by $^1$H-NHR (400 MHz, CDCl$_3$). The results are given below.

δ 8.57 (s, 1H), 8.47 (s, 1H), 8.40 (s, 1H), 8.03-7.99 (m, 2H), 7.98 (d, J=8 Hz, 1H), 7.79 (dd, J=1 Hz, 1H), 7.48-7.45 (m, 2H), 1.41 (s, 12H)

[Synthesis of Intermediate A2]

In a four-necked 200 mL round bottomed flask, intermediate A1 (3.6 g, 12 mmol), 2-bromo-5-chlorobenzaldehyde (2.4 g, 11 mmol) and tetrakis(triphenylphosphine)palladium (0) (0.38 g, 0.33 mmol) were placed, and dissolved in dimethoxyethane (40 mL). 20 mL of an aqueous solution of sodium carbonate (3.8 g, 36 mmol) was added to the reaction solution, and the resulting mixture was heated under reflux for 11 hours. After completion of the reaction, water was added. The solid obtained was filtered and washed with water and methanol. The resulting crude product was purified by column chromatography, whereby intermediate A2 was obtained (3.4 g, yield 98%).

The intermediate A2 was identified by $^1$H-NHR (400 MHz, $CDCl_3$). The results are shown below.

δ 10.03 (s, 1H), 8.50 (s, 1H), 8.48 (s, 1H), 8.12 (d, J=9 Hz, 1H), 8.06-8.03 (m, 3H), 7.95 (s, 1H), 7.66 (dd, J=8.2 Hz, 1H), 7.57 (d, J=8 Hz, 1H), 7.53-7.47 (m, 3H)

[Synthesis of Intermediate A3]

In a four-necked 300 mL round bottomed flask having, (methoxymethyl)triphenylphosphoniumchloride (5.5 g, 16 mmol) was dissolved in anhydrous tetrahydrofuran (120 mL). To this reaction solution, potassium tert-butoxide (1.8 g, 16 mmol) was added, and the resulting mixture was stirred at room temperature for an hour. Furthermore, intermediate A2 (3.4 g, 11 mmol) was added, and the resulting mixture was stirred at room temperature for 10 hours. After completion of the reaction, water and toluene were added. An organic phase was extracted with toluene, dried over magnesium sulfate, followed by concentration under reduced pressure. The resulting crude product was purified by column chromatography, whereby intermediate A3 (4.1 g) was obtained in the form of a mixture of two isomers (quant. E isomer: Z isomer=2:3).

The intermediate A3 was identified by $^1$H-NHR (400 MHz, $CDCl_3$). The results are shown below. Here, for calculation of a value of integral, one unit of hydrogen in Z isomer was taken 1H.

δ 8.44 (s, 2H), 8.42 (s, 3H), 8.18 (d, J=2 Hz, 1H), 8.03-7.99 (m, 6H), 7.53 (d, J=10 Hz, 2.6H), 7.49-7.43 (m, 8H), 7.39-7.23 (m, 8H), 6.49 (d, J=13 Hz, 1.6H), 6.10 (d, J=7 Hz, 1H), 5.76 (d, J=13 Hz, 1.6H), 5.19 (d, J=7 Hz, 1H), 3.78 (s, 3H), 3.49 (s, 5H)

[Synthesis of Intermediate A4]

In a four-necked 300 mL round bottomed recovery flask, intermediate A3 (3.8 g, 11 mmol) was dissolved in anhydrous dichloromethane (160 mL). The reaction mixture was cooled in an ice bath. To this was added drop-wise methanesulfonic acid (0.7 mL, 11 mmol), and the resulting mixture was stirred at 5° C. for an hour and then at room, temperature for 8 hours. After completion of the reaction, the resulting solution was concentrated. Methanol was added thereto, and then the resulting solids were filtered, whereby intermediate A4 was obtained (2.8 g, yield 81%).

The intermediate A4 was identified by $^1$H-NHR (400 MHz, $CDCl_3$). The results are shown below.

δ 9.29 (s, 1H), 8.94 (d, J=9 Hz, 1H), 8.69 (d, J=9 Hz, 1H), 8.56 (d, J=9 Hz, 1H), 8.51 (s, 1H), 8.19-8.08 (m, 3H), 8.00-7.98 (m, 2H), 7.65 (dd, J=9.2 Hz, 1H), 7.61-7.57 (m, 2H)

[Synthesis of Compound A8]

In a four-necked 300 mL round bottomed flask, intermediate A4 (0.70 g, 2.2 mmol) and [1,3-bis(diphenylphosphino) propane]nickel(II)dichloride (0.06 g, 0.11 mmol, 5 mol %) were dissolved in anhydrous THF (20 mL) under Ar atmosphere. The 1.0M THF solution of octylmagnesium bromide (3.4 mL, 3.4 mmol, 1.5 eq) was added thereto, and the resulting mixture was stirred for 2 days. Dilute hydrochloric acid was added to the resulting mixture to quench the reaction, and an organic phase was extracted. After drying the organic phase over magnesium sulfate, and concentrated under reduced pressure. The resulting crude product was purified by column chromatography, whereby compound (A8) was obtained (0.68 g, 78%).

The compound (A8) was identified by $^1$H-NHR (400 MHz, $CDCl_3$). The results are shown below.

δ 9.29 (s, 1H), 8.88 (d, J=10 Hz, 1H), 8.67 (d, J=9 Hz, 1H), 8.62 (d, J=9 Hz, 1H), 8.50 (s, 1H), 8.18-8.16 (m, 1H), 8.08 (m, 2H), 7.80 (s, 1H), 7.57-7.56 (m, 3H), 2.86 (t, J=8 Hz, 2H), 1.78 (t, J=8 Hz, 2H), 1.43-1.26 (m, 10H), 0.89 (t, J=8 Hz, 3H)

The FD-MS (Field Desorption Mass Spectrometry) analysis of the compound (A-8) was shown below.

Calculated value for $C_{30}H_{30}$=390. Found value m/z=390 ($M^+$, 100)

For the compound (A8) obtained, the solubility and stability to oxidization were evaluated according to the following methods. The results are shown in Table 1.

(1) Solubility 0.5 mg of the compound (A8) was weighed, and toluene was added at room temperature so that the mixture was a 0.4 wt % toluene solution. This solution was stirred for 5 minutes, and then the generation of precipitate was visually confirmed. The evaluation was described as follows:

No precipitates were generated: "○",

Precipitates were generated: "X"

Meanwhile, the compound (A8) was dissolved at room temperature in toluene at the concentration of 1 wt % or more.

(2) Stability to Oxidization

The compound (A8) was dissolved in tetrahydrofuran, and the resulting solution was left under fluorescent lights for 40 minutes. HPLC purities before and after light irradiation were measured. The evaluation was described as follows:

A decrease in purity is 1% or less: "○"

A decrease in purity is 1% or more: "X"

[Production of Organic Thin Film Transistor]

A glass substrate was subjected to ultrasonic cleaning in neutral detergent, pure water, acetone and ethanol, each for 30 minutes. After that, gold (Au) was deposited with a thickness of 40 nm by sputtering to form a gate electrode. Subsequently, this substrate was mounted in the film-formation part of heating CVD apparatus. On the other hand, a 250 mg of polyparaxylene derivative [polyparaxylene chloride (Parylene)] (product name; diX-C, manufactured by DAISAN KASEI CO., LTD.) as a precursor material for an insulating layer was put in a petri dish and set in the evaporation part. The heating CVD apparatus was vacuumed using a vacuum pump to reduce the pressure to 5 Pa. After that, the evaporation part was heated to 180° C., the polymerizing part was heated to 680° C., and then the both parts were left for 2 hours. As a result, a 1 µm-thick insulating layer was formed on the gate electrode. Subsequently, the compound (A8) was dissolved in chloroform to obtain a 0.5 wt % solution. Using this stock solution, organic semiconductor layer was formed onto the above-prepared insulating layer by spin coater (1H-D7; produced by MIKASA CO., LTD.) The resulting substrate was dried at 80° C. in a nitrogen atmosphere to remove remaining solvent. By forming a gold film of a thickness of 50 nm through a metal mask, a source electrode and a drain electrode, which were not in contact with each other, were formed so that the interval (channel length: L) was 75 μm. At this time, the width between the source electrode and the drain electrode (channel width: W) was 5 mm, whereby an organic thin film transistor was produced.

A gate voltage ($V_G$) of −70V was applied to the gate electrode in the organic thin film transistor obtained, thereby to lead to p-type driving. A current on/off between the source electrode and the drain electrode was measured to calculate the field effect mobility p of a hole. The results are shown in Table 1.

Example 2

Compound (A12) was synthesized in the same manner as in Example 1, except that dodecylmagnesium bromide was used instead of octylmagnesium bromide in the synthesis of compound (A8).

The compound (A12) was identified by $^1$H-NHR (400 MHz, $CDCl_3$). The results are shown below.

δ 9.29 (s, 1H), 8.88 (d, J=10 Hz, 1H), 8.67 (d, J=9 Hz, 1H), 8.62 (d, J=9 Hz, 1H), 8.50 (s, 1H), 8.18-8.16 (m, 1H), 8.08 (m, 2H), 7.80 (s, 1H), 7.57-7.56 (m, 3H), 2.86 (t, J=8 Hz, 2H), 1.78 (t, J=8 Hz, 2H), 1.43-1.26 (m, 18H), 0.88 (t, J=8 Hz, 3H)

The FD-MS (Field Desorption Mass Spectrometry) analysis of the compound (A12) was shown below.

Calculated value for $C_{34}H_{38}$=446. Found value m/z=446 ($M^+$, 100)

For the compound (A12) obtained, the solubility and stability to oxidization were evaluated in the same manner as in Example 1. An organic thin film transistor was produced and evaluated in the same manner as in Example 1, except that the compound (A12) was used instead of the compound (A8). The results are shown in Table 1.

Meanwhile, the compound (A12) was dissolved at room temperature in toluene at the concentration of 0.4 wt % or more.

Example 3

Intermediate (A7) was synthesized according to the following synthesis scheme:

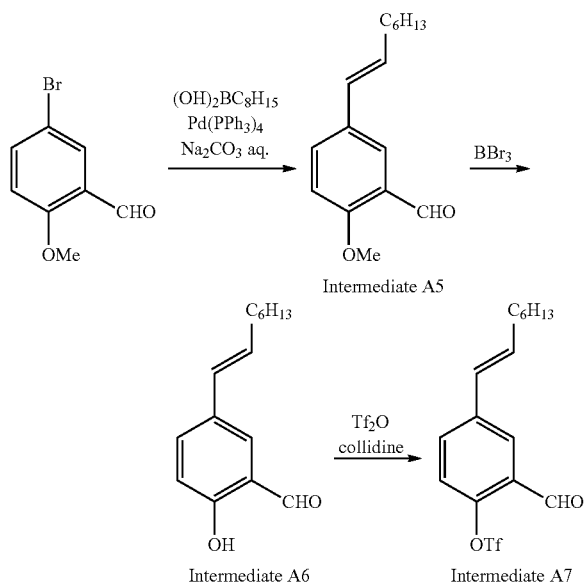

[Synthesis of Intermediate A5]

In a four-necked 300 mL round bottomed flask, boronic acid (2.2 g, 14 mmol), 5-bromo-2-methoxybenzaldehyde (2.8 g, 13 mmol), and tetrakis(triphenylphosphine)palladium(0) (0.5 g, 0.43 mmol) were dissolved in dimethoxyethane (60 mL). To the reaction solution, a 30 mL aqueous solution of sodium carbonate (4.0 g, 38 mmol) was added, and the resulting solution was heated under reflux for 11 hours. After completion of the reaction, water was added. Following extraction with ethyl acetate and drying with magnesium sulfate anhydrous, the solvent was removed under reduced pressure. The resulting crude product was purified by column chromatography, whereby intermediate A5 was obtained (1.6 g, yield 50%).

[Synthesis of Intermediate A6]

In a 100 mL round bottomed flask, intermediate A5 (1.0 g, 3.8 mmol) was dissolved in dichloromethane (10 mL). To the solution, a 1M dichloromethane solution of boron tribromide (5.0 ml, 5.0 mmol) was added at 0° C., and the resulting solution was stirred for an hour. After completion of the reaction, water was added. Following extraction with ethyl acetate and drying over anhydrous magnesium sulfate, the solvent was removed under reduced pressure. The resulting crude product was purified by column chromatography, whereby intermediate A6 was obtained (0.38 g, yield 40%).

[Synthesis of intermediate A7]

In a round bottomed flask, intermediate A6 (0.30 g, 1.3 mmol) and collidine (0.35 ml, 2.7 mmol) were dissolved in dichloromethane (15 mL). To the reaction solution, trifluoromethane sulfonic anhydride (0.35 ml, 2.1 mmol) was added, and the resulting solution was stirred at room temperature for 12 hours. After completion of the reaction, water was added. Following extraction with ethyl acetate and drying over anhydrous magnesium sulfate, the solvent was removed under reduced pressure. The resulting crude product was purified by column chromatography, whereby intermediate A7 was obtained (0.37 g, yield 80%).

[Synthesis of Compound A40]

Compound A40 was obtained in the same manner as in Example 1, except that intermediate A7 was used instead of 2-bromo-5-chlorobenzaldehyde in the synthesis of intermediate A2.

The FD-MS (Field Desorption Mass Spectrometry) analysis of the compound (A40) was shown below.

Calculated value for $C_{30}H_{28}$=388. Found value m/z=388 ($M^+$, 100)

For the compound (A40) obtained, the solubility and stability to oxidization were evaluated in the same manner as in Example 1. An organic thin film transistor was produced and evaluated in the same manner as in Example 1, except that the compound (A40) was used instead of the compound (A8). The results are shown in Table 1.

Meanwhile, the compound (A40) was dissolved at room temperature in toluene at the concentration of 0.4 wt % or more.

Example 4

Intermediate A8 was synthesized according to the following synthesis scheme:

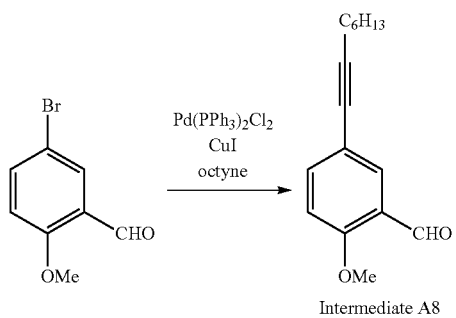

Intermediate A8

[Synthesis of Intermediate A8]

In a four-necked 300 mL round bottomed flask, 1-octyne (1.4 ml, 9.5 mmol), 5-bromo-2-methoxybenzaldehyde (1.7 g, 7.9 mmol), dichlorobis(triphenylphosphine)palladium(II) (0.50 g, 0.71 mmol) and copper iodide (0.27 g, 1.4 mmol) were dissolved in tetrahydrofuran (20 mL). To the reaction solution, triethylamine (20 mL) was added, and the resulting solution was heated under reflux for 12 hours. After completion of the reaction, the reaction mixture was filtered through Celite, followed by concentration under reduced pressure. The resulting crude product was purified by column chromatography, whereby intermediate A8 was obtained (0.77 g, yield 40%).

[Synthesis of Compound A41]

Compound A41 was obtained in the same manner as in Example 3, except that intermediate A8 was used instead of intermediate A5 in the synthesis of intermediate A6.

The FD-MS (Field Desorption Mass Spectrometry) analysis of the compound (A41) was shown below.

Calculated value for $C_{30}H_{26}$=386. Found value m/z=386 ($M^+$, 100)

For the compound (A41) obtained, the solubility and stability to oxidization were evaluated in the same manner as in Example 1. An organic thin film transistor was produced and evaluated in the same manner as in Example 1, except that the compound (A41) was used instead of the compound (A8). The results are shown in Table 1.

Meanwhile, the compound (A41) was dissolved at room temperature in toluene at the concentration of 0.4 wt % or more.

Comparative Example 1

The solubility and stability of oxidization of pentacene were evaluated in the same manner as in Example 1. The results are shown in Table 1. As seen in Table 1, a 0.4 wt % toluene solution of pentacene was not obtained due to insolubility. Furthermore, an organic thin film transistor was tried to produce in the same manner as in Example 1, except that pentacene was used instead of the compound (A8). However, a 0.5 wt % chloroform solution of pentacene was not obtained, whereby the organic thin film transistor could not be produced:

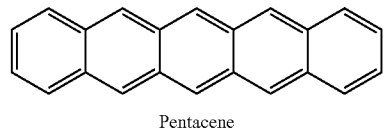 [SMILES: c1ccc2cc3cc4cc5ccccc5cc4cc3cc2c1]

Pentacene

Comparative Example 2

The solubility and stability to oxidization of picene were evaluated in the same manner as in Example 1. The results are shown in Table 1. As seen in Table 1, a tetrahydrofuran solution of picene was not obtained, whereby the stability to oxidization thereof could not be evaluated. Furthermore, an organic thin film transistor was tried to produce in the same manner as in Example 1, except that picene was used instead of the compound (A8). However, a 0.5 wt % chloroform solution of picene was not obtained, whereby the organic thin film transistor could not be produced.

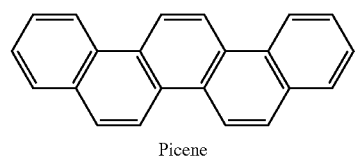 [SMILES: c1ccc2c(c1)ccc1c2ccc2c3ccccc3ccc21]

Picene

TABLE 1

| | Organic semiconductor layer | Solubility | Stability to oxidization | Type of transistor | Field effect mobility [cm²/Vs] |
|---|---|---|---|---|---|
| Example 1 | Compound (A8) | ○ | ○ | p | $1.1 \times 10^0$ |
| Example 2 | Compound (A12) | ○ | ○ | p | $6.6 \times 10^{-5}$ |
| Com. Ex. 1 | Pentacene | x | x | — | — |
| Com. Ex. 2 | Picene | x | — | — | — |
| Example 3 | Compound (A40) | ○ | ○ | p | $5.3 \times 10^{-1}$ |
| Example 4 | Compound (A41) | ○ | ○ | p | $2.1 \times 10^{-1}$ |

Example 5

Compound (B1) was synthesized according to the following synthesis scheme:

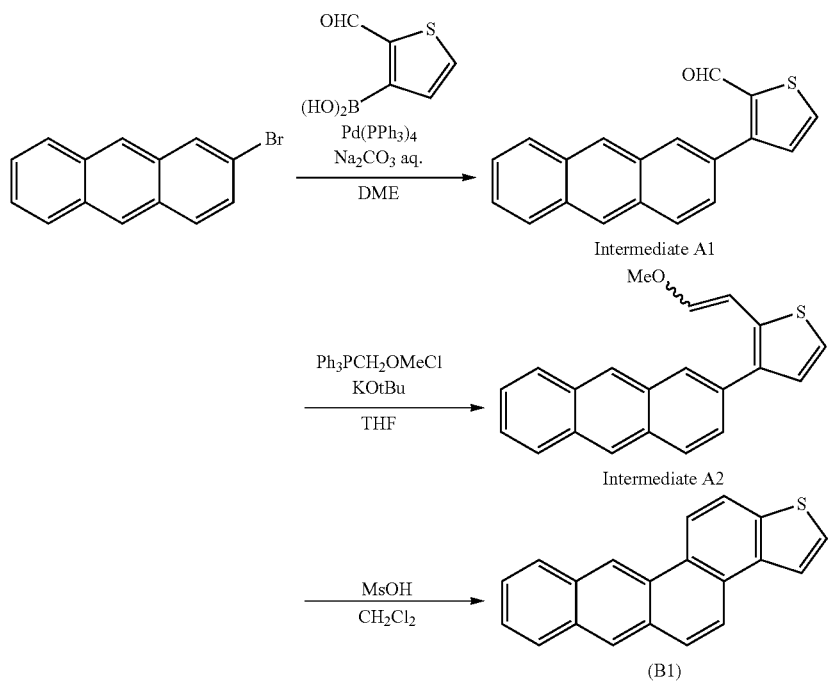

Intermediate A1

Intermediate A2

(B1)

[Synthesis of Intermediate A1]

In a four-necked 300 mL round bottomed flask, 2-bromoanthracene (6.3 g, 25 mmol), (2-formylthiophene-3-yl) boronic acid (5.0 g, 32 mmol, 1.3 eq.) and tetrakis(triphenylphosphine)palladium(0) (1.0 g, 0.87 mmol, 3 mol %) were placed. After the inside of the flask was replaced with argon gas, dimethoxyethane (75 mL) and a 2M aqueous solution of sodium carbonate (35 mL, 70 mmol, 2.8 eq.) was added thereto, and the resulting mixture was heated under reflux for 1 day. After completion of the reaction, toluene and water were added. An organic phase was extracted with toluene, and dried over magnesium sulfate. The resulting crude product was purified by column chromatography, whereby intermediate A1 was obtained (3.5 g, yield 49%).

[Synthesis of Intermediate A2]

In a four-necked 300 mL round bottomed flask, (methoxymethyl)triphenylphosphonium chloride (13 g, 37 mmol, 3.1 eq.) was suspended in anhydrous THF (90 mL). To this solution, potassium tert-butoxide (3.6 g, 32 mmol, 2.7 eq.) was added, and the resulting mixture was stirred at room temperature for an hour. Intermediate A1 (3.5 g, 14 mmol) was added to the reaction solution, and the resulting mixture was stirred at room temperature for 1 day. After completion of the reaction, water and toluene were added. An organic phase was extracted with toluene, and dried over magnesium sulfate. The resulting crude product was purified by column chromatography, whereby intermediate A2 (1.2 g, yield 32%) was obtained in the form of a mixture of two isomers (E isomer: Z isomer=3:1).

[Synthesis of Compound (B1)]

In a 200 mL round bottomed flask, intermediate A2 (1.2 g, 3.8 mmol) was dissolved in anhydrous dichloromethane (60 mL). The reaction solution was cooled in an ice bath. Methanesulfonic acid was added dropwise thereto slowly, and the resulting mixture was stirred at 5° C. for an hour and then at room temperature for 8 hours. After completion of the reaction, the resulting solution was concentrated. Methanol was added thereto, and then the resulting solid was filtered, whereby compound (B1) (0.6 g, yield 65%) was obtained.

The compound (B1) was identified by $^1$H-NHR (400 MHz, CDCl$_3$). The results are shown below.

δ 9.26 (s, 1H), 8.84 (d, 7 Hz, 1H), 8.47 (s, 1H), 8.25 (d, 8 Hz, 1H), 8.16 (d, 9 Hz, 2H), 8.07 (d, 9 Hz, 1H), 8.03 (d, 5 Hz, 1H), 8.00 (d, 9 Hz, 1H), 7.65 (d, 5 Hz, 1H), 7.59-7.52 (m, 2H)

The FD-MS (Field Desorption Mass Spectrometry) analysis of the compound (B1) was shown below.

Calculated value for $C_{20}H_{12}S$=284. Found value m/z=284 (M$^+$, 100)

The solid (0.28 g) of prepared compound (B1) was sublimed under a gentle flow of nitrogen of 1.0 ccm at 180° C./20 Pa, whereby a pale yellow crystal (0.1 g) of the compound (B1) was obtained.

The purity of the pale yellow crystal (purified compound (B1)) was confirmed by HPLC (UV 254 nm). As a result, the main component peak (compound (B1)) had an area % of 96.1.

For the compound (B1) obtained by sublimation purification, the solubility and stability to oxidization were evaluated according to the following method. The results are shown in Table 2.

(I) Solubility 0.5 mg of the compound (B1) was weighed, and toluene was added so that the mixture was a 0.4 wt % toluene solution at room temperature. This solution was stirred for 5 minutes, and then generation of precipitate was visually confirmed. The evaluation was as below:

No precipitates generated: "◯"

Precipitates generated: "X"

(II) Stability to Oxidization

The compound (B1) was dissolved in tetrahydrofuran, and the resulting solution was left under fluorescent lights for 40 minutes. HPLC purities before and after light irradiation were measured. The evaluation was made as below:

A decrease in purity is less than 1%: ◯ (having stability to oxidization)

A decrease in purity is 1% or more: X (having no stability to oxidization)

[Production of Organic Thin Film Transistor Using Application Process]

A glass substrate was subjected to ultrasonic cleaning in neutral detergent, pure water, acetone and ethanol, each for 30 minutes. After that, gold (Au) was deposited with a thickness of 40 nm by sputtering to form a gate electrode. Subsequently, this substrate was mounted in the film-formation part of heating CVD apparatus. On the other hand, a 250 mg of polyparaxylene derivative [polyparaxylene chloride (Parylene)] (diX-C, manufactured by DAISAN KASEI CO., LTD.) as a precursor material for an insulating layer was put in a petri dish and set in the evaporation part. The heating CVD apparatus was vacuumed using a vacuum pump to reduce the pressure to 5 Pa. After that, the evaporation part is heated to 180° C., the polymerizing part is heated to 680° C., and then the both parts are left for 2 hours. As a result, a 1 μm-thick insulating layer was formed on the gate electrode. Subsequently, the compound (B1) was dissolved in chloroform to obtain a 0.5 wt % chloroform solution. Using this stock solution, organic semiconductor layer was formed onto the above-prepared insulating layer by spin coater (1H-D7; produced by MIKASA CO., LTD.) The resulting substrate was dried at 80° C. in a nitrogen atmosphere to remove remaining solvent. By using film formation of gold in a thickness of 50 nm through a metal mask, a source electrode and a drain electrode which are not in contact with each other was formed so that the interval (channel length: L) is 75 μm. At this time, the width between the source electrode and the drain electrode (channel width: W) is 5 mm. In this way, an organic thin film transistor was produced.

A gate voltage ($V_G$) of −70V was applied to the gate electrode in the organic thin film transistor obtained, thereby to lead to p-type driving. A current on/off between the source electrode and the drain electrode was measured to calculate the field effect mobility p of a hole. The results were shown in Table 2.

Example 6

Compound (B17) was synthesized according to the following synthesis scheme:

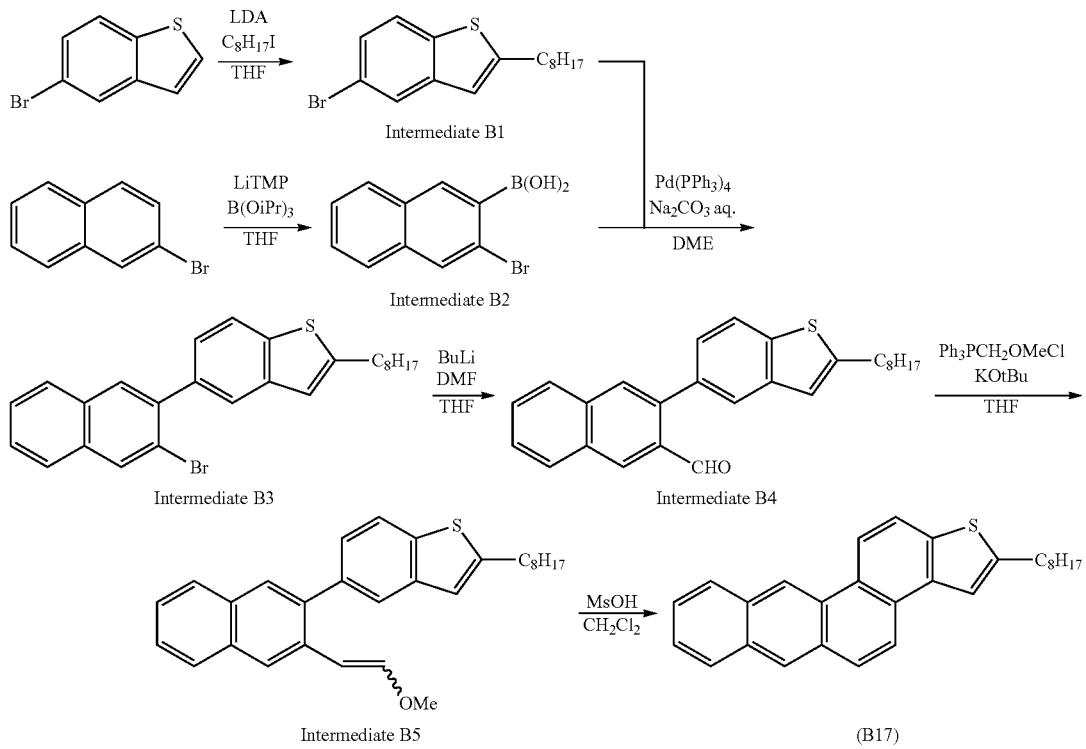

[Synthesis of Intermediate B1]

In a four-necked 300 mL round bottomed flask, 5-bromobenzo[b]thiophene (10.8 g, 50.7 mmol) was dissolved in anhydrous THF (120 mL). The reaction solution was cooled at −78° C. A 1.08M lithium diisopropylamide/hexane solution (56.0 mL, 60.5 mmol, 1.2 eq.) was added thereto, and the mixture solution was allowed to warm to 0° C. and stirred for an hour. After the reaction solution was cooled to −78° C. again, 1-iodo octane (18.0 mL, 99.7 mmol, 2.0 eq.) was added. Then, the mixture was allowed to warm to room temperature, and stirred at room temperature for a day. After completion of the reaction, water and ethyl acetate were added. An organic phase was extracted with ethyl acetate, and dried over magnesium sulfate. The resulting crude product was purified by column chromatography, whereby intermediate B1 was obtained (16.5 g, yield 100%).

[Synthesis of Intermediate B2]

In a nitrogen atmosphere, 2,2,6,6-tetramethylpiperidine (8.2 g, 58 mmol, 1.5 eq.) was dissolved in anhydrous THF (80 ml), and the resulting solution was cooled to −30° C. in dry ice/methanol bath. To this solution, an n-butyllithium/hexane solution (1.6 mol/L, 37 mL, 59 mmol, 1 eq. to TMP) was added dropwise, followed stirring at −20° C. for 20 minutes. The reaction mixture was cooled to −74° C., and triisopropyl borate (18 mL, 78 mmol, 2 eq.) was added. After 5 minutes, a 2-bromonaphthalene/anhydrous THF solution (8 g, 39 mmol/15 mL) was dropped over 10 minutes. The reaction mixture was stirred for 10 hours in a range of −74° C. and room temperature, and left for a night. The reaction mixture was cooled in water bath, quenched with a 5% solution of hydrochloric acid (100 ml) gradually, and washed with toluene (100 ml). This was extracted with a 5% solution of sodium hydroxide (150 ml), a water phase was collected and cooled in ice bath, and the pH of the resultant was adjusted to 2 by adding concentrated hydrochloric acid gradually. The resulting solids were separated by filtration and washed with water to obtain intermediate B2 which are white solids (8.0 g, yield 82%).

[Synthesis of Intermediate B3]

In a round bottomed flask, intermediate B1 (21.0 g, 64.6 mmol, 1.6 eq.), intermediate B2 (10.0 g, 39.9 mmol) and tetrakis(triphenylphosphine) palladium (0) (1.00 g, 0.865 mmol, 2 mol %) were dissolved in dimethoxyethane (200 mL). To this reaction solution, a 2M aqueous sodium carbonate solution (12.6 g/H$_2$O 100 mL, 119 mmol, 3.0 eq.) was added, and the resultant was heated under reflux for 6 hours. After completion of the reaction, water and toluene were added, and an organic phase was extracted with toluene and dried with sodium sulfate. The resulting crude product was purified by column chromatography, whereby intermediate B3 was obtained (8.40, yield 47%).

[Synthesis of Intermediate B4]

In a round bottomed flask, intermediate B3 (8.4 g, 19 mmol) was dissolved in anhydrous THF (180 mL) and anhydrous toluene (100 mL). After the reaction solution was cooled to −60° C., a 1.6M n-butyllithium/hexane solution (18 mL, 28 mmol, 1.5 eq.) was added, followed by stirring for an hour. Then anhydrous DMF (2.9 mL, 38 mmol, 2.0 eq.) was added, the mixture was heated to room temperature and stirred for a day. Water and toluene were added. An organic phase was extracted with toluene, and dried over sodium sulfate. The resulting crude product was purified by column chromatography, whereby intermediate B4 was obtained (4.1 g, yield 55%).

[Synthesis of Intermediate B5]

In a four-necked 300 mL round bottomed flask, (methoxymethyl)triphenylphosphonium chloride (10 g, 30 mmol, 2.9 eq.) was suspended in anhydrous THF (100 mL). To this solution, potassium tert-butoxide (2.8 g, 25 mmol, 2.5 eq.) was added, and the resulting solution was stirred at room temperature for 30 minutes. An anhydrous THF solution (30 mL) of intermediate B4 (4.1 g, 10 mmol) was added, followed stirring at room temperature for a day. Water and toluene were added. An organic phase was extracted with toluene, and dried over magnesium sulfate. The resulting crude product was purified by column chromatography, whereby intermediate B5 was obtained in the form of a mixture of two isomers (4.3 g, yield 100%).

[Synthesis of Compound (B17)]

In a four-necked 300 mL round bottomed flask, intermediate B5 (4.3 g, 10 mmol) was dissolved in anhydrous dichloromethane (200 mL). The reaction solution was cooled in an ice bath. Methanesulfonic acid (2 drops) was added thereto slowly, and the resulting mixture was stirred in an ice bath for a day. After completion of the reaction, water was added. An organic phase was extracted with dichloromethane and dried over sodium sulfate. The resulting crude product was purified by column chromatography, whereby intermediate (B17) was obtained (1.2 g, yield 31%).

The intermediate (B17) was identified by $^1$H-NHR (400 MHz, CDCl$_3$). The results are shown below.

δ 9.23 (s, 1H), 8.74 (d, j=9 Hz, 1H), 8.44 (s, 1H), 8.15 (t, j=9 Hz, 2H), 8.07-8.02 (m, 2H), 7.95 (d, j=9 Hz, 1H), 7.68 (s, 1H), 7.57-7.54 (m, 2H), 3.03 (t, j=9 Hz, 2H), 1.87-1.82 (m, 2H), 1.49-1.29 (m, 10H), 0.89 (t, j=7 Hz, 3H)

The FD-MS (Field Desorption Mass Spectrometry) analysis of the compound (B17) was shown below.

Calculated value for $C_{28}H_{28}S$=396. Found value m/z=396 (M$^+$, 100)

The solid (1.0 g) of prepared compound (B17) was sublimed under a gentle stream of nitrogen of 1.0 ccm at 220° C./18 Pa, whereby a pale yellow crystal (0.9 g) of the compound (B17) was obtained.

The purity of the pale yellow crystal (purified compound (B17)) was confirmed by HPLC (UV 254 nm). As a result, the main component peak (compound (B17)) had an area % of 99.3.

For the compound (B17) obtained, the solubility and stability to oxidization were evaluated in the same manner as in Example 5. An organic thin film transistor was produced by using application process and evaluated in the same manner as in Example 5, except that the compound (B17) was used instead of the compound (B1). The results are shown in Table 2.

Example 7

Compound (B552) was synthesized according to the following synthesis scheme:

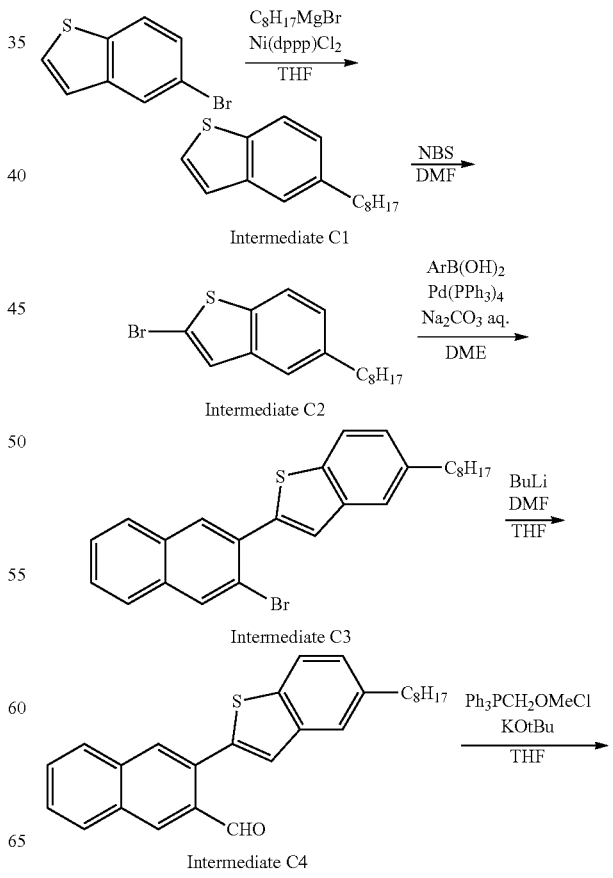

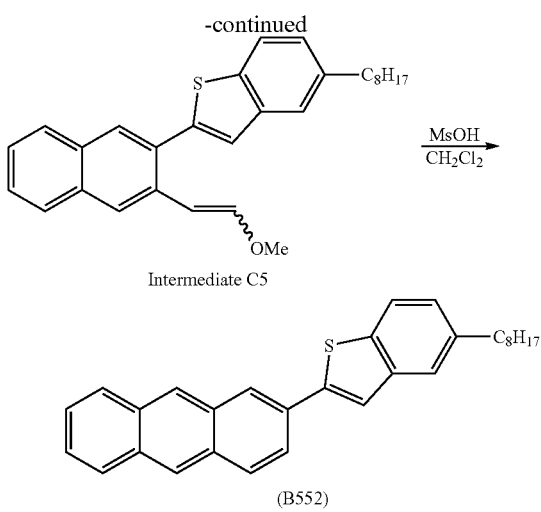

Intermediate C5

(B552)

[Synthesis of Intermediate C1]

In a 300 mL round bottomed flask, 5-bromobenzo[b]thiophene (5.6 g, 26 mmol) and dichloro(diphenylphosphinopropyne)nickel (0.54 g, 1.0 mol, 4 mol %) were dissolved in anhydrous THF (50 mL). A 1.0M octylmagnesium bromide solution (31 mL, 31 mmol, 1.2 eq.) was added thereto, and the mixture solution was stirred at room temperature for one day. After the completion of the reaction, hydrochloric acid and toluene were added, and an organic phase was extracted with toluene, and dried over sodium sulfate. The resulting crude product was purified by column chromatography, whereby intermediate C1 was obtained (4.1 g, yield 62%).

[Synthesis of Intermediate C2]

In a four-necked 300 mL round bottomed flask, intermediate C1 (4.1 g, 16 mmol) was dissolved in anhydrous DMF (80 mL). To this reaction solution, N-bromosuccinimide (3.8 g, 21 mmol, 1.3 eq.) was added. The resultant solution was stirred at room temperature for one day. After completion of the reaction, water and ethyl acetate were added, and an organic phase was extracted with ethyl acetate and dried with sodium sulfate. The resulting crude product was purified by column chromatography, whereby intermediate C2 was obtained (5.0 g, yield 100%).

[Synthesis of Intermediate C3]

In a four-necked 300 mL round bottomed flask, intermediate C3 (5.0 g, 15 mmol), 3-bromonapthalene-2-ylborinic acid (3.9 g, 15 mmol) and tetrakis(triphenylphosphine) palladium (0) (1.0 g, 0.87 mmol, 6 mol %) were dissolved in dimethoxyethane (100 mL). To this reaction solution, a 2M aqueous sodium carbonate solution (5.0 g/$H_2O$, 50 mL, 47 mmol, 3.1 eq.) was added. The reaction mixture was heated under reflux for 2 days. After completion of the reaction, water and toluene were added, and an organic phase was extracted with toluene, and dried with sodium sulfate. The resulting crude product was purified by column chromatography, whereby intermediate C3 was obtained (5.5 g, yield 80%).

[Synthesis of Intermediate C4]

In a four-necked 300 mL round bottomed flask, the intermediate C4 (5.5 g, 12 mmol) was dissolved in anhydrous THF (50 mL). The reaction solution was cooled to −78° C. A 1.67M n-butyllithium/hexane solution (11 mL, 18 mmol, 1.5 eq.) was added thereto, and the mixture solution was stirred for an hour. Then, anhydrous DMF (2 mL, 14 mmol, 1.2 eq.) was added, and the reaction mixture was warmed to room temperature, for 5 hours. Water and toluene were added. An organic phase was extracted with toluene, and dried over sodium sulfate. The resulting crude product was purified by column chromatography, whereby intermediate C4 was obtained (3.2 g, yield 67%).

[Synthesis of Intermediate C5]

In a four-neck flask, (methoxymethyl)triphenylphosphonium chloride (8.2 g, 24 mmol, 3.0 eq.) was suspended in anhydrous THF (50 mL). Potassium tert-butoxide (2.3 g, 21 mmol, 2.6 eq.) was added, and the resultant mixture was stirred at room temperature for 30 minutes. Then an anhydrous THF solution (20 mL) of the intermediate C4 (3.2 g, 8.0 mmol) was added, and the resultant mixture was stirred at room temperature for a day. Water and toluene were added, and an organic phase was extracted with toluene and dried with magnesium sulfate. The resulting crude product was purified by column chromatography, whereby intermediate C5 was obtained (1.5 g, yield 44%) was obtained as a mixture of two types of isomers.

[Synthesis of Compound (B552)]

In a four-necked 300 mL round bottomed flask, the intermediate C5 (1.5 g, 3.5 mmol) was dissolved in anhydrous dichloromethane (70 ml). The reaction solution was cooled in an ice bath, and methanesulfonic acid (5 drops) was added dropwise slowly. The resultant mixture was stirred in an ice bath for a day. After completion of the reaction, water was added, and an organic phase was extracted with dichloromethane and dried over sodium sulfate. The resulting crude product was purified by column chromatography, whereby compound (6552) was obtained (0.6 g, yield 29%).

The compound (B552) was identified by $^1$H-NHR (400 MHz, $CDCl_3$). The results are shown below.)

δ9.05, (d, 9 Hz, 1H), 8.81 (d, 6 Hz, 1H), 8.80 (d, 6 Hz, 1), 8.71 (s, 1H), 8.10 (d, 9 Hz, 1H), 8.05 (d, 9H, 1H), 8.00 (d, 8 Hz, 1H), 7.91 (d, 8 Hz, 1H), 7.72 (t, 8 Hz, 1H), 7.64 (t, 8 Hz, 1H), 7.37 (d, 8H, 1H), 2.91 (t, 8 Hz, 2H), 1.83-1.76 (m, 2H), 1.47-1.30 (m, 10H), 0.88 (t, 6 Hz, 3H)

The FD-MS (Field Desorption Mass Spectrometry) analysis of the compound (B552) was shown below.

Calculated value for $C_{28}H_{28}S$=396. Found value m/z=396 ($M^+$, 100)

The solid (0.6 g) of prepared compound (B552) was sublimed under a gentle stream of nitrogen of 1.0 ccm at 220° C./19 Pa, whereby a pale yellow crystal (0.5 g) of the compound (6552) was obtained.

The purity of the pale yellow crystal (purified compound (6552)) was confirmed by HPLC (UV 254 nm). As a result, the main component peak (compound (B552)) had an area % of 99.3.

For the compound (B552) obtained, the solubility and stability to oxidization were evaluated in the same manner as in Example 5. An organic thin film transistor was produced by using application process and evaluated in the same manner as in Example 5, except that the compound (B552) was used instead of the compound (B1). The results are shown in Table 2.

Comparative Example 3

The solubility and stability to oxidization of the following pentacene (A) were evaluated in the same manner as in Example 5. The results are shown in Table 2. As seen in Table 2, a 0.4 wt % toluene solution of pentacene (A) was not obtained. Furthermore, an organic thin film transistor was tried to produce in the same manner as in Example 5, except that pentacene (A) was used instead of the compound (B1).

However, a 0.5 wt % chloroform solution of pentacene (A) was not obtained, whereby the manic thin film transistor could not be produced.

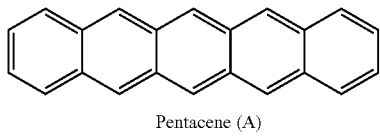 [SMILES: c1ccc2cc3cc4cc5ccccc5cc4cc3cc2c1]

Pentacene (A)

Comparative Example 4

The solubility and stability to oxidization of picene (B) were evaluated in the same manner as in Example 5. The results are shown in Table 2. As seen in Table 2, since a tetrahydrofuran solution of picene (B) was not obtained, it was not able to evaluate the stability to oxidization. Furthermore, an organic thin film transistor was tried to produce in the same manner as in Example 5, except that picene (B) was used instead of the compound (B1). However, a 0.5 wt % chloroform solution of picene (B) was not obtained, whereby the organic thin film transistor could not be produced.

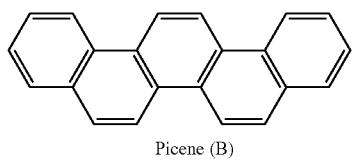 [SMILES: c1ccc2c(c1)ccc1c2ccc2c3ccccc3ccc21]

Picene (B)

TABLE 2

| Organic semiconductor layer | | Solubility | Stability to oxidization | Type of transistor | Field effect mobility [cm²/Vs] |
|---|---|---|---|---|---|
| Example 5 | Compound (B1) | ○ | ○ | p | $1.1 \times 10^{-3}$ |
| Example 6 | Compound (B17) | ○ | ○ | p | $4.1 \times 10^{-1}$ |
| Example 7 | Compound (B552) | ○ | ○ | p | $1.9 \times 10^{-4}$ |
| Com. Ex. 3 | Pentacene (A) | x | x | — | — |
| Com. Ex 4 | Picene (B) | x | — | — | — |

Example 8

Compound (C56) was synthesized according to the following synthesis scheme:

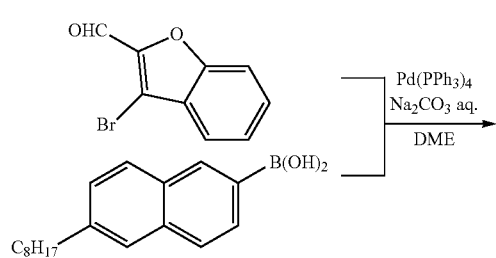

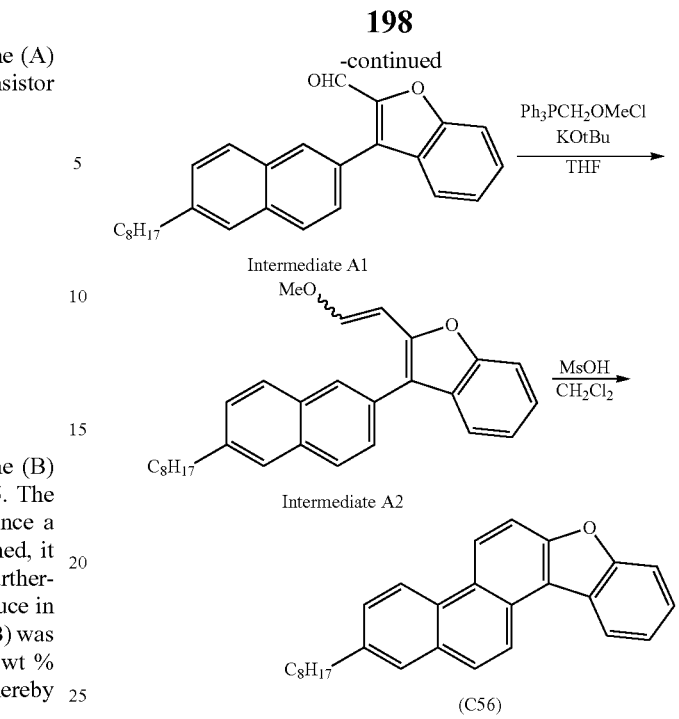

[Synthesis of Intermediate A1]

In a four-necked 300 mL round bottomed flask, 3-bromobenzofuran-2-carbaldehyde (2.96 g, 13.2 mmol), 6-octyl-naphtnalene-2-ylboronic acid (4.38 g, 15.4 mmol, 1.2 eq.) and tetrakis(triphenylphosphine)palladium (0) (1.00 g, 0.865 mmol, 7 mol %) were dissolved in DME (100 mL). 1.0M of an aqueous sodium carbonate solution (40.0 mL, 40.0 mmol, 3.0 eq.) was added, and the resultant was heated under reflux for 4 hours. An organic phase was extracted with toluene, dried with sodium sulfate and concentrated under reduced pressure. The resulting crude product was purified by column chromatography, whereby intermediate (A1) (5.33 g, quant.) was obtained.

[Synthesis of Intermediate A2]

In a four-necked 300 mL round bottomed flask, (methoxymethyl)triphenylphosphonium chloride (14 g, 41 mmol, 3.0 eq.) was suspended in anhydrous TFT (70 mL). To this reaction solution, potassium tert-butoxide (3.9 g, 35 mmol, 2.5 eq.) was added, and the resulting mixture was stirred at room temperature for 30 minutes. Then an aqueous TFT solution (30 mL) of intermediate A1 (5.3 g, 14 mmol) was added, and the resulting mixture was stirred at room temperature for a day. An organic phase was extracted with water and toluene, dried over magnesium sulfate, followed by concentration under reduced pressure. The resulting crude product was purified by column chromatography, whereby intermediate A2 (5.1 g, yield 90%) was obtained in the form of a mixture of two isomers.

[Synthesis of Compound (C56)]

In a four-necked 300 mL round bottomed flask, the intermediate A2 (5.1 g, 12 mmol) was dissolved in anhydrous dichloromethane (30 ml). The reaction solution was cooled in an ice bath. Methansulfonic acid (2 drops) was added dropwise slowly, and the resultant mixture was stirred for a day at room temperature. After the completion of the reaction, methanol was added, and resulting precipitates were filtered, whereby compound (C56) (1.8 g, yield 38%) was obtained.

The compound (C56) was identified by ¹H-NHR (400 MHz, CDCl₃).

The FD-MS (Field Desorption Mass Spectrometry) analysis of the compound (C56) is shown below.

Calculated value for $C_{28}H_{28}O=380$. Found value m/z=380 (M+, 100)<

FD-MS Measurement>
Apparatus: HX110 (manufactured by JEOL Ltd.)
Conditions: accelerated voltage 8 kV
Scan range m/s=50 to 1500

The solid (1.44 g) of prepared compound (C56) sublimed at 220° C./$3.1 \times 10^{-2}$ Pa, whereby a white crystal (0.40 g) was obtained.

The purity of the pale yellow crystal of purified compound (C56) was confirmed by HPLC (UV 254 nm). As a result, the main component peak (compound (C56)) had an area % of 98.8.

For the compound (C56) obtained by sublimation purification, the solubility and stability to oxidization were evaluated by the following methods. The results are shown in Table 3.

(I) Solubility 0.5 mg of the compound (C56) was weighed, and each solvent (hexane and toluene) was added so that the mixture was a 0.4 wt % solution at room temperature. This solution was stirred for 5 minutes, and then the generation of precipitate was visually confirmed. The evaluation was described as follows:

No precipitates generated: "○" (dissolved)
Precipitates were generated: "X" (not dissolved)

(II) Stability to Oxidation

The compound (C56) was dissolved in tetrahydrofuran, and the resulting solution was left under fluorescent lights for 40 minutes. HPLC purities before and after light irradiation were measured. The evaluation was conducted as follows:

A decrease in purity is less than 1%: "○" (having stability to oxidation)

A decrease in purity is 1% or more: "X" (having no stability to oxidation)

[Formation of Organic Thin Film Transistor Using Application Process]

A glass substrate was subjected to ultrasonic cleaning for 30 minutes each with a neutral detergent, pure water, acetone and ethanol. Then, gold (Au) was formed into a film of 40 nm by sputtering, thereby to form a gate electrode. Subsequently, this substrate was installed on the film-forming part of a thermal CVD apparatus. 250 mg of a polyparaxylene derivative [polyparaxylene chloride (Parylene)] (trade name: diX-C; manufactured by Daisan KASEI CO., LTD.) as a material for an insulator layer was placed in a petri dish and installed in the evaporation part of the raw material. After vacuuming the thermal CVD apparatus by means of a vacuum pump to a pressure of 5 Pa, the evaporation part was heated to 180° C. and a polymerization part was heated to 680° C., and the material was allowed to stand for 2 hours, whereby an insulator layer with a thickness of 1 μm was formed on the gate electrode. Subsequently, the compound (C56) was dissolved in chloroform to obtain a 0.5 wt % chloroform solution. Using this stock solution, organic semiconductor layer was formed onto the above-prepared substrate by means of a spin coater (1H-D7; manufactured by Mikasa Co., Ltd.) on which the gate electrode and the insulating layer had been formed and dried at 80° C. in the nitrogen atmosphere, to remove remaining solvent (film thickness: 50 nm). Subsequently, a source electrode and a drain electrode which did not contact each other were formed such that the distance between them (channel length: L) became 75 μm by forming gold into a 50 nm-thick film through a metal mask. Film formation was conducted such that the width (channel width W) of the source electrode and the drain electrode become 5 mm, whereby an organic thin film transistor was formed.

A gate voltage $V_G$ of −70 V was applied to the gate electrode of the resulting organic thin film transistor to allow it drive as a p-type transistor. The on/off of the current flowing between the source electrode and the drain electrode was measured, thereby to calculate the field effect mobility p of the hole. The results are shown in Table 3.

$$I_D = (W/2L) \cdot C\mu \cdot (V_G - V_T)^2$$

In the formula, $I_D$ is source-drain current, W is a channel width, L is a channel length, C is an electric capacitance per unit area of the gate insulator layer, $V_T$ is a gate threshold voltage and $V_G$ is a gate voltage.

Example 9

Compound (C146) was synthesized according to the following synthesis scheme:

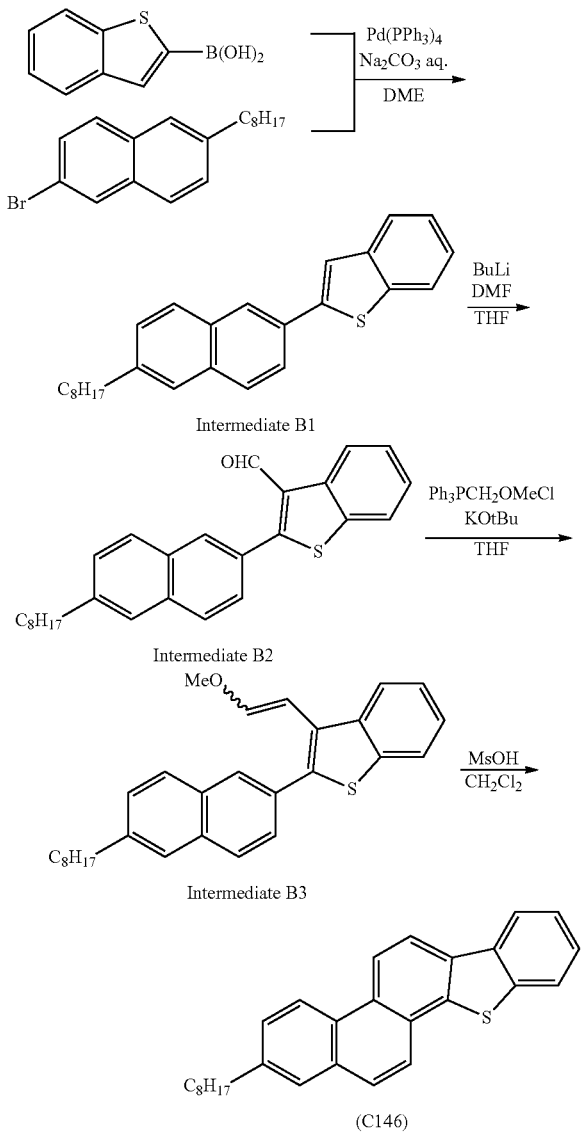

[Synthesis of Intermediate B1]

In a four-necked 300 mL round bottomed flask, benzo[b]thiophene-2-ylboronic acid (5.32 g, 30.0 mmol), 2-bromo-6-octylnaphthalene (9.54 g, 30.0 mmol, 1.0 eq.) and tetrakis(triphenylphosphine)palladium(0) (1.00 g, 0.865 mmol, 3 mol %) were dissolved in DME (150 mL). An aqueous solution (100 mL) of sodium carbonate (9.54 g, 90.0 mmol, 3.0 eq.) was added, and the resultant mixture was heated under reflux for 2 days. An organic phase was extracted with toluene, dried over magnesium sulfate, followed by concentration under reduced pressure. The resulting crude product was purified by column chromatography, whereby intermediate B1 (5.59 g, yield 50%) was obtained.

[Synthesis of Intermediate B2]

In a four-necked 300 mL round bottomed flask, intermediate B1 (3.0 g, 8.6 mmol) was dissolved in anhydrous THF (35 mL). After the reaction solution was cooled at −78° C., a 1.67M n-butyllithium/hexane solution (5.7 mL, 9.5 mmol, 1.1 eq.) was added. The resultant mixture was allowed to warm to room temperature, followed by stirring for an hour. The reaction solution was cooled in an ice bath, and anhydrous DMF (1.0 mL, 12 mmol, 1.5 eq.) was added, the mixture was stirred for a day. Water was added. An organic phase was extracted with toluene, and dried over magnesium sulfate. The resulting crude product was purified by column chromatography, whereby intermediate B2 was obtained (0.6 g, yield 17%).

[Synthesis of Intermediate B3]

In a four-necked 300 mL round bottomed flask, (methoxymethyl)triphenylphosphonium chloride (4.1 g, 12 mmol, 3.0 eq.) was suspended in anhydrous THF (25 mL). To this reaction solution, potassium tert-butoxide (1.2 g, 10 mmol, 2.7 eq.) was added, and the resulting mixture was stirred at room temperature for 30 minutes. Then anhydrous THF solution (10 mL) of the intermediate B2 (1.5 g, 3.9 mmol) was added, and the resulting mixture was stirred at room temperature for a day. Water and toluene were added. An organic phase was extracted with toluene, dried over magnesium sulfate, followed by concentration under reduced pressure. The resulting crude product was purified by column chromatography, whereby intermediate B3 (1.7 g, quant.) was obtained in the form of a mixture of two isomers.

[Synthesis of Compound (C146)]

In a four-necked 300 mL round bottomed flask, the intermediate B3 (1.7 g, 3.9 mmol) was dissolved in anhydrous dichloromethane (30 mL). The reaction solution was cooled in an ice bath. Methanesulfonic acid (2 drops) was dropped thereto slowly, and the resulting mixture was stirred at room temperature for a day. After completion of the reaction, water was added. An organic phase was extracted with dichloromethane and dried over sodium sulfate, followed by concentration under reduced pressure. The resulting crude product was purified by column chromatography, whereby intermediate (C146) was obtained (1.1 g, yield 69%).

The intermediate (C146) was identified by $^1$H-NHR (400 MHz, CDCl$_3$).

The FD-MS (Field Desorption Mass Spectrometry) analysis of the compound (C146) was shown below.

Calculated value for $C_{28}H_{28}S$=396. Found value m/z=396 (M$^+$, 100)

The solid (1.06 g) of prepared compound (C146) was sublimed at 240° C./19 Pa under 1.0 ccm nitrogen flow, whereby a white crystal (1.01 g) of the compound (C146) was obtained.

The purity of the pale yellow crystal of purified compound (C146) was confirmed by HPLC (UV 254 nm). As a result, the main component peak (compound (C146)) had an area % of 99.6.

For the compound (C146) obtained, the solubility and stability to oxidization were evaluated in the same manner as in Example 8. Further, an organic thin film transistor was produced and evaluated by a coating process in the same manner as in Example 8, except that the compound (C146) was used instead of the compound (C56). The results are shown in Table 3.

Example 10

Compound (C191) was synthesized according to the following synthesis scheme:

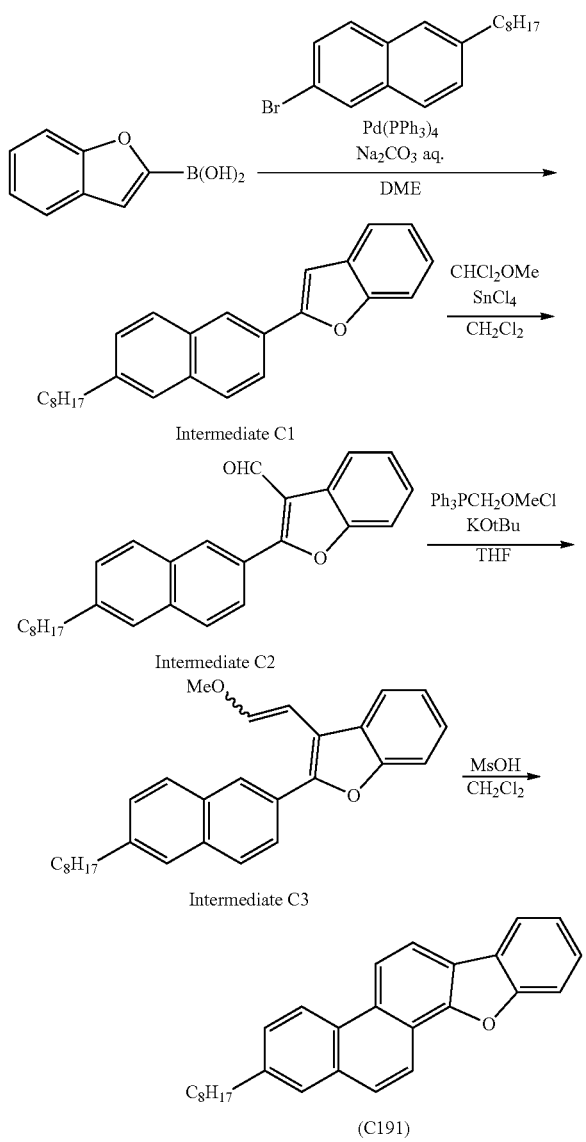

[Synthesis of Intermediate C1]

In a four-necked 300 mL round bottomed flask, 2-bromo-6-octylnaphthalene (8.2 g, 26 mmol), benzofurane-2-ylboronic acid (5.0 g, 31 mmol, 1.2 eq.) and tetrakistriphenylphosphine palladium (0) (1.0 g, 0.87 mmol, 5 mol %) were dissolved in DME (100 mL). An aqueous solution (100 mL) of sodium carbonate (10 g, 96 mmol, 3.7 eq.) was added, and the resultant mixture was heated under reflux for a day. An organic phase was extracted with toluene, dried over sodium sulfate, followed by concentration under reduced pressure. The resulting crude product was purified by column chromatography, whereby intermediate (C1) was obtained (3.7 g, yield 40%).

[Synthesis of Intermediate C2]

In a round bottomed flask, the starting material (1.0 g, 2.8 mmol) was dissolved in anhydrous dichloroethane (18 mL). The reaction solution was cooled in an ice bath, tin tetrachloride (0.6 mL, 5.3 mmo, 1.9 eq.) and dichloromethylmethylether (0.3 mL, 3.4 mmol, 1.2 eq.) was added, and the resultant solution was stirred for 8 hours. After completion of the reaction, hydrochloric acid was added, and an organic phase was extracted with toluene, dried over sodium sulfate, followed by concentration under reduced pressure. The resulting crude product was purified by column chromatography, whereby intermediate (C2) was obtained (1.0 g, yield 93%).

[Synthesis of Intermediate C3]

In a four-necked 300 mL round bottomed flask, (methoxymethyl)triphenylphosphonium chloride (2.7 g, 7.9 mmol, 3.0 eq.) was dissolved in anhydrous THF (26 mL). Potassium tert-butoxide (0.73 g, 6.5 mmol, 2.5 eq.) was added, and the resultant mixture was stirred at room temperature for 30 minutes. The aldehyde (1.0 g, 2.6 mmol) was added, and the resultant mixture was stirred at room temperature for a day. Water and toluene were added, and an organic phase was extracted with toluene, dried over sodium sulfate, followed by concentration under reduced pressure. The resulting crude product was purified by column chromatography, whereby intermediate (C3) was obtained (1.1 g, yield 100%) in the form of a mixture of two isomers.

[Synthesis of Compound (C191)]

In a 1-necked 200 mL round bottomed flask, starting material (1.1 g, 2.8 mmol) was dissolved in anhydrous dichloroethane (40 mL). The reaction solution was cooled in an ice bath, and methanesulfonic acid (10 drops) was added, followed by stirring for 1 hours. Methanesulfonic acid (20 drops) was further added, followed by stirring for 4 hours. After completion of the reaction, water was added, and an organic phase was extracted with chloroform, dried over sodium sulfate, followed by concentration under reduced pressure. The resulting crude product was purified by column chromatography, whereby intermediate (C191) was obtained (0.7 g, yield 71%).

The compound (C191) was identified by $^1$H-NHR (400 MHz, CDCl$_3$).

The FD-MS (Field Desorption Mass Spectrometry) analysis of the compound (C191) is shown below.

Calculated value for $C_{28}H_{28}S$=380. Found value m/z=380 (M$^+$, 100)

The solid (0.54 g) of prepared compound (C191) was sublimed under a flow of nitrogen of 1.0 ccm at 240° C./19 Pa, whereby a white crystal (0.51 g) was obtained.

The purity of the pale yellow crystal of purified compound (C191) was confirmed by HPLC (UV 254 nm). As a result, the main component peak (compound (C191)) had an area % of 99.7.

For the compound (C191) obtained, the solubility and stability to oxidization were evaluated in the same manner as in Example 8. Further, an organic thin film transistor was produced and evaluated by a coating process in the same manner as in Example 8, except that the compound (C191) was used instead of the compound (C56). The results are shown in Table 3.

Comparative Example 5

The solubility and stability to oxidization of the following pentacene (A) were evaluated in the same manner as in Example 8. The results are shown in Table 3. As seen in Table 3, a 0.4 wt % toluene solution and a 0.4 wt % hexane solution of pentacene (A) were not obtained. Furthermore, an organic thin film transistor was tried to produce in the same manner as in Example 8, except that pentacene (A) was used instead of the compound (C56). However, a 0.5 wt % chloroform solution of pentacene (A) was not obtained, whereby the organic thin film transistor could not be produced.

Pentacene (A)

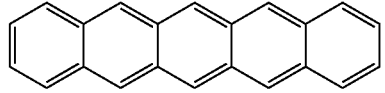

Comparative Example 6

The solubility and stability to oxidization of picene (B) were evaluated in the same manner as in Example 8. The results are shown in Table 3. As seen in Table 3, a tetrahydrofuran solution of picene (B) was not obtained and hence the stability to oxidization could not be evaluated. Furthermore, an organic thin film transistor was tried to produce in the same manner as in Example 8, except that picene (B) was used instead of the compound (C56). However, a 0.5 wt % chloroform solution of picene (B) was not obtained, whereby the organic thin film transistor could not be produced.

Picene (B)

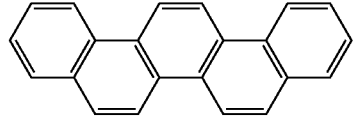

TABLE 3

| | Organic semiconductor layer | Solubility (hexane) | Solubility (toluene) | Stability to oxidization | Type of transistor | Field effect mobility (cm$^2$/Vs) |
|---|---|---|---|---|---|---|
| Example 8 | Compound (C56) | ○ | ○ | ○ | p | $1.5 \times 10^{-2}$ |
| Example 9 | Compound (C146) | ○ | ○ | ○ | p | $2.0 \times 10^{-1}$ |
| Example 10 | Compound (C191) | ○ | ○ | ○ | p | $1.5 \times 10^{-2}$ |
| Com. Ex. 5 | Pentacene (A) | x | x | x | — | — |
| Com. Ex. 6 | Picene (B) | x | x | — | — | — |

From the results shown in Table 3, it can be understood that the compound of the invention is well soluble in toluene or hexane, which is a non-halogen solvent in which pentance or picene is insoluble. Further, the results demonstrate that the compound of the invention is excellent in stability against oxidation. Also, it can be understood from the results that the compound of the invention is excellent in field effect mobility.

INDUSTRIAL APPLICABILITY

The compound of the invention can be applied to a wet coating process, and enables an organic thin film transistor which has stability against oxidation to be obtained. Further, the organic thin film transistor of the invention can be used in an electronic device for a display such as an electronic device for a thin film display, a wearable electronic device such as plastic IC cards or information tags, medical devices such as a bio-sensor or a measurement apparatus.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A compound represented by the following formula (I):

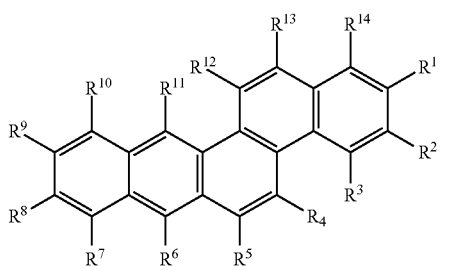

(I)

wherein $R^1$ to $R^{14}$ are independently a hydrogen atom, a halogen atom, an alkyl group having 2 to 30 carbon atoms, an alkenyl group having 3 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups further may have one or more substituents; and the two alkyl groups of the dialkylamino group having 2 to 60 carbon atoms may combine with each other to form a cyclic structure containing a nitrogen atom;

provided that the compound in which all of $R^1$ to $R^{14}$ are hydrogen atoms is excluded.

2. The compound according to claim 1 wherein at least one of $R^1$ to $R^{14}$ is an alkenyl group having 3 to 30 carbon atoms, an alkynyl group having 2 to 30 carbon atoms, a halolalkyl group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an alkylsilyl group having 3 to 20 carbon atoms, an alkylsilylethynyl group having 5 to 60 carbon atoms or a cyano group.

3. A compound for an organic thin film transistor represented by the following formula (A-1):

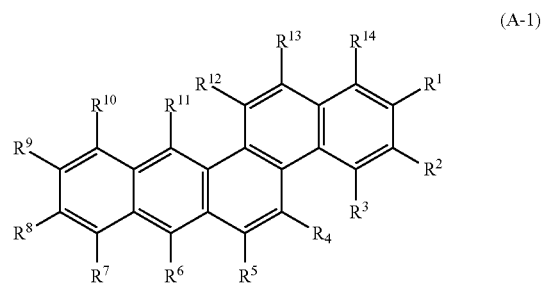

(A-1)

wherein $R^1$ to $R^{14}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups further may have one or more substituents; and the two alkyl groups of the dialkylamino group having 2 to 60 carbon atoms may combine with each other to form a cyclic structure containing a nitrogen atom;

provided that the compound in which all of $R^1$ to $R^{14}$ are hydrogen atoms is excluded.

4. An organic thin film transistor comprising the compound for an organic thin film transistor according to claim 3.

5. An apparatus comprising the organic thin film transistor according to claim 4.

6. An organic thin film transistor comprising at least three terminals of a gate electrode, a source electrode and a drain electrode, an insulating layer and an organic semiconductor layer, on a substrate, current flowing between the source electrode and the drain electrode being controlled by applying a voltage to the gate electrode, the organic semiconductor layer comprising the compound for an organic thin film transistor according to claim 3.

7. A compound for an organic thin film transistor represented by the following formula (A-2):

(A-2)

[structure]

wherein R¹, R², R⁷, R⁸, R⁹, R¹⁰ and R¹⁴ are the same as R¹, R², R⁷, R⁸, R⁹, R¹⁰ and R¹⁴ in the formula (A-1).

8. An organic thin film transistor comprising the compound for an organic thin film transistor according to claim 7.

9. An organic thin film transistor comprising at least three terminals of a gate electrode, a source electrode and a drain electrode, an insulating layer and an organic semiconductor layer, on a substrate, current flowing between the source electrode and the drain electrode being controlled by applying a voltage to the gate electrode, the organic semiconductor layer comprising the compound for an organic thin film transistor according to claim 7.

10. An apparatus comprising the organic thin film transistor according to claim 9.

11. A compound represented by the following formula (B-1):

(B-1)

[structure]

wherein R¹ to R⁴ independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents;

the two alkyl groups of the above-mentioned dialkylamino group having 2 to 60 carbon atoms may combine with each other to form a ring structure containing a nitrogen atom; and the ring Ar¹ is a fused ring which is represented by any of the following formulas (B-2) to (B-5):

(B-2)

[structure]

(B-3)

[structure]

(B-4)

[structure]

(B-5)

[structure]

wherein the numerals 7 and 8 in a bold line respectively correspond to the 7ᵗʰ and 8ᵗʰ positions of the anthracene skeleton of the compound represented by the formula (B-1):

X¹ is —S—, —O—, or —N(R²¹)—;

R⁵ to R²¹ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that compounds in which all of R¹³ to R¹⁶ and all of R¹⁷ to R²⁰ are hydrogen atoms are excluded.

12. A compound according to claim 11 which is represented by the following formula (B-6):

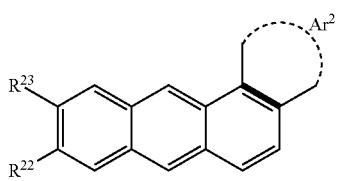
(B-6)

wherein $R^{22}$ and $R^{23}$ are independently a hydrogen atom, a halogen atom,
an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, which groups may further have one or more substituents;

the two alkyl groups of the dialkylamino group having 2 to 60 carbon atoms may combine with each other to form a ring structure containing a nitrogen atom; and the ring $Ar^2$ is a fused ring represented by any of the following formulas (B-7) to (B-10):

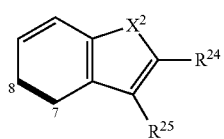
(B-7)

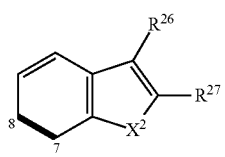
(B-8)

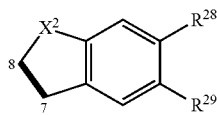
(B-9)

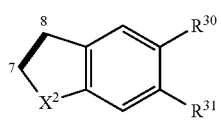
(B-10)

wherein the numerals 7 and 8 in a bold line respectively correspond to the 7$^{th}$ and 8$^{th}$ positions of the anthracene skeleton of the compound represented by the formula (B-6):

$X^2$ is —S—, —O—, or —N($R^{32}$)—;

$R^{24}$ to $R^{32}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that compounds in which all of $R^{28}$ to $R^{29}$ and all of $R^{30}$ to $R^{31}$ are hydrogen atoms are excluded.

13. A compound for an organic thin film transistor represented by the following formula (B-1):

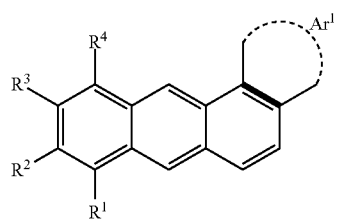
(B-1)

wherein $R^1$ to $R^4$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents;

the two alkyl groups of the dialkylamino group having 2 to 60 carbon atoms may combine with each other to form a ring structure containing a nitrogen atom; and the ring $Ar^1$ is a fused ring which is represented by any of the following formulas (B-2) to (B-5):

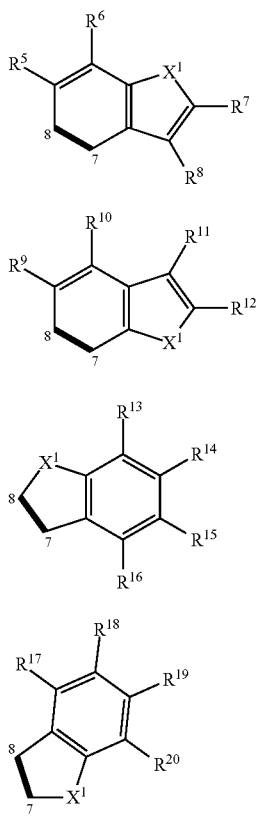

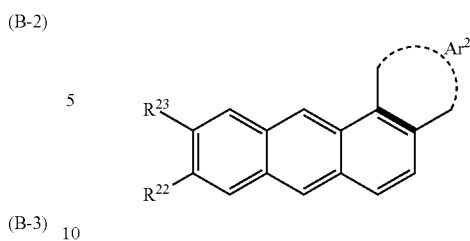

wherein the numerals 7 and 8 in a bold line respectively correspond to the 7<sup>th</sup> and 8<sup>th</sup> positions of the anthracene skeleton of the compound represented by the formula (B–1):

$X^1$ is —S—, —O—, or —N($R^{21}$)—;

$R^5$ to $R^{21}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that compounds in which all of $R^{13}$ to $R^{16}$ and all of $R^{17}$ to $R^{20}$ are hydrogen atoms are excluded.

14. A compound for an organic thin film transistor according to claim 13 which is represented by the following formula (B-6):

wherein $R^{22}$ and $R^{23}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, which groups may further have one or more substituents;

the two alkyl groups of the dialkylamino group having 2 to 60 carbon atoms may combine with each other to form a ring structure containing a nitrogen atom; and the ring $Ar^2$ is a fused ring represented by any of the following formulas (B-7) to (B-10):

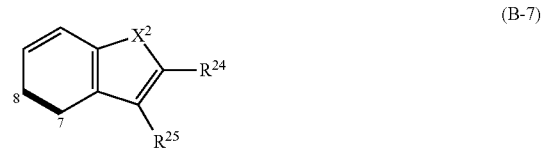

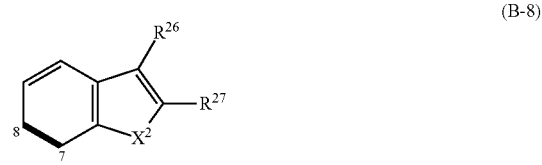

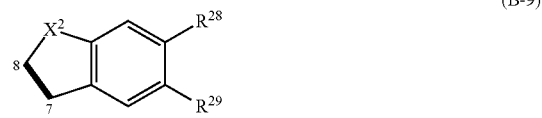

wherein the numerals 7 and 8 in a bold line respectively correspond to the 7<sup>th</sup> and 8<sup>th</sup> positions of the anthracene skeleton of the compound represented by the formula (B-6):

$X^2$ is —S—, —O—, or —N($R^{32}$)—;

$R^{24}$ to $R^{32}$ are independently a hydrogen atom, a halogen atom, an alkyl group having 1 to 30 carbon atoms, an alkenyl group having 2 to 30 carbon atoms, an alkynyl group having 2 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the above-mentioned dialkylamino group having 2 to 60 carbon atoms may combine with each other to form a ring structure containing a nitrogen atom;

provided that compounds in which all of $R^{28}$ to $R^{29}$ and all of $R^{30}$ to $R^{31}$ are hydrogen atoms are excluded.

15. An organic thin film transistor comprising the compound for an organic thin film transistor according to claim 13.

16. An apparatus comprising the organic thin film transistor according to claim 15.

17. An organic thin film transistor comprising at least three terminals of a gate electrode, a source electrode and a drain electrode, an insulating layer and an organic semiconductor layer, on a substrate, current flowing between the source electrode and the drain electrode being controlled by applying a voltage to the gate electrode, the organic semiconductor layer comprising the compound for an organic thin film transistor according to claim 13.

18. A method for producing an organic thin film transistor wherein an organic semiconductor layer is formed by applying the compound for an organic thin film transistor according to claim 13.

19. A compound represented by the following formula (C-1) or (C-2):

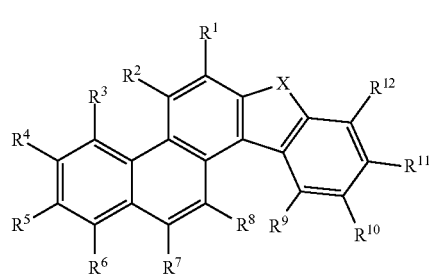

(C-1)

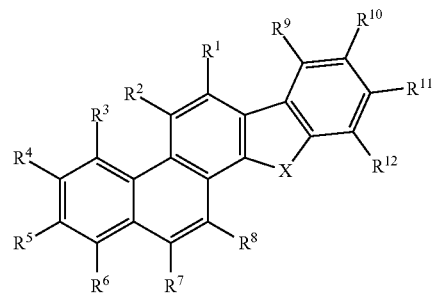

(C-2)

wherein $R^1$ to $R^8$ are independently a hydrogen atom, a halogen atom, an alkyl group having 2 to 30 carbon atoms, an alkenyl group having 2 to 30 carbon atoms, an alkynyl group having 2 to 30 carbon atoms, a haloalkyl group having 1 to 30 carbon atoms, an alkoxy group having 2 to 30 carbon atoms, a haloalkoxy group having 1 to 30 carbon atoms, an alkylthio group having 2 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms or an alkylsilylethynyl group having 5 to 60 carbon atoms, which groups may further have one or more substituents;

the two alkyl groups of the dialkylamino group having 2 to 60 carbon atoms may combine with each other to form a ring structure containing a nitrogen atoms;

X is —S—, —O—, or —N($R^{13}$)—;

$R^9$ to $R^{13}$ are independently a hydrogen atom, a halogen atom, an alkyl group having 2 to 30 carbon atoms ($R^{13}$ may be a methyl group), an alkenyl group having 2 to 30 carbon atoms, an alkynyl group having 2 to 30 carbon atoms, a haloalkyl group having 1 to 30 carbon atoms, an alkoxy group having 2 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, an arylamino group having 6 to 60 carbon atoms, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylethynyl group having 5 to 60 carbon atoms or a cyano group, which groups may further have one or more substituents; and the two alkyl groups of the dialkylamino group having 2 to 60 carbon atoms may combine with each other to form a ring structure containing a nitrogen atom;

provided that at least one of $R^1$ to $R^{12}$ is a group other than hydrogen.

20. The compound according to claim 19 wherein the compound represented by the formula (C-1) is a compound represented by the following formula (C-3) and the compound represented by the formula (C-2) is a compound represented by the following formula (C-4):

(C-3) 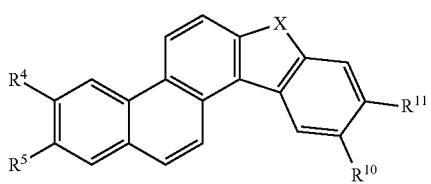

(C-4) 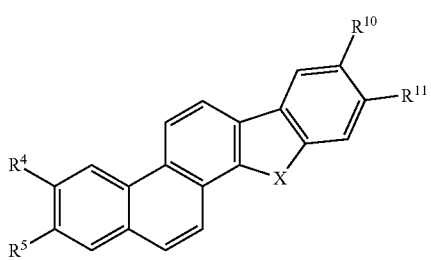

wherein X, $R^4$, $R^5$, $R^{10}$ and $R^{11}$ are the same as those in the formulas (C-1) and (C-2); and at least one of $R^4$, $R^5$, $R^{10}$ and $R^{11}$ is a group other than hydrogen.

21. The compound according to claim 19 which is a compound for an organic thin film transistor.

22. An organic thin film transistor which comprises the compound according to claim 21.

23. An organic thin film transistor comprising at least three terminals of a gate electrode, a source electrode and a drain electrode, an insulating layer and an organic semiconductor layer, on a substrate, current flowing between the source electrode and the drain electrode being controlled by applying a voltage to the gate electrode, the organic semiconductor layer comprising the compound according to claim 21.

24. An apparatus comprising the organic thin film transistor according to claim 22.

* * * * *